(12) United States Patent
Andrae et al.

(10) Patent No.: US 11,384,340 B2
(45) Date of Patent: *Jul. 12, 2022

(54) ALCOHOL DEHYDROGENASE VARIANTS

(71) Applicant: Genomatica, Inc., San Diego, CA (US)

(72) Inventors: Stefan Andrae, San Diego, CA (US);
Michael Patrick Kuchinskas, San Diego, CA (US); Jingyi Li, San Diego, CA (US); Harish Nagarajan, San Diego, CA (US); Priti Pharkya, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/792,592

(22) Filed: Feb. 17, 2020

(65) Prior Publication Data

US 2020/0354692 A1 Nov. 12, 2020

Related U.S. Application Data

(63) Continuation of application No. 15/027,169, filed as application No. PCT/US2014/059135 on Oct. 3, 2014, now Pat. No. 10,563,180.

(60) Provisional application No. 61/887,251, filed on Oct. 4, 2013.

(51) Int. Cl.
| | | |
|---|---|---|
| *C12N 9/04* | (2006.01) | |
| *C12P 7/24* | (2006.01) | |
| *C12P 7/18* | (2006.01) | |

(52) U.S. Cl.
CPC .............. *C12N 9/0006* (2013.01); *C12P 7/18* (2013.01); *C12P 7/24* (2013.01); *C12Y 101/01244* (2013.01); *C12Y 101/01001* (2013.01); *Y02P 20/10* (2015.11)

(58) Field of Classification Search
None
See application file for complete search history.

(56) References Cited

U.S. PATENT DOCUMENTS

| | | |
|---|---|---|
| 6,280,972 B1 | 8/2001 | Yasueda |
| 6,440,711 B1 | 8/2002 | Dave |
| 6,558,933 B2 | 5/2003 | Donald et al. |
| 8,163,516 B2 | 4/2012 | Dehring et al. |
| 9,346,902 B2 | 5/2016 | Burgard |
| 9,518,278 B2 | 12/2016 | Liao et al. |
| 10,563,180 B2 | 2/2020 | Andrae et al. |
| 2002/0010946 A1 | 1/2002 | Meyers |

FOREIGN PATENT DOCUMENTS

| | | |
|---|---|---|
| CN | 101328260 A | 12/2008 |
| CN | 101415758 A | 4/2009 |
| CN | 101668861 A | 3/2010 |
| WO | 2009141607 A1 | 11/2009 |
| WO | 2013110797 A1 | 8/2013 |

OTHER PUBLICATIONS

Brautaset et al. (2004) "Plasmid-Dependent Methylotrophy in Thermotolerant Bacillus methanolicus", Journal of Bacteriology, 186:1229-1238.
Hektor et al. (2002) "Identification of a Magnesium-dependent NAD(P)(H)-binding Domain in the Nicotinoprotein methanol Dehydrogenase from Bacillus methanolicus," Journal of Biol. Chem., 277:46966-46973.
Kloosterman et al. (2002) "Molecular, Biochemical and Functional Characterization of a Nudix Hydrolase Protein That Stimulates the Activity of a Nicotinoprotein Alcohol Dehydrogenase", J. Biol. Chem., 277:34785-34792.
Krog et al. (2013) "Methylotrophic Bacillus methanolicus Encodes Two Chromosomal and One Plasmid Born NAD+ Dependent Methanol Dehydrogenase Paralogs with Different Catalytic and Biochemical Properties," PLoS ONE, 8 (3): 1-11.
Ochsner et al. (2014) "In Vitro Activation of NAD-Dependent Alcohol Dehydrogenases by Nudix Hydrolases is More Widespread Than Assumed", Federation of European Biochemical Societies, 588:2993-2999.
Bailey, J. E. (1991) "Toward a Science of Metabolic Engineering", Science, 252:1668-1675.
Keasling, J.D. (2010) "Manufacturing Molecules Through Metabolic Engineering", Science, 330:1355-1358.
Yadav et al. (2012) "The future of metabolic engineering and synthetic biology: Towards a systematic practice", Metabolic Engineering, 14:233-241.
Arnold, F. H. (2001) "Combinatorial and computational challenges for biocatalyst design", Nature, 409:253-257.

*Primary Examiner* — Marsha Tsay
(74) *Attorney, Agent, or Firm* — Kagan Binder, PLLC

(57) ABSTRACT

Described herein are non-natural $NAD^+$-dependent alcohol dehydrogenases (ADHs) capable of at least two fold greater conversion of methanol or ethanol to formaldehyde or acetaldehyde, respectively, as compared to its unmodified counterpart. Nucleic acids encoding the non-natural alcohol dehydrogenases, as well as expression constructs including the nucleic acids, and engineered cells comprising the nucleic acids or expression constructs are described. Also described are engineered cells expressing a non-natural $NAD^+$-dependent alcohol dehydrogenase, optionally include one or more additional metabolic pathway transgene(s), methanol metabolic pathway genes, target product pathway genes, cell culture compositions including the cells, methods for promoting production of the target product or intermediate thereof from the cells, compositions including the target product or intermediate, and products made from the target product or intermediate.

18 Claims, 10 Drawing Sheets
Specification includes a Sequence Listing.

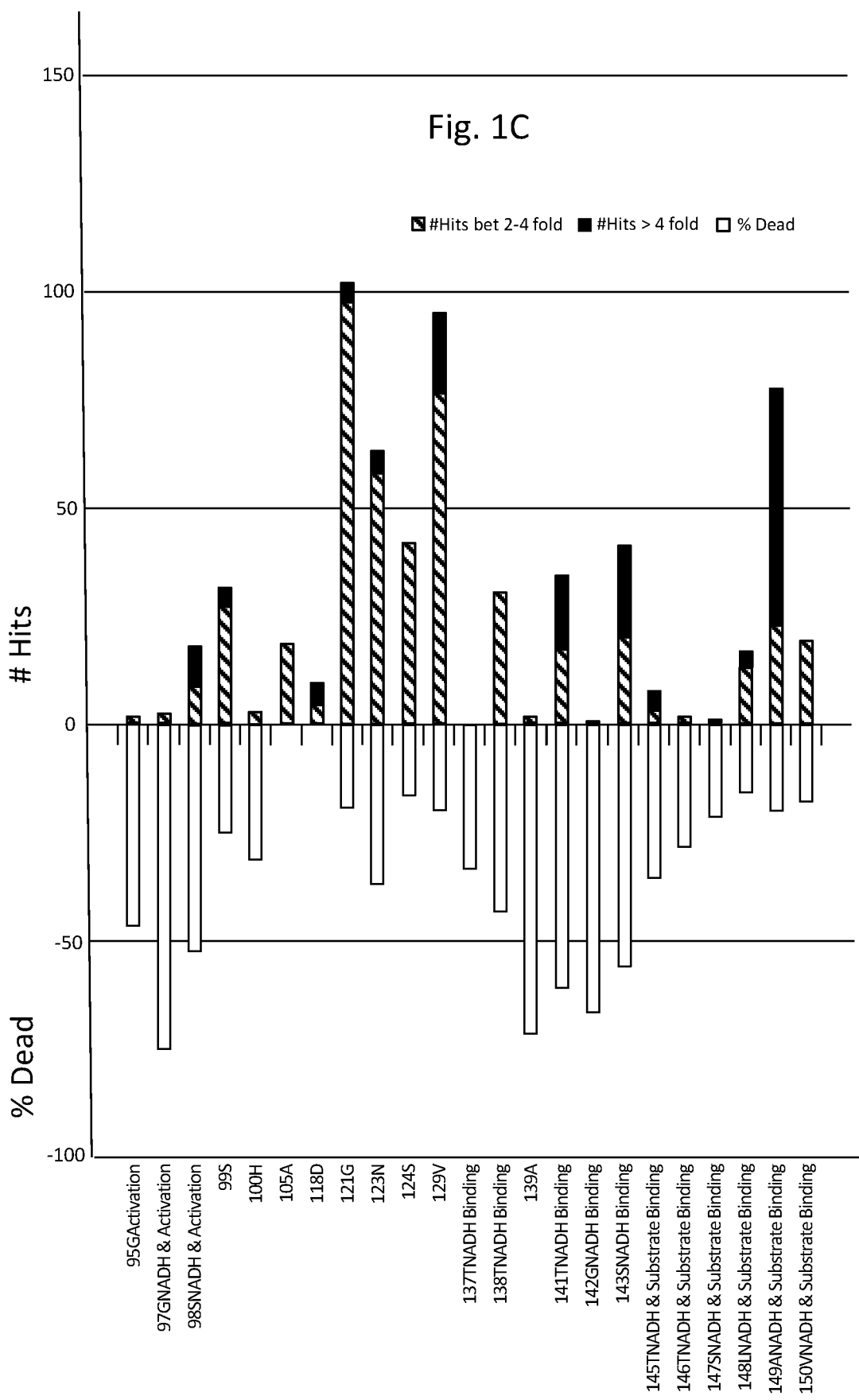

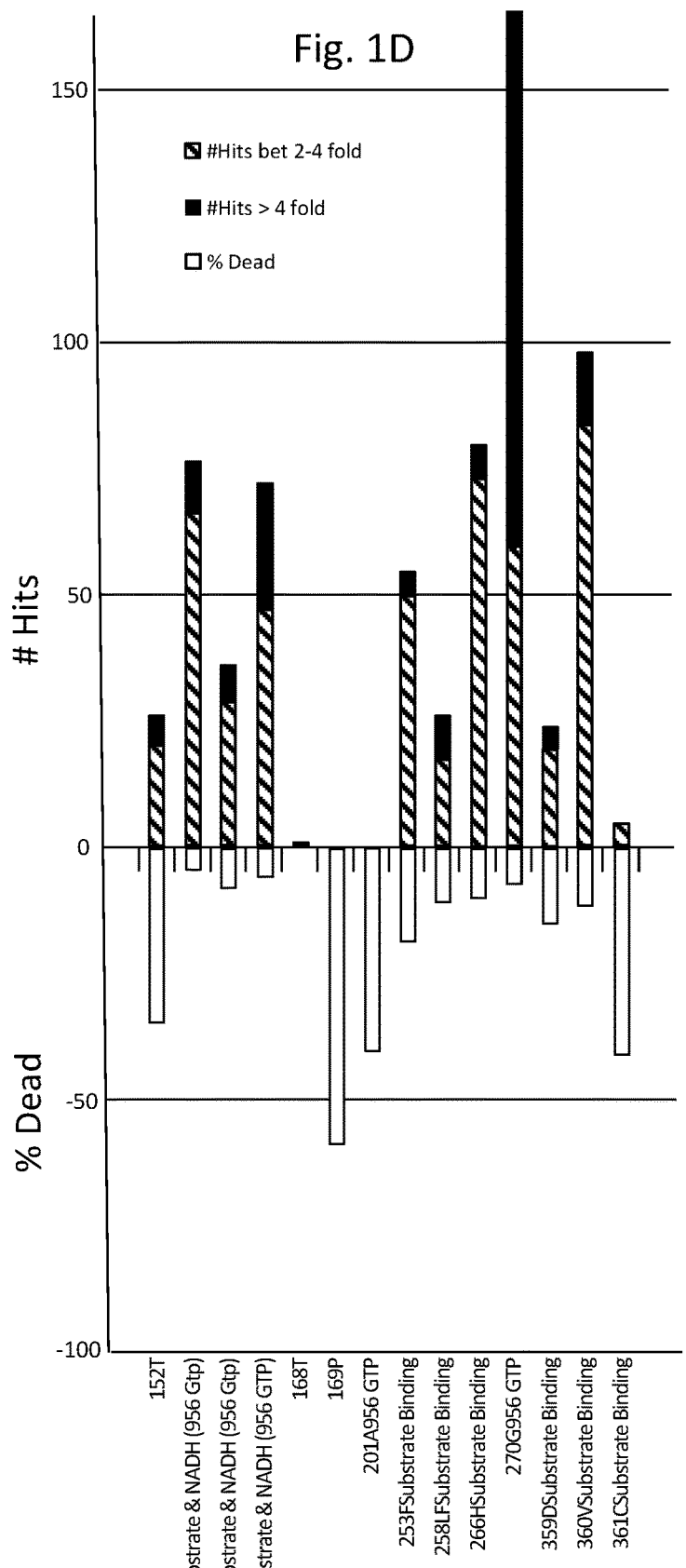

```
              10         20         30         40         50         60
1. Bacillus MeDH                                         MTMFIPASVIGRGAVKEVGTRLKQIGAKKALIVTDAFLHST--GLSEEVAKNIR
2. K. pneumoniae dhaT       MSYRMFDYLVPNVNFFGFMAISVVGERCQLLGGKKALIVTDKGLRAIKDGAVDKTLHYLR
3. Z. mobilis ADH                  MASSTFYIFFVNEMSEGSLERAIKDLNGSGFKMALIVSDAFMNKS--GVVRQVADLLK
4. E. coli FucO                    MANRMILNETAWFGRGAVGALTDEVKRRGYQKALIVDKTHVQC--GVVAKVTDKMD 70         80         90        100        110        120        130
1. Bacillus MeDH    HHHHHHGILMWANRMILNETAWFGRGAVGALTDEVKRRGYQKALIVDKTHVQC--GVVAKVTDKMD
2. K. pneumoniae dhaT  EAGLDVAIFPKAQPDPADTQVHEGVEKQENCDALVSIGGGSSHDTAKAIGLVAANG--GRINDYQ
3. Z. mobilis ADH      EAGIEVAIFDGSVEPNPKDTNVRDGLAVFRREQCDIITVTVGGGSPHDCGKGIGIAATHE--GDLYQYA
4. E. coli FucO        AQGINSAVYDGVMPNFVTAVLEGLKILKDNNSDFVISLGGGSPHDCAKAIALVATNG--GEVKDYE 140        150        160        170        180        190        200
1. Bacillus MeDH    AAGLAWAIYDGVVPNPTITVVKESLGVFQNSGADYLIAIGGGSFQDTCKAIGIISWNPEADVRSLE
2. K. pneumoniae dhaT  GVNSVEKPVVPVVAITTAGTGSETTSLAVITDSARKVKMPVIDEKITPTVAIVDFELMVKKPAGLT
3. Z. mobilis ADH      GIETIFMPLPPIVAVNTTAGTASEVTRHCVLTNTETKVKFVIVSWRNLPSVSINDPLLMIGKPAALT
4. E. coli FucO        GIDKSKKPALPLMSINTTAGTASEMTRECIITDEVRHVRKMAIVDRHVTPMVSVNDPLMVGMPKGLT 210        220        230        240        250        260
1. Bacillus MeDH    GLSPTNKPSVPILAIPTTAGTAAEVTINYVITDEEKRRKFVCVDPHDIPQVAFIDADMDGMPFALK
2. K. pneumoniae dhaT  IATGMDALSHAIEAYVAKGATPVTDAFAIQAMNLINEYLPKAVANGEDIEAREAMAYAQYMAGVAEN
3. Z. mobilis ADH      AATGMDALTHAVEAYISKDANPVTDAAAMQAIRPLIARNLRQAVALGSMLQARENMAYASLLAGMAFN
4. E. coli FucO        AATGMDALTHAFEAYSSTARTFITDACALKAASMIAKNLKTTCDMGKDMPAREAMAYAQFLAGMAFN 270        280        290        300        310        320        330
1. Bacillus MeDH    AATGVDALTHAIEGYITRGAWALTDALHIRAIEIIAGALRGSVAG   DKDAGEEMALGQYVAGMGFS
2. K. pneumoniae dhaT  NGGLGLVHSISHQVGGVYKLQHGICNSVNMPHVCAENLIAKTERFAHIAELLGENVSGLSTAAAAER
3. Z. mobilis ADH      NAMLGYVHAMAHQLGGLVHDMPHGVANAVLLPHVARYNLIAMPEKFADIAELMGENITGLSTLDAAEK
4. E. coli FucO        NASLGYVHAMAHQLGGYNLPHGVCNAVILPHVCLAVNASVVAGRLKDVGVAMSLDIANLGDKECAEA
                       NVGLGLVHSGMAHPLGAFYNTPHGVANAILLPHVMRYNADFTGEKYRDIARVMGVKVEGMSLEEARNA 340        350        360        370        380        390
1. Bacillus MeDH    AIVALEEYMKNEGIPSSGYAEMGVKEEDIELLAKMAFEDVCTQSNPRVATVQDIAQIIKNAL
2. K. pneumoniae dhaT  AIAAITRLSMDIGIFQHLRDLGVKEABFPYMAEMALKBGNAFSMPRKGMECEIAAIFRQAE
3. Z. mobilis ADH      TIQAVRDLAASIGIPANLTELGAKKEDVPLLADHALKDACALTNPRQGDQKEVEELFLSAF
4. E. coli FucO        AVEAVEAVLNRDVGIPFHLRDVGVRNEDIPALAQAALDDVCTGGNPREATLEDIVELYHTAW
```

Fig. 4

ALCOHOL DEHYDROGENASE VARIANTS

PRIORITY CLAIM

This application is a continuation of U.S. patent application Ser. No. 15/027,169, filed Apr. 4, 2016, which claims priority to International Patent Application No. PCT/US14/59135, filed Oct. 3, 2014, which claims the benefit of U.S. Provisional Patent Application No. 61/887,251, filed Oct. 4, 2013, entitled ALCOHOL DEHYDROGENASE VARIANTS, the disclosure of which is incorporated herein by reference. Also, the entire contents of the ASCII text file entitled "GN00003WO_Sequence_Listing_V2_ST25.txt" created on Aug. 26, 2019, having a size of 207 kilobytes is incorporated herein by reference.

BACKGROUND

Alcohol dehydrogenases (ADHs; EC 1.1.1.1) promote the conversion of alcohols to and aldehydes or ketones, typically along with the reduction of nicotinamide adenine dinucleotide ($NAD^+$ to NADH). ADHs are instrumental in the generation of important compounds having aldehyde, ketone, and alcohol groups during biosynthesis of various metabolites.

One class of alcohol dehydrogenase is methanol dehydrogenases (MDHs). MDHs, converts methanol (MeOH) to formaldehyde (Fald), may be used in an enzymatic pathway engineered into a microbe to enable MeOH as a sole carbon source or as a co-carbon source with other feed stocks such as, for example, glucose, dextrose, plant biomass or syngas, to produce valuable products. Microorganisms have been reported that metabolize methanol, and in some instances do so via a methanol dehydrogenase, and in even fewer instances produce valuable products. Increasing MDH activity will enable improved use of MeOH, improving MeOH as a sole carbon source, decreasing production costs, decreasing amounts of any more expensive secondary or co-carbon source, e.g. glucose, increasing product yields, and providing faster rate of MeOH use.

SUMMARY

Generally, presented herein are non-natural $NAD^+$-dependent alcohol dehydrogenases (ADHs) (i.e. engineered enzymes and their encoding-polynucleotides) capable of at least two fold greater conversion of methanol or ethanol to formaldehyde or acetaldehyde, respectively, as compared to its original or unmodified counterpart. Exemplary aspects describe non-natural $NAD^+$-dependent methanol dehydrogenases (MDHs), in particular enzymes of the class EC 1.1.1.244.

The ADHs and MDHs have at least one amino acid substitution as compared to its corresponding natural or unmodified alcohol dehydrogenase. By unmodified alcohol dehydrogenase is meant that the ADH or MDH may have been previously engineered (e.g., need not be naturally-occurring), prior to incorporating any modification described herein. Such alcohol dehydrogenases that are starting sequences for incorporating a modification described herein to generate the novel engineered enzyme may be alternatively referred to herein as wild-type, template, starting sequence, natural, naturally-occurring, unmodified, corresponding natural alcohol dehydrogenase, corresponding natural alcohol dehydrogenase without the amino acid substitution, corresponding alcohol dehydrogenase or corresponding alcohol dehydrogenase without the amino acid substitution. Experimental studies described herein demonstrate for the first time that a number of amino acid positions along the length of the amino acid sequence can be substituted to provide a non-natural dehydrogenase having increased substrate conversion. The studies also show that combinations of substitutions (e.g., two, three, four, five, six, seven, eight, nine, ten, eleven, or twelve, etc.) in an amino acid sequence can also provide even further increased substrate conversion. Provided herein therefore are single and combination variants of a starting or template or corresponding alcohol dehydrogenase, e.g., in particular enzymes of the class EC 1.1.1.244, having increased substrate conversion.

Embodiments of the disclosure provide a non-natural $NAD^+$-dependent alcohol dehydrogenase comprising at least one amino acid substitution as compared to a corresponding alcohol dehydrogenase, and capable of at least two fold greater conversion of methanol or ethanol to formaldehyde or acetaldehyde, as measured relative to a corresponding alcohol dehydrogenase without amino acid substitution. Embodiments of the disclosure also provide a non-natural $NAD^+$-dependent alcohol dehydrogenase comprising at least one amino acid substitution capable of at least two fold greater conversion of methanol or ethanol to formaldehyde or acetaldehyde, respectively, as compared a second sequence that is an $NAD^+$-dependent alcohol dehydrogenase, wherein the first and second sequences differ with regards to the at least one amino acid substitution. Embodiments are also directed to engineered cells expressing the non-natural $NAD^+$-dependent alcohol dehydrogenase capable of at least two fold greater conversion of methanol or ethanol to formaldehyde or acetaldehyde as described.

Some embodiments of the current disclosure are directed to an engineered cell expressing a non-natural $NAD^+$-dependent alcohol dehydrogenase comprising at least one amino acid substitution (including single and combination variants). The cells can be used to promote production of a target product or intermediate thereof. For example, the cell may provide either or both an increased amount of reducing equivalents, e.g. NADH, for an increase in a target product or may provide for increased fixation of carbon from formaldehyde and/or acetaldehyde into a target product. Exemplary products include (a) 1,4-butanediol and intermediates thereto, such as 4-hydroxybutanoic acid (4-hydroxybutanoate, 4-hydroxybutyrate, 4-HB), (b) butadiene and intermediates thereto, such as 1,4-butanediol, 1,3-butanediol, crotyl alcohol, 3-buten-2-ol (methyl vinyl carbinol) and 3-buten-1-ol, (c) 1,3-butanediol and intermediates thereto, such as 2,4-pentadienoate, crotyl alcohol or 3-buten-1-ol, (d) adipate, 6-aminocaproic acid, caprolactam, hexamethylenediamine and levulinic acid and their intermediates, e.g. 4-aminobutyryl-CoA, (e) methacrylic acid (2-methyl-2-propenoic acid) and its esters known collectively as methacrylates, such as methyl methacrylate, methyl methacrylate, 3-hydroxyisobutyrate and/or 2-hydroxyisobutyrate and their intermediates, (f) 1,2-propanediol (propylene glycol), n-propanol, 1,3-propanediol and glycerol, and their intermediates and (g) succinic acid and intermediates thereto.

Embodiments of the engineered cell may further optionally include one or more additional metabolic pathway transgene(s) to further promote production of the target product or intermediate thereof. In exemplary embodiments the cell further comprises one or more methanol metabolic pathway (MMP) transgene(s), such as a formaldehyde dehydrogenase transgene, allowing expression of the encoded pathway enzyme or accessory protein.

In exemplary embodiments the cell further comprises a product pathway comprising enzymes (and their encoding polynucleotides) for production of a target product, such as the enzymes described herein for production of 1,4-butanediol from glucose.

Other embodiments are directed to compositions including engineered cell, such as cell culture compositions, and also compositions including one or more product(s) produced from the engineered cell. For example, a composition can include a target product or intermediate thereof produced by the cells, where the composition has been purified to remove cells or other components useful for cell culturing. The composition may be treated to enrich or purify the target product or intermediate thereof.

Other embodiments of the disclosure are directed to products made from the target product obtained from methods using the engineered cell. Exemplary products include polymers made with target products, such as polymers made from diol target products combined with diacids, including target product succinic acid, such as polybutylene terephthalate (PBT) and polybutylene succinate (PBS) made from 1,4-butanediol polymerized with terephthalic acid or succinic acid respectively.

Other embodiments of the disclosure are directed to nucleic acids encoding the non-natural alcohol dehydrogenases with one or more variant amino acids, as well as expression constructs including the nucleic acids, and engineered cells comprising the nucleic acids or expression constructs.

In other embodiments the disclosure also provides methods for generating non-natural NAD$^+$-dependent alcohol dehydrogenases capable of at least two-fold greater conversion of methanol or ethanol to formaldehyde or acetaldehyde, respectively, as compared to its unmodified (original; template) counterpart. In some embodiments, the method includes steps of (a) identifying a variant amino acid that provides increased conversion in a template sequence, (b) identifying corresponding amino acid position in a target sequence having identify to the template sequence, and (c) changing the amino acid at the corresponding amino acid position in a target sequence to the variant amino acid. The starting template for incorporation of modifications described herein can be a naturally-occurring enzyme sequence or a previously engineered enzyme sequence.

In other embodiments, the methods includes steps of (a) identifying an amino acid position in a non-natural NAD$^+$-dependent alcohol dehydrogenases that is not a variant position, (b) providing, in a original template, a variation at an amino acid position that is a non-variant position, and (c) identifying variants from step (b) that provide increased conversion of the substrate.

DESCRIPTION OF THE DRAWINGS

FIGS. 1A-D are graphs listing amino acid positions of methanol dehydrogenase (2315A) and the effect of substitution of those positions on enzyme activity.

FIG. 3D illustrates using enzymes to fix carbon from methanol via formaldehyde assimilation into a product pathway of interest. The "Product Pathway" can be that of 1,4-butanediol as described herein or other product pathway.

FIG. 4 is an amino acid sequence alignment of various Fe-dependent alcohol dehydrogenases with Bacillus MeDH.

DETAILED DESCRIPTION

Figure 1A:
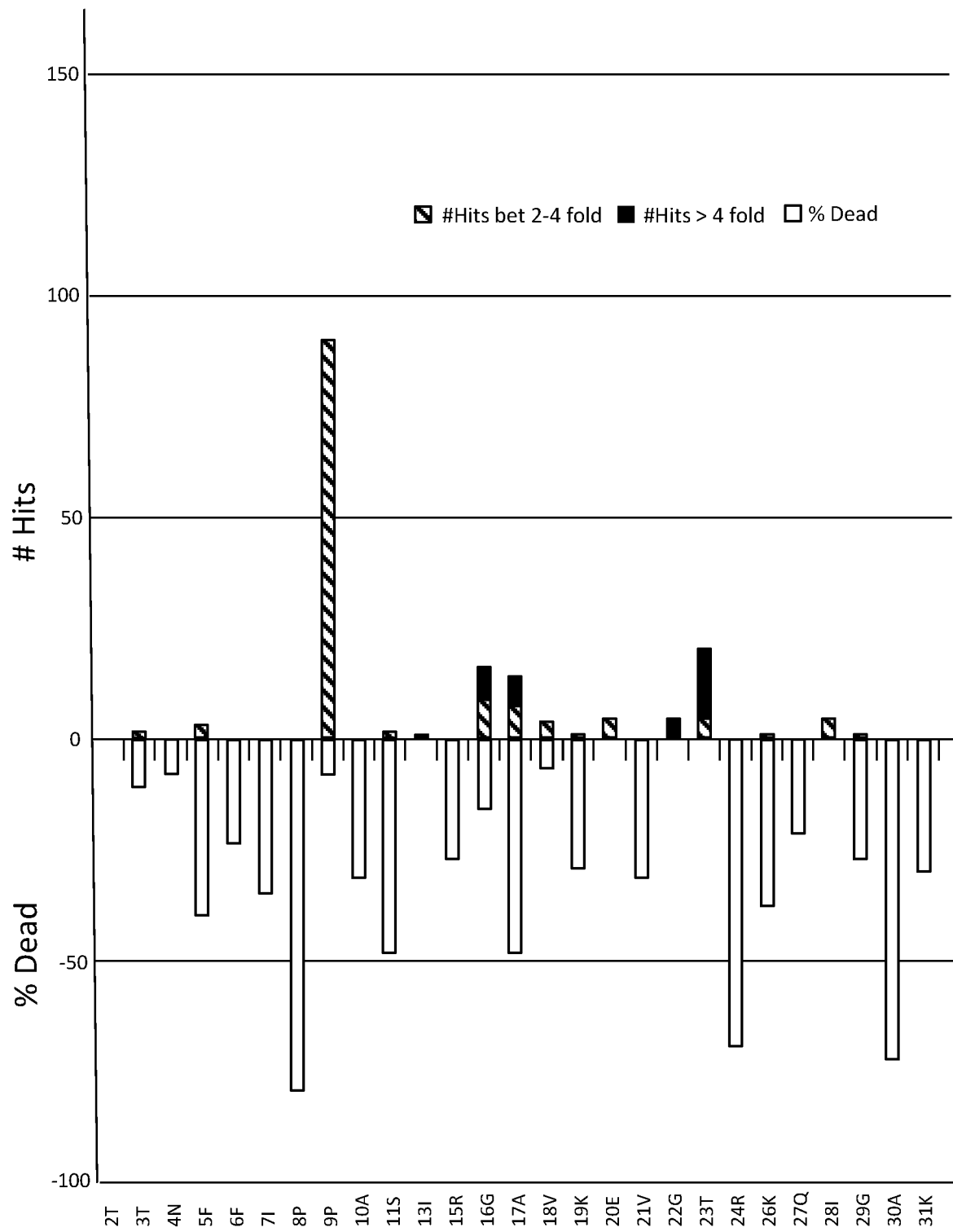

The embodiments of the description described herein are not intended to be exhaustive or to limit the disclosure to the precise forms disclosed in the following detailed description. Rather, the embodiments are chosen and described so that others skilled in the art can appreciate and understand the principles and practices of the description.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Generally, the disclosure provides non-natural NAD$^+$-dependent alcohol dehydrogenases (ADHs) capable of at least two fold greater conversion of methanol or ethanol to formaldehyde or acetaldehyde, respectively, as compared to its unmodified counterpart. Nucleic acids encoding the non-natural alcohol dehydrogenases, as well as expression constructs including the nucleic acids, and engineered cells comprising the nucleic acids or expression constructs are described.

Also described are engineered cells expressing a non-natural NAD$^+$-dependent alcohol dehydrogenase, optionally including one or more additional metabolic pathway transgene(s), methanol metabolic pathway genes, and/or target product pathway genes; cell culture compositions including the cells; methods for promoting production of the target product or intermediate thereof from the cells; compositions including the target product or intermediate; and products made from the target product or intermediate.

The term "non-naturally occurring", when used in reference to an organism (e.g., microbial) is intended to mean that the organism has at least one genetic alteration not normally found in a naturally occurring organism of the referenced species. Naturally-occurring organisms can be referred to as "wild-type" such as wild type strains of the referenced species. Likewise, a "non-natural" polypeptide or nucleic acid can include at least one genetic alteration not normally found in a naturally-occurring polypeptide or nucleic acid. Naturally-occurring organisms, nucleic acids, and polypeptides can be referred to as "wild-type" or "original" such as wild type strains of the referenced species. Likewise, amino acids found in the wild type organism can be referred to as "original" with regards to any amino acid position.

A genetic alteration that makes an organism non-natural can include, for example, modifications introducing expressible nucleic acids encoding metabolic polypeptides, other nucleic acid additions, nucleic acid deletions and/or other functional disruption of the organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon.

An NAD(P)+-dependent methanol dehydrogenase from Bacillus methanolicus MGA3 (Genbank Accession number EIJ77596.1, GI number: 387585261; designated herein as MDH 2315, 382 amino acids long; SEQ ID NO: 1), was selected as a template for mutagenesis to identify variants with improved activity. This sequence was selected as it was surprisingly found to be very active on methanol, typically nearly twice as active as other alcohol dehydrogenases tested, and used NAD+ and thus able to regenerate NADH that can be useful to enzymes in target pathways. MDH 2315 is reported in the literature as an NAD(P)-dependent methanol dehydrogenase from *Bacillus methanolicus* MGA3 and its sequence was described in Brautaset et al., "Plasmid-Dependent Methylotrophy in Thermotolerant *Bacillus methanolicus*", Journal of Bacteriology, vol. 186, pp 1229-1238 (2004). It is also referred to as MDH MGA3 in WO2013/110797 to Brautaset and MDH "M" in Krog et al., "Methylotrophic *Bacillus methanolicus* Encodes Two Chromosomal and One Plasmid Born NAD+ Dependent Mathanol Dehydrogenase Paralogs with Different Catalytic and Biochemical Properties", PLOS ONE, pp. 1-11, (2013), which report additional wild-type *Bacillus* MDHs.

MDH 2315A was expressed in *E. coli* and a library of variants was generated by error prone PCR (the epPCR Library). Specifically, MDH 2315A was expressed in *E. coli* and subjected to saturation mutagenesis at 375 of 382 positions to generate a library of all single point substitutions of the common 20 amino acids (the NNK library).

In the primary screen, the NNK Library was screened by assaying individual colony cell extracts for MeOH to Fald conversion. The library was screened for variants that had greater than 2-fold activity over wild-type (defined as a positive). Such a library can contain variants with multiple mutations, deletions, etc. However, variants with single point substitutions were identified. In that primary screen about 150 positions gave colonies whose extracts had activity reliably 2-fold greater than wild-type. Of those, 21 positions gave colonies with activity reliably greater than 4-fold wild-type.

The primary screen of the NNK library identified about 10 positions where 90% or more of the colonies were inactive, suggesting that any amino acid other than wild-type at those positions led to enzyme inactivity (or rapid degradation). About 30 positions were identified in which less than 5% of the colonies were inactive. Many positions were identified in which no positives were observed but the total number of inactives was less than 90%. Many positions were identified in which the total number of positives and inactives were less than 95%.

Secondary in vitro assays in triplicate and sequencing were done on all positives greater than 4-fold, and many greater than 2-fold activity. At 40 positions, a total of 90 substitutions were determined to be responsible for the activity increase either greater than 2-fold or in many cases greater than 4-fold, and up to 10-fold. In many positions, only a single specific amino acid gave improvement, in other positions several amino acid substitutions gave improvement (e.g., at 213 only N213D, but at 121 both G121D, G121V, etc).

Secondary screening of the epPCR library revealed about 20 positions whose substitutions gave activity greater than 3-fold wild-type. Sequencing of these colonies revealed the specific substitutions at each position, for example, N213D (nomenclature: N is original or unmodified amino acid at position 213; D is the substitution). At these 20 positions, a total of 30 substitutions provided greater than 3-fold wild-type activity of which about 15 variants provided greater than 4-fold activity.

Some of the colonies whose MDH variant sequence were identified were also assayed in vivo by measuring MeOH conversion to formaldehyde in a strain background in which genes for use of formaldehyde were inactivated, thus enabling accumulation of formaldehyde. Generally, all MDH variants that were positive (greater than wild-type) in in vitro screening also enabled greater than wild-type activity in vivo, although the in vitro to in vivo activities did not always correlate exactly.

At some positions the frequency of a particular substitution in the total population of colonies at that position in a library was zero or less than statistically expected. Thus some substitutions at some positions may not have been present or present and not detected.

Figure 1B:
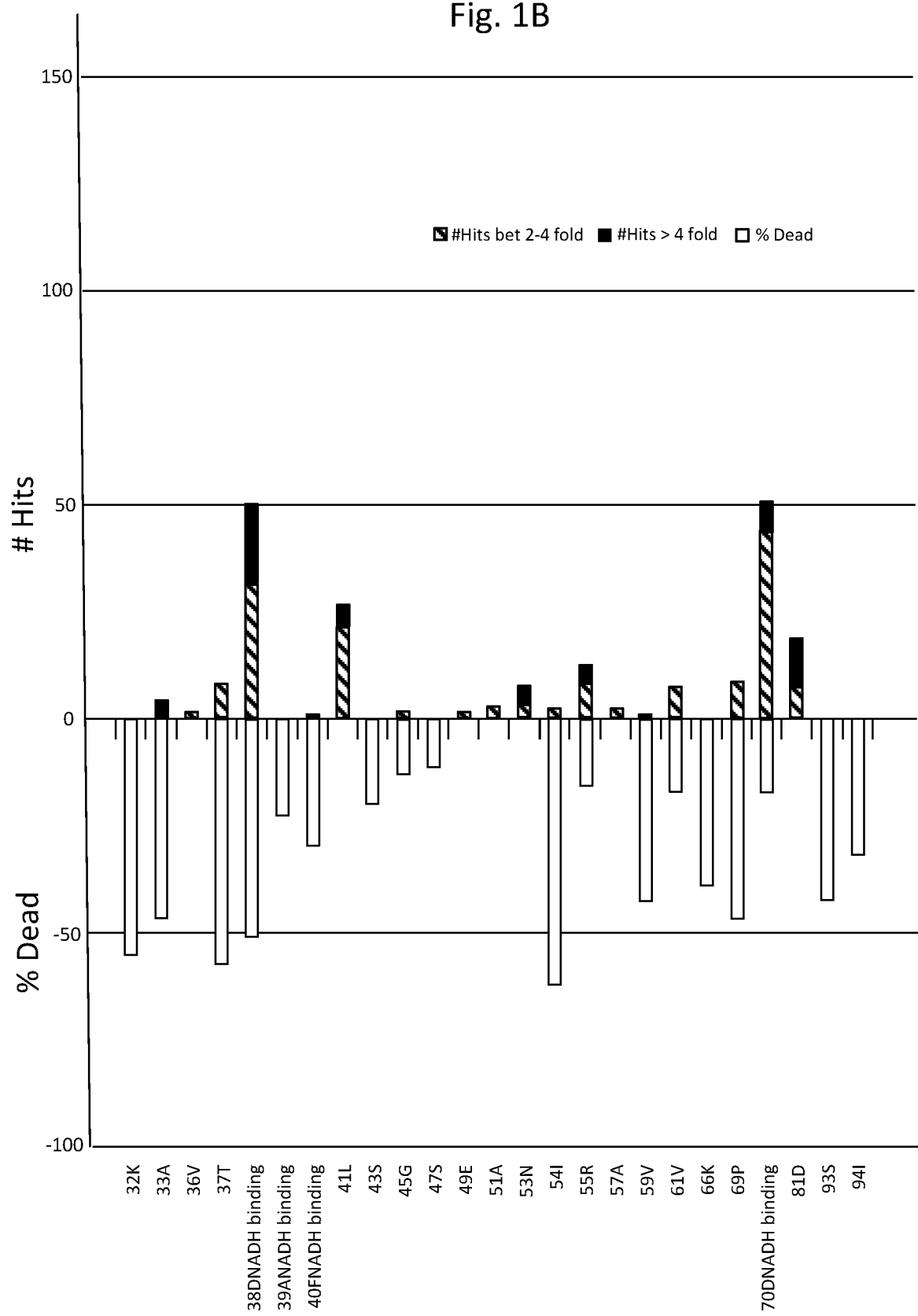

Table 1 lists amino acids mutations with respect to SEQ ID NO: 1, providing greater than two fold activity when present as single mutations. While not to be bound by theory, as depicted in FIG. 1, functional features associated with amino acid positions of methanol dehydrogenase designated 2315A and corresponding positions in other methanol dehydrogenase described herein include: NADH cofactor binding correlating with positions 38D, 39A, 40F, 70D, 97G, 98S, 137T, 138T, 141T, 142G, 143S, 145T, 146T, 147S, 148L, 149A, 150V, 161P, 162V, 163I; activation site correlating with positions 95G, 97G, 98S; and substrate correlating with positions 145T, 146T, 147S, 148L, 149A, 150V, 161P, 162V, 163I, 253F, 258L, 266H, 359D, 360V, 361C.

As can be seen from FIG. 1 depicting site saturation mutagenesis, numerous amino acid positions of methanol dehydrogenase designated 2315A are tolerant to substitution (indicated by a percentage of colonies having greater than 2-fold (designated "hits") or from 0.2 to less than 2-fold activity of wild-type enzyme) and others less tolerant (indicated by percentage of colonies where enzyme activity was less than 20% of wild-type enzyme activity (designated "dead"). For example, 168T and 270G are very tolerant to change, where substitutions at 168T generally had little effect on activity, whereas substitutions at 270G predominantly improved activity.

Art known methods can be used for the testing the enzymatic activity of alcohol dehydrogenases, and such methods can be used to test activity of alcohol dehydrogenase (ADH) variant enzymes as well. As a general matter, a reaction composition including the alcohol dehydrogenase (ADH) variant, an alcohol (substrate) and NAD (cofactor) can be converted to a dehydrogenated product. For example, conversion of ethanol is shown as follows:

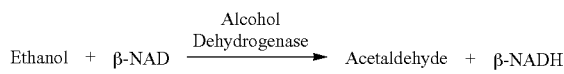

$$\text{Ethanol} + \beta\text{-NAD} \xrightarrow{\text{Alcohol Dehydrogenase}} \text{Acetaldehyde} + \beta\text{-NADH}$$

Reaction can be carried out at a desired temperature, such as 25° C., and pH, such as pH 7.

The ADH variant can be defined in terms of its enzymatic activity with one unit of enzyme converting 1.0 µmole of alcohol to dehydrogenated product per minute at pH 8.8 @ 25° C. See, for example, Kagi, J. H. R. and Vallee, B. L. (1960) *Journal of Biological Chemistry* 235, 3188-3192

Of particular interest herein is conversion of methanol to formaldehyde to regenerate NADH. This conversion can be followed by either or both conversion to formate or fixation of the formaldehyde carbon into target product. The formate can be either or both converted to $CO_2$ or have its carbon fixed into target product, such as by conversion back to formaldehyde. See the attached figures.

A representative in vivo assay was developed to determine the activity of methanol dehydrogenase variants in organisms is reported in U.S. application Ser. No. 13/975,678. This assay relies on the detection of formaldehyde (Palp), thus measuring the forward activity of the enzyme (oxidation of methanol). To this end, a strain comprising a BDOP and lacking frmA, frmB, frmR was created using Lamba Red recombinase technology (Datsenko and Wanner, *Proc. Natl. Acad. Sci. USA*, 6 97(12): 6640-5 (2000). Plasmids expressing methanol dehydrogenases were transformed into the strain, then grown to saturation in LB medium+antibiotic at 37° C. with shaking. Transformation of the strain with an empty vector served as a negative control. Cultures were adjusted by O.D. and then diluted 1:10 into M9 medium+0.5% glucose+antibiotic and cultured at 37° C. with shaking for 6-8 hours until late log phase. Methanol was added to 2% v/v and the cultures were further incubated for 30 min. with shaking at 37° C. Cultures were spun down and the supernatant was assayed for formaldehyde produced using DETECTX Formaldehyde Detection kit (Arbor Assays; Ann Arbor, Mich.) according to manufacturer's instructions. The frmA, frmB, frmR deletions resulted in the native formaldehyde utilization pathway to be deleted, which enables the formation of formaldehyde that can be used to detect methanol dehydrogenase activity in the organism. These genes are deleted in this case solely to facilitate measurement of methanol conversion by preventing loss of the measured analyte, formaldehyde.

Enzymatic kinetic assays were done for 10 single point variants, and that 2-10 fold improvements in activity were reflected in 2-10 fold improvements in Km, Vmax or both. Co-factor binding nor substrate or product on-off rates were not measured.

Table 7 shows enzymology data from various wild type ADH proteins. Tables 8 and 9 show data for wild type and variant enzymes, with Table 8 showing activity using either methanol or 1,4-butanediol, and Table 9 showing 1,4-butanediol-dependent steady-state kinetic parameters for wild-type and variant methanol dehydrogenase.

Results of the mutagenesis procedures and rationale design and screening of the positives (by "positive" is meant a sequence modified as described herein having at least a two (2) fold increase in activity compared to the unmodified template sequence) revealed a number of amino acid variants along the MDH protein 2315A template for use in the invention. Positives showing greater than two fold increase in activity are shown in Table 1, and listed as follows: S11T, D38N, H42Q, E48D, N53I, E56K, D60E, V61A, I63F, P65Q, D70N, P71I, P71T, P71V, T74S, D81G, K84R, E86K, N87K, I94V, S99P, S99T, A103V, I106L, G107S, L108V, L108W, V109Y, N112K, N112R, R115H, I116F, N117D, N117Q, N117Y, Q120H, Q120R, G121A, G121D, G121E, G121L, G121M, G121R, G121S, G121T, G121V, G121W, G121Y, V122A, V122P, N123D, N123I, N123L, N123R, N123Y, S124I, S124L, S124R, V125C, V125G, V125W, E126G, E126V, K127C, K127R, P128A, P128R, P128S, V129A, V129M, V129P, V129S, V130F, V130I, V130Y, A134T, S143T, T145M, T146N, S147R, L148A, L148F, L148G, L148I, L148T, L148V, L148W, A149L, A149M, A149T, A149V, V150A, V150I, T152M, A155V, K157N, V158E, V158H, V158K, V158W, P161A, P161G, P161Q, P161S, P161V, I163F, I163N, I163Q, I163T, D164G, D164N, E165G, K181R, A184T, L186M, T190A, T190S, I199V, Q217K, L226M, G256C, Q267H, G269S, G270M, G270S, G270Y, T296S, R298H, A300T, I302V, G312V, A316V, I323M, F333L, P336L, S337C, G343D, V344A, V344G, K345E, E350K, K354M, N355D, N355I, N355K, E358G, V360A, V360G, V360K, V360R, V360S, C361N, C361R, Q363K, and K379M. These changes, their positions in SEQ ID NO: 1, and their corresponding positions in other template sequences are described further in the tables and elsewhere herein.

Of more interest are positives showing greater than two fold increase in activity as single mutations shown in Table 1, and listed as follows: D38N, D60E, P71I, P71V, N87K, S99T, A103V, G107S, L108V, L108W, V109Y, R115H, I116F, N117D, N117Q, G121D, G121E, G121L, G121M, G121R, G121S, G121T, G121V, G121W, G121Y, V122P, N123D, N123I, N123L, N123R, N123Y, S124I, S124L, V125C, V125G, V125W, E126G, K127C, K127R, P128A, P128R, P128S, V129A, V129M, V129P, V129S, V130F, V130I, V130Y, A134T, S143T, T146N, A149L, A149M, A149T, A149V, V150A, K157N, V158E, V158H, V158K, V158W, I163Q, D164N, Q267H, G270M, G270S, G270Y, K345E, N355D, V360G, V360K, V360R, V360S, C361R. These changes, their positions in SEQ ID NO: 1, and their corresponding positions in other template sequences are described further in the tables and elsewhere herein.

Results of the rationale design mutagenesis procedures and the other library generation procedures described herein and screening of the positive revealed a number of combination amino acid variants along the MDH protein 2315A template. Positives showing greater than two fold increase in activity are shown in Tables 2-4, and listed as variations in the following sets: (a) D70N, L148G, P161G, V360A; (b) D70N, L148G, V360A, C361N; (c) D70N, L148V, V150I, P161A, V360G; (d) D70N, L148V, V360G; (e) D70N, P161A, V360A; (f) D70N, P161V, V360G, C361N; (g) D70N, V150I, P161A, V360A; (h) D70N, V150I, P161V, V360G, C361N; (i) E48D, L148V, P161A, V360A; (j) L148G, P161A, V360A, C361N; (k) L148G, P161A, V360G; (l) L148G, P161A, V360G, C361N; (m) L148G, P161G, V360A; (n) L148G, P161G, V360G, C361N; (o) L148G, V360A, C361N; (p) L148G, V360G, C361N; (q) L148I, P161G, V360G; (r) L148I, P161V, V360G; (s) L148T, V150I, V360A; (t) L148T, V360G; (u) L148V, P161A, V360A; (v) L148V, V150I, P161A, V360A; (w) L148V, V150I, P161A, V360A, C361N; (x) L148V, V150I, P161A, V360G; (y) L148V, V150I, P161A, V360G, C361N; (z) L148V, V150I, P161A, V360G, C361N; (aa) L148V, V150I, P161G, V360A; (ab) L148V, V150I, P161V, V360G, C361N; (ac) L148W, P161A, V360A, C361N; (ad) N112K, S147R, P161A, V360A; (ae) P161A, Q217K, V360A, C361N; (af) P161A, V360A, C361N; (ag) P161A, V360G; (ah) P161V, E358G, V360G; (ai) P161V, V360A, C361N; (aj) L148W, P161A, V360A, C361N; (ak) N112K, S147R, P161A, V360A; (al) P161A, Q217K, V360A, C361N; (am) P161A, V360A, C361N; (an) P161A, V360G; (ao) P161V, E358G, V360G; (ap) P161V, V360A, C361N; (aq) P161V, V360G; (ar) P65Q, L148G, V150I, P161A, V360G, C361N; (as) S147R, L148A, V150I, P161A, V360G; (at) S147R, L148F, V150I, P161G, V360G; (au) S147R, L148V, P161G, V360A; (av) P161V, V360G; (aw) P65Q, L148G, V150I, P161A, V360G, C361N; (ax) S147R, L148A, V150I, P161A, V360G; (ay) S147R, L148F, V150I, P161G, V360G; (az) S147R, L148V, P161G, V360A; (aaa) S147R, L148V, P161V, V360G; (aab) S147R, L148V, V150I, P161A, C361N; (aac) S147R, L148V, V150I, P161G, V360G; (aad) S147R, P161A, V360A; (aae) S147R, P161A, V360A, C361N; (aaf) S147R, P161A, V360G; (aag) S147R, P161V, V360G; (aah) S147R, P161V, V360G, C361N; (aai) S147R, V150I, P161V, V360A; (aaj) S147R, V150I, V360A, C361N; (aak) T145M, L148I, V360G; (aal) V150I, I302V, V360G, C361N; (aam) V150I, P161A, C361N; (aan) V150I, P161G, V360A, C361N; (aao) V150I, P161G, V360G; (aap) V150I, P161G, V360G, C361N; (aaq) V150I, P161V, C361N; (aar) V150I, P161V, K354R, V360A, C361N; (aas) V150I, P161V, V360A, C361N; (aat) V150I, P161V, V360G, C361N; (aau) V150I, V360A, C361N; (aav)

V150I, V360G; (aaw) S11T, T74S, G269S, V344A; (aax) K84R, I163T; (aay) V122A, I163N; (aaz) G107S, F333L; (aaaa) V129M, T152M, G343D; (aaab) I63F, N355K; (aaac) G107S, F333L; (aaad) E86K, S99T, A149V; (aaae) N53I, V158E; (aaaf) N355I, K379M; (aaag) H42Q, G107S; (aaah) Q120H, I163N; (aaai) A149V, I323M; (aaaj) G107S, F333L; (aaak) D164G, K181R; (aaal) A155V, R298H, N355D; (aaam) N123D, E165G; (aaan) I163F, L186M; (aaao) G121A, T296S; (aaap) I94V, S99P, N123I; (aaaq) E126V, V129M, V344G; (aaar) Q120R, S143T; (aaas) G256C, A316V; (aaat) P161Q, G312V; (aaau) L226M, A300T, V360A; (aaav) S337C, E350K, N355D, Q363K; (aaaw) D81G, V158E; (aaax) I106L, N117Y, E126V; (aaay) G107S, G121D; (aaaz) V61A, V158E; (aaaaa) N53I, V158E; (aaaab) N117Y, T190S; (aaaac) S124R, I199V; (aaaad) K354M, C361R; (aaaae) A184T, C361R; (aaaag) E56K, Q267H; (aaaag) S124R, E126G; (aaaah) T190A, N355K; (aaaai) P71T, F333L; (aaaaj) G107S, F333L; and (aaaak) N123I, P336L, (aaaal) D38D/A149V, (aaaam) D38N/V163V, (aaaan) D73D/L108V, (aaaao) G121R/P161S, and (aaaap) N112R/P161S.

Also identified were positions in SEQ ID NO:1 that are generally intolerant to substitution, including P8, V132, E177, A207, T208, Q246, 1264, P285, E308, Y339, A340, A353, T362, R367, P369, D373, and 1377; where original amino acids are of particular interest at these positions in SEQ ID NO:1 and their corresponding positions in other templates as described herein.

Also identified were positions in SEQ ID NO:1 that are generally very tolerant to substitution, including E56, E78, E86, T2, N4, E237, E240, E327, E341, E347, P9, V18, R24, T44, L46, K52, D60, A62, F64, A67, P71, A72, D73, T74, V80, K84, Q85, I106, V109, R115, I116, N117, V122, K127, 1135, T136, S154, A155, R156, P161, V162, 1163, P169, T170, V171, V174, L178, M179, A184, G185, L186, A189, T190, A194, A198, Y202, V203, T211, F214, 1216, Q217, K220, L221, N223, Y225, A229, Y244, A245, M248, A252, N254, H266, G270, Y272, 1278, M284, H286, V287, N291, 1293, A294, R298, H301, I302, L305, N309, A311, G312, T315, A317, R321, V324, 1329, S332, S337, M342, K345, K354, N355, A356, Y357, T370, A375, and I378 in SEQ ID NO:1 and their corresponding positions in other templates; where it was observed that typically all amino acids, except for occasionally 1 or 2, were neutral, beneficial, or less than an 80% decrease to activity at these positions. Of these, D60, I378, L46, A62, A67, N117, K52, 1135, Y202, 1216, M248, N291, M342, T2, E240, T44, I116, V203, S332, and thus their corresponding positions in other templates, were tolerant to all changes.

Positions for additional interest for substitution to increase activity include 23T, 81D, 141T, 174V, 189A, 332S, 372Q and 379K and their corresponding positions in other templates.

Embodiments of the disclosure are also directed to the preparation and use of other alcohol dehydrogenase (ADH) variant enzymes including methanol dehydrogenases variant enzymes, based on the single and combination amino acid variants identified in and with respect to the MDH protein 2315A template. In these embodiments generation of non-natural $NAD^+$-dependent alcohol dehydrogenases (that are not 2315A) capable of at least two fold greater conversion of methanol or ethanol to formaldehyde or acetaldehyde, respectively, as compared to its original unmodified counterpart can be based on information of those MDH 2315A variants that provided increased activity.

In some embodiments, the method for preparing other ADH variants includes steps of (a) identifying a variant amino acid that provides increased conversion when present in the 2315A template sequence, (b) identifying a corresponding amino acid position in a target sequence (i.e., other ADH or MDH sequence) having identity to the template sequence, and (c) changing the amino acid at the corresponding amino acid position in the target sequence to the variant amino acid. For example, the D at position 38 of 2315A when substituted with N provides greater than two fold increase in activity compared to the unmodified 2315A sequence. A position corresponding to D38 is identified in the new target ADH or MDH template sequence, e.g., it may be D38 or D39 appropriate, and replaced with N to generate the new non-naturally-occurring ADH or MDH.

In some cases an "ortholog" of the NAD(P)-dependent methanol dehydrogenase from *Bacillus methanolicus* MGA3 (2315A), SEQ ID NO: 1, is first identified. An ortholog is a gene or genes that are related by vertical descent and are responsible for substantially the same or identical functions in different organisms. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 45% to 100% amino acid sequence identity, and more preferably about 60% to 100% amino acid sequence identity.

Genes sharing a desired amount of identify (e.g., 45%, 50%, 55%, or 60% or greater) to the NAD(P)-dependent methanol dehydrogenase from *Bacillus methanolicus* MGA3 (2315A), including orthologs and paralogs, can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor.

Computational approaches to sequence alignment and generation of sequence identity include global alignments and local alignments. Global alignment uses global optimization to forces alignment to span the entire length of all query sequences. Local alignments, by contrast, identify regions of similarity within long sequences that are often widely divergent overall. For understanding the identity of a target sequence to the *Bacillus methanolicus* MGA3 (2315A) template a global alignment can be used. Optionally, amino terminal and/or carboxy-terminal sequences of the target sequence that share little or no identify with the template sequence can be excluded for a global alignment and generation of an identify score.

Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 45% to 100% sequence identity. Proteins that are unrelated can have an identity which is essentially the same as would be expected to occur by chance, if a database of sufficient size is scanned (about 5%).

Pairwise global sequence alignment was carried out for each of the template polypeptides with SEQ ID No.1 (2315A) as the reference. The alignment was performed using the Needleman-Wunsch algorithm (Needleman, S. & Wunsch, C. A general method applicable to the search for similarities in the amino acid sequence of two proteins J. Mol. Biol, 1970, 48, 443-453) implemented through the BALIGN tool (balign.sourceforge.net). Default parameters were used for the alignment and BLOSUM62 was used as the scoring matrix.

Table 10 provides target polypeptides details and alignment to SEQ ID NO. 1 (2315A). These sequences represent target sequences in which one or more amino acid variations, based on the variant amino acids in the *Bacillus methanolicus* MGA3 (2315A) variants showing increased conversion, can be made. For example, as a general matter, this process can involve steps of aligning the template 2315A sequence to a target sequence, such as any sequence listed in Table 10. Next a position of the amino acid substitution/variant (or set of substitutions) in the template 2315A sequence providing the increased conversion of methanol or ethanol is identified. The amino acid alignment at the substitution/variant position is inspected to identify what amino acid position in the target sequence corresponds to that of the template 2315A sequence. Preferred target sequences for substitution with the amino acid variants based on the 2315A variants are highlighted.

In some cases the original amino acid and its position on the template 2315A sequence will precisely correlate with the original amino acid and position on the target. In other cases the original amino acid and its position on the template 2315A sequence will correlate with the original amino acid, but its position on the target will not be in the corresponding template position. However, the corresponding amino acid on the target can be a predetermined distance from the position on the template, such as within 10, 9, 8, 7, 6, 5, 4, 3, 2, or 1 amino acid positions from the template position. In other cases the original amino acid on the template 2315A sequence will not precisely correlate with the original amino acid on the target. However one can understand what the corresponding amino acid on the target sequence is based on the general location of the amino acid on the template and the sequence of amino acids in the vicinity of the target amino acid. For example, amino acids in the vicinity of the target amino acids may be viewed as a "sequence motif" having a certain amount of identity or similarity to between the template and target sequences.

In some cases, it can be useful to use the Basic Local Alignment Search Tool (BLAST) algorithm to understand the sequence identity between an amino acid motif in a template sequence and a target sequence. Therefore, in preferred modes of practice, BLAST is used to identify or understand the identity of a shorter stretch of amino acids (e.g. a sequence motif) between a template and a target protein. BLAST finds similar sequences using a heuristic method that approximates the Smith-Waterman algorithm by locating short matches between the two sequences. The (BLAST) algorithm can identify library sequences that resemble the query sequence above a certain threshold. Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In view of and following the teachings herein, using methods known in the art such as sequence alignment and 3D modeling, the "corresponding positions and amino acids" for substitution in template polypeptides other than SEQ ID NO: 1 are readily determined. Table 11 indicates for each template the corresponding positions for substitution to improve polypeptide activity, from which each original amino acid, its location and substitution is specifically contemplated as if expressly listed. For example, using the 385 amino acid template polypeptide of EIJ83020.1, GI:387590701 (SEQ ID NO:7), from *Bacillus methanolicus* MGA3, having 61% global identity and 79% similarity to SEQ ID NO:1, the formula $R^1XR^2$ is directly and unambiguously derived, is evident, and is contemplated, as if expressly listed herein and is from which the group of positions for $R^1XR^2$ are readily envisioned as: D41, E63, P74, N91, S102, G106, A110, L111, V112, K118, I119, H120, G124, V125, D126, V127, S128, K129, E130, P131, M132, V134, S146, T149, T152, I153, K160, V161, V166, D167, Q270, G273, K348, N358, A363, C364. This is readily derived as evident in the following that depicts the amino acid position for each amino acid for substitution (corresponding to those of SEQ ID NO: 1 and accepting the corresponding substitution). The above approach applies to obtain a resulting $R^1XR^2$ formula for each template polypeptide herein, as well as for polypeptides sharing identity thereto as described herein.

```
GI:          MTNTQSAFFMPSVNLFGAGSVNEVGTRLADLGVKKALLVTD41AGLH
387590701    GLGLSEKISSIIRAAGVE63VSIFPKAEPNP74TDKNVAEGLEAYNAEN91
             CDSIVTLGGGSS102HDAG106KAIA110L111V112AANGGK118I119H120
             DYEG124V125D126V127S128K129E130P131M132V134PLIAINTTAGTG
             S146ELT149KFT152I153ITDTERK160V161KMAIV166D167KHVTPTLSI
             NDPELMVGMPPSLTAATGLDALTHAIEAYVSTGATPITDALAIQAIKIIS
             KYLPRAVANGKDIEAREQMAFAQSLAGMAFNNAGLGYVHAIAHQ270
             LGG273FYNFPIIGVCNAVLLPYVCRFNLISKVERYAEIAAFLGENVDGL
             STYDAAEKAIKAIERMAKDLNIPKGFKELGAK348EEDIETLAKN358AM
             KDA363C364ALTNPRKPKLEEVIQIIKNAM
```

In another example, the amino acids and positions for substitution $R^1XR^2$ in 387 amino acid template polypeptide YP_002138168.1 GI: 197117741 (SEQ ID NO:17) from *Geobac 71% similarity to SEQ ID NO:1 are: D43, S65, P76, G92, S104, A108, G112, M113, V114, H120, I121, R122, G126, V127, N128, K129, T130, T131, K132, P133, M134, P135, S148, T151, C154, I155, H162, V163, V168, D169, Q272, G275, K350, N360, A365, C366. The following, readily derivable from the tables herein, indicates these positions.

```
GI:         MALGEQTYGFYIPTVSLMGIGSAKETGGQIKALGASKALIVTD43KGLS
197117741   AMGVADKIKSQVEEAGVS65AVIFDGAEPNP76TDINVHDGVKVYQDN
            G92CDAIISLGGGSS104HDCA108KGIG112M113V114IGNGGH120I121R
            122DLEG126V127N128K129T130T131K132P133M134P135AFVAINTTA
            GTAS148EMT151RFC154I155ITNTDTH162V163KMAIV168D169WRCTP
            NVAINDPLLMVGKPAALTAATGMDALTHAVEAYVSTIATPITDACAIK
            AIELIAEFLSKAVANGEDLEARDKMAYAEYLAGMAFNNASLGYVHSM
            AHQ272LGG275FYNLPHGVCNAILLPAVSQYNLIACPKRFADIAKALGE
            NIDGLSVTEAGQKAIDRIRTLSASIGIPTGLKALNVK350EADLTIMAEN3
            60AKKDA365C366QFTNPRKATLEQVVQIFKDAM
```

Table 11 provides amino acid sequences of target polypeptides, having underlined target amino acids for substitution with the variant amino acids generated in the *Bacillus methanolicus* MGA3 (2315A) variants. It is understood that upon replacement of amino acid in the target sequence (with a variant amino acid from the corresponding location in the 2315A variant), the substituted target sequence can be considered a "template sequence," useful in some embodiments for the further screening of polypeptides sequences for substitution.

Table 11 also illustrates a consensus of the templates of 60% or better identity to SEQ ID NO: 1 with positions for substitution indicated by underlining. Non-underlined positions are not required for substitution and, in embodiments, remain constant (identical across all templates). These positions can be tolerant to change by selection from at least amongst the wild-type alternatives indicated at a specific position, and tolerant sites for substitution with the substitutions at the variant amino acid positions.

Site-directed mutagenesis or sequence alteration (e.g., site-specific mutagenesis or oligonucleotide-directed) can be used to make specific changes to a target alcohol dehydrogenase DNA sequence to provide a variant DNA sequence encoding alcohol dehydrogenase with the desired amino acid substitution. As a general matter, an oligonucleotide having a sequence that provides a codon encoding the variant amino acid is used. Alternatively, artificial gene sequence of the entire coding region of the variant alcohol dehydrogenase DNA sequence can be performed as preferred alcohol dehydrogenases targeted for substitution are generally less than 400 amino acids long.

Exemplary techniques using mutagenic oligonucleotides for generation of a variant ADH sequence include the Kunkel method which may utilize an ADH gene sequence placed into a phagemid. The phagemid in *E. coli* produces ADH ssDNA which is template for mutagenesis using an oligonucleotide which is primer extended on the template.

Depending on the restriction enzyme sites flanking a location of interest in the ADH DNA, cassette mutagenesis may be used to create a variant sequence of interest. For cassette mutagenesis, a DNA fragment is synthesized inserted into a plasmid, cleaved with a restriction enzyme, and and then subsequently ligated to a pair of complementary oligonucleotides containing the ADH variant mutation The restriction fragments of the plasmid and oligonucleotide can be ligated to one another.

Another technique that can be used to generate the variant ADH sequence is PCR site directed mutagenesis. Mutagenic oligonucleotide primers are used to introduce the desired mutation and to provide a PCR fragment carrying the mutated sequence. Additional oligonucleotides may be used to extend the ends of the mutated fragment to provide restriction sites suitable for restriction enzyme digestion and insertion into the gene.

Commercial kits for site-directed mutagenesis techniques are also available. For example, the Quikchange™ kit uses complementary mutagenic primers to PCR amplify a gene region using a high-fidelity non-strand-displacing DNA polymerase such as pfu polymerase. The reaction generates a nicked, circular DNA which is relaxed. The template DNA is eliminated by enzymatic digestion with a restriction enzyme such as DpnI which is specific for methylated DNA.

An expression vector or vectors can be constructed to include one or more variant ADH encoding nucleic acids as exemplified herein operably linked to expression control sequences functional in the host organism. Expression vectors applicable for use in the microbial host organisms provided include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The term "exogenous" is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid can utilize either or both a heterologous or homologous encoding nucleic acid.

It is understood that when more than one exogenous nucleic acid is included in a microbial organism, the more than one exogenous nucleic acids refers to the referenced encoding nucleic acid or biosynthetic activity, as discussed above. It is further understood, as disclosed herein, that more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

Exogenous variant ADH-encoding nucleic acid sequences can be introduced stably or transiently into a host cell using techniques well known in the art including, but not limited to, conjugation, electroporation, chemical transformation, transduction, transfection, and ultrasound transformation. Optionally, for exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

The terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

The term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments.

In some aspects the ADH variant gene is introduced into a cell with a gene disruption. The term "gene disruption," or grammatical equivalents thereof, is intended to mean a genetic alteration that renders the encoded gene product inactive or attenuated. The genetic alteration can be, for example, deletion of the entire gene, deletion of a regulatory sequence required for transcription or translation, deletion of a portion of the gene which results in a truncated gene product, or by any of various mutation strategies that inactivate or attenuate the encoded gene product. One particularly useful method of gene disruption is complete gene deletion because it reduces or eliminates the occurrence of genetic reversions. The phenotypic effect of a gene disruption can be a null mutation, which can arise from many types of mutations including inactivating point mutations, entire gene deletions, and deletions of chromosomal segments or entire chromosomes. Specific antisense nucleic acid compounds and enzyme inhibitors, such as antibiotics, can also produce null mutant phenotype, therefore being equivalent to gene disruption.

A metabolic modification refers to a biochemical reaction that is altered from its naturally occurring state. Therefore, microorganisms may have genetic modifications to nucleic acids encoding metabolic polypeptides, or functional fragments thereof. Exemplary metabolic modifications are disclosed herein.

The microorganisms provided herein can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

A variety of microorganism may be suitable for the incorporating the variant ADH, optionally with one or more other transgenes Such organisms include both prokaryotic and eukaryotic organisms including, but not limited to, bacteria, including archaea and eubacteria, and eukaryotes, including yeast, plant, insect, animal, and mammal, including human. Exemplary species are reported in U.S. application Ser. No. 13/975,678 (filed Aug. 26, 2013), which is incorporated herein by reference, and include, for example, *Escherichia coli, Saccharomyces cerevisiae, Saccharomyces kluyveri, Candida boidinii, Clostridium kluyveri, Clostridium acetobutylicum, Clostridium beijerinckii, Clostridium saccharoperbutylacetonicum, Clostridium perfringens, Clostridium difficile, Clostridium botulinum, Clostridium tyrobutyricum, Clostridium tetanomorphum, Clostridium tetani, Clostridium propionicum, Clostridium aminobutyricum, Clostridium subterminale, Clostridium sticklandii, Ralstonia eutropha, Mycobacterium bovis, Mycobacterium tuberculosis, Porphyromonas gingivalis, Arabidopsis thaliana, Thermus thermophilus, Pseudomonas* species, including *Pseudomonas aeruginosa, Pseudomonas putida, Pseudomonas stutzeri, Pseudomonas fluorescens, Homo sapiens, Oryctolagus cuniculus, Rhodobacter spaeroides, Thermoanaerobacter brockii, Metallosphaera sedula, Leuconostoc mesenteroides, Chloroflexus aurantiacus, Roseiflexus castenholzii, Erythrobacter, Simmondsia chinensis, Acinetobacter* species, including *Acinetobacter calcoaceticus* and *Acinetobacter baylyi, Porphyromonas gingivalis, Sulfolobus tokodaii, Sulfolobus solfataricus, Sulfolobus acidocaldarius, Bacillus subtilis, Bacillus cereus, Bacillus megaterium, Bacillus brevis, Bacillus pumilus, Rattus norvegicus, Klebsiella pneumonia, Klebsiella oxytoca, Euglena gracilis, Treponema denticola, Moorella thermoacetica, Thermotoga maritima, Halobacterium salinarum, Geobacillus stearothermophilus, Aeropyrum pernix, Sus scrofa, Caenorhabditis elegans, Corynebacterium glutamicum, Acidaminococcus fermentans, Lactococcus lactis, Lactobacillus plantarum, Streptococcus thermophilus, Enterobacter aerogenes, Candida, Aspergillus terreus, Pedicoccus pentosaceus, Zymomonas mobilus, Acetobacter pasteurians, Kluyveromyces lactis, Eubacterium barkeri, Bacteroides capillosus, Anaerotruncus colihominis, Natranaerobius thermophilusm, Campylobacter jejuni, Haemophilus influenzae, Serratia marcescens, Citrobacter amalonaticus, Myxococcus xanthus, Fusobacterium nuleatum, Penicillium chrysogenum,* marine gamma proteobacterium, butyrate producing bacterium, *Nocardia iowensis, Nocardia farcinica, Streptomyces griseus, Schizosaccharomyces pombe, Geobacillus thermoglucosidasius, Salmonella typhimurium, Vibrio cholera, Heliobacter pylori, Nicotiana tabacum, Oryza sativa, Haloferax mediterranei, Agrobacterium tumefaciens, Achromobacter denitrificans, Fusobacterium nucleatum, Streptomyces clavuligenus, Acinetobacter baumanii, Mus musculus, Lachancea kluyveri, Trichomonas vaginalis, Trypanosoma brucei, Pseudomonas stutzeri, Bradyrhizobium japonicum, Mesorhizobium loti, Bos taurus, Nicotiana glutinosa, Vibrio vulnificus, Selenomonas ruminantium, Vibrio parahaemolyticus, Archaeoglobus fulgidus, Haloarcula marismortui, Pyrobaculum aerophilum, Mycobacterium smegmatis* MC2 155, *Mycobacterium avium* subsp. paratuberculosis K-10, *Mycobacterium marinum Tsukamurella paurometabola* DSM 20162, *Cyanobium* PCC7001, *Dictyostelium discoideum* AX4, as well as other exemplary species disclosed herein or available as source organisms for corresponding genes.

In certain embodiments, suitable organisms include *Acinetobacter baumannii* Naval-82, *Acinetobacter* sp. ADP1, *Acinetobacter* sp. strain M-1, *Actinobacillus succinogenes* 130Z, *Allochromatium vinosum* DSM 180, *Amycolatopsis methanolica, Arabidopsis thaliana, Atopobium parvulum* DSM 20469, *Azotobacter vinelandii* DJ, *Bacillus alcalophilus* ATCC 27647, *Bacillus azotoformans* LMG 9581, *Bacillus coagulans* 36D1, *Bacillus megaterium, Bacillus methanolicus* MGA3, *Bacillus methanolicus* PB1, *Bacillus methanolicus* PB-1, *Bacillus selenitireducens* MLS10, *Bacillus smithii, Bacillus subtilis, Burkholderia cenocepacia, Burkholderia cepacia, Burkholderia multivorans, Burkholderia pyrrocinia, Burkholderia stabilis, Burkholderia thailandensis* E264, *Burkholderiales bacterium* Joshi_001, Butyrate-producing bacterium L2-50, *Campylobacter jejuni, Candida albicans, Candida boidinii, Candida methylica, Carboxydothermus hydrogenoformans, Carboxydothermus* hydrogenoformans Z-2901, *Caulobacter* sp. AP07, *Chloroflexus aggregans* DSM 9485, *Chloroflexus aurantiacus* J-10-fl, *Citrobacter freundii, Citrobacter koseri* ATCC BAA-895, *Citrobacter youngae, Clostridium, Clostridium acetobutylicum, Clostridium acetobutylicum* ATCC 824, *Clostridium acidurici, Clostridium aminobutyricum, Clostridium asparagiforme* DSM 15981, *Clostridium beijerinckii, Clostridium beijerinckii* NCIMB 8052, *Clostridium bolteae* ATCC BAA-613, *Clostridium carboxidivorans* P7, *Clostridium cellulovorans* 743B, *Clostridium difficile, Clostridium hiranonis* DSM 13275, *Clostridium hylemonae* DSM 15053, *Clostridium kluyveri, Clostridium kluyveri* DSM 555, *Clostridium ljungdahli, Clostridium ljungdahlii* DSM 13528, *Clostridium methylpentosum* DSM 5476, *Clostridium pasteurianum, Clostridium pasteurianum* DSM 525, *Clostridium perfringens, Clostridium perfringens* ATCC 13124, *Clostridium perfringens* str. 13, *Clostridium phytofermentans* ISDg, *Clostridium saccharobutylicum, Clostridium saccharoperbutylacetonicum, Clostridium saccharoperbutylacetonicum* N1-4, *Clostridium tetani, Corynebacterium glutamicum* ATCC 14067, *Corynebacterium glutamicum* R, *Corynebacterium* sp. U-96, *Corynebacterium variabile, Cupriavidus necator* N-1, *Cyanobium* PCC7001, *Desulfatibacillum alkenivorans* AK-01, *Desulfitobacterium hafniense, Desulfitobacterium metallireducens* DSM 15288, *Desulfotomaculum reducens* MI-1, *Desulfovibrio africanus* str. Walvis Bay, *Desulfovibrio fructosovorans* JJ, *Desulfovibrio vulgaris* str. Hildenborough, *Desulfovibrio vulgaris* str. 'Miyazaki F', *Dictyostelium discoideum* AX4, *Escherichia coli, Escherichia coli* K-12, *Escherichia coli* K-12 MG1655, *Eubacterium hallii* DSM 3353, *Flavobacterium frigoris, Fusobacterium nucleatum* subsp. polymorphum ATCC 10953, *Geobacillus* sp. Y4.1MC1, *Geobacillus themodenitrificans* NG80-2, *Geobacter bemidjiensis* Bem, *Geobacter sulfurreducens, Geobacter sulfurreducens* PCA,

*Geobacillus stearothermophilus* DSM 2334, *Haemophilus influenzae*, *Helicobacter pylori*, *Homo sapiens*, *Hydrogenobacter thermophilus*, *Hydrogenobacter thermophilus* TK-6, *Hyphomicrobium denitrificans* ATCC 51888, *Hyphomicrobium zavarzinii*, *Klebsiella pneumoniae*, *Klebsiella pneumoniae* subsp. *pneumoniae* MGH 78578, *Lactobacillus brevis* ATCC 367, *Leuconostoc mesenteroides*, *Lysinibacillus fusiformis*, *Lysinibacillus sphaericus*, *Mesorhizobium loti* MAFF303099, *Metallosphaera sedula*, *Methanosarcina acetivorans*, *Methanosarcina acetivorans* C2A, *Methanosarcina barkeri*, *Methanosarcina mazei* Tuc01, *Methylobacter marinus*, *Methylobacterium extorquens*, *Methylobacterium extorquens* AM1, *Methylococcus capsulatas*, *Methylomonas aminofaciens*, *Moorella thermoacetica*, *Mycobacter* sp. strain JC1 DSM 3803, *Mycobacterium avium* subsp. *paratuberculosis* K-10, *Mycobacterium bovis* BCG, *Mycobacterium gastri*, *Mycobacterium marinum M*, *Mycobacterium smegmatis*, *Mycobacterium smegmatis* MC2 155, *Mycobacterium tuberculosis*, *Nitrosopumilus salaria* BD31, *Nitrososphaera gargensis* Ga9.2, *Nocardia farcinica* IFM 10152, *Nocardia iowensis* (sp. NRRL 5646), *Nostoc* sp. PCC 7120, *Ogataea angusta*, *Ogataea parapolymorpha* DL-1 (*Hansenula polymorpha* DL-1), *Paenibacillus peoriae* KCTC 3763, *Paracoccus denitrificans*, *Penicillium chrysogenum*, *Photobacterium profundum* 3TCK, *Phytofermentans* ISDg, *Pichia pastoris*, *Picrophilus torridus* DSM9790, *Porphyromonas gingivalis*, *Porphyromonas gingivalis* W83, *Pseudomonas aeruginosa* PA01, *Pseudomonas denitrificans*, *Pseudomonas knackmussii*, *Pseudomonas putida*, *Pseudomonas* sp, *Pseudomonas syringae* pv. *syringae* B728a, *Pyrobaculum islandicum* DSM 4184, *Pyrococcus abyssi*, *Pyrococcus furiosus*, *Pyrococcus horikoshii* OT3, *Ralstonia eutropha*, *Ralstonia eutropha* H16, *Rhodobacter capsulatus*, *Rhodobacter sphaeroides*, *Rhodobacter sphaeroides* ATCC 17025, *Rhodopseudomonas palustris*, *Rhodopseudomonas palustris* CGA009, *Rhodopseudomonas palustris* DX-1, *Rhodospirillum rubrum*, *Rhodospirillum rubrum* ATCC 11170, *Ruminococcus obeum* ATCC 29174, *Saccharomyces cerevisiae*, *Saccharomyces cerevisiae* S288c, *Salmonella enterica*, *Salmonella enterica* subsp. *enterica* serovar *Typhimurium* str. LT2, *Salmonella enterica typhimurium*, *Salmonella typhimurium*, *Schizosaccharomyces pombe*, *Sebaldella termitidis* ATCC 33386, *Shewanella oneidensis* MR-1, *Sinorhizobium meliloti* 1021, *Streptomyces coelicolor*, *Streptomyces griseus* subsp. *griseus* NBRC 13350, *Sulfolobus acidocalarius*, *Sulfolobus solfataricus* P-2, *Synechocystis* str. PCC 6803, *Syntrophobacter fumaroxidans*, *Thauera aromatica*, *Thermoanaerobacter* sp. X514, *Thermococcus kodakaraensis*, *Thermococcus litoralis*, *Thermoplasma acidophilum*, *Thermoproteus neutrophilus*, *Thermotoga maritima*, *Thiocapsa roseopersicina*, *Tolumonas auensis* DSM 9187, *Trichomonas vaginalis* G3, *Trypanosoma brucei*, *Tsukamurella paurometabola* DSM 20162, *Vibrio cholera*, *Vibrio harveyi* ATCC BAA-1116, *Xanthobacter autotrophicus* Py2, *Yersinia intermedia*, or *Zea mays*.

In some aspects the variant ADH gene is introduced into a cell engineered with increased of levels of 1,4-butanediol (BDO) or hydroxylbutyrate (4-HB) biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

With the complete genome sequence available for now more than 550 species (with more than half of these available on public databases such as the NCBI), including 395 microorganism genomes and a variety of yeast, fungi, plant, and mammalian genomes, the identification of genes encoding the requisite BDO or 4-HB biosynthetic pathway as well as other known biosynthetic pathways for 1,3-butanediol (13BDO), butadiene, 6-amino caproic acid (6ACA), hexamethyldiamine (HMDA), adipic acid or derivatives thereof, croytl alcohol, methyl vinyl carbinol, 3-buten-1-ol, succinic acid or derivatives thereof, n-propanol, isopropanol, propylene, methacrylic acid or derivatives thereof, methanol metabolic and/or formaldehyde assimilation activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of various target products including 1,3-butanediol (13BDO), 1,4-butanediol (BDO), 4-HB, butadiene, 6-amino caproic acid (6ACA), hexamethyldiamine (HMDA), adipic acid or derivatives thereof, croytl alcohol, methyl vinyl carbinol, 3-buten-1-ol, succinic acid or derivatives thereof, n-propanol, isopropanol, propylene, methacrylic acid or derivatives thereof, metabolism of methanol and/or assimilation of formaldehyde described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

Therefore, the engineered cell including the non-natural NAD$^+$-dependent alcohol dehydrogenase, can include one or more genetic alterations, such as inserted transgenes, deletions, attenuation, mutations, etc., desired to increase levels of one or more intermediates or a product thereof, and include those genetic modifications as described in U.S. application Ser. No. 13/975,678 (filed Aug. 26, 2013), which is incorporated herein by reference.

Exemplary alcohol metabolic pathway gene(s), such as described in U.S. application Ser. No. 13/975,678, encode a protein selected from the group consisting of a), a formate dehydrogenase (EM8), a formaldehyde activating enzyme (EM10), a formaldehyde dehydrogenase (EM11), a S-(hydroxymethyl)glutathione synthase (EM12), a glutathione-dependent formaldehyde dehydrogenase (EM13), a S-formylglutathione hydrolase (EM14), a formate hydrogen lyase (EM15), and a hydrogenase (EM16), any or more can be coexpressed with the non-natural NAD$^+$-dependent alcohol dehydrogenase in the engineered cell.

Other exemplary alcohol metabolic pathway gene(s), such as described in U.S. application Ser. No. 13/975,678, encode an alcohol metabolic pathway gene(s) encoding a protein selected from the group consisting of a succinyl-CoA reductase (aldehyde forming) (EB3), a 4-hydroxybutyrate (4-HB) dehydrogenase (EB4), a 4-HB kinase (EB5), a phosphotrans-4-hydroxybutyrylase (EB6), a 4-hydroxybutyryl-CoA reductase (aldehyde forming) (EB7), a 1,4-butanediol dehydrogenase (EB8); a succinate reductase (EB9), a succinyl-CoA reductase (alcohol forming) (EB10), 4-hydroxybutyryl-CoA transferase (EB11), a 4-hydroxybutyryl-CoA synthetase (EB12), a 4-HB reductase (EB13), and a 4-hydroxybutyryl-CoA reductase (alcohol forming) (EB15), a succinyl-CoA transferase (EB1), and a succinyl-CoA synthetase (EB2A), any or more can be coexpressed with the non-natural NAD$^+$-dependent alcohol dehydrogenase in the engineered cell.

Target products obtained from, and product pathways suitable for producing in, host cells expressing the engineered NAD+-dependent methanol or ethanol dehydrogenases described herein include the following. Of particular interest are a target product obtained using pyruvate and acetyl-CoA as entry point or precursor to its product pathway(s), in part because the methanol metabolic pathway using the novel enzymes enables fixing the carbon of methanol into pathways to pyruvate and acetyl-CoA. Target products include (a) 1,4-butanediol and intermediates thereto, such as 4-hydroxybutanoic acid (4-hydroxybutanoate, 4-hydroxybutyrate, 4-HB), (b) butadiene and intermediates thereto, such as 1,4-butanediol, 1,3-butanediol, crotyl alcohol, 3-buten-2-ol (methyl vinyl carbinol) and 3-buten-1-ol, (c) 1,3-butanediol and intermediates thereto, such as 2,4-pentadienoate, crotyl alcohol or 3-buten-1-ol, (d) adipate, 6-aminocaproic acid, caprolactam, hexamethylenediamine and levulinic acid and their intermediates, e.g. 4-aminobutyryl-CoA, (e) methacrylic acid (2-methyl-2-propenoic acid) and its esters known collectively as methacrylates, such as methyl methacrylate, methyl methacrylate, 3-hydroxyisobutyrate and/or 2-hydroxyisobutyrate and their intermediates, (f) 1,2-propanediol (propylene glycol), n-propanol, 1,3-propanediol and glycerol, and their intermediates and (g) succinic acid and intermediates thereto.

1,4-butanediol and intermediates thereto, such as 4-hydroxybutanoic acid (4-hydroxybutanoate, 4-hydroxybutyrate, 4-HB), are target products that can be made by co-expressing the novel alcohol dehydrogenases described herein with a product pathway described herein as well as in the following documents. Suitable product pathways and enzymes, methods for screening and methods for isolating are found herein as well as in the following documents, incorporated herein by reference: WO2008115840A2 published 25 Sep. 2008 entitled Compositions and Methods for the Biosynthesis of 1,4-Butanediol and Its Precursors; WO2010141780A1 published 9 Dec. 2010 entitled Process of Separating Components of A Fermentation Broth; WO2010141920A2 published 9 Dec. 2010 entitled Microorganisms for the Production of 1,4-Butanediol and Related Methods; WO2010030711A2 published 18 Mar. 2010 entitled Microorganisms for the Production of 1,4-Butanediol; WO2010071697A1 published 24 Jun. 2010 Microorganisms and Methods for Conversion of Syngas and Other Carbon Sources to Useful Products; WO2009094485A1 published 30 Jul. 2009 Methods and Organisms for Utilizing Synthesis Gas or Other Gaseous Carbon Sources and Methanol; WO2009023493A1 published 19 Feb. 2009 entitled Methods and Organisms for the Growth-Coupled Production of 1,4-Butanediol; WO2008115840A2 published 25 Sep. 2008 entitled Compositions and Methods for the Biosynthesis of 1,4-Butanediol and Its Precursors; and International Application No. PCT/US13/56725 filed 27 Aug. 2013 entitled Microorganisms an Methods for Enhancing the Availability of Reducing Equivalents in the Presence of Methanol, and for Producing 1,4-Butanediol Related Thereto.

Butadiene and intermediates thereto, such as 1,4-butanediol, 1,3-butanediol, crotyl alcohol, 3-buten-2-ol (methyl vinyl carbinol) and 3-buten-1-ol, are target products that can be made by co-expressing the novel alcohol dehydrogenases described herein with a product pathway described in the following documents. In addition to direct fermentation to produce butadiene, 1,3-butanediol, 1,4-butanediol, crotyl alcohol, 3-buten-2-ol (methyl vinyl carbinol) and 3-buten-1-ol can be separated, purified (for any use), and then dehydrated to butadiene in a second step involving metal-based catalysis. Suitable product pathways and enzymes, methods for screening and methods for isolating are found in the following documents, incorporated herein by reference: WO2011140171A2 published 10 Nov. 2011 entitled Microorganisms and Methods for the Biosynthesis of Butadiene; WO2012018624A2 published 9 Feb. 2012 entitled Microorganisms and Methods for the Biosynthesis of Aromatics, 2,4-Pentadienoate and 1,3-Butadiene; WO2011140171A2 published 10 Nov. 2011 entitled Microorganisms and Methods for the Biosynthesis of Butadiene; WO2013040383A1 published 21 Mar. 2013 entitled Microorganisms and Methods for Producing Alkenes; WO2012177710A1 published 27 Dec. 2012 entitled Microorganisms for Producing Butadiene and Methods Related thereto; WO2012106516A1 published 9 Aug. 2012 entitled Microorganisms and Methods for the Biosynthesis of Butadiene; WO2013028519A1 published 28 Feb. 2013 entitled Microorganisms and Methods for Producing 2,4-Pentadienoate, Butadiene, Propylene, 1,3-Butanediol and Related Alcohols; and U.S. Ser. No. 61/799,255 filed 15 Mar. 2013.

1,3-butanediol and intermediates thereto, such as 2,4-pentadienoate, crotyl alcohol or 3-buten-1-ol, are target products that can be made by co-expressing the novel alcohol dehydrogenases described herein with a product pathway described herein as well as in the following documents. Suitable product pathways and enzymes, methods for screening and methods for isolating are found herein as well as in the following documents, incorporated herein by reference: WO2011071682A1 published 16 Jun. 2011 entitled Methods and Organisms for Converting Synthesis Gas or Other Gaseous Carbon Sources and Methanol to 1,3-Butanediol; WO2011031897A published 17 Mar. 2011 entitled Microorganisms and Methods for the Co-Production of Isopropanol with Primary Alcohols, Diols and Acids; WO2010127319A2 published 4 Nov. 2010 entitled Organisms for the Production of 1,3-Butanediol; WO2013071226A1 published 16 May 2013 entitled Eukaryotic Organisms and Methods for Increasing the Availability of Cytosolic Acetyl-CoA, and for Producing 1,3-Butanediol; WO2013028519A1 published 28 Feb. 2013 entitled Microorganisms and Methods for Producing 2,4-Pentadienoate, Butadiene, Propylene, 1,3-Butanediol and Related Alcohols; WO2013036764A1 published 14 Mar. 2013 entitled Eukaryotic Organisms and Methods for Producing 1,3-Butanediol; WO2013012975A1 published 24 Jan. 2013 entitled Methods for Increasing Product Yields; WO2012177619A2 published 27 Dec. 2012 entitled Microorganisms for Producing 1,3-Butanediol and Methods Related Thereto; and U.S. Ser. No. 61/799,255 filed 15 Mar. 2013.

Adipate, 6-aminocaproic acid, caprolactam, hexamethylenediamine and levulinic acid, and their intermediates, e.g. 4-aminobutyryl-CoA, are target products, useful for example for making nylon polymers, that can be made by co-expressing the novel alcohol dehydrogenases described herein with a product pathway described herein as well as in the following documents. Suitable product pathways and enzymes, methods for screening and methods for isolating are found herein as well as in the following documents, incorporated herein by reference: WO2010129936A1 published 11 Nov. 2010 entitled Microorganisms and Methods for the Biosynthesis of Adipate, Hexamethylenediamine and 6-Aminocaproic Acid; WO2013012975A1 published 24

Jan. 2013 entitled Methods for Increasing Product Yields; WO2012177721A1 published 27 Dec. 2012 entitled Microorganisms for Producing 6-Aminocaproic Acid; WO2012099621A1 published 26 Jul. 2012 entitled Methods for Increasing Product Yields; and application U.S. Ser. No. 61/766,620 filed 19 Feb. 2013 entitled Microorganisms an Methods for Enhancing the Availability of Reducing Equivalents in the Presence of Methanol, and for Producing Adipate, 6-Aminocaproate, Hexamethylenediamine or Caprolactam Related Thereto.

Methacrylic acid (2-methyl-2-propenoic acid; used in the preparation of its esters known collectively as methacrylates, such as methyl methacrylate, which is used most notably in the manufacture of polymers), methacrylate ester such as methyl methacrylate, 3-hydroxyisobutyrate and/or 2-hydroxyisobutyrate and their intermediates are target products, useful for example for making polymers, that can be made by co-expressing the novel alcohol dehydrogenases described herein with a product pathway described herein as well as in the following documents. Suitable product pathways and enzymes, methods for screening and methods for isolating are found herein as well as in the following documents, incorporated herein by reference: WO2012135789A2 published 4 Oct. 2012 entitled Microorganisms for Producing Methacrylic Acid and Methacrylate Esters and Methods Related Thereto; WO2009135074A2 published 5 Nov. 2009 entitled Microorganisms for the Production of Methacrylic Acid; and application U.S. Ser. No. 61/766,660 filed 19 Feb. 2013 entitled Microorganisms an Methods for Enhancing the Availability of Reducing Equivalents in the Presence of Methanol, and for Producing 3-Hydroxyisobutyrate or Methacrylic Acid Related Thereto.

1,2-propanediol (propylene glycol), n-propanol, 1,3-propanediol and glycerol, and their intermediates are target products, useful for example for making polymers, that can be made by co-expressing the novel alcohol dehydrogenases described herein with a product pathway described herein as well as in the following documents. Suitable product pathways and enzymes, methods for screening and methods for isolating are found herein as well as in the following documents, incorporated herein by reference: WO2009111672A1 published 9 Nov. 2009 entitled Primary Alcohol Producing Organisms; WO2011031897A1 17 Mar. 2011 entitled Microorganisms and Methods for the Co-Production of Isopropanol with Primary Alcohols, Diols and Acids; WO2012177599A2 published 27 Dec. 2012 entitled Microorganisms for Producing N-Propanol 1,3-Propanediol, 1,2-Propanediol or Glycerol and Methods Related Thereto; and application U.S. Ser. No. 61/766,635 filed 19 Feb. 2013 entitled Microorganisms an Methods for Enhancing the Availability of Reducing Equivalents in the Presence of Methanol, and for Producing 1,2-Propanediol, n-Propanol, 1,3-Propanediol, or Glycerol Related Thereto.

Succinic acid and intermediates thereto (useful to produce products including polymers, e.g. PBS, 1,4-butanediol, tetrahydrofuran, pyrrolidone, solvents, paints, deicers, plastics, fuel additives, fabrics, carpets, pigments, and detergents) are target products that can be made by co-expressing the novel alcohol dehydrogenases described herein with a product pathway described herein as well as in the following documents. Suitable product pathways and enzymes, methods for screening and methods for isolating are found herein as well as in the following documents, incorporated herein by reference: EP1937821A2 published 2 Jul. 2008 entitled Methods and Organisms for the Growth-Coupled Production of Succinate; and application U.S. Ser. No. 61/766,635 filed 19 Feb. 2013 entitled Microorganisms and Methods for Enhancing the Availability of Reducing Equivalents in the Presence of Methanol, and for Producing Succinate Related Thereto.

Target products obtained from, and product pathways suitable for producing in, host cells co-expressing the engineered NAD+-dependent methanol or ethanol dehydrogenases described herein include the following.

Butadiene and intermediates thereto, such as 1,4-butanediol, 1,3-butanediol, crotyl alcohol, 3-buten-2-ol (methyl vinyl carbinol) and 3-buten-1-ol, are target products that can be made by co-expressing the novel alcohol dehydrogenases described herein with a product pathway described in the following documents. In addition to direct fermentation to produce butadiene, 1,3-butanediol, 1,4-butanediol, crotyl alcohol, 3-buten-2-ol (methyl vinyl carbinol) and 3-buten-1-ol can be separated, purified (for any use), and then dehydrated to butadiene in a second step involving metal-based catalysis. Suitable product pathways and enzymes, methods for screening and methods for isolating are found in: WO2011140171A2 published 10 Nov. 2011 entitled Microorganisms and Methods for the Biosynthesis of Butadiene; WO2012018624A2 published 9 Feb. 2012 entitled Microorganisms and Methods for the Biosynthesis of Aromatics, 2,4-Pentadienoate and 1,3-Butadiene; 02011140171A2 published 10 Nov. 2011 entitled Microorganisms and Methods for the Biosynthesis of Butadiene; WO2013040383A1 published 21 Mar. 2013 entitled Microorganisms and Methods for Producing Alkenes; WO2012177710A1 published 27 Dec. 2012 entitled Microorganisms for Producing Butadiene and Methods Related thereto; WO2012106516A1 published 9 Aug. 2012 entitled Microorganisms and Methods for the Biosynthesis of Butadiene; WO2013028519A1 published 28 Feb. 2013 entitled Microorganisms and Methods for Producing 2,4-Pentadienoate, Butadiene, Propylene, 1,3-Butanediol and Related Alcohols; and U.S. Ser. No. 61/799,255 filed 15 Mar. 2013.

In some embodiments, the disclosure provides organisms comprising a MDH variant and that are engineered to improve the availability of reducing equivalents or utilizing formaldehyde resulting from methanol via a formaldehyde assimilation pathway (FAB), which can be used for the production of target product molecules. It will be recognized by one skilled in the art that any product molecule that utilizes reducing equivalents in its production can exhibit enhanced production through other biosynthetic pathways.

BDO is a valuable chemical for the production of high performance polymers, solvents, and fine chemicals. It is the basis for producing other high value chemicals such as tetrahydrofuran (THF) and gamma-butyrolactone (GBL). The value chain is comprised of three main segments including: (1) polymers, (2) THF derivatives, and (3) GBL derivatives. In the case of polymers, BDO is a comonomer for polybutylene terephthalate (PBT) production. PBT is a medium performance engineering thermoplastic used in automotive, electrical, water systems, and small appliance applications. Conversion to THF, and subsequently to polytetramethylene ether glycol (PTMEG), provides an intermediate used to manufacture spandex products such as LYCRA® fibers. PTMEG is also combined with BDO in the production of specialty polyester ethers (COPE). COPEs are high modulus elastomers with excellent mechanical properties and oil/environmental resistance, allowing them to operate at high and low temperature extremes. PTMEG and BDO also make thermoplastic polyurethanes processed on standard thermoplastic extrusion, calendaring, and molding equipment, and are characterized by their outstanding toughness and abrasion resistance. The GBL produced from BDO provides the feedstock for making pyrrolidones, as well as serving the agrochemical market. The pyrrolidones are used as high performance solvents for extraction processes of increasing use, including for example, in the electronics industry and in pharmaceutical production. Accordingly, provided herein is bioderived BDO produced according to the methods described herein and biobased products comprising or obtained using the bioderived BDO.

In numerous engineered pathways, realization of maximum product yields based on carbohydrate feedstock is hampered by insufficient reducing equivalents or by loss of reducing equivalents to byproducts. Methanol is a relatively inexpensive organic feedstock that can be used to generate reducing equivalents by employing one or more methanol metabolic enzymes as shown in FIG. 3a. The reducing equivalents produced by the metabolism of methanol can then be used to power the glucose to BDO production pathways, for example, as shown in FIG. 2.

Figure 2:
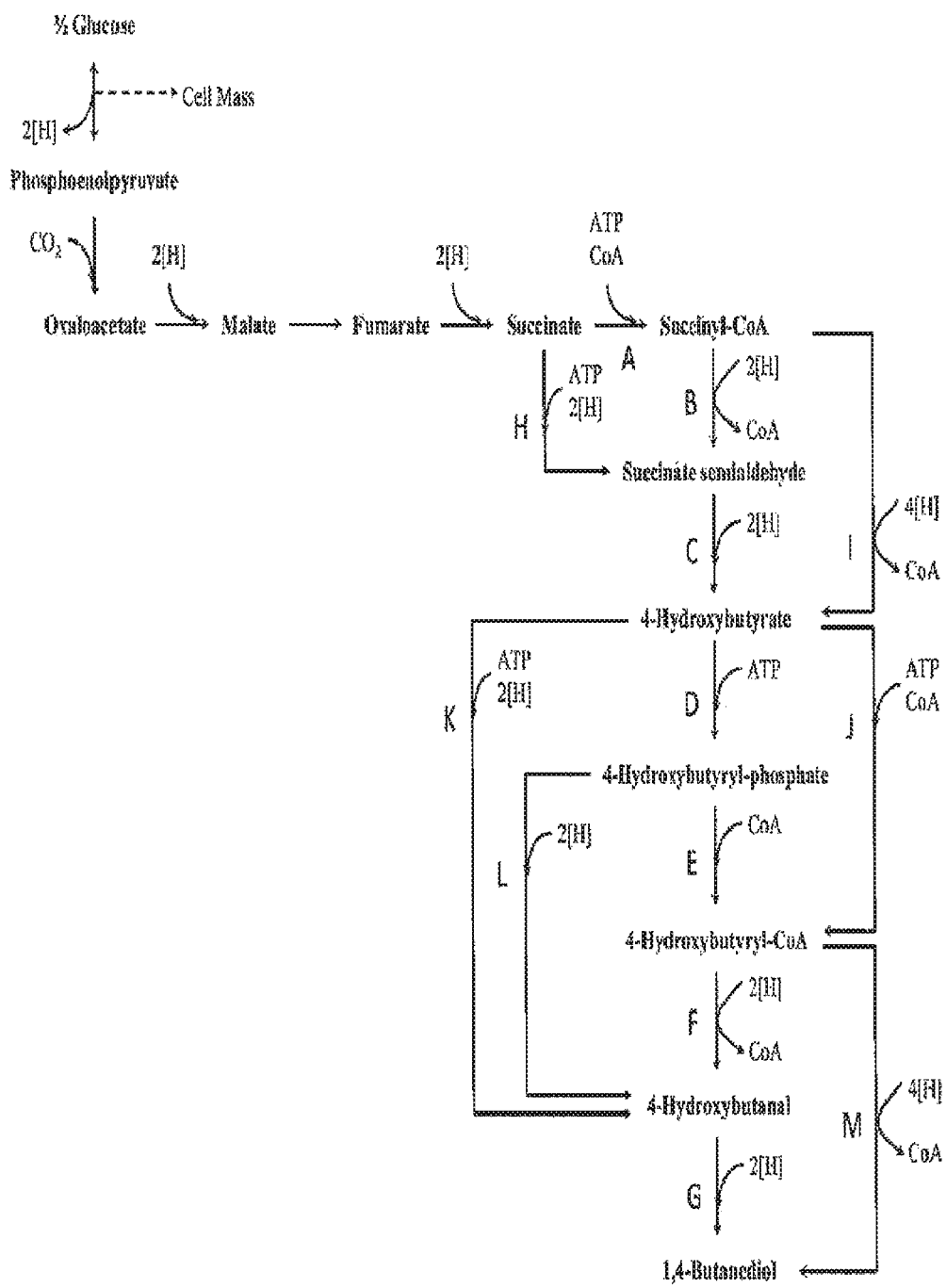
FIG. 2 illustrates a pathway using MDH to produce 1,4-butanediol (BDO) in organism such as E. coli.
Figure 3A:
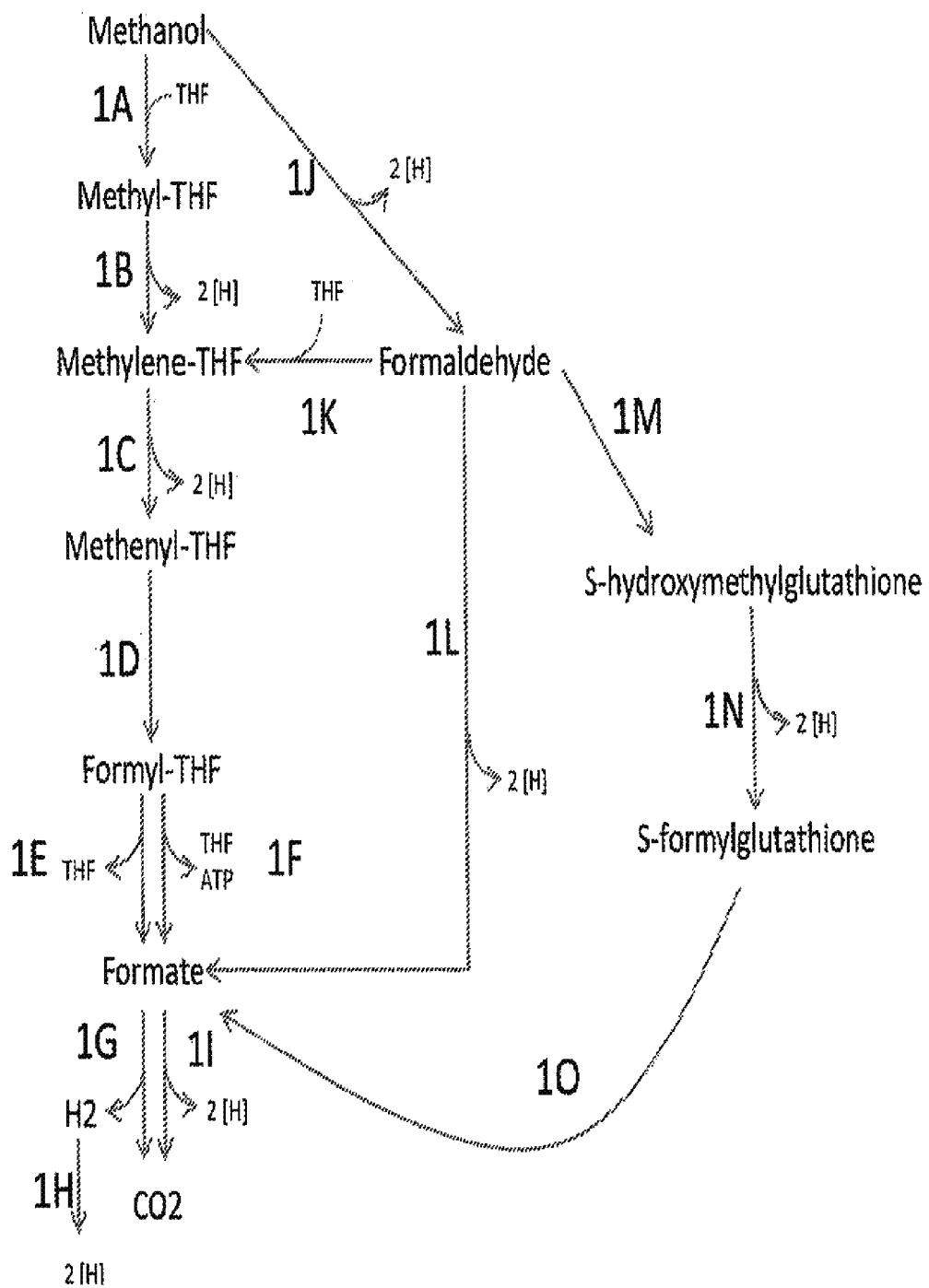
FIGS. 3A-D illustrate pathways using certain methanol metabolizing enzymes.

IN FIG. 2, the organism comprises at least one exogenous nucleic acid encoding a BDOPE expressed in a sufficient amount to produce BDO. In certain embodiments, the BDOPE is selected from the group consisting of a succinyl-CoA transferase (EB1) or a succinyl-CoA synthetase (EB2A) (or succinyl-CoA ligase); a succinyl-CoA reductase (aldehyde forming) (EB3); a 4-hydroxybutyrate (4-HB) dehydrogenase (EB4); a 4-HB kinase (EB5); a phosphotrans-4-hydroxybutyrylase (EB6); a 4-hydroxybutyryl-CoA reductase (aldehyde forming) (EB7); a 1,4-butanediol dehydrogenase (EB8); a succinate reductase (EB9); a succinyl-CoA reductase (alcohol forming) (EB10); a 4-hydroxybutyryl-CoA transferase (EB11) or a 4-hydroxybutyryl-CoA synthetase (EB12); a 4-HB reductase (EB13); a 4-hydroxybutyryl-phosphate reductase (EB14); and a 4-hydroxybutyryl-CoA reductase (alcohol forming) (EB15).

Enzymes, genes and methods for engineering pathways from succinate and succinyl-CoA to various products, such as BDO, into a microorganism, are now known in the art (see, e.g., U.S. Publ. No. 2011/0201089). A set of BDOPEs represents a group of enzymes that can convert succinate to BDO as shown in FIG. 2. The additional reducing equivalents obtained from the MDH pathway, as disclosed herein, improve the yields of all these products when utilizing carbohydrate-based feedstock. For example, BDO can be produced from succinyl-CoA via previously disclosed pathways (see for example, Burk et al., WO 2008/115840). Exemplary enzymes for the conversion succinyl-CoA to BDO include EB3 (FIG. 2, Step B), EB4 (FIG. 2, Step C), EB5 (FIG. 2, Step D), EB6 (FIG. 2, Step E), EB7 (FIG. 2, Step F), EB8 (FIG. 2, Step G), EB10 (FIG. 1, Step I), EB11 (FIG. 2, Step J), EB12 (FIG. 2, Step J), EB14 (FIG. 2, Step L), EB13 (FIG. 2, Step K), and EB15 (FIG. 2, Step M). EB9 (FIG. 2, Step H) can be additionally useful in converting succinate directly to the BDOP intermediate, succinate semialdehyde.

The maximum theoretical yield of BDO via the pathway shown in FIG. 2 supplemented with the reactions of the oxidative TCA cycle (e.g., citrate synthase, aconitase, isocitrate dehydrogenase, alpha-ketoglutarate dehydrogenase) is 1.09 mol/mol.

$$1C_6H_{12}O_6 \rightarrow 1.09C_4H_{10}O_2 + 1.64CO_2 + 0.55H_2O$$

When both feedstocks of sugar and methanol are available, the methanol can be utilized to generate reducing equivalents by employing one or more of the enzymes shown in FIG. 1. The reducing equivalents generated from methanol can be utilized to power the glucose to BDO production pathways, e.g., as shown in FIG. 2. Theoretically, all carbons in glucose will be conserved, thus resulting in a maximal theoretical yield to produce BDO from glucose at 2 mol BDO per mol of glucose under either aerobic or anaerobic conditions as shown in FIG. 2:

$$10CH_3OH + 3C_6H_{12}O_6 = 6C_4H_{10}O_2 + 8H_2O + 4CO_2$$

In a similar manner, the maximum theoretical yields of succinate and 4-HB can reach 2 mol/mol glucose using the reactions shown in FIGS. 1 and 2.

$$C_6H_{12}O_6 + 0.667CH_3OH + 1.333CO_2 \rightarrow 2C_4H_6O_4 + 1.333H_2O$$

$$C_6H_{12}O_6 + 2CH_3OH \rightarrow 2C_4H_8O_3 + 2H_2O$$

In other embodiments, the organism having a MDH protein, either alone or in combination with a BDOP, as provided herein, may further comprises a formaldehyde assimilation pathway (FAP) that utilizes formaldehyde, e.g., obtained from the oxidation of methanol, in the formation of intermediates of certain central metabolic pathways that can be used, for example, in the formation of biomass. In certain embodiments, the organism further comprises a FAP, wherein said organism comprises at least one exogenous nucleic acid encoding a formaldehyde assimilation pathway enzyme (FAPE) expressed in a sufficient amount to produce an intermediate of glycolysis and/or a metabolic pathway that can be used in the formation of biomass. In one embodiment, the FAPE is expressed in a sufficient amount to produce an intermediate of glycolysis. In another embodiment, the FAPE is expressed in a sufficient amount to produce an intermediate of a metabolic pathway that can be used in the formation of biomass. In some of the embodiments, the FAP comprises a hexulose-6-phosphate (H6P) synthase (EF1), a 6-phospho-3-hexuloisomerase (EF2), a dihydroxyacetone (DHA) synthase (EF3) or a DHA kinase (EF4). In one embodiment, the FAP comprises an EF1 and an EF2. In one embodiment, the intermediate is a H6P, a fructose-6-phosphate (F6P), or a combination thereof. In other embodiments, the FAP comprises an EF3 or an EF4. In one embodiment, the intermediate is a DHA, a DHA phosphate, or a combination thereof. In certain embodiments, the organism comprises two exogenous nucleic acids, each encoding a FAPE.

Figure 3B:
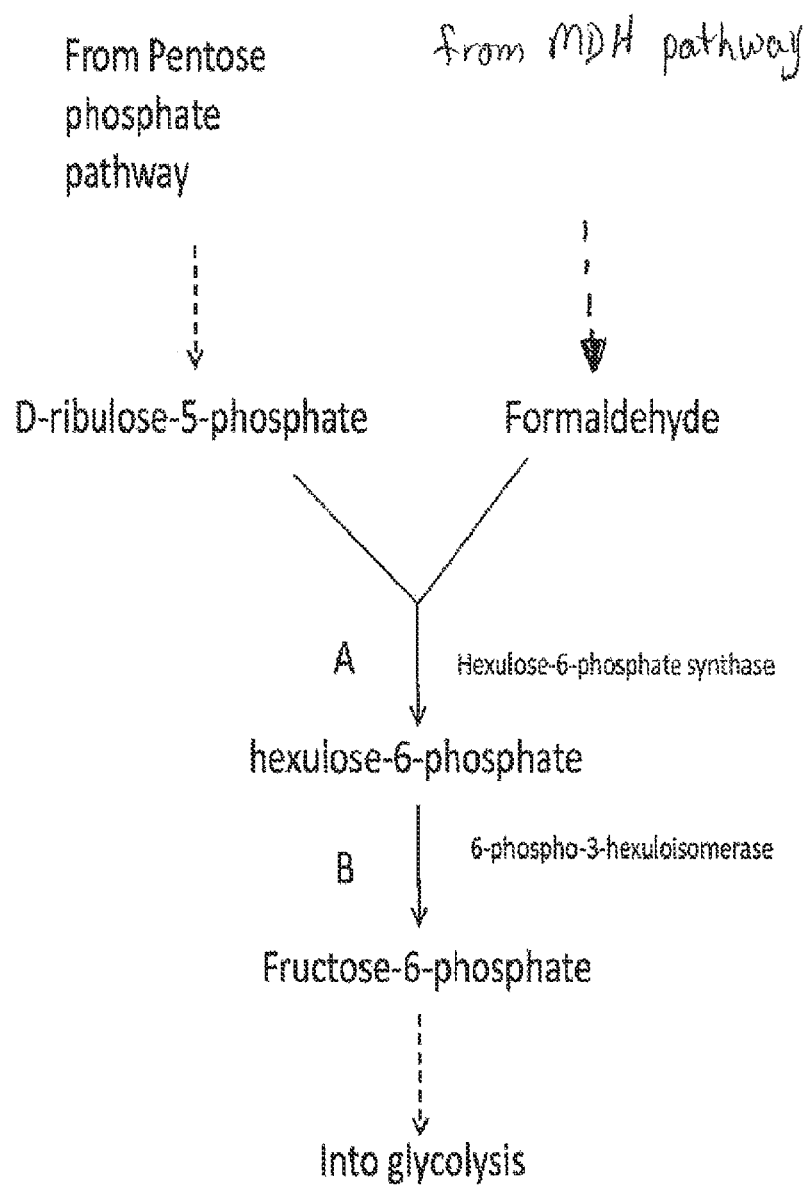
Figure 3C:
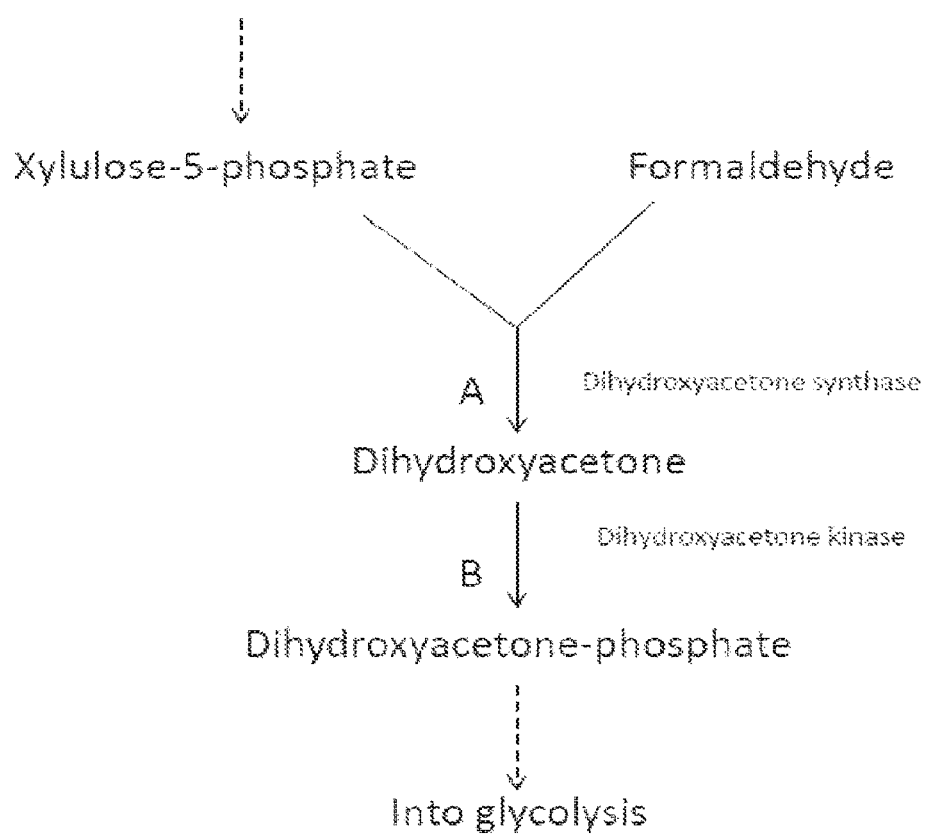
Figure 3D:
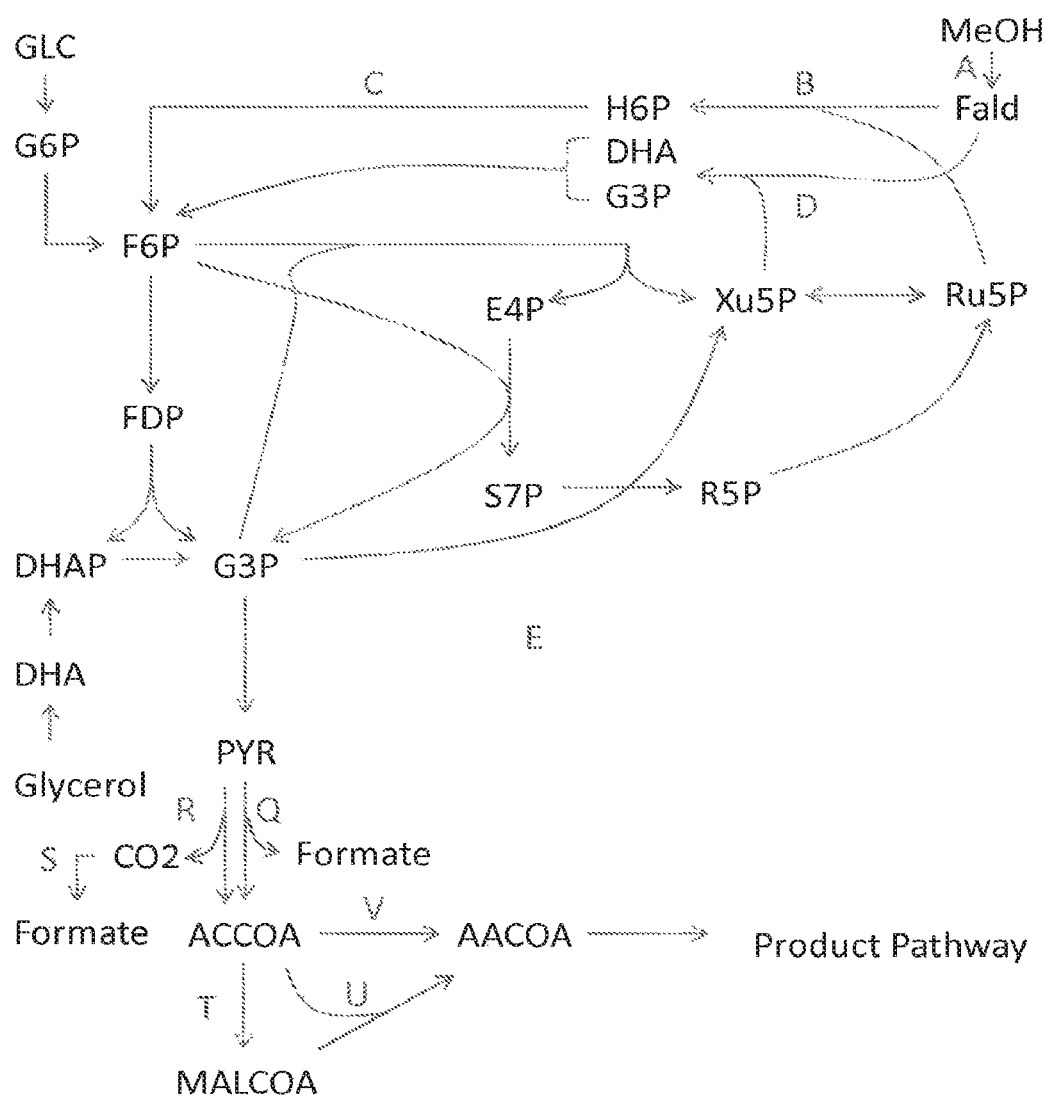

Also provided herein are exemplary pathways, which utilize formaldehyde produced from the oxidation of methanol (e.g., as provided in FIG. 3A, step J) in the formation of intermediates of certain central metabolic pathways that can be used for the formation of biomass. One exemplary FAP that can utilize formaldehyde produced from the oxidation of methanol (e.g., as provided in FIG. 3A) is shown in FIG. 3b, which involves condensation of formaldehyde and D-ribulose-5-phosphate to form H6P by EF1 (FIG. 3b, step A). The enzyme can use $Mg^{2+}$ or $Mn^{2+}$ for maximal activity, although other metal ions are useful, and even non-metal-ion-dependent mechanisms are contemplated. H6P is converted into F6P by EF2 (FIG. 3b, step B). Another exemplary pathway that involves the detoxification and assimilation of formaldehyde produced from the oxidation of methanol (e.g., as provided in FIG. 3a) is shown in FIG. 3c and proceeds through DHA. EF3 is a special transketolase that first transfers a glycoaldehyde group from xylulose-5-phosphate to formaldehyde, resulting in the formation of DHA and G3P, which is an intermediate in glycolysis (FIG. 3c, step A). The DHA obtained from DHA synthase is then further phosphorylated to form DHA phosphate by a DHA kinase (FIG. 3c, step B). DHAP can be assimilated into glycolysis and several other pathways. Rather than converting formaldehyde to formate and on to $CO_2$ off-gassed, the pathways provided in FIGS. 3b and 3c show that carbon is assimilated, going into the final product.

Thus, in one embodiment, an organism having a MDH protein, either alone or in combination with a BDOP, as provided herein, further comprises a FAP that utilizes formaldehyde, e.g., obtained from the oxidation of methanol, in the formation of intermediates of certain central metabolic pathways that can be used, for example, in the formation of biomass. In some embodiments, the FAP comprises 3A or 3B, wherein 3A is an EF1 and 3B is an EF2 In other embodiments, the FAP comprises 4A or 4B, wherein 4A is an EF3 and 4B is an EF4. In certain embodiments, provided herein is a organism having a MDH protein, wherein said organism comprises at least one exogenous nucleic acid encoding an EM9 expressed in a sufficient amount to enhance the availability of reducing equivalents in the presence of methanol and/or expressed in a sufficient amount to convert methanol to formaldehyde. In some embodiments, the organism comprises at least one exogenous nucleic acid encoding an EM9 expressed in a sufficient amount to enhance the availability of reducing equivalents in the presence of methanol. In other embodiments, the organism comprises at least one exogenous nucleic acid encoding an EM9 expressed in a sufficient amount to convert methanol to formaldehyde. In some embodiments, the microbial organism further comprises a FAP.

In certain embodiments, the organism further comprises at least one exogenous nucleic acid encoding a FAPE expressed in a sufficient amount to produce an intermediate of glycolysis. In certain embodiments, the FAPE is selected from the group consisting of an EF1, an EF2, an EF3 and an EF4.

Exemplary enzymes suitable for the reactions described herein to metabolize methanol for either or both reducing equivalents or carbon include the following, with respect to FIG. 3A, particularly as regards to Steps J, L, I, G, H, M, N and O.

FIG. 3, Step G—Formate Hydrogen Lyase (EM15)

An EM15 enzyme can be employed to convert formate to carbon dioxide and hydrogen. An exemplary EM15 enzyme can be found in *Escherichia coli*. The *E. coli* EM15 consists of hydrogenase 3 and formate dehydrogenase-H (Maeda et al., *Appl Microbiol Biotechnol* 77:879-890 (2007)). It is activated by the gene product of fhlA. (Maeda et al., *Appl Microbiol Biotechnol* 77:879-890 (2007)). The addition of the trace elements, selenium, nickel and molybdenum, to a fermentation broth has been shown to enhance EM15 activity (Soini et al., *Microb. Cell Fact.* 7:26 (2008)). Various hydrogenase 3, EM8 and transcriptional activator genes are shown below.

| Protein | GenBank ID | GI number | Organism |
| --- | --- | --- | --- |
| hycA | NP_417205 | 16130632 | *Escherichia coli* K-12 MG1655 |
| hycB | NP_417204 | 16130631 | *Escherichia coli* K-12 MG1655 |
| hycC | NP_417203 | 16130630 | *Escherichia coli* K-12 MG1655 |
| hycD | NP_417202 | 16130629 | *Escherichia coli* K-12 MG1655 |
| hycE | NP_417201 | 16130628 | *Escherichia coli* K-12 MG1655 |
| hycF | NP_417200 | 16130627 | *Escherichia coli* K-12 MG1655 |
| hycG | NP_417199 | 16130626 | *Escherichia coli* K-12 MG1655 |
| hycH | NP_417198 | 16130625 | *Escherichia coli* K-12 MG1655 |
| hycI | NP_417197 | 16130624 | *Escherichia coli* K-12 MG1655 |
| fdhF | NP_418503 | 16131905 | *Escherichia coli* K-12 MG1655 |
| fhlA | NP_417211 | 16130638 | *Escherichia coli* K-12 MG1655 |

An EM15 enzyme also exists in the hyperthermophilic archaeon, *Thermococcus litoralis* (Takacs et al., *BMC. Microbiol* 8:88 (2008)).

| Protein | GenBank ID | GI number | Organism |
| --- | --- | --- | --- |
| mhyC | ABW05543 | 157954626 | |
| mhyD | ABW05544 | 157954627 | *Thermococcus litoralis* |
| mhyE | ABW05545 | 157954628 | *Thermococcus litoralis* |
| myhF | ABW05546 | 157954629 | *Thermococcus litoralis* |
| myhG | ABW05547 | 157954630 | *Thermococcus litoralis* |
| myhH | ABW05548 | 157954631 | *Thermococcus litoralis* |
| fdhA | AAB94932 | 2746736 | *Thermococcus litoralis* |
| fdhB | AAB94931 | 157954625 | *Thermococcus litoralis* |

Additional EM15 systems have been found in *Salmonella typhimurium, Klebsiella pneumoniae, Rhodospirillum rubrum, Methanobacterium formicicum* (Vardar-Schara et al., Microbial Biotechnology 1:107-125 (2008)).

FIG. 3, Step H—Hydrogenase (EM16)

Hydrogenase enzymes can convert hydrogen gas to protons and transfer electrons to acceptors such as ferredoxins, NAD+, or NADP+. *Ralstonia eutropha* H16 uses hydrogen as an energy source with oxygen as a terminal electron acceptor. Its membrane-bound uptake [NiFe]-hydrogenase is an "O2-tolerant" EM16 (Cracknell, et al. Proc Nat Acad Sci, 106(49) 20681-20686 (2009)) that is periplasmically-oriented and connected to the respiratory chain via a b-type cytochrome (Schink and Schlegel, *Biochim. Biophys. Acta,* 567, 315-324 (1979); Bernhard et al., *Eur. J. Biochem.* 248, 179-186 (1997)). *R. eutropha* also contains an $O_2$-tolerant soluble EM16 encoded by the Hox operon which is cytoplasmic and directly reduces NAD+ at the expense of hydrogen (Schneider and Schlegel, Biochim. Biophys. Acta 452, 66-80 (1976); Burgdorf, *J. Bact.* 187(9) 3122-3132 (2005)). Soluble EM16 enzymes are additionally present in several other organisms including *Geobacter sulfurreducens* (Coppi, *Microbiology* 151, 1239-1254 (2005)), *Synechocystis* str. PCC 6803 (Germer, *J. Biol. Chem.*, 284(52), 36462-36472 (2009)), and *Thiocapsa roseopersicina* (Rakhely, *Appl. Environ. Microbiol.* 70(2) 722-728 (2004)). The *Synechocystis* enzyme is capable of generating NADPH from hydrogen. Overexpression of both the Hox operon from *Synechocystis* str. PCC 6803 and the accessory genes encoded by the Hyp operon from *Nostoc* sp. PCC 7120 led to increased EM16 activity compared to expression of the Hox genes alone (Germer, *J. Biol. Chem.* 284(52), 36462-36472 (2009)).

| Protein | GenBank ID | GI Number | Organism |
| --- | --- | --- | --- |
| HoxF | NP_942727.1 | 38637753 | *Ralstonia eutropha* H16 |
| HoxU | NP_942728.1 | 38637754 | *Ralstonia eutropha* H16 |
| HoxY | NP_942729.1 | 38637755 | *Ralstonia eutropha* H16 |
| HoxH | NP_942730.1 | 38637756 | *Ralstonia eutropha* H16 |
| HoxW | NP_942731.1 | 38637757 | *Ralstonia eutropha* H16 |
| HoxI | NP_942732.1 | 38637758 | *Ralstonia eutropha* H16 |
| HoxE | NP_953767.1 | 39997816 | *Geobacter sulfurreducens* |
| HoxF | NP_953766.1 | 39997815 | *Geobacter sulfurreducens* |
| HoxU | NP_953765.1 | 39997814 | *Geobacter sulfurreducens* |
| HoxY | NP_953764.1 | 39997813 | *Geobacter sulfurreducens* |
| HoxH | NP_953763.1 | 39997812 | *Geobacter sulfurreducens* |
| GSU2717 | NP_953762.1 | 39997811 | *Geobacter sulfurreducens* |
| HoxE | NP_441418.1 | 16330690 | *Synechocystis* str. PCC 6803 |
| HoxF | NP_441417.1 | 16330689 | *Synechocystis* str. PCC 6803 |
| Unknown function | NP_441416.1 | 16330688 | *Synechocystis* str. PCC 6803 |
| HoxU | NP_441415.1 | 16330687 | *Synechocystis* str. PCC 6803 |
| HoxY | NP_441414.1 | 16330686 | *Synechocystis* str. PCC 6803 |

| Protein | GenBank ID | GI Number | Organism |
| --- | --- | --- | --- |
| Unknown function | NP_441413.1 | 16330685 | *Synechocystis* str. PCC 6803 |
| Unknown function | NP_441412.1 | 16330684 | *Synechocystis* str. PCC 6803 |
| HoxH | NP_441411.1 | 16330683 | *Synechocystis* str. PCC 6803 |
| HypF | NP_484737.1 | 17228189 | *Nostoc* sp. PCC 7120 |
| HypC | NP_484738.1 | 17228190 | *Nostoc* sp. PCC 7120 |
| HypD | NP_484739.1 | 17228191 | *Nostoc* sp. PCC 7120 |
| Unknown function | NP_484740.1 | 17228192 | *Nostoc* sp. PCC 7120 |
| HypE | NP_484741.1 | 17228193 | *Nostoc* sp. PCC 7120 |
| HypA | NP_484742.1 | 17228194 | *Nostoc* sp. PCC 7120 |
| HypB | NP_484743.1 | 17228195 | *Nostoc* sp. PCC 7120 |
| Hox1E | AAP50519.1 | 37787351 | *Thiocapsa roseopersicina* |
| Hox1F | AAP50520.1 | 37787352 | *Thiocapsa roseopersicina* |
| Hox1U | AAP50521.1 | 37787353 | *Thiocapsa roseopersicina* |
| Hox1Y | AAP50522.1 | 37787354 | *Thiocapsa roseopersicina* |
| Hox1H | AAP50523.1 | 37787355 | *Thiocapsa roseopersicina* |

The genomes of *E. coli* and other enteric bacteria encode up to four EM16 enzymes (Sawers, G., *Antonie Van Leeuwenhoek* 66:57-88 (1994); Sawers et al., *J Bacteriol.* 164: 1324-1331 (1985); Sawers and Boxer, *Eur. J Biochem.* 156:265-275 (1986); Sawers et al., *J Bacteriol.* 168:398-404 (1986)). Given the multiplicity of enzyme activities *E. coli* or another host organism can provide sufficient EM16 activity to split incoming molecular hydrogen and reduce the corresponding acceptor. Endogenous hydrogen-lyase enzymes of *E. coli* include hydrogenase 3, a membrane-bound enzyme complex using ferredoxin as an acceptor, and hydrogenase 4 that also uses a ferredoxin acceptor. Hydrogenase 3 and 4 are encoded by the hyc and hyf gene clusters, respectively. EM16 activity in *E. coli* is also dependent upon the expression of the hyp genes whose corresponding proteins are involved in the assembly of the EM16 complexes (Jacobi et al., *Arch. Microbiol* 158:444-451 (1992); Rangarajan et al., *J Bacteriol.* 190:1447-1458 (2008)). The *M. thermoacetica* and *Clostridium ljungdahli* EM16s are suitable for a host that lacks sufficient endogenous EM16 activity. *M. thermoacetica* and *C. ljungdahli* can grow with $CO_2$ as the exclusive carbon source indicating that reducing equivalents are extracted from $H_2$ to enable acetyl-CoA synthesis via the Wood-Ljungdahl pathway (Drake, H. L., *J Bacteriol.* 150:702-709 (1982); Drake and Daniel, *Res Microbiol* 155:869-883 (2004); Kellum and Drake, *J Bacteriol.* 160:466-469 (1984)). *M. thermoacetica* has homologs to several hyp, hyc, and hyf genes from *E. coli*. These protein sequences encoded for by these genes are identified by the following GenBank accession numbers. In addition, several gene clusters encoding EM16 functionality are present in *M. thermoacetica* and *C. ljungdahli* (see for example US 2012/0003652).

| Protein | GenBank ID | GI Number | Organism |
| --- | --- | --- | --- |
| HypA | NP_417206 | 16130633 | *Escherichia coli* |
| HypB | NP_417207 | 16130634 | *Escherichia coli* |
| HypC | NP_417208 | 16130635 | *Escherichia coli* |
| HypD | NP_417209 | 16130636 | *Escherichia coli* |
| HypE | NP_417210 | 226524740 | *Escherichia coli* |
| HypF | NP_417192 | 16130619 | *Escherichia coli* |
| HycA | NP_417205 | 16130632 | *Escherichia coli* |
| HycB | NP_417204 | 16130631 | *Escherichia coli* |
| HycC | NP_417203 | 16130630 | *Escherichia coli* |
| HycD | NP_417202 | 16130629 | *Escherichia coli* |
| HycE | NP_417201 | 16130628 | *Escherichia coli* |
| HycF | NP_417200 | 16130627 | *Escherichia coli* |
| HycG | NP_417199 | 16130626 | *Escherichia coli* |
| HycH | NP_417198 | 16130625 | *Escherichia coli* |
| HycI | NP_417197 | 16130624 | *Escherichia coli* |
| HyfA | NP_416976 | 90111444 | *Escherichia coli* |
| HyfB | NP_416977 | 16130407 | *Escherichia coli* |
| HyfC | NP_416978 | 90111445 | *Escherichia coli* |
| HyfD | NP_416979 | 16130409 | *Escherichia coli* |
| HyfE | NP_416980 | 16130410 | *Escherichia coli* |
| HyfF | NP_416981 | 16130411 | *Escherichia coli* |
| HyfG | NP_416982 | 16130412 | *Escherichia coli* |
| HyfH | NP_416983 | 16130413 | *Escherichia coli* |
| HyfI | NP_416984 | 16130414 | *Escherichia coli* |
| HyfJ | NP_416985 | 90111446 | *Escherichia coli* |
| HyfR | NP_416986 | 90111447 | *Escherichia coli* |

Proteins in *M. thermoacetica* whose genes are homologous to the *E. coli* EM16 genes are shown below.

| Protein | GenBank ID | GI Number | Organism |
| --- | --- | --- | --- |
| Moth_2175 | YP_431007 | 83590998 | *Moorella thermoacetica* |
| Moth_2176 | YP_431008 | 83590999 | *Moorella thermoacetica* |
| Moth_2177 | YP_431009 | 83591000 | *Moorella thermoacetica* |
| Moth_2178 | YP_431010 | 83591001 | *Moorella thermoacetica* |
| Moth_2179 | YP_431011 | 83591002 | *Moorella thermoacetica* |
| Moth_2180 | YP_431012 | 83591003 | *Moorella thermoacetica* |
| Moth_2181 | YP_431013 | 83591004 | *Moorella thermoacetica* |
| Moth_2182 | YP_431014 | 83591005 | *Moorella thermoacetica* |
| Moth_2183 | YP_431015 | 83591006 | *Moorella thermoacetica* |
| Moth_2184 | YP_431016 | 83591007 | *Moorella thermoacetica* |
| Moth_2185 | YP_431017 | 83591008 | *Moorella thermoacetica* |
| Moth_2186 | YP_431018 | 83591009 | *Moorella thermoacetica* |
| Moth_2187 | YP_431019 | 83591010 | *Moorella thermoacetica* |
| Moth_2188 | YP_431020 | 83591011 | *Moorella thermoacetica* |
| Moth_2189 | YP_431021 | 83591012 | *Moorella thermoacetica* |
| Moth_2190 | YP_431022 | 83591013 | *Moorella thermoacetica* |
| Moth_2191 | YP_431023 | 83591014 | *Moorella thermoacetica* |
| Moth_2192 | YP_431024 | 83591015 | *Moorella thermoacetica* |
| Moth_0439 | YP_429313 | 83589304 | *Moorella thermoacetica* |
| Moth_0440 | YP_429314 | 83589305 | *Moorella thermoacetica* |
| Moth_0441 | YP_429315 | 83589306 | *Moorella thermoacetica* |
| Moth_0442 | YP_429316 | 83589307 | *Moorella thermoacetica* |
| Moth_0809 | YP_429670 | 83589661 | *Moorella thermoacetica* |
| Moth_0810 | YP_429671 | 83589662 | *Moorella thermoacetica* |
| Moth_0811 | YP_429672 | 83589663 | *Moorella thermoacetica* |
| Moth_0812 | YP_429673 | 83589664 | *Moorella thermoacetica* |
| Moth_0814 | YP_429674 | 83589665 | *Moorella thermoacetica* |
| Moth_0815 | YP_429675 | 83589666 | *Moorella thermoacetica* |
| Moth_0816 | YP_429676 | 83589667 | *Moorella thermoacetica* |
| Moth_1193 | YP_430050 | 83590041 | *Moorella thermoacetica* |
| Moth_1194 | YP_430051 | 83590042 | *Moorella thermoacetica* |
| Moth_1195 | YP_430052 | 83590043 | *Moorella thermoacetica* |
| Moth_1196 | YP_430053 | 83590044 | *Moorella thermoacetica* |
| Moth_1717 | YP_430562 | 83590553 | *Moorella thermoacetica* |
| Moth_1718 | YP_430563 | 83590554 | *Moorella thermoacetica* |
| Moth_1719 | YP_430564 | 83590555 | *Moorella thermoacetica* |
| Moth_1883 | YP_430726 | 83590717 | *Moorella thermoacetica* |
| Moth_1884 | YP_430727 | 83590718 | *Moorella thermoacetica* |
| Moth_1885 | YP_430728 | 83590719 | *Moorella thermoacetica* |
| Moth_1886 | YP_430729 | 83590720 | *Moorella thermoacetica* |
| Moth_1887 | YP_430730 | 83590721 | *Moorella thermoacetica* |
| Moth_1888 | YP_430731 | 83590722 | *Moorella thermoacetica* |
| Moth_1452 | YP_430305 | 83590296 | *Moorella thermoacetica* |
| Moth_1453 | YP_430306 | 83590297 | *Moorella thermoacetica* |
| Moth_1454 | YP_430307 | 83590298 | *Moorella thermoacetica* |

Genes encoding EM16 enzymes from *C. ljungdahli* are shown below.

| Protein | GenBank ID | GI Number | Organism |
| --- | --- | --- | --- |
| CLJU_c20290 | ADK15091.1 | 300435324 | *Clostridium ljungdahli* |
| CLJU_c07030 | ADK13773.1 | 300434006 | *Clostridium ljungdahli* |
| CLJU_c07040 | ADK13774.1 | 300434007 | *Clostridium ljungdahli* |

| Protein | GenBank ID | GI Number | Organism |
| --- | --- | --- | --- |
| CLJU_c07050 | ADK13775.1 | 300434008 | *Clostridium ljungdahli* |
| CLJU_c07060 | ADK13776.1 | 300434009 | *Clostridium ljungdahli* |
| CLJU_c07070 | ADK13777.1 | 300434010 | *Clostridium ljungdahli* |
| CLJU_c07080 | ADK13778.1 | 300434011 | *Clostridium ljungdahli* |
| CLJU_c14730 | ADK14541.1 | 300434774 | *Clostridium ljungdahli* |
| CLJU_c14720 | ADK14540.1 | 300434773 | *Clostridium ljungdahli* |
| CLJU_c14710 | ADK14539.1 | 300434772 | *Clostridium ljungdahli* |
| CLJU_c14700 | ADK14538.1 | 300434771 | *Clostridium ljungdahli* |
| CLJU_c28670 | ADK15915.1 | 300436148 | *Clostridium ljungdahli* |
| CLJU_c28660 | ADK15914.1 | 300436147 | *Clostridium ljungdahli* |
| CLJU_c28650 | ADK15913.1 | 300436146 | *Clostridium ljungdahli* |
| CLJU_c28640 | ADK15912.1 | 300436145 | *Clostridium ljungdahli* |

In some cases, EM16 encoding genes are located adjacent to a CODH. In *Rhodospirillum rubrum*, the encoded CODH/hydrogenase proteins form a membrane-bound enzyme complex that has been indicated to be a site where energy, in the form of a proton gradient, is generated from the conversion of CO and $H_2O$ to $CO_2$ and $H_2$ (Fox et al., *J Bacteriol.* 178:6200-6208 (1996)). The CODH-I of *C. hydrogenoformans* and its adjacent genes have been proposed to catalyze a similar functional role based on their similarity to the *R. rubrum* CODH/hydrogenase gene cluster (Wu et al., *PLoS Genet.* 1:e65 (2005)). The *C. hydrogenoformans* CODH-I was also shown to exhibit intense CO oxidation and $CO_2$ reduction activities when linked to an electrode (Parkin et al., *J Am. Chem. Soc.* 129:10328-10329 (2007)).

| Protein | GenBank ID | GI Number | Organism |
| --- | --- | --- | --- |
| CooL | AAC45118 | 1515468 | *Rhodospirillum rubrum* |
| CooX | AAC45119 | 1515469 | *Rhodospirillum rubrum* |
| CooU | AAC45120 | 1515470 | *Rhodospirillum rubrum* |
| CooH | AAC45121 | 1498746 | *Rhodospirillum rubrum* |
| CooF | AAC45122 | 1498747 | *Rhodospirillum rubrum* |
| CODH (CooS) | AAC45123 | 1498748 | *Rhodospirillum rubrum* |
| CooC | AAC45124 | 1498749 | *Rhodospirillum rubrum* |
| CooT | AAC45125 | 1498750 | *Rhodospirillum rubrum* |
| CooJ | AAC45126 | 1498751 | *Rhodospirillum rubrum* |
| CODH-I (CooS-I) | YP_360644 | 78043418 | *Carboxydothermus hydrogenoformans* |
| CooF | YP_360645 | 78044791 | *Carboxydothermus hydrogenoformans* |
| HypA | YP_360646 | 78044340 | *Carboxydothermus hydrogenoformans* |
| CooH | YP_360647 | 78043871 | *Carboxydothermus hydrogenoformans* |
| CooU | YP_360648 | 78044023 | *Carboxydothermus hydrogenoformans* |
| CooX | YP_360649 | 78043124 | *Carboxydothermus hydrogenoformans* |
| CooL | YP_360650 | 78043938 | *Carboxydothermus hydrogenoformans* |
| CooK | YP_360651 | 78044700 | *Carboxydothermus hydrogenoformans* |
| CooM | YP_360652 | 78043942 | *Carboxydothermus hydrogenoformans* |
| CooC | YP_360654.1 | 78043296 | *Carboxydothermus hydrogenoformans* |
| CooA-1 | YP_360655.1 | 78044021 | *Carboxydothermus hydrogenoformans* |

Some EM16 and CODH enzymes transfer electrons to ferredoxins. Ferredoxins are small acidic proteins containing one or more iron-sulfur clusters that function as intracellular electron carriers with a low reduction potential. Reduced ferredoxins donate electrons to Fe-dependent enzymes such as ferredoxin-$NADP^+$ oxidoreductase, pyruvate:ferredoxin oxidoreductase (PFOR) and 2-oxoglutarate:ferredoxin oxidoreductase (OFOR). The *H. thermophilus* gene fdx1 encodes a [4Fe-4S]-type ferredoxin that is required for the reversible carboxylation of 2-oxoglutarate and pyruvate by OFOR and PFOR, respectively (Yamamoto et al., *Extremophiles* 14:79-85 (2010)). The ferredoxin associated with the *Sulfolobus solfataricus* 2-oxoacid:ferredoxin reductase is a monomeric dicluster [3Fe-4S][4Fe-4S] type ferredoxin (Park et al. 2006). While the gene associated with this protein has not been fully sequenced, the N-terminal domain shares 93% homology with the zfx ferredoxin from *S. acidocaldarius*. The *E. coli* genome encodes a soluble ferredoxin of unknown physiological function, fdx. Some evidence indicates that this protein can function in iron-sulfur cluster assembly (Takahashi and Nakamura, 1999). Additional ferredoxin proteins have been characterized in *Helicobacter pylori* (Mukhopadhyay et al. 2003) and *Campylobacter jejuni* (van Vliet et al. 2001). A 2Fe-2S ferredoxin from *Clostridium pasteurianum* has been cloned and expressed in *E. coli* (Fujinaga and Meyer, *Biochemical and Biophysical Research Communications*, 192(3): (1993)). Acetogenic bacteria such as *Moorella thermoacetica*, *Clostridium carboxidivorans* P7, *Clostridium ljungdahli* and *Rhodospirillum rubrum* are predicted to encode several ferredoxins, listed below.

| Protein | GenBank ID | GI Number | Organism |
| --- | --- | --- | --- |
| fdx1 | BAE02673.1 | 68163284 | *Hydrogenobacter thermophilus* |
| M11214.1 | AAA83524.1 | 144806 | *Clostridium pasteurianum* |
| Zfx | AAY79867.1 | 68566938 | *Sulfolobus acidocalarius* |
| Fdx | AAC75578.1 | 1788874 | *Escherichia coli* |
| hp_0277 | AAD07340.1 | 2313367 | *Helicobacter pylori* |
| fdxA | CAL34484.1 | 112359698 | *Campylobacter jejuni* |
| Moth_0061 | ABC18400.1 | 83571848 | *Moorella thermoacetica* |
| Moth_1200 | ABC19514.1 | 83572962 | *Moorella thermoacetica* |
| Moth_1888 | ABC20188.1 | 83573636 | *Moorella thermoacetica* |
| Moth_2112 | ABC20404.1 | 83573852 | *Moorella thermoacetica* |
| Moth_1037 | ABC19351.1 | 83572799 | *Moorella thermoacetica* |
| CcarbDRAFT_4383 | ZP_05394383.1 | 255527515 | *Clostridium carboxidivorans* P7 |
| CcarbDRAFT_2958 | ZP_05392958.1 | 255526034 | *Clostridium carboxidivorans* P7 |
| CcarbDRAFT_2281 | ZP_05392281.1 | 255525342 | *Clostridium carboxidivorans* P7 |
| CcarbDRAFT_5296 | ZP_05395295.1 | 255528511 | *Clostridium carboxidivorans* P7 |
| CcarbDRAFT_1615 | ZP_05391615.1 | 255524662 | *Clostridium carboxidivorans* P7 |
| CcarbDRAFT_1304 | ZP_05391304.1 | 255524347 | *Clostridium carboxidivorans* P7 |
| cooF | AAG29808.1 | 11095245 | *Carboxydothermus hydrogenoformans* |
| fdxN | CAA35699.1 | 46143 | *Rhodobacter capsulatus* |

| Protein | GenBank ID | GI Number | Organism |
| --- | --- | --- | --- |
| Rru_A2264 | ABC23064.1 | 83576513 | Rhodospirillum rubrum |
| Rru_A1916 | ABC22716.1 | 83576165 | Rhodospirillum rubrum |
| Rru_A2026 | ABC22826.1 | 83576275 | Rhodospirillum rubrum |
| cooF | AAC45122.1 | 1498747 | Rhodospirillum rubrum |
| fdxN | AAA26460.1 | 152605 | Rhodospirillum rubrum |
| Alvin_2884 | ADC63789.1 | 288897953 | Allochromatium vinosum DSM 180 |
| Fdx | YP_002801146.1 | 226946073 | Azotobacter vinelandii DJ |
| CKL_3790 | YP_001397146.1 | 153956381 | Clostridium kluyveri DSM 555 |
| fer1 | NP_949965.1 | 39937689 | Rhodopseudomonas palustris CGA009 |
| Fdx | CAA12251.1 | 3724172 | Thauera aromatica |
| CHY_2405 | YP_361202.1 | 78044690 | Carboxydothermus hydrogenoformans |
| Fer | YP_359966.1 | 78045103 | Carboxydothermus hydrogenoformans |
| Fer | AAC83945.1 | 1146198 | Bacillus subtilis |
| fdx1 | NP_249053.1 | 15595559 | Pseudomonas aeruginosa PA01 |
| yfhL | AP_003148.1 | 89109368 | Escherichia coli K-12 |
| CLJU_c00930 | ADK13195.1 | 300433428 | Clostridium ljungdahli |
| CLJU_c00010 | ADK13115.1 | 300433348 | Clostridium ljungdahli |
| CLJU_c01820 | ADK13272.1 | 300433505 | Clostridium ljungdahli |
| CLJU_c17980 | ADK14861.1 | 300435094 | Clostridium ljungdahli |
| CLJU_c17970 | ADK14860.1 | 300435093 | Clostridium ljungdahli |
| CLJU_c22510 | ADK15311.1 | 300435544 | Clostridium ljungdahli |
| CLJU_c26680 | ADK15726.1 | 300435959 | Clostridium ljungdahli |
| CLJU_c29400 | ADK15988.1 | 300436221 | Clostridium ljungdahli |

Ferredoxin oxidoreductase enzymes transfer electrons from ferredoxins or flavodoxins to NAD(P)H. Two enzymes catalyzing the reversible transfer of electrons from reduced ferredoxins to NAD(P)+ are ferredoxin:NAD+ oxidoreductase (EC 1.18.1.3) and ferredoxin:NADP+ oxidoreductase (FNR, EC 1.18.1.2). Ferredoxin:NADP+ oxidoreductase (FNR, EC 1.18.1.2) has a noncovalently bound FAD cofactor that facilitates the reversible transfer of electrons from NADPH to low-potential acceptors such as ferredoxins or flavodoxins (Blaschkowski et al., Eur. J. Biochem. 123:563-569 (1982); Fujii et al., 1977). The Helicobacter pylori FNR, encoded by HP1164 (fqrB), is coupled to the activity of pyruvate:ferredoxin oxidoreductase (PFOR) resulting in the pyruvate-dependent production of NADPH (St et al. 2007). An analogous enzyme is found in Campylobacter jejuni (St Maurice et al., J. Bacteriol. 189: 4764-4773 (2007)). A ferredoxin:NADP+ oxidoreductase enzyme is encoded in the E. coli genome by fpr (Bianchi et al. 1993). Ferredoxin:NAD+ oxidoreductase utilizes reduced ferredoxin to generate NADH from NAD+. In several organisms, including E. coli, this enzyme is a component of multifunctional dioxygenase enzyme complexes. The ferredoxin:NAD+ oxidoreductase of E. coli, encoded by hcaD, is a component of the 3-phenylpropionate dioxygenase system involved in involved in aromatic acid utilization (Diaz et al. 1998). NADH:ferredoxin reductase activity was detected in cell extracts of Hydrogenobacter thermophilus, although a gene with this activity has not yet been indicated (Yoon et al. 2006). Additional ferredoxin: NAD(P)+ oxidoreductases have been annotated in Clostridium carboxydivorans P7. The NADH-dependent reduced ferredoxin:NADP oxidoreductase of C. kluyveri, encoded by nfnAB, catalyzes the concomitant reduction of ferredoxin and NAD+ with two equivalents of NADPH (Wang et al, J Bacteriol 192: 5115-5123 (2010)). Finally, the energy-conserving membrane-associated Rnf-type proteins (Seedorf et al, PNAS 105:2128-2133 (2008); and Herrmann, J Bacteriol 190:784-791 (2008)) provide a means to generate NADH or NADPH from reduced ferredoxin.

| Protein | GenBank ID | GI Number | Organism |
| --- | --- | --- | --- |
| fqrB | NP_207955.1 | 15645778 | Helicobacter pylori |
| fqrB | YP_001482096.1 | 157414840 | Campylobacter jejuni |
| RPA3954 | CAE29395.1 | 39650872 | Rhodopseudomonas palustris |
| Fpr | BAH29712.1 | 225320633 | Hydrogenobacter thermophilus |
| yumC | NP_391091.2 | 255767736 | Bacillus subtilis |
| Fpr | P28861.4 | 399486 | Escherichia coli |
| hcaD | AAC75595.1 | 1788892 | Escherichia coli |
| LOC100282643 | NP_001149023.1 | 226497434 | Zea mays |
| NfnA | YP_001393861.1 | 153953096 | Clostridium kluyveri |
| NfnB | YP_001393862.1 | 153953097 | Clostridium kluyveri |
| CcarbDRAFT_2639 | ZP_05392639.1 | 255525707 | Clostridium carboxidivorans P7 |
| CcarbDRAFT_2638 | ZP_05392638.1 | 255525706 | Clostridium carboxidivorans P7 |
| CcarbDRAFT_2636 | ZP_05392636.1 | 255525704 | Clostridium carboxidivorans P7 |
| CcarbDRAFT_5060 | ZP_05395060.1 | 255528241 | Clostridium carboxidivorans P7 |
| CcarbDRAFT_2450 | ZP_05392450.1 | 255525514 | Clostridium carboxidivorans P7 |
| CcarbDRAFT_1084 | ZP_05391084.1 | 255524124 | Clostridium carboxidivorans P7 |
| RnfC | EDK33306.1 | 146346770 | Clostridium kluyveri |
| RnfD | EDK33307.1 | 146346771 | Clostridium kluyveri |
| RnfG | EDK33308.1 | 146346772 | Clostridium kluyveri |
| RnfE | EDK33309.1 | 146346773 | Clostridium kluyveri |
| RnfA | EDK33310.1 | 146346774 | Clostridium kluyveri |
| RnfB | EDK33311.1 | 146346775 | Clostridium kluyveri |
| CLJU_c11410 (Rnff) | ADK14209.1 | 300434442 | Clostridium ljungdahlii |

-continued

| Protein | GenBank ID | GI Number | Organism |
|---|---|---|---|
| CLJU_c11400 (RnfA) | ADK14208.1 | 300434441 | *Clostridium ljungdahlii* |
| CLJU_c11390 (RnfE) | ADK14207.1 | 300434440 | *Clostridium ljungdahlii* |
| CLJU_c11380 (RnfG) | ADK14206.1 | 300434439 | *Clostridium ljungdahlii* |
| CLJU_c11370 (RnfD) | ADK14205.1 | 300434438 | *Clostridium ljungdahlii* |
| CLJU_c11360 (RnfC) | ADK14204.1 | 300434437 | *Clostridium ljungdahlii* |
| MOTH_1518 (NfnA) | YP_430370.1 | 83590361 | *Moorella thermoacetica* |
| MOTH_1517(NfnB) | YP_430369.1 | 83590360 | *Moorella thermoacetica* |
| CHY_1992 (NfnA) | YP_360811.1 | 78045020 | *Carboxydothermus hydrogenoformans* |
| CHY_1993 (NfnB) | YP_360812.1 | 78044266 | *Carboxydothermus hydrogenoformans* |
| CLJU_c37220 (NfnAB) | YP_003781850.1 | 300856866 | *Clostridium ljungdahlii* |

FIG. 3, Step I—Formate Dehydrogenase (EM8)

Formate dehydrogenase (FDH; EM8) catalyzes the reversible transfer of electrons from formate to an acceptor. Enzymes with FDH activity utilize various electron carriers such as, for example, NADH (EC 1.2.1.2), NADPH (EC 1.2.1.43), quinols (EC 1.1.5.6), cytochromes (EC 1.2.2.3) and EM16s (EC 1.1.99.33). FDH enzymes have been characterized from *Moorella thermoacetica* (Andreesen and Ljungdahl, *J Bacteriol* 116:867-873 (1973); Li et al., *J Bacteriol* 92:405-412 (1966); Yamamoto et al., *J Biol Chem.* 258:1826-1832 (1983). The loci, Moth_2312 is responsible for encoding the alpha subunit of EM8 while the beta subunit is encoded by Moth_2314 (Pierce et al., *Environ Microbiol* (2008)). Another set of genes encoding EM8 activity with a propensity for $CO_2$ reduction is encoded by Sfum_2703 through Sfum_2706 in *Syntrophobacter fumaroxidans* (de Bok et al., *Eur J Biochem.* 270:2476-2485 (2003)); Reda et al., *PNAS* 105:10654-10658 (2008)). A similar set of genes presumed to carry out the same function are encoded by CHY_0731, CHY_0732, and CHY_0733 in *C. hydrogenoformans* (Wu et al., *PLoS Genet* 1:e65 (2005)).

EM8s are also found many additional organisms including *C. carboxidivorans* P7, *Bacillus methanolicus*, *Burkholderia stabilis*, *Moorella thermoacetica* ATCC 39073, *Candida boidinii*, *Candida methylica*, and *Saccharomyces cerevisiae* S288c. The soluble EM8 from *Ralstonia eutropha* reduces $NAD^+$ (fdsG, –B, –A, –C, –D) (Oh and Bowien, 1998).

Several EM8 enzymes have been identified that have higher specificity for NADP as the cofactor as compared to NAD. This enzyme has been deemed as the NADP-dependent formate dehydrogenase and has been reported from 5 species of the *Burkholderia cepacia* complex. It was tested and verified in multiple strains of *Burkholderia multivorans*, *Burkholderia stabilis*, *Burkholderia pyrrocinia*, and *Burkholderia cenocepacia* (Hatrongjit et al., *Enzyme and Microbial Tech.*, 46: 557-561 (2010)). The enzyme from *Burkholderia stabilis* has been characterized and the apparent $K_m$ of the enzyme were reported to be 55.5 mM, 0.16 mM and 1.43 mM for formate, NADP, and NAD respectively. More gene candidates can be identified using sequence homology of proteins deposited in Public databases such as NCBI, JGI and the metagenomic databases.

| Protein | GenBank ID | GI Number | Organism |
|---|---|---|---|
| Moth_2312 | YP_431142 | 148283121 | *Moorella thermoacetica* |
| Moth_2314 | YP_431144 | 83591135 | *Moorella thermoacetica* |
| Sfum_2703 | YP_846816.1 | 116750129 | *Syntrophobacter fumaroxidans* |
| Sfum_2704 | YP_846817.1 | 116750130 | *Syntrophobacter fumaroxidans* |
| Sfum_2705 | YP_846818.1 | 116750131 | *Syntrophobacter fumaroxidans* |
| Sfum_2706 | YP_846819.1 | 116750132 | *Syntrophobacter fumaroxidans* |
| CHY_0731 | YP_359585.1 | 78044572 | *Carboxydothermus hydrogenoformans* |
| CHY_0732 | YP_359586.1 | 78044500 | *Carboxydothermus hydrogenoformans* |
| CHY_0733 | YP_359587.1 | 78044647 | *Carboxydothermus hydrogenoformans* |
| CcarbDRAFT_0901 | ZP_05390901.1 | 255523938 | *Clostridium carboxidivorans* P7 |
| CcarbDRAFT_4380 | ZP_05394380.1 | 255527512 | *Clostridium carboxidivorans* P7 |
| fdhA, MGA3_06625 | EIJ82879.1 | 387590560 | *Bacillus methanolicus* MGA3 |
| fdhA, PB1_11719 | ZP_10131761.1 | 387929084 | *Bacillus methanolicus* PB1 |
| fdhD, MGA3_06630 | EIJ82880.1 | 387590561 | *Bacillus methanolicus* MGA3 |
| fdhD, PB1_11724 | ZP_10131762.1 | 387929085 | *Bacillus methanolicus* PB1 |
| fdh | ACF35003.1 | 194220249 | *Burkholderia stabilis* |
| fdh | ACF35004.1 | 194220251 | *Burkholderia pyrrocinia* |
| fdh | ACF35002.1 | 194220247 | *Burkholderia cenocepacia* |
| fdh | ACF35001.1 | 194220245 | *Burkholderia multivorans* |
| fdh | ACF35000.1 | 194220243 | *Burkholderia cepacia* |
| FDH1 | AAC49766.1 | 2276465 | *Candida boidinii* |
| fdh | CAA57036.1 | 1181204 | *Candida methylica* |
| FDH2 | P0CF35.1 | 294956522 | *Saccharomyces cerevisiae* S288c |
| FDH1 | NP_015033.1 | 6324964 | *Saccharomyces cerevisiae* S288c |
| fdsG | YP_725156.1 | 113866667 | *Ralstonia eutropha* |

| Protein | GenBank ID | GI Number | Organism |
|---------|------------|-----------|----------|
| fdsB | YP_725157.1 | 113866668 | Ralstonia eutropha |
| fdsA | YP_725158.1 | 113866669 | Ralstonia eutropha |
| fdsC | YP_725159.1 | 113866670 | Ralstonia eutropha |
| fdsD | YP_725160.1 | 113866671 | Ralstonia eutropha |

FIG. 3, Step J—Methanol Dehydrogenase (EM9)

NAD+ dependent EM9 enzymes (EC 1.1.1.244) catalyze the conversion of methanol and NAD+ to formaldehyde and NADH. See the present invention as described herein.

FIG. 3, Step L—Formaldehyde Dehydrogenase (EM11)

Oxidation of formaldehyde to formate is catalyzed by EM11. A NAD+ dependent EM11 enzyme is encoded by fdhA of *Pseudomonas putida* (Ito et al, *J Bacteriol* 176: 2483-2491 (1994)). Additional EM11 enzymes include the NAD+ and glutathione independent EM11 from *Hyphomicrobium zavarzinii* (Jerome et al, *Appl Microbiol Biotechnol* 77:779-88 (2007)), the glutathione dependent EM11 of *Pichia pastoris* (Sunga et al, *Gene* 330:39-47 (2004)) and the NAD(P)+ dependent EM11 of *Methylobacter marinus* (Speer et al, FEMS Microbiol Lett, 121(3):349-55 (1994)).

| Protein | GenBank ID | GI number | Organism |
|---------|------------|-----------|----------|
| fdhA | P46154.3 | 1169603 | Pseudomonas putida |
| faoA | CAC85637.1 | 19912992 | Hyphomicrobium zavarzinii |
| Fld1 | CCA39112.1 | 328352714 | Pichia pastoris |
| fdh | P47734.2 | 221222447 | Methylobacter marinus |

In addition to the EM11 enzymes listed above, alternate enzymes and pathways for converting formaldehyde to formate are known in the art. For example, many organisms employ glutathione-dependent formaldehyde oxidation pathways, in which formaldehyde is converted to formate in three steps via the intermediates S-hydroxymethylglutathione and S-formylglutathione (Vorholt et al, *J Bacteriol* 182:6645-50 (2000)). The enzymes of this pathway are EM12 (EC 4.4.1.22), EM13 (EC 1.1.1.284) and EM14 (EC 3.1.2.12).

FIG. 3, Step M—Spontaneous or S-(hydroxymethyl)glutathione Synthase (EM12) While conversion of formaldehyde to S-hydroxymethylglutathione can occur spontaneously in the presence of glutathione, it has been shown by Goenrich et al (Goenrich, et al., *J Biol Chem* 277(5); 3069-72 (2002)) that an enzyme from *Paracoccus denitrificans* can accelerate this spontaneous condensation reaction. The enzyme catalyzing the conversion of formaldehyde and glutathione was purified and named glutathione-dependent formaldehyde-activating enzyme (Gfa). The gene encoding it, which was named gfa, is located directly upstream of the gene for EM13, which catalyzes the subsequent oxidation of S-hydroxymethylglutathione. Putative proteins with sequence identity to Gfa from *P. denitrificans* are present also in *Rhodobacter sphaeroides*, *Sinorhizobium meliloti*, and *Mesorhizobium loti*.

| Protein | GenBank ID | GI Number | Organism |
|---------|------------|-----------|----------|
| Gfa | Q51669.3 | 38257308 | Paracoccus denitrificans |
| Gfa | ABP71667.1 | 145557054 | Rhodobacter sphaeroides ATCC 17025 |
| Gfa | Q92WX6.1 | 38257348 | Sinorhizobium meliloti 1021 |
| Gfa | Q98LU4.2 | 38257349 | Mesorhizobium loti MAFF303099 |

FIG. 3, Step N—Glutathione-Dependent Formaldehyde Dehydrogenase (EM13)

EM13 (GS-FDH) belongs to the family of class III alcohol dehydrogenases. Glutathione and formaldehyde combine non-enzymatically to form hydroxymethylglutathione, the true substrate of the GS-FDH catalyzed reaction. The product, S-formylglutathione, is further metabolized to formic acid.

| Protein | GenBank ID | GI Number | Organism |
|---------|------------|-----------|----------|
| frmA | YP_488650.1 | 388476464 | Escherichia coli K-12 MG1655 |
| SFA1 | NP_010113.1 | 6320033 | Saccharomyces cerevisiae S288c |
| flhA | AAC44551.1 | 1002865 | Paracoccus denitrificans |
| adhI | AAB09774.1 | 986949 | Rhodobacter sphaeroides |

FIG. 3, Step O—S-formylglutathione Hydrolase (EM14)

EM14 is a glutathione thiol esterase found in bacteria, plants and animals. It catalyzes conversion of S-formylglutathione to formate and glutathione. The fghA gene of *P. denitrificans* is located in the same operon with gfa and flhA, two genes involved in the oxidation of formaldehyde to formate in this organism. In *E. coli*, FrmB is encoded in an operon with FrmR and FrmA, which are proteins involved in the oxidation of formaldehyde. YeiG of *E. coli* is a promiscuous serine hydrolase; its highest specific activity is with the substrate S-formylglutathione.

| Protein | GenBank ID | GI Number | Organism |
|---------|------------|-----------|----------|
| frmB | NP_414889.1 | 16128340 | Escherichia coli K-12 MG1655 |
| yeiG | AAC75215.1 | 1788477 | Escherichia coli K-12 MG1655 |
| fghA | AAC44554.1 | 1002868 | Paracoccus denitrificans |

Exemplary enzymes for the methods of using formaldehyde produced from the oxidation of methanol in the formation of intermediates of central metabolic pathways for the formation of target product or biomass are further described, particularly with respect to FIGS. 3B and 3C.

Provided herein are exemplary pathways, which utilize formaldehyde produced from the oxidation of methanol (see, e.g., FIG. 3, step J) in the formation of intermediates of certain central metabolic pathways that can be used for the formation of biomass. Exemplary MMPs for enhancing the availability of reducing equivalents, as well as the producing formaldehyde from methanol (step J), are provided in FIG. 3.

One exemplary pathway that can utilize formaldehyde produced from the oxidation of methanol (e.g., as provided in FIG. 3) is shown in FIG. 3B, which involves condensation of formaldehyde and D-ribulose-5-phosphate to form H6P by EF1 (FIG. 3B, step A). The enzyme can use $Mg^{2+}$ or $Mn^{2+}$ for maximal activity, although other metal ions are useful, and even non-metal-ion-dependent mechanisms are contemplated. H6P is converted into F6P by EF2 (FIG. 3B, step B).

Another exemplary pathway that involves the detoxification and assimilation of formaldehyde produced from the oxidation of methanol (e.g., as provided in FIG. 3) is shown in FIG. 3C and proceeds through DHA. EF3 is a special transketolase that first transfers a glycoaldehyde group from xylulose-5-phosphate to formaldehyde, resulting in the formation of DHA and G3P, which is an intermediate in glycolysis (FIG. 3C, step A). The DHA obtained from DHA synthase is then further phosphorylated to form DHA phosphate by a DHA kinase (FIG. 3C, step B). DHAP can be assimilated into glycolysis and several other pathways.

FIG. 3B, Steps A and B—Hexulose-6-phosphate synthase (EF1) (Step A) and 6-phospho-3-hexuloisomerase (EF2) (Step B)

Both of the EF1 and EF2 enzymes are found in several organisms, including methanotrops and methylotrophs where they have been purified (Kato et al., 2006, BioSci Biotechnol Biochem. 70(1):10-21. In addition, these enzymes have been reported in heterotrophs such as *Bacillus subtilis* also where they are reported to be involved in formaldehyde detoxification (Mitsui et al., 2003, AEM 69(10):6128-32, Yasueda et al., 1999. J Bac 181(23):7154-60. Genes for these two enzymes from the methylotrophic bacterium *Mycobacterium gastri* MB19 have been fused and *E. coli* strains harboring the hps-phi construct showed more efficient utilization of formaldehyde (Orita et al., 2007, Appl Microbiol Biotechnol. 76:439-445). In some organisms, these two enzymes naturally exist as a fused version that is bifunctional.

Exemplary candidate genes for H6P synthase are:

| Protein | GenBank ID | GI number | Organism |
|---|---|---|---|
| Hps | AAR39392.1 | 40074227 | *Bacillus methanolicus* MGA3 |
| Hps | EIJ81375.1 | 387589055 | *Bacillus methanolicus* PB1 |
| RmpA | BAA83096.1 | 5706381 | *Methylomonas aminofaciens* |
| RmpA | BAA90546.1 | 6899861 | *Mycobacterium gastri* |
| YckG | BAA08980.1 | 1805418 | *Bacillus subtilis* |

Exemplary gene candidates for EF2 are:

| Protein | GenBank ID | GI number | Organism |
|---|---|---|---|
| Phi | AAR39393.1 | 40074228 | *Bacillus methanolicus* MGA3 |
| Phi | EIJ81376.1 | 387589056 | *Bacillus methanolicus* PB1 |
| Phi | BAA83098.1 | 5706383 | *Methylomonas aminofaciens* |
| RmpB | BAA90545.1 | 6899860 | *Mycobacterium gastri* |

Candidates for enzymes where both of these functions have been fused into a single open reading frame include the following.

| Protein | GenBank ID | GI number | Organism |
|---|---|---|---|
| PH1938 | NP_143767.1 | 14591680 | *Pyrococcus horikoshii* OT3 |
| PF0220 | NP_577949.1 | 18976592 | *Pyrococcus furiosus* |
| TK0475 | YP_182888.1 | 57640410 | *Thermococcus kodakaraensis* |
|  | NP_127388.1 | 14521911 | *Pyrococcus abyssi* |
| MCA2738 | YP_115138.1 | 53803128 | *Methylococcus capsulatas* |

FIG. 3C, Step A—Dihydroxyacetone synthase (EF3)

Another exemplary pathway that involves the detoxification and assimilation of formaldehyde produced from the oxidation of methanol (e.g., as provided in FIG. 3) is shown in FIG. 3C and proceeds through DHA. EF3 is a special transketolase that first transfers a glycoaldehyde group from xylulose-5-phosphate to formaldehyde, resulting in the formation of DHA and G3P, which is an intermediate in glycolysis (FIG. 3C, step A). The DHA obtained from DHA synthase is then further phosphorylated to form DHA phosphate by a DHA kinase (FIG. 3C, step B). DHAP can be assimilated into glycolysis and several other pathways.

The EF3 enzyme in *Candida boidinii* uses thiamine pyrophosphate and $Mg^{2+}$ as cofactors and is localized in the peroxisome. The enzyme from the methanol-growing carboxydobacterium, *Mycobacter* sp. strain JC1 DSM 3803, was also found to have DHA synthase and kinase activities (Ro et al., 1997, JBac 179(19):6041-7). DHA synthase from this organism also has similar cofactor requirements as the enzyme from *C. boidinii*. The $K_m$s for formaldehyde and xylulose 5-phosphate were reported to be 1.86 mM and 33.3 microM, respectively. Several other mycobacteria, excluding only *Mycobacterium tuberculosis*, can use methanol as the sole source of carbon and energy and are reported to use EF3 (Part et al., 2003, JBac 185(1):142-7.

| Protein | GenBank ID | GI number | Organism |
|---|---|---|---|
| DAS1 | AAC83349.1 | 3978466 | *Candida boidinii* |
| HPODL_2613 | EFW95760.1 | 320581540 | *Ogataea parapolymorpha* DL-1 (*Hansenula polymorpha* DL-1) |
|  | AAG12171.2 | 18497328 | *Mycobacter* sp. strain JC1 DSM 3803 |

FIG. 3C, Step B—Dihydroxyacetone (DHA) Kinase

DHA obtained from DHA synthase is further phosphorylated to form DHA phosphate by a DHA kinase. DHAP can be assimilated into glycolysis and several other pathways. EF4 has been purified from *Ogataea angusta* to homogeneity (Bystrkh, 1983, Biokhimiia, 48(10):1611-6). The enzyme, which phosphorylates DHA and, to a lesser degree, glyceraldehyde, is a homodimeric protein of 139 kDa. ATP is the preferred phosphate group donor for the enzyme. When ITP, GTP, CTP and UTP are used, the activity drops to about 30%. In several organisms such as *Klebsiella pneumoniae* and *Citrobacter fruendii* (Daniel et al., 1995, JBac 177(15):4392-40), DHA is formed as a result of oxidation of glycerol and is converted into DHAP by the kinase DHA kinase of *K. pneumoniae* has been characterized (Jonathan et al, 1984, JBac 160(1):55-60). It is very specific for DHA, with a $K_m$ of 4 μM, and has two apparent $K_m$ values for ATP, one at 25 to 35 μM, and the other at 200 to 300 μM. DHA can also be phosphorylated by glycerol kinases but the DHA kinase from *K. puemoniae* is different from glycerol kinase in several respects. While both enzymes can phosphorylate DHA, DHA kinase does not phosphorylate glycerol, neither is it inhibited by fructose-1,6-diphosphate. In *Saccharomyces cerevisiae*, DHA kinases (I and II) are involved in rescuing the cells from toxic effects of DHA (Molin et al., 2003, J Biol Chem. 17; 278(3):1415-23).

In *Escherichia coli*, DHA kinase is composed of the three subunits DhaK, DhaL, and DhaM and it functions similarly to a phosphotransferase system (PTS) in that it utilizes phosphoenolpyruvate as a phosphoryl donor (Gutknecht et al., 2001, EMBO J. 20(10):2480-6). It differs in not being involved in transport. The phosphorylation reaction requires the presence of the EI and HPr proteins of the PTS system. The DhaM subunit is phosphorylated at multiple sites. DhaK contains the substrate binding site (Garcia-Alles et al., 2004, 43(41):13037-45; Siebold et al., 2003, PNAS. 100(14): 8188-92). The $K_M$ for DHA for the *E. coli* enzyme has been reported to be 6 μM. The K subunit is similar to the N-terminal half of ATP-dependent EF4 of *Citrobacter freundii* and eukaryotes.

Exemplary DHA kinase gene candidates for this step are:

| Protein | GenBank ID | GI number | Organism |
| --- | --- | --- | --- |
| DAK1 | P54838.1 | 1706391 | *Saccharomyces cerevisiae* S288c |
| DAK2 | P43550.1 | 1169289 | *Saccharomyces cerevisiae* S288c |
| D186_20916 | ZP_16280678.1 | 421847542 | *Citrobacter freundii* |
| DAK2 | ZP_18488498.1 | 425085405 | *Klebsiella pneumoniae* |
| DAK | AAC27705.1 | 3171001 | *Ogataea angusta* |
| DhaK | NP_415718.6 | 162135900 | *Escherichia coli* |
| DhaL | NP_415717.1 | 16129162 | *Escherichia coli* |
| DhaM | NP_415716.4 | 226524708 | *Escherichia coli* |

Suitable purification and/or assays to test, e.g., for the production of BDO can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art.

The BDO or other target molecules may separated from other components in the culture using a variety of methods well known in the art. Such separation methods include, for example, extraction procedures as well as methods that include continuous liquid-liquid extraction, pervaporation, evaporation, filtration, membrane filtration (including reverse osmosis, nanofiltration, ultrafiltration, and microfiltration), membrane filtration with diafiltration, membrane separation, reverse osmosis, electrodialysis, distillation, extractive distillation, reactive distillation, azeotropic distillation, crystallization and recrystallization, centrifugation, extractive filtration, ion exchange chromatography, size exclusion chromatography, adsorption chromatography, carbon adsorption, hydrogenation, and ultrafiltration. All of the above methods are well known in the art.

Examples of target molecule isolation processes include distillation for 13BDO, 14BDO, butadiene, methyl vinyl carbinol, 3-buten-1-ol, n-propanol, isopropanol, propylene, and crotyl alcohol; crystallization for 6ACA (alternatively it can be converted to caprolactam and then purified via distillation as a final step), HMDA, adipic acid or derivatives thereof, succinic acid or derivatives thereof, or any of crystallization, distillation, or extraction for methacrylic acid or derivatives thereof.

Target molecules such as 13BDO, 14BDO, butadiene, methyl vinyl carbinol n-propanol, isopropanol, propylene, crotyl alcohol; 3-buten-1-ol, 6ACA, HMDA, adipic acid or derviaties thereof, succinic acid or derivatives thereof, or methacrylic acid or derivatives thereof are chemicals used in commercial and industrial applications. In some embodiments, BDO and/or 4-HB are used in various commercial and industrial applications. Non-limiting examples of such applications include production of plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like. Moreover, BDO and/or 4-HB are also used as a raw material in the production of a wide range of products including plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like.

Accordingly, in some embodiments, provided are biobased plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like, comprising one or more bioderived BDO and/or 4-HB or bioderived BDO and/or 4-HB intermediate thereof produced by an organism provided herein or produced using a method disclosed herein.

As used herein, the term "bioderived" means derived from or synthesized by a biological organism and can be considered a renewable resource since it can be generated by a biological organism. Such a biological organism, in particular the microbial organisms disclosed herein, can utilize feedstock or biomass, such as, sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound of the disclosure. A biobased or bioderived product is in contrast to a petroleum derived product, wherein such a product is derived from or synthesized from petroleum or a petrochemical feedstock.

In some embodiments, the disclosure provides plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like, comprising bioderived BDO and/or 4-HB or bioderived BDO and/or 4-HB intermediate thereof, wherein the bioderived BDO and/or 4-HB or bioderived BDO and/or 4-HB intermediate thereof includes all or part of the BDO and/or 4-HB or BDO and/or 4-HB intermediate thereof used in the production of plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like. Thus, in some aspects, the disclosure provides a biobased plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like, comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived BDO and/or 4-HB or bioderived BDO and/or 4-HB intermediate thereof as disclosed herein. Additionally, in some aspects, the disclosure provides a biobased plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like, wherein the BDO and/or 4-HB or BDO and/or 4-HB intermediate thereof used in its production is a combination of bioderived and petroleum derived BDO and/or 4-HB or BDO and/or 4-HB intermediate thereof. For example, a biobased plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like, can be produced using 50% bioderived BDO and/or 4-HB and 50% petroleum derived BDO and/or 4-HB or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the microbial organisms disclosed herein. It is understood that methods for producing plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like, using the bioderived BDO and/or 4-HB or bioderived BDO and/or 4-HB intermediate thereof of the disclosure are well known in the art.

In one embodiment, the product is a plastic. In one embodiment, the product is an elastic fiber. In one embodiment, the product is a polyurethane. In one embodiment, the product is a polyester. In one embodiment, the product is a polyhydroxyalkanoate. In one embodiment, the product is a poly-4-HB. In one embodiment, the product is a co-polymer of poly-4-HB. In one embodiment, the product is a poly(tetramethylene ether) glycol. In one embodiment, the product is a polyurethane-polyurea copolymer. In one embodiment, the product is a spandex. In one embodiment, the product is an elastane. In one embodiment, the product is a Lycra™. In one embodiment, the product is a nylon.

In some embodiments, provided herein is a culture medium comprising bioderived BDO. In some embodiments, the bioderived BDO is produced by culturing an organism having a MDH protein and BDOP, as provided herein. In certain embodiments, the bioderived BDO has a carbon-12, carbon-13 and carbon-14 isotope ratio that reflects an atmospheric carbon dioxide uptake source. In one embodiment, the culture medium is separated from a organism having a MDH protein and BDOP.

In other embodiments, provided herein is a bioderived BDO. In some embodiments, the bioderived BDO is produced by culturing an organism having a MDH protein and BDOP, as provided herein. In some embodiments, the bioderived BDO has an Fm value of at least 80%, at least 85%, at least 90%, at least 95% or at least 98%. In certain embodiments, the bioderived BDO is a component of culture medium.

In certain embodiments, provided herein is a composition comprising a bioderived BDO provided herein, for example, a bioderived BDO produced by culturing an organism having a MDH protein and BDOP, as provided herein. In some embodiments, the composition further comprises a compound other than said bioderived BDO. In certain embodiments, the compound other than said bioderived BDO is a trace amount of a cellular portion of an organism having a MDH protein and a BDOP, as provided herein.

In some embodiments, provided herein is a biobased product comprising a bioderived BDO provided herein. In certain embodiments, the biobased product is a plastic, elastic fiber, polyurethane, polyester, polyhydroxyalkanoate, poly-4-HB, co-polymer of poly-4-HB, poly(tetramethylene ether) glycol, polyurethane-polyurea copolymer, spandex, elastane, Lycra™, or nylon. In certain embodiments, the biobased product comprises at least 5% bioderived BDO. In certain embodiments, the biobased product is (i) a polymer, THF or a THF derivative, or GBL or a GBL derivative; (ii) a plastic, elastic fiber, polyurethane, polyester, polyhydroxyalkanoate, poly-4-HB, co-polymer of poly-4-HB, poly(tetramethylene ether) glycol, polyurethane-polyurea copolymer, spandex, elastane, Lycra™, or nylon; (iii) a polymer, a resin, a fiber, a bead, a granule, a pellet, a chip, a plastic, a polyester, a thermoplastic polyester, a molded article, an injection-molded article, an injection-molded part, an automotive part, an extrusion resin, an electrical part and a casing; and optionally where the biobased product is reinforced or filled and further where the biobased product is glass-reinforced or -filled or mineral-reinforced or -filled; (iv) a polymer, wherein the polymer comprises polybutylene terephthalate (PBT); (v) a polymer, wherein the polymer comprises PBT and the biobased product is a resin, a fiber, a bead, a granule, a pellet, a chip, a plastic, a polyester, a thermoplastic polyester, a molded article, an injection-molded article, an injection-molded part, an automotive part, an extrusion resin, an electrical part and a casing; and optionally where the biobased product is reinforced or filled and further where the biobased product is glass-reinforced or -filled or mineral-reinforced or -filled; (vi) a THF or a THF derivative, wherein the THF derivative is polytetramethylene ether glycol (PTMEG), a polyester ether (COPE) or a thermoplastic polyurethane; (viii) a THF derivative, wherein the THF derivative comprises a fiber; or (ix) a GBL or a GBL derivative, wherein the GBL derivative is a pyrrolidone. In certain embodiments, the biobased product comprises at least 10% bioderived BDO. In some embodiments, the biobased product comprises at least 20% bioderived BDO. In other embodiments, the biobased product comprises at least 30% bioderived BDO. In some embodiments, the biobased product comprises at least 40% bioderived BDO. In other embodiments, the biobased product comprises at least 50% bioderived BDO. In one embodiment, the biobased product comprises a portion of said bioderived BDO as a repeating unit. In another embodiment, provided herein is a molded product obtained by molding the biobased product provided herein. In other embodiments, provided herein is a process for producing a biobased product provided herein, comprising chemically reacting said bioderived-BDO with itself or another compound in a reaction that produces said biobased product. In certain embodiments, provided herein is a polymer comprising or obtained by converting the bioderived BDO. In other embodiments, provided herein is a method for producing a polymer, comprising chemically or enzymatically converting the bioderived BDO to the polymer. In yet other embodiments, provided herein is a composition comprising the bioderived BDO, or a cell lysate or culture supernatant thereof.

In some embodiments, the carbon feedstock and other cellular uptake sources such as phosphate, ammonia, sulfate, chloride and other halogens can be chosen to alter the isotopic distribution of the atoms present in BDO and/or 4-HB or any BDO and/or 4-HB pathway intermediate. The various carbon feedstock and other uptake sources enumerated above will be referred to herein, collectively, as "uptake sources." Uptake sources can provide isotopic enrichment for any atom present in the product BDO and/or 4-HB or BDO and/or 4-HB pathway intermediate, or for side products generated in reactions diverging away from a BDO and/or 4-HB pathway. Isotopic enrichment can be achieved for any target atom including, for example, carbon, hydrogen, oxygen, nitrogen, sulfur, phosphorus, chloride or other halogens. The same holds true for the MMPs and FAPs, as well as intermediates thereof, provided herein.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target isotopic ratio of an uptake source can be obtained by selecting a desired origin of the uptake source as found in nature. For example, as discussed herein, a natural source can be a biobased derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as $CO_2$, which can possess a larger amount of carbon-14 than its petroleum-derived counterpart.

Isotopic enrichment is readily assessed by mass spectrometry using techniques known in the art such as Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC) and/or high performance liquid chromatography (HPLC).

The unstable carbon isotope carbon-14 or radiocarbon makes up for roughly 1 in $10^{12}$ carbon atoms in the earth's atmosphere and has a half-life of about 5700 years. The stock of carbon is replenished in the upper atmosphere by a nuclear reaction involving cosmic rays and ordinary nitrogen ($^{14}N$). Fossil fuels contain no carbon-14, as it decayed long ago. Burning of fossil fuels lowers the atmospheric carbon-14 fraction, the so-called "Suess effect".

Methods of determining the isotopic ratios of atoms in a compound are well known to those skilled in the art. Isotopic enrichment is readily assessed by mass spectrometry using techniques known in the art such as accelerated mass spectrometry (AMS), Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC), high performance liquid chromatography (HPLC) and/or gas chromatography, and the like.

In the case of carbon, ASTM D6866 was developed in the United States as a standardized analytical method for determining the biobased content of solid, liquid, and gaseous samples using radiocarbon dating by the American Society for Testing and Materials (ASTM) International. The standard is based on the use of radiocarbon dating for the determination of a product's biobased content. ASTM D6866 was first published in 2004, and the current active version of the standard is ASTM D6866-11 (effective Apr. 1, 2011). Radiocarbon dating techniques are well known to those skilled in the art, including those described herein.

The biobased content of a compound is estimated by the ratio of carbon-14 ($^{14}C$) to carbon-12 ($^{12}C$). Specifically, the Fraction Modern (Fm) is computed from the expression: Fm=(S−B)/(M−B), where B, S and M represent the $^{14}C/12C$ ratios of the blank, the sample and the modern reference, respectively. Fraction Modern is a measurement of the deviation of the $^{14}C/12C$ ratio of a sample from "Modern." Modern is defined as 95% of the radiocarbon concentration (in AD 1950) of National Bureau of Standards (NBS) Oxalic Acid I (i.e., standard reference materials (SRM) 4990b) normalized to $\delta^{13}C_{VPDB}$=−19 per mil (Olsson, The use of Oxalic acid as a Standard. in, Radiocarbon Variations and Absolute Chronology, Nobel Symposium, 12th Proc., John Wiley & Sons, New York (1970)). Mass spectrometry results, for example, measured by ASM, are calculated using the internationally agreed upon definition of 0.95 times the specific activity of NBS Oxalic Acid I (SRM 4990b) normalized to $\delta^{13}C_{VPDB}$=−19 per mil. This is equivalent to an absolute (AD 1950) $^{14}C/^{12}C$ ratio of $1.176\pm0.010\times10^{-12}$ (Karlen et al., Arkiv Geofisik, 4:465-471 (1968)). The standard calculations take into account the differential uptake of one isotope with respect to another, for example, the preferential uptake in biological systems of $C^{12}$ over $C^{13}$ over $C^{14}$, and these corrections are reflected as a Fm corrected for $\delta^{13}$.

An oxalic acid standard (SRM 4990b or HOx 1) was made from a crop of 1955 sugar beet. Although there were 1000 lbs made, this oxalic acid standard is no longer commercially available. The Oxalic Acid II standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is 1.2933±0.001 (the weighted mean). The isotopic ratio of HOx II is −17.8 per mile. ASTM D6866-11 suggests use of the available Oxalic Acid II standard SRM 4990 C (Hox2) for the modern standard (see discussion of original vs. currently available oxalic acid standards in Mann, Radiocarbon, 25(2):519-527 (1983)). A Fm=0% represents the entire lack of carbon-14 atoms in a material, thus indicating a fossil (for example, petroleum based) carbon source. A Fm=100%, after correction for the post-1950 injection of carbon-14 into the atmosphere from nuclear bomb testing, indicates an entirely modern carbon source. As described herein, such a "modern" source includes biobased sources.

As described in ASTM D6866, the percent modern carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new biobased products are produced in a post-bomb environment, all pMC values (after correction for isotopic fraction) must be multiplied by 0.95 (as of 2010) to better reflect the true biobased content of the sample. A biobased content that is greater than 103% suggests that either an analytical error has occurred, or that the source of biobased carbon is more than several years old.

ASTM D6866 quantifies the biobased content relative to the material's total organic content and does not consider the inorganic carbon and other non-carbon containing substances present. For example, a product that is 50% starch-based material and 50% water would be considered to have a Biobased Content=100% (50% organic content that is 100% biobased) based on ASTM D6866. In another example, a product that is 50% starch-based material, 25% petroleum-based, and 25% water would have a Biobased Content=66.7% (75% organic content but only 50% of the product is biobased). In another example, a product that is 50% organic carbon and is a petroleum-based product would be considered to have a Biobased Content=0% (50% organic carbon but from fossil sources). Thus, based on the well known methods and known standards for determining the biobased content of a compound or material, one skilled in the art can readily determine the biobased content and/or prepared downstream products having a desired biobased content.

Applications of carbon-14 dating techniques to quantify bio-based content of materials are known in the art (Currie et al., *Nuclear Instruments and Methods in Physics Research B*, 172:281-287 (2000)). For example, carbon-14 dating has been used to quantify bio-based content in terephthalate-containing materials (Colonna et al., *Green Chemistry*, 13:2543-2548 (2011)). Notably, polypropylene terephthalate (PPT) polymers derived from renewable 1,3-propanediol and petroleum-derived terephthalic acid resulted in Fm values near 30% (i.e., since 3/11 of the polymeric carbon derives from renewable 1,3-propanediol and 8/11 from the fossil end member terephthalic acid) (Currie et al., supra, 2000). In contrast, polybutylene terephthalate polymer derived from both renewable BDO and renewable terephthalic acid resulted in bio-based content exceeding 90% (Colonna et al., supra, 2011).

Accordingly, in some embodiments, provided are BDO and/or 4-HB or a BDO and/or 4-HB pathway intermediate thereof that has a carbon-12, carbon-13, and carbon-14 ratio that reflects an atmospheric carbon, also referred to as environmental carbon, uptake source. For example, in some aspects the BDO and/or 4-HB or a BDO and/or 4-HB intermediate thereof can have an Fm value of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or as much as 100%. In some such embodiments, the uptake source is $CO_2$. In some embodiments, provided is BDO and/or 4-HB or a BDO and/or 4-HB intermediate thereof that has a carbon-12, carbon-13, and carbon-14 ratio that reflects petroleum-based carbon uptake source. In this aspect, the BDO and/or 4-HB or a BDO and/or 4-HB intermediate thereof can have an Fm value of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2% or less than 1%. In some embodiments, provided is BDO and/or 4-HB or a BDO and/or 4-HB intermediate thereof that has a carbon-12, carbon-13, and carbon-14 ratio that is obtained by a combination of an atmospheric carbon uptake source with a petroleum-based uptake source. Using such a combination of uptake sources is one way by which the carbon-12, carbon-13, and carbon-14 ratio can be varied, and the respective ratios would reflect the proportions of the uptake sources.

Further, the disclosure relates, in part, to biologically produced BDO and/or 4-HB or BDO and/or 4-HB intermediate thereof as disclosed herein, and to the products derived therefrom, wherein the BDO and/or 4-HB or a BDO and/or 4-HB intermediate thereof has a carbon-12, carbon-13, and carbon-14 isotope ratio of about the same value as the $CO_2$ that occurs in the environment. For example, in some aspects, provided are a bioderived BDO and/or 4-HB or a bioderived BDO and/or 4-HB intermediate thereof having a carbon-12 versus carbon-13 versus carbon-14 isotope ratio of about the same value as the $CO_2$ that occurs in the environment, or any of the other ratios disclosed herein. It is understood, as disclosed herein, that a product can have a carbon-12 versus carbon-13 versus carbon-14 isotope ratio of about the same value as the $CO_2$ that occurs in the environment, or any of the ratios disclosed herein, wherein the product is generated from bioderived BDO and/or 4-HB or a bioderived BDO and/or 4-HB intermediate thereof as disclosed herein, wherein the bioderived product is chemically modified to generate a final product. Methods of chemically modifying a bioderived product of BDO and/or 4-HB, or an intermediate thereof, to generate a desired product are well known to those skilled in the art, as described herein. Also provided are plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide) and polyurethane-polyurea copolymers, referred to as spandex, elastane or Lycra™, nylons, and the like, having a carbon-12 versus carbon-13 versus carbon-14 isotope ratio of about the same value as the $CO_2$ that occurs in the environment, wherein the plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like, are generated directly from or in combination with bioderived BDO and/or 4-HB or a bioderived BDO and/or 4-HB intermediate thereof as disclosed herein.

Those skilled in the art will understand that an organism can be engineered that secretes the biosynthesized compounds when grown on a carbon source such as a methanol alone or combined with other carbohydrates. Such compounds include, for example, BDO and any of the intermediate metabolites in the BDOP. All that is required is to engineer in one or more of the required enzyme or protein activities to achieve biosynthesis of the desired compound or intermediate including, for example, inclusion of some or all of the BDO biosynthetic pathways. Accordingly, provided herein is an organism that produces and/or secretes BDO when grown on a carbohydrate or other carbon source and produces and/or secretes any of the intermediate metabolites shown in the BDOP when grown on a carbohydrate or other carbon source. The BDO producing microbial organisms provided herein can initiate synthesis from an intermediate. The same holds true for intermediates in the formaldehyde assimilation.

In one embodiment, the carbon source is methanol or formate. In certain embodiments, methanol is used as a carbon source. In one embodiment, the carbon source is methanol or formate. In other embodiments, formate is used as a carbon source. In specific embodiments, methanol is used as a carbon source in the organisms provided herein, either alone or in combination with the product pathways provided herein.

In one embodiment, the carbon source comprises methanol, and sugar (e.g., glucose) or a sugar-containing biomass. In another embodiment, the carbon source comprises formate, and sugar (e.g., glucose) or a sugar-containing biomass. In one embodiment, the carbon source comprises methanol, formate, and sugar (e.g., glucose) or a sugar-containing biomass. In specific embodiments, the methanol or formate, or both, in the fermentation feed is provided as a mixture with sugar (e.g., glucose) or sugar-comprising biomass. In certain embodiments, sugar is provided for sufficient strain growth.

In some embodiments, the sugar (e.g., glucose) is provided at a molar concentration ratio of methanol to sugar of from 200:1 to 1:200. In some embodiments, the sugar (e.g., glucose) is provided at a molar concentration ratio of methanol to sugar of from 100:1 to 1:100. In some embodiments, the sugar (e.g., glucose) is provided at a molar concentration ratio of methanol to sugar of from 100:1 to 5:1. In some embodiments, the sugar (e.g., glucose) is provided at a molar concentration ratio of methanol to sugar of from 50:1 to 5:1. In certain embodiments, the sugar (e.g., glucose) is provided at a molar concentration ratio of methanol to sugar of 100:1. In one embodiment, the sugar (e.g., glucose) is provided at a molar concentration ratio of methanol to sugar of 90:1. In one embodiment, the sugar (e.g., glucose) is provided at a molar concentration ratio of methanol to sugar of 80:1. In one embodiment, the sugar (e.g., glucose) is provided at a molar concentration ratio of methanol to sugar of 70:1. In one embodiment, the sugar (e.g., glucose) is provided at a molar concentration ratio of methanol to sugar of 60:1. In one embodiment, the sugar (e.g., glucose) is provided at a molar concentration ratio of methanol to sugar of 50:1. In one embodiment, the sugar (e.g., glucose) is provided at a molar concentration ratio of methanol to sugar of 40:1. In one embodiment, the sugar (e.g., glucose) is provided at a molar concentration ratio of methanol to sugar of 30:1. In one embodiment, the sugar (e.g., glucose) is provided at a molar concentration ratio of methanol to sugar of 20:1. In one embodiment, the sugar (e.g., glucose) is provided at a molar concentration ratio of methanol to sugar of 10:1. In one embodiment, the sugar (e.g., glucose) is provided at a molar concentration ratio of methanol to sugar of 5:1. In one embodiment, the sugar (e.g., glucose) is provided at a molar concentration ratio of methanol to sugar of 2:1. In one embodiment, the sugar (e.g., glucose) is provided at a molar concentration ratio of methanol to sugar of 1:1. In certain embodiments, the sugar (e.g., glucose) is provided at a molar concentration ratio of methanol to sugar of 1:100. In one embodiment, the sugar (e.g., glucose) is provided at a molar concentration ratio of methanol to sugar of 1:90. In one embodiment, the sugar (e.g., glucose) is provided at a molar concentration ratio of methanol to sugar of 1:80. In one embodiment, the sugar (e.g., glucose) is provided at a molar concentration ratio of methanol to sugar of 1:70. In one embodiment, the sugar (e.g., glucose) is provided at a molar concentration ratio of methanol to sugar of 1:60. In one embodiment, the sugar (e.g., glucose) is provided at a molar concentration ratio of methanol to sugar of 1:50. In one embodiment, the sugar (e.g., glucose) is provided at a molar concentration ratio of methanol to sugar of 1:40. In one embodiment, the sugar (e.g., glucose) is provided at a molar concentration ratio of methanol to sugar of 1:30. In one embodiment, the sugar (e.g., glucose) is provided at a molar concentration ratio of methanol to sugar of 1:20. In one embodiment, the sugar (e.g., glucose) is provided at a molar concentration ratio of methanol to sugar of 1:10. In one embodiment, the sugar (e.g., glucose) is provided at a molar concentration ratio of methanol to sugar of 1:5. In one embodiment, the sugar (e.g., glucose) is provided at a molar concentration ratio of methanol to sugar of 1:2. In certain embodiments of the ratios provided above, the sugar is a sugar-containing biomass.

In certain embodiments, the carbon source comprises formate and a sugar (e.g., glucose). In some embodiments, the sugar (e.g., glucose) is provided at a molar concentration ratio of formate to sugar of from 200:1 to 1:200. In some embodiments, the sugar (e.g., glucose) is provided at a molar concentration ratio of formate to sugar of from 100:1 to 1:100. In some embodiments, the sugar (e.g., glucose) is provided at a molar concentration ratio of formate to sugar of from 100:1 to 5:1. In some embodiments, the sugar (e.g., glucose) is provided at a molar concentration ratio of formate to sugar of from 50:1 to 5:1. In certain embodiments, the sugar (e.g., glucose) is provided at a molar concentration ratio of formate to sugar of 100:1. In one embodiment, the sugar (e.g., glucose) is provided at a molar concentration ratio of formate to sugar of 90:1. In one embodiment, the sugar (e.g., glucose) is provided at a molar concentration ratio of formate to sugar of 80:1. In one embodiment, the sugar (e.g., glucose) is provided at a molar concentration ratio of formate to sugar of 70:1. In one embodiment, the sugar (e.g., glucose) is provided at a molar concentration ratio of formate to sugar of 60:1. In one embodiment, the sugar (e.g., glucose) is provided at a molar concentration ratio of formate to sugar of 50:1. In one embodiment, the sugar (e.g., glucose) is provided at a molar concentration ratio of formate to sugar of 40:1. In one embodiment, the sugar (e.g., glucose) is provided at a molar concentration ratio of formate to sugar of 30:1. In one embodiment, the sugar (e.g., glucose) is provided at a molar concentration ratio of formate to sugar of 20:1. In one embodiment, the sugar (e.g., glucose) is provided at a molar concentration ratio of formate to sugar of 10:1. In one embodiment, the sugar (e.g., glucose) is provided at a molar concentration ratio of formate to sugar of 5:1. In one embodiment, the sugar (e.g., glucose) is provided at a molar concentration ratio of formate to sugar of 2:1. In one embodiment, the sugar (e.g., glucose) is provided at a molar concentration ratio of formate to sugar of 1:1. In certain embodiments, the sugar (e.g., glucose) is provided at a molar concentration ratio of formate to sugar of 1:100. In one embodiment, the sugar (e.g., glucose) is provided at a molar concentration ratio of formate to sugar of 1:90. In one embodiment, the sugar (e.g., glucose) is provided at a molar concentration ratio of formate to sugar of 1:80. In one embodiment, the sugar (e.g., glucose) is provided at a molar concentration ratio of formate to sugar of 1:70. In one embodiment, the sugar (e.g., glucose) is provided at a molar concentration ratio of formate to sugar of 1:60. In one embodiment, the sugar (e.g., glucose) is provided at a molar concentration ratio of formate to sugar of 1:50. In one embodiment, the sugar (e.g., glucose) is provided at a molar concentration ratio of formate to sugar of 1:40. In one embodiment, the sugar (e.g., glucose) is provided at a molar concentration ratio of formate to sugar of 1:30. In one embodiment, the sugar (e.g., glucose) is provided at a molar concentration ratio of formate to sugar of 1:20. In one embodiment, the sugar (e.g., glucose) is provided at a molar concentration ratio of formate to sugar of 1:10. In one embodiment, the sugar (e.g., glucose) is provided at a molar concentration ratio of formate to sugar of 1:5. In one embodiment, the sugar (e.g., glucose) is provided at a molar concentration ratio of formate to sugar of 1:2. In certain embodiments of the ratios provided above, the sugar is a sugar-containing biomass.

In certain embodiments, the carbon source comprises a mixture of methanol and formate, and a sugar (e.g., glucose). In certain embodiments, sugar is provided for sufficient strain growth. In some embodiments, the sugar (e.g., glucose) is provided at a molar concentration ratio of methanol and formate to sugar of from 200:1 to 1:200. In some embodiments, the sugar (e.g., glucose) is provided at a molar concentration ratio of methanol and formate to sugar of from 100:1 to 1:100. In some embodiments, the sugar (e.g., glucose) is provided at a molar concentration ratio of methanol and formate to sugar of from 100:1 to 5:1. In some embodiments, the sugar (e.g., glucose) is provided at a molar concentration ratio of methanol and formate to sugar of from 50:1 to 5:1. In certain embodiments, the sugar (e.g., glucose) is provided at a molar concentration ratio of methanol and formate to sugar of 100:1. In one embodiment, the sugar (e.g., glucose) is provided at a molar concentration ratio of methanol and formate to sugar of 90:1. In one embodiment, the sugar (e.g., glucose) is provided at a molar concentration ratio of methanol and formate to sugar of 80:1. In one embodiment, the sugar (e.g., glucose) is provided at a molar concentration ratio of methanol and formate to sugar of 70:1. In one embodiment, the sugar (e.g., glucose) is provided at a molar concentration ratio of methanol and formate to sugar of 60:1. In one embodiment, the sugar (e.g., glucose) is provided at a molar concentration ratio of methanol and formate to sugar of 50:1. In one embodiment, the sugar (e.g., glucose) is provided at a molar concentration ratio of methanol and formate to sugar of 40:1. In one embodiment, the sugar (e.g., glucose) is provided at a molar concentration ratio of methanol and formate to sugar of 30:1. In one embodiment, the sugar (e.g., glucose) is provided at a molar concentration ratio of methanol and formate to sugar of 20:1. In one embodiment, the sugar (e.g., glucose) is provided at a molar concentration ratio of methanol and formate to sugar of 10:1. In one embodiment, the sugar (e.g., glucose) is provided at a molar concentration ratio of methanol and formate to sugar of 5:1. In one embodiment, the sugar (e.g., glucose) is provided at a molar concentration ratio of methanol and formate to sugar of 2:1. In one embodiment, the sugar (e.g., glucose) is provided at a molar concentration ratio of methanol and formate to sugar of 1:1. In certain embodiments, the sugar (e.g., glucose) is provided at a molar concentration ratio of methanol and formate to sugar of 1:100. In one embodiment, the sugar (e.g., glucose) is provided at a molar concentration ratio of methanol and formate to sugar of 1:90. In one embodiment, the sugar (e.g., glucose) is provided at a molar concentration ratio of methanol and formate to sugar of 1:80. In one embodiment, the sugar (e.g., glucose) is provided at a molar concentration ratio of methanol and formate to sugar of 1:70. In one embodiment, the sugar (e.g., glucose) is provided at a molar concentration ratio of methanol and formate to sugar of 1:60. In one embodiment, the sugar (e.g., glucose) is provided at a molar concentration ratio of methanol and formate to sugar of 1:50. In one embodiment, the sugar (e.g., glucose) is provided at a molar concentration ratio of methanol and formate to sugar of 1:40. In one embodiment, the sugar (e.g., glucose) is provided at a molar concentration ratio of methanol and formate to sugar of 1:30. In one embodiment, the sugar (e.g., glucose) is provided at a molar concentration ratio of methanol and formate to sugar of 1:20. In one embodiment, the sugar (e.g., glucose) is provided at a molar concentration ratio of methanol and formate to sugar of 1:10. In one embodiment, the sugar (e.g., glucose) is provided at a molar concentration ratio of methanol and formate to sugar of 1:5. In one embodiment, the sugar (e.g., glucose) is provided at a molar concentration ratio of methanol and formate to sugar of 1:2. In certain embodiments of the ratios provided above, the sugar is a sugar-containing biomass.

1. An engineered cell either (a) expressing a non-natural $NAD^+$-dependent alcohol dehydrogenase comprising at least one amino acid substitution as compared to a corresponding alcohol dehydrogenase and capable of at least two fold greater conversion of methanol or ethanol to formaldehyde or acetaldehyde, respectively, as compared to an engineered cell expressing the corresponding alcohol dehydrogenase without amino acid substitution or (b) expressing a first sequence that is a non-natural $NAD^+$-dependent alcohol dehydrogenase comprising at least one amino acid substitution capable of at least two fold greater conversion of methanol or ethanol to formaldehyde or acetaldehyde, respectively, as compared to an engineered cell expressing a second sequence that is a non-natural $NAD^+$-dependent alcohol dehydrogenase, wherein the first and second sequences differ with regards to the at least one amino acid substitution.

2. The engineered cell of embodiment 1 further comprising one or more metabolic pathway transgene(s) encoding a protein of a metabolic pathway that promotes production of a target product or intermediate thereof.

3. The engineered cell of embodiments 1 or 2, wherein expression of the non-natural alcohol dehydrogenase provides an increased amount of reducing equivalents for an increase in a target product and/or for increased fixation of carbon from the formaldehyde into a target product.

4. The engineered cell of embodiment any of the previous embodiments further comprising a transgene encoding an enzyme to convert the formaldehyde to formate thereby generating reducing equivalents useful to product the target product and/or able to fix carbon of formate into the target product.

5. The engineered cell of any of the previous embodiments wherein the target product is selected from the group consisting of a diol, 1,4-butadiol, 1,3-butadiol, butadiene, succinate, adipate, HMDA, 6-aminocaproic acid (6ACA), or an intermediate compound thereof.

6. The engineered cell of any of the previous embodiments further comprising one or more alcohol metabolic pathway gene(s) encoding a protein selected from the group consisting of a), a formate dehydrogenase (EM8), a formaldehyde activating enzyme (EM10), a formaldehyde dehydrogenase (EM11), a S-(hydroxymethyl)glutathione synthase (EM12), a glutathione-dependent formaldehyde dehydrogenase (EM13), a S-formylglutathione hydrolase (EM14), a formate hydrogen lyase (EM15), and a hydrogenase (EM16).

7. The engineered cell of any of the previous embodiments further comprising one or more alcohol metabolic pathway gene(s) encoding a protein selected from the group consisting of a succinyl-CoA reductase (aldehyde forming) (EB3), a 4-hydroxybutyrate (4-HB) dehydrogenase (EB4), a 4-HB kinase (EB5), a phosphotrans-4-hydroxybutyrylase (EB6), a 4-hydroxybutyryl-CoA reductase (aldehyde forming) (EB7), a 1,4-butanediol dehydrogenase (EB8); a succinate reductase (EB9), a succinyl-CoA reductase (alcohol forming) (EB10), 4-hydroxybutyryl-CoA transferase (EB11), a 4-hydroxybutyryl-CoA synthetase (EB12), a 4-HB reductase (EB13), and a 4-hydroxybutyryl-CoA reductase (alcohol forming) (EB15), a succinyl-CoA transferase (EB1), and a succinyl-CoA synthetase (EB2A).

8. A composition comprising the cell of any of the previous embodiments, or a cell extract thereof.

9. The composition of embodiment 8 wherein the composition is a cell culture composition, optionally comprising a target product or intermediate thereof.

10. A cell culture composition comprising a target product or intermediate thereof produced by the cell of any of the previous embodiments.

11. A composition comprising a target product or intermediate thereof produced by the cell of any of the previous embodiments, optionally comprising cell debris and/or residual culture medium.

12. The composition of embodiment 11 comprising target product or intermediate thereof. which is at least 50%, 60%, 70%, 80%, 90%, 95%, 96, 97, 98, 99 or 99.9% pure in the composition.

13. The composition of embodiment 11 or 12 comprising a detectable trace amount of a nucleic acid encoding the non-natural NAD$^+$-dependent alcohol dehydrogenase, or a detectable trace amount of a metabolic pathway intermediate or product not produced in the corresponding original cell absent expression of the non-natural NAD+-dependent alcohol dehydrogenase.

14. The composition of embodiment 11 wherein the metabolic pathway intermediate or product is 4-hydroxybutyrate (4-HB) and 1,3 propanediol (1,3-PDO).

15. The composition of embodiment 14 comprising an amount of 1,4-butanediol or 1,3-butanediol in the range of 70-90% (vol/vol) and an amount of water in the range of 10-30% (vol/vol).

16. A method for increasing the conversion of methanol or ethanol to formaldehyde or acetaldehyde, respectively, comprising a step of (a) culturing an engineered cell expressing a NAD$^+$-dependent non-natural alcohol dehydrogenase comprising at least one amino acid substitution as compared to a corresponding alcohol dehydrogenase in a culture medium comprising methanol or ethanol, where in said culturing the cell provides at least two fold greater conversion of the methanol or ethanol to formaldehyde or acetaldehyde respectively, as compared to an engineered cell expressing the corresponding alcohol dehydrogenase without amino acid substitution.

17. A method for increasing the conversion of methanol or ethanol to formaldehyde or acetaldehyde, respectively, comprising a step of (a) providing a reaction composition having a pH in the range of 6-8, the composition comprising a NAD$^+$-dependent non-natural alcohol dehydrogenase comprising at least one amino acid substitution as compared to a corresponding alcohol dehydrogenase and methanol or ethanol, where in the composition said NAD$^+$-dependent non-natural alcohol dehydrogenase provides at least two fold greater conversion of methanol or ethanol to a formaldehyde or acetaldehyde respectively, as compared to the corresponding alcohol dehydrogenase without amino acid substitution.

18. A nucleic acid encoding a NAD$^+$-dependent non-natural alcohol dehydrogenase comprising at least one amino acid substitution as compared to a corresponding alcohol dehydrogenase capable, when expressed in a cell, of at least two fold greater conversion of methanol or ethanol to formaldehyde or acetaldehyde respectively, as compared to the corresponding alcohol dehydrogenase without amino acid substitution.

19. An expression construct comprising the nucleic acid of embodiment 18.

20. A NAD$^+$-dependent non-natural alcohol dehydrogenase comprising at least one amino acid substitution as compared to a corresponding alcohol dehydrogenase capable, when expressed in a cell, of at least two fold greater conversion of a methanol or ethanol to formaldehyde or acetaldehyde respectively, as compared to the corresponding alcohol dehydrogenase without amino acid substitution.

21. The subject matter of any of the previous embodiments wherein the methanol is converted to formaldehyde.

22. The subject matter of any of the previous embodiments wherein the non-natural alcohol dehydrogenase is capable of at least three fold greater, of at least four fold, of at least five fold, of at least six fold, of at least seven fold, at least 8 fold, at least 9 fold, at least 10 fold, or at least 11 fold, conversion of methanol or ethanol to a formaldehyde or acetaldehyde, respectively, in vivo, as compared to the corresponding alcohol dehydrogenase without amino acid substitution.

23. The subject matter of any of the previous embodiments wherein the non-natural alcohol dehydrogenase is capable of at least three fold greater, of at least four fold, of at least five fold, of at least six fold, of at least seven fold, at least 8 fold, at least 9 fold, at least 10 fold, or at least 11 fold, conversion of methanol or ethanol to a formaldehyde or acetaldehyde, respectively, in vitro, as compared to the corresponding alcohol dehydrogenase without amino acid substitution.

24. The subject matter of any of the previous embodiments wherein the non-natural alcohol dehydrogenase is capable of an increase in conversion of methanol or ethanol to a formaldehyde or acetaldehyde respectively, as compared to the corresponding alcohol dehydrogenase without amino acid substitution, in the range of two fold to twelve fold greater, in the range of two fold to eleven fold greater, in the range of two fold to ten fold greater, in the range of two fold to nine fold greater, in the range of two fold to eight fold greater, in the range of two fold to seven fold greater, in the range of two fold to six fold greater, in the range of two fold to five fold greater, or in the range of two fold to four fold greater.

25. A NAD$^+$-dependent non-natural alcohol dehydrogenase comprising at least one amino acid substitution as compared to a corresponding alcohol dehydrogenase having a catalytic efficiency ($k_{cat}/K_m$) for the conversion of methanol to formaldehyde of $8.6 \times 10^4$ or greater.

26. The subject matter of any of the previous embodiments comprising an activator protein that is an Act Nudix hydrolase.

27. A method of producing a target product or its intermediate comprising culturing the engineered cell of embodiment any of embodiments 1-7 in a culture medium comprising methanol or ethanol to produce the the target product (TP) or its intermediate (INT).

28. The method of embodiment 27 further comprising a step of isolating or purifying target product (TP) or its intermediate (INT).

29. The method of embodiment 28 wherein the step of isolating or purifying comprises one or more of continuous liquid-liquid extraction, pervaporation, evaporation, filtration, membrane filtration (including reverse osmosis, nanofiltration, ultrafiltration, and microfiltration), membrane filtration with diafiltration, membrane separation, reverse osmosis, electrodialysis, distillation, extractive distillation, reactive distillation, azeotropic distillation, crystallization and recrystallization, centrifugation, extractive filtration, ion exchange chromatography, size exclusion chromatography, adsorption chromatography, carbon adsorption, hydrogenation, and ultrafiltration.

30. The method of embodiment 29 selected from the group consisting of: (a) target product: 1,4-butanediol, purification: distillation; (b) target product: 1,3-butanediol, purification: distillation; (c) target product: Butadiene, purification: distillation; (d) target product: 6-AminoCaproic Acid, purification: crystallization, (a) target product: caprolactam, purification: distillation as a final step; (e) target product: hexamethylenediame (HMDA), purification: crystallization; (f) target product: Adipic acid, purification: crystallization (adipic acid crystals); (g) target product: Crotyl alcohol, purification: distillation (h) target product: methyl vinyl carbinol, purification: distillation; (i) target product: succinic acid—crystallization (succinic acid crystals); (j) target product: n-propanol, purification: distillation; (k) target product: isopropanol, purification: distillation; (1) target product: propylene, purification: distillation; (m) target product: methacrylic acid, purification: crystallization, distillation, or extraction (n) target product: methylmethacrylate (MMA) or another ester, purification: distillation or crystallization.

31. The method of any of embodiments 31 wherein the step of isolating or purifying further comprises distillation.

32. The method of embodiments 28-31 wherein the target product is a diol.

33. The method of embodiments 28-32 wherein the target product is a diol is 1,4-butanediol or 1,3-butanediol.

34. The method of embodiments 28-32 comprising purifying the target product to at least 50%, 60%, 70%, 80%, 90%, 95%, 96, 97, 98, 99 or 99.9% purity in a composition.

35. A method of preparing a polymer comprising obtaining a target product produced by the engineered cell of any of embodiments 1-7 or method of any of the embodiments 27-34 and polymerizing the target product, optionally with one or more other monomeric compounds, to provide a polymeric product.

36. The method of embodiment 35 further comprising a step of isolating or purifying the polymeric product.

37. The method of embodiments 35 or 36 comprising purifying the polymer product to at least 50%, 60%, 70%, 80%, 90%, 95%, 96, 97, 98, 99 or 99.9% purity in a composition.

38. A polymer prepared according to the method of any of embodiments 35-37.

39. The polymer of embodiment 38 which is a homopolymer or copolymer.

40. The polymer of embodiment 39 that is selected from the group consisting of polybutylene terephthalate (PBT) and polybutylene succinate (PBS).

41. A composition comprising a polymer blend comprising the polymer of any ones of embodiments 38-40.

42. An article comprising the polymer or composition any one of embodiments 38-41.

43. The article of embodiment 42 which is a plastic article.

44. The article of embodiment 17d or 17e which is molded, extruded, or shaped from the polymer or composition any one of embodiments 41-43.

45. A biobased product comprising target product produced by the engineered cell of any of embodiments 1-7 or the polymer of any ones of embodiments 38-40 wherein said biobased product is
(i) a polymer, THF or a THF derivative, or GBL or a GBL derivative;
(ii) a plastic, elastic fiber, polyurethane, polyester, polyhydroxyalkanoate, poly-4-HB, co-polymer of poly-4-HB, poly(tetramethylene ether) glycol, polyurethanepolyurea copolymer, spandex, elastane, Lycra™, or nylon;
(iii) a polymer, a resin, a fiber, a bead, a granule, a pellet, a chip, a plastic, a polyester, a thermoplastic polyester, a molded article, an injection-molded article, an injection-molded part, an automotive part, an extrusion resin, an electrical part and a casing; and optionally where the biobased product is reinforced or filled and further where the biobased product is glass-reinforced or -filled or mineral-reinforced or -filled;
(iv) a polymer, wherein the polymer comprises polybutylene terephthalate (PBT);
(v) a polymer, wherein the polymer comprises PBT and the biobased product is a resin, a fiber, a bead, a granule, a pellet, a chip, a plastic, a polyester, a thermoplastic polyester, a molded article, an injection-molded article, an injection-molded part, an automotive part, an extrusion resin, an electrical part and a casing; and optionally where the biobased product is reinforced or filled and further where the biobased product is glass-reinforced or -filled or mineral-reinforced or -filled;
(vi) a THF or a THF derivative, wherein the THF derivative is polytetramethylene ether glycol (PTMEG), a polyester ether (COPE) or a thermoplastic polyurethane;
(viii) a THF derivative, wherein the THF derivative comprises a fiber; or (ix) a GBL or a GBL derivative, wherein the GBL derivative is a pyrrolidone;
wherein said biobased product optionally comprises at least 5%, at least 10%, at least 20%, at least 30%, at least 40% or at least 50% bioderived BDO; and/or wherein said biobased product optionally comprises a portion of said bioderived BDO as a repeating unit.

46. A molded product obtained by molding the biobased product of embodiment 10.

47. A process for producing the biobased product of embodiment 45, comprising chemically reacting said bioderived BDO with itself or another compound in a reaction that produces said biobased product.

48. A polymer comprising or obtained by converting the bioderived BDO of embodiment 45.

49. A method for producing a polymer, comprising chemically of enzymatically converting the bioderived BDO of embodiment 45 to the polymer.

50. A composition comprising the bioderived BDO of embodiment 45, or a cell lysate or culture supernatant thereof.

51. A method of producing an intermediate of glycolysis and/or an intermediate of a metabolic pathway that can be used in the formation of biomass, comprising culturing the engineered cell of any one of embodiments 1-7 under conditions and for a sufficient period of time to produce the intermediate, and optionally wherein the intermediate is consumed to provide a reducing equivalent or to incorporate into BDO or target product.

52. The method of embodiment 51, wherein the organism is cultured in a medium comprising biomass, glucose, xylose, arabinose, galactose, mannose, fructose, sucrose, starch, glycerol, methanol, carbon dioxide, formate, methane, or any combination thereof as a carbon source.

53. The subject matter of any of the previous embodiments wherein the non-natural alcohol dehydrogenase has sequence identity of 45% or greater, 55% or greater, 65% or greater, 75% or greater, 85% or greater, 90% or greater, 92.5% or greater, 95% or greater, 96% or greater, 97% or greater, 98% or greater, or 99% or greater to an NAD$^+$-dependent alcohol dehydrogenase template selected from the group consisting of SEQ ID NO:1 (MDH MGA3_17392), n177596.1, AAA22593.1, n177618.1, EIJ78790.1, EIJ80770.1, n178397.1, n183020.1, EFI69743.1, YP_004860127.1, YP_001699778.1, ZP_11313277.1, ZP_05587334.1, YP_004681552.1, AGF87161, YP_002138168.1, YP_359772.1, YP_001343716.1, ZP_16224338.1, AAC45651.1, YP_007491369.1, YP_002434746, YP_005052855, NP 561852.1, YP_001447544, YP_001113612.1, YP_011618, ZP_01220157.1, YP_003990729.1, ZP_07335453.1, NP_717107, YP_003310546.1, ZP_10241531.1, YP_001337153.1, YP_026233.1, YP_694908, YP_725376.1, YP_001663549, EKC54576, YP_001126968.1 or a fragment of said template having said dehydrogenase activity with an amino-terminal deletion, carboxy-terminal deletion, or both, the fragment having a sequence identity of 45% or greater, 55% or greater, 65% or greater, 75% or greater, 85% or greater, 90% or greater, 92.5% or greater, 95% or greater, 96% or greater, 97% or greater, 98% or greater, or 99% or greater to the template.

54. The subject matter of any of the previous embodiments said template is selected from the group consisting of EIJ77596.1, E1178397.1, EFI69743.1, YP_001699778.1, YP_002138168.1, YP_359772.1, YP_005052855, NP_561852.1, YP_001447544, ZP_01220157.1, YP_003990729.1, ZP_10241531.1, and YP_026233.1.

55. The subject matter of any of the previous embodiments wherein the alcohol dehydrogenase is a methanol dehydrogenase.

56. The subject matter of embodiment 55 wherein the methanol dehydrogenase is from bacteria.

57. The subject matter of embodiment 56 wherein the methanol dehydrogenase is from *Bacillus*.

58. The subject matter of embodiment 57 wherein the methanol dehydrogenase is from *Bacillus methanolicus* MGA3 or *Bacillus methanolicus* PB1.

59. The subject matter of any of the previous embodiments wherein the non-natural alcohol dehydrogenase has a sequence identity of 45% or greater, 55% or greater, 65% or greater, 75% or greater, 85% or greater, 90% or greater, 92.5% or greater, 95% or greater, 96% or greater, 97% or greater, 98% or greater, or 99% or greater to any one of the templates of embodiment 53, and wherein the dehydrogenase comprises one or more amino acid substitutions based on formula: $R^1XR^2$, where $R^1$ is an original amino acid at position X of the template, and $R^2$ is the variant amino acid that replaces $R^1$ eat a position on the template corresponding to X, wherein $XR^2$ is selected from the group consisting of (a) 11T, 38N, 42Q, 48D, 53I, 56K, 60E, 61A, 63F, 65Q, 70N, 71I, 71T, 71V, 74S, 81G, 84R, 86K, 87K, 94V, 99P, 99T, 103V, 106L, 107S, 108V, 108W, 109Y, 112K, 112R, 115H, 116F, 117D, 117Q, 117Y, 120H, 120R, 121A, 121D, 121E, 121L, 121M, 121R, 121S, 121T, 121V, 121W, 121Y, 122A, 122P, 123D, 123I, 123L, 123R, 123Y, 124I, 124L, 124R, 125C, 125G, 125W, 126G, 126V, 127C, 127R, 128A, 128R, 128S, 129A, 129M, 129P, 129S, 130F, 130I, 130Y, 134T, 143T, 145M, 146N, 147R, 148A, 148F, 148G, 148I, 148T, 148V, 148W, 149L, 149M, 149T, 149V, 150A, 150I, 152M, 155V, 157N, 158E, 158H, 158K, 158W, 161A, 161G, 161Q, 161S, 161V, 163F, 163N, 163Q, 163T, 164G, 164N, 165G, 181R, 184T, 186M, 190A, 190S, 199V, 217K, 226M, 256C, 267H, 269S, 270M, 270S, 270Y, 296S, 298H, 300T, 302V, 312V, 316V, 323M, 333L, 336L, 337C, 343D, 344A, 344G, 345E, 350K, 354M, 355D, 355I, 355K, 358G, 360A, 360G, 360K, 360R, 360S, 361N, 361R, 363K, and 379M or group consisting of (b) 38N, 60E, 71I, 71V, 87K, 99T, 103V, 107S, 108V, 108W, 109Y, 115H, 116F, 117D, 117Q, 121D, 121E, 121L, 121M, 121R, 121S, 121T, 121V, 121W, 121Y, 122P, 123D, 123I, 123L, 123R, 123Y, 124I, 124L, 125C, 125G, 125V, 125W, 126G, 127C, 127R, 128A, 128R, 128S, 129A, 129M, 129P, 129S, 129V, 130F, 130I, 130Y, 134T, 143T, 146N, 149L, 149M, 149T, 149V, 150A, 157N, 158E, 158H, 158K, 158W, 163Q, 164N, 267H, 270M, 270S, 270Y, 345E, 355D, 360G, 360K, 360R, 360S, and 361R.

60. The subject matter of embodiment 59 wherein $XR^2$ is selected from the group consisting of 107S, 121D, 123D, 123I, 123L, 123R, 123Y, 129A, 129M, 129P, 129S, 129V, 130F, 130I, 130Y, 143T, 146N, 149L, 149M, 149T, 149V, 158E, 158H, 158K, 158W, 267H, 270M, 270S, 270Y, 355D, 360G, 360K, 360R, and 360S 61. The subject matter of embodiment 60 wherein $R^1XR^2$ is selected from the group consisting of (a) 511T, D38N, H42Q, E48D, N53I, E56K, D60E, V61A, I63F, P65Q, D70N, P71I, P71T, P71V, T74S, D81G, K84R, E86K, N87K, I94V, S99P, S99T, A103V, I106L, G107S, L108V, L108W, V109Y, N112K, N112R, R115H, I116F, N117D, N117Q, N117Y, Q120H, Q120R, G121A, G121D, G121E, G121L, G121M, G121R, G121S, G121T, G121V, G121W, G121Y, V122A, V122P, N123D, N123I, N123L, N123R, N123Y, S124I, S124L, S124R, V125C, V125G, V125W, E126G, E126V, K127C, K127R, P128A, P128R, P128S, V129A, V129M, V129P, V129S, V130F, V130I, V130Y, A134T, S143T, T145M, T146N, S147R, L148A, L148F, L148G, L148I, L148T, L148V, L148W, A149L, A149M, A149T, A149V, V150A, V150I, T152M, A155V, K157N, V158E, V158H, V158K, V158W, P161A, P161G, P161Q, P161S, P161V, I163F, I163N, I163Q, I163T, D164G, D164N, E165G, K181R, A184T, L186M, T190A, T190S, I199V, Q217K, L226M, G256C, Q267H, G269S, G270M, G270S, G270Y, T296S, R298H, A300T, I302V, G312V, A316V, I323M, F333L, P336L, S337C, G343D, V344A, V344G, K345E, E350K, K354M, N355D, N355I, N355K, E358G, V360A, V360G, V360K, V360R, V360S, C361N, C361R, Q363K, and K379M or (b) D38N, D60E, P71I, P71V, N87K, S99T, A103V, G107S, L108V, L108W, V109Y, R115H, I116F, N117D, N117Q, G121D, G121E, G121L, G121M, G121R, G121S, G121T, G121V, G121W, G121Y, V122P, N123D, N123I, N123L, N123R, N123Y, S124I, S124L, V125C, V125G, V125W, E126G, K127C, K127R, P128A, P128R, P128S, V129A, V129M, V129P, V129S, V130F, V130I, V130Y, A134T, S143T, T146N, A149L, A149M, A149T, A149V, V150A, K157N, V158E, V158H, V158K, V158W, I163Q, D164N, Q267H, G270M, G270S, G270Y, K345E, N355D, V360G, V360K, V360R, V360S, and C361R.

62. The subject matter of any of the previous embodiments wherein the non-natural alcohol dehydrogenase has sequence identity of 45% or greater, 55% or greater, 65% or greater, 75% or greater, 85% or greater, 90% or greater, 92.5% or greater, 95% or greater, 96% or greater, 97% or greater, 98% or greater, or 99% or greater to any one of the templates of embodiment 53, and comprises a original amino acid at all positions that are not substituted at amino acid position numbers of group (a) 11, 38, 42, 48, 53, 56, 60, 61, 63, 65, 70, 71, 74, 81, 84, 86, 87, 94, 99, 103, 106, 107, 108, 109, 112, 115, 116, 117, 117, 120, 121, 122, 123, 124, 125, 126, 127, 128, 129, 130, 134, 143, 145, 146, 147, 148, 149, 150, 152, 155, 157, 158, 161, 163, 164, 165, 181, 184, 186, 190, 199, 217, 226, 256, 267, 269, 270, 296, 298, 300, 302, 312, 316, 323, 333, 336, 337, 343, 344, 345, 350, 354, 355, 358, 360, 361, 363 and 379; or of group (b) 38, 60, 71, 87, 99, 103, 107, 108, 109, 115, 116, 117, 121, 122, 123, 124, 125, 126, 127, 128, 129, 130, 134, 143, 146, 149, 150, 157, 158, 163, 164, 267, 270, 345, 355, 360, and 361.

63. The subject matter of any of the previous embodiments wherein the non-natural alcohol dehydrogenase has sequence identity of 45% or greater, 55% or greater, 65% or greater, 75% or greater, 85% or greater, 90% or greater, 92.5% or greater, 95% or greater, 96% or greater, 97% or greater, 98% or greater, or 99% or greater to any one of the templates of embodiment 53, and comprises a original amino acid at all positions that are not amino acid position numbers 107, 121, 123, 129, 130, 143, 146, 149, 158, 267, 270, 355, 360.

64. The subject matter of any of the previous embodiments wherein the non-natural alcohol dehydrogenase comprises two, three, four, five, six, seven, eight, nine, ten, eleven or twelve, amino acid substitutions selected from the group consisting of: (a) S11T, D38N, H42Q, E48D, N53I, E56K, D60E, V61A, I63F, P65Q, D70N, P71I, P71T, P71V, T74S, D81G, K84R, E86K, N87K, I94V, S99P, S99T, A103V, I106L, G107S, L108V, L108W, V109Y, N112K, N112R, R115H, I116F, N117D, N117Q, N117Y, Q120H, Q120R, G121A, G121D, G121E, G121L, G121M, G121R, G121S, G121T, G121V, G121W, G121Y, V122A, V122P, N123D, N123I, N123L, N123R, N123Y, S124I, S124L, S124R, V125C, V125G, V125W, E126G, E126V, K127C, K127R, P128A, P128R, P128S, V129A, V129M, V129P, V129S, V130F, V130I, V130Y, A134T, S143T, T145M, T146N, S147R, L148A, L148F, L148G, L148I, L148T, L148V, L148W, A149L, A149M, A149T, A149V, V150A, V150I, T152M, A155V, K157N, V158E, V158H, V158K, V158W, P161A, P161G, P161Q, P161S, P161V, I163F, I163N, I163Q, I163T, D164G, D164N, E165G, K181R, A184T, L186M, T190A, T190S, I199V, Q217K, L226M, G256C, Q267H, G269S, G270M, G270S, G270Y, T296S, R298H, A300T, I302V, G312V, A316V, I323M, F333L, P336L, S337C, G343D, V344A, V344G, K345E, E350K, K354M, N355D, N355I, N355K, E358G, V360A, V360G, V360K, V360R, V360S, C361N, C361R, Q363K, and K379M or (b) D38N, D60E, P71I, P71V, N87K, S99T, A103V, G107S, L108V, L108W, V109Y, R115H, I116F, N117D, N117Q, G121D, G121E, G121L, G121M, G121R, G121S, G121T, G121V, G121W, G121Y, V122P, N123D, N123I, N123L, N123R, N123Y, S124I, S124L, V125C, V125G, V125W, E126G, K127C, K127R, P128A, P128R, P128S, V129A, V129M, V129P, V129S, V130F, V130I, V130Y, A134T, S143T, T146N, A149L, A149M, A149T, A149V, V150A, K157N, V158E, V158H, V158K, V158W, I163Q, D164N, Q267H, G270M, G270S, G270Y, K345E, N355D, V360G, V360K, V360R, V360S and C361R.

65. The subject matter of any of the previous embodiments wherein the non-natural alcohol dehydrogenase comprises a set of amino acid substitutions selected from the group consisting of (a) D70N, L148G, P161G, V360A; (b) D70N, L148G, V360A, C361N; (c) D70N, L148V, V150I, P161A, V360G; (d) D70N, L148V, V360G; (e) D70N, P161A, V360A; (f) D70N, P161V, V360G, C361N; (g) D70N, V150I, P161A, V360A; (h) D70N, V150I, P161V, V360G, C361N; (i) E48D, L148V, P161A, V360A; (j) L148G, P161A, V360A, C361N; (k) L148G, P161A, V360G; (l) L148G, P161A, V360G, C361N; (m) L148G, P161G, V360A; (n) L148G, P161G, V360G, C361N; (o) L148G, V360A, C361N; (p) L148G, V360G, C361N; (q) L148I, P161G, V360G; (r) L148I, P161V, V360G; (s) L148T, V150I, V360A; (t) L148T, V360G; (u) L148V, P161A, V360A; (v) L148V, V150I, P161A, V360A; (w) L148V, V150I, P161A, V360A, C361N; (x) L148V, V150I, P161A, V360G; (y) L148V, V150I, P161A, V360G, C361N; (z) L148V, V150I, P161A, V360G, C361N; (aa) L148V, V150I, P161G, V360A; (ab) L148V, V150I, P161V, V360G, C361N; (ac) L148W, P161A, V360A, C361N; (ad) N112K, S147R, P161A, V360A; (ae) P161A, Q217K, V360A, C361N; (af) P161A, V360A, C361N; (ag) P161A, V360G; (ah) P161V, E358G, V360G; (ai) P161V, V360A, C361N; (aj) L148W, P161A, V360A, C361N; (ak) N112K, S147R, P161A, V360A; (al) P161A, Q217K, V360A, C361N; (am) P161A, V360A, C361N; (an) P161A, V360G; (ao) P161V, E358G, V360G; (ap) P161V, V360A, C361N; (aq) P161V, V360G; (ar) P65Q, L148G, V150I, P161A, V360G, C361N; (as) S147R, L148A, V150I, P161A, V360G; (at) S147R, L148F, V150I, P161G, V360G; (au) S147R, L148V, P161G, V360A; (av) P161V, V360G; (aw) P65Q, L148G, V150I, P161A, V360G, C361N; (ax) S147R, L148A, V150I, P161A, V360G; (ay) S147R, L148F, V150I, P161G, V360G; (az) S147R, L148V, P161G, V360A; (aaa) S147R, L148V, P161V, V360G; (aab) S147R, L148V, V150I, P161A, C361N; (aac) S147R, L148V, V150I, P161G, V360G; (aad) S147R, P161A, V360A; (aae) S147R, P161A, V360A, C361N; (aaf) S147R, P161A, V360G; (aag) S147R, P161V, V360G; (aah) S147R, P161V, V360G, C361N; (aai) S147R, V150I, P161V, V360A; (aaj) S147R, V150I, V360A, C361N; (aak) T145M, L148I, V360G; (aal) V150I, I302V, V360G, C361N; (aam) V150I, P161A, C361N; (aan) V150I, P161G, V360A, C361N; (aao) V150I, P161G, V360G, C361N; (aap) V150I, P161G, V360G, C361N; (aaq) V150I, P161V, C361N; (aar) V150I, P161V, K354R, V360A, C361N; (aas) V150I, P161V, V360A, C361N; (aat) V150I, P161V, V360G, C361N; (aau) V150I, V360A, C361N; (aav) V150I, V360G; (aaw) S11T, T74S, G269S, V344A; (aax) K84R, I63T; (aay) V122A, I163N; (aaz) G107S, F333L; (aaaa) V129M, T152M, G343D; (aaab) I63F, N355K; (aaac) G107S, F333L; (aaad) E86K, S99T, A149V; (aaae) N53I, V158E; (aaaf) N355I, K379M; (aaag) H42Q, G107S; (aaah) Q120H, I163N; (aaai) A149V, I323M; (aaaj) G107S, F333L; (aaak) D164G, K181R; (aaal) A155V, R298H, N355D; (aaam) N123D, E165G; (aaan) I63F, L186M; (aaao) G121A, T296S; (aaap) I94V, S99P, N123I; (aaaq) E126V, V129M, V344G; (aaar) Q120R, S143T; (aaas) G256C, A316V; (aaat) P161Q, G312V; (aaau) L226M, A300T, V360A; (aaav) S337C, E350K, N355D, Q363K; (aaaw) D81G, V158E; (aaax) I106L, N117Y, E126V; (aaay) G107S, G121D; (aaaz) V61A, V158E; (aaaaa) N53I, V158E; (aaaab) N117Y, T190S; (aaaac) S124R, I199V; (aaaad) K354M, C361R; (aaaae) A184T, C361R; (aaaag) E56K, Q267H; (aaaag) S124R, E126G; (aaaah) T190A, N355K; (aaaai) P71T, F333L; (aaaaj) G107S, F333L; and (aaaak) N123I, P336L, (aaaal) D38D/A149V, (aaaam) D38N/V163V, (aaaan) D73D/L108V, (aaaao) G121R/P161S, and (aaaap) N112R/P161S.

66. The subject matter of any of the previous embodiments wherein the non-natural alcohol dehydrogenase comprises a sequence motif selected from the group consisting of TNA and VTNAF (SEQ ID NO: 79).

67. The subject matter of any of the previous embodiments wherein the non-natural alcohol dehydrogenase comprises a sequence motif selected from the group consisting of VEV and GVEVA (SEQ ID NO: 80).

68. The subject matter of any of the previous embodiments wherein the non-natural alcohol dehydrogenase comprises a sequence motif selected from the group consisting of DIA, PDIAD (SEQ ID NO: 81), DVA, and PDVAD (SEQ ID NO: 82).

69. The subject matter of any of the previous embodiments wherein the non-natural alcohol dehydrogenase comprises a sequence motif selected from the group consisting of EKC and QEKCD (SEQ ID NO: 83). 70. The subject matter of any of the previous embodiments wherein the non-natural alcohol dehydrogenase comprises a sequence motif selected from the group consisting of STH and GSTHD (SEQ ID NO: 84).

71. The subject matter of any of the previous embodiments wherein the non-natural alcohol dehydrogenase comprises a sequence motif selected from the group consisting of TVK and DTVKA (SEQ ID NO: 85).

72. The subject matter of any of the previous embodiments wherein the non-natural alcohol dehydrogenase comprises a sequence motif selected from the group consisting of SLV, GVV, GWV, GLY, ISLVA (SEQ ID NO: 86), IGVVA (SEQ ID NO: 87), IGWVA (SEQ ID NO: 88), and IGLYA (SEQ ID NO: 89)

73. The subject matter of any of the previous embodiments wherein the non-natural alcohol dehydrogenase comprises a sequence motif selected from the group consisting of HIN, RFN, RID, RIQ, GHIND (SEQ ID NO: 90), GRFND (SEQ ID NO: 91), GRIDD (SEQ ID NO: 92), and GRIQD (SEQ ID NO: 93).

74. The subject matter of any of the previous embodiments wherein the non-natural alcohol dehydrogenase comprises a sequence motif selected from the group consisting of DVNSVEKPVV (SEQ ID NO: 94), EVNSVEKPVV (SEQ ID NO: 95), LVNSVEKPVV (SEQ ID NO: 96), MVNSVEKPVV (SEQ ID NO: 97), RVNSVEKPVV (SEQ ID NO: 98), SVNSVEKPVV (SEQ ID NO: 99), TVNSVEKPVV (SEQ ID NO: 100), VVNSVEKPVV (SEQ ID NO: 101), WVNSVEKPVV (SEQ ID NO: 102), YVNSVEKPVV (SEQ ID NO: 103), GPNSVEKPVV (SEQ ID NO: 104), GVDSVEKPVV (SEQ ID NO: 105), GVISVEKPVV (SEQ ID NO: 106), GVLSVEKPVV (SEQ ID NO: 107), GVRSVEKPVV (SEQ ID NO: 108), GVYSVEKPVV (SEQ ID NO: 109). GVNIVEKPVV (SEQ ID NO: 110), GVNLVEKPVV (SEQ ID NO: 111), GVNSCEKPVV (SEQ ID NO: 112), GVNSGEKPVV (SEQ ID NO: 113), GVNSWEKPVV (SEQ ID NO: 114), GVNSVGKPVV (SEQ ID NO: 115), GVNSVECPVV (SEQ ID NO: 116), GVNSVERPVV (SEQ ID NO: 117), GVNSVEKAVV (SEQ ID NO: 118). GVNSVEKRVV (SEQ ID NO: 119). GVNSVEKSVV (SEQ ID NO: 120). GVNSVEKPAV (SEQ ID NO: 121). GVNSVEKPMV (SEQ ID NO: 122). GVNSVEKPPV (SEQ ID NO: 123). GVNSVEKPSV (SEQ ID NO: 124). GVNSVEKPVF (SEQ ID NO: 125). GVNSVEKPVI (SEQ ID NO: 126), and GVNSVEKPVY (SEQ ID NO: 127).

75. The subject matter of any of the previous embodiments wherein the non-natural alcohol dehydrogenase comprises a sequence motif selected from the group consisting of TETT (SEQ ID NO: 128), SETN (SEQ ID NO: 129), GTETTS (SEQ ID NO: 130), and GSETNS (SEQ ID NO: 131).

76. The subject matter of any of the previous embodiments wherein the non-natural alcohol dehydrogenase comprises a sequence motif selected from the group consisting of LLVI (SEQ ID NO: 132), LMVI (SEQ ID NO: 133), LTVI (SEQ ID NO: 134), LVVI (SEQ ID NO: 135), and LAAI (SEQ ID NO: 136).

77. The subject matter of any of the previous embodiments wherein the non-natural alcohol dehydrogenase comprises a sequence motif selected from the group consisting of NVKMPVID (SEQ ID NO: 137), KEKMPVID (SEQ ID NO: 138), KHKMPVID (SEQ ID NO: 139), KKKMPVID (SEQ ID NO: 140), KWKMPVID (SEQ ID NO: 141), KVKMPVQD (SEQ ID NO: 142), and KVKMPVIN (SEQ ID NO: 143).

78. The subject matter of any of the previous embodiments wherein the non-natural alcohol dehydrogenase comprises a sequence motif selected from the group consisting of HVGG (SEQ ID NO: 144), QVGM (SEQ ID NO: 145), QVGS (SEQ ID NO: 146), and QVGY (SEQ ID NO: 147).

79. The subject matter of any of the previous embodiments wherein the non-natural alcohol dehydrogenase comprises a sequence motif selected from the group consisting of VEE and GVEEE (SEQ ID NO: 148).

80. The subject matter of any of the previous embodiments wherein the non-natural alcohol dehydrogenase comprises a sequence motif selected from the group consisting of DAYEDVC (SEQ ID NO: 149), NAYEDGC (SEQ ID NO: 150), NAYEDKC (SEQ ID NO: 151), and NAYEDRC (SEQ ID NO: 152), and NAYEDSC (SEQ ID NO: 153), and NAYEDVR (SEQ ID NO: 154).

81. A nucleic acid encoding the non-natural alcohol dehydrogenase of any of embodiments 53-80.

82. A non-natural alcohol dehydrogenase has sequence identity of 45% or greater, 55% or greater, 65% or greater, 75% or greater, 85% or greater, 90% or greater, 92.5% or greater, 95% or greater, 96% or greater, 97% or greater, 98% or greater, or 99% or greater to an NAD$^+$-dependent alcohol dehydrogenase template selected from the group consisting of SEQ ID NO:1 (MDH MGA3_17392), EI177596.1, AAA22593.1, n177618.1, EIJ78790.1, EIJ80770.1, n178397.1, n183020.1, EFI69743.1, YP_004860127.1, YP_001699778.1, ZP_11313277.1, ZP_05587334.1, YP_004681552.1, AGF87161, YP_002138168.1, YP_359772.1, YP_001343716.1, ZP_16224338.1, AAC45651.1, YP_007491369.1, YP_002434746, YP_005052855, NP_561852.1, YP_001447544, YP_001113612.1, YP_011618, ZP_01220157.1, YP_003990729.1, ZP_07335453.1, NP_717107, YP_003310546.1, ZP_10241531.1, YP_001337153.1, YP_026233.1, YP_694908, YP_725376.1, YP_001663549, EKC54576, YP_001126968.1 or a fragment of said template having said dehydrogenase activity with an amino-terminal deletion, carboxy-terminal deletion, or both, the fragment having a sequence identity of 45% or greater, 55% or greater, 65% or greater, 75% or greater, 85% or greater, 90% or greater, 92.5% or greater, 95% or greater, 96% or greater, 97% or greater, 98% or greater, or 99% or greater to the template.

83. A non-natural alcohol dehydrogenase of embodiment 82 wherein said template is selected from the group consisting of EIJ77596.1, EI178397.1, EFI69743.1, YP_001699778.1, YP_002138168.1, YP_359772.1, YP_005052855, NP_561852.1, YP_001447544, ZP_01220157.1, YP_003990729.1, ZP_10241531.1, and YP_026233.1.

84. A non-natural alcohol dehydrogenase of embodiment 82 wherein the non-natural alcohol dehydrogenase has a sequence identity of 45% or greater, 55% or greater, 65% or greater, 75% or greater, 85% or greater, 90% or greater, 92.5% or greater, 95% or greater, 96% or greater, 97% or greater, 98% or greater, or 99% or greater to any one of the templates of embodiment 53, and wherein the dehydrogenase comprises one or more amino acid substitutions based on formula: $R^1XR^2$, where $R^1$ is a original amino acid at position X of the template, and $R^2$ is the variant amino acid that replaces $R^1$ at a position on the template corresponding to X, wherein $XR^2$ is selected from the group consisting of (a) 11T, 38N, 42Q, 48D, 53I, 56K, 60E, 61A, 63F, 65Q, 70N, 71I, 71T, 71V, 74S, 81G, 84R, 86K, 87K, 94V, 99P, 99T, 103V, 106L, 107S, 108V, 108W, 109Y, 112K, 112R, 115H, 116F, 117D, 117Q, 117Y, 120H, 120R, 121A, 121D, 121E, 121L, 121M, 121R, 121S, 121T, 121V, 121W, 121Y, 122A, 122P, 123D, 123I, 123L, 123R, 123Y, 124I, 124L, 124R, 125C, 125G, 125W, 126G, 126V, 127C, 127R, 128A, 128R, 128S, 129A, 129M, 129P, 129S, 130F, 130I, 130Y, 134T, 143T, 145M, 146N, 147R, 148A, 148F, 148G, 148I, 148T, 148V, 148W, 149L, 149M, 149T, 149V, 150A, 150I, 152M, 155V, 157N, 158E, 158H, 158K, 158W, 161A, 161G, 161Q, 161S, 161V, 163F, 163N, 163Q, 163T, 164G, 164N, 165G, 181R, 184T, 186M, 190A, 190S, 199V, 217K, 226M, 256C, 267H, 269S, 270M, 270S, 270Y, 296S, 298H, 300T, 302V, 312V, 316V, 323M, 333L, 336L, 337C, 343D, 344A, 344G, 345E, 350K, 354M, 355D, 355I, 355K, 358G, 360A, 360G, 360K, 360R, 360S, 361N, 361R, 363K, and 379M or the group consisting of (b) 38N, 60E, 71I, 71V, 87K, 99T, 103V, 107S, 108V, 108W, 109Y, 115H, 116F, 117D, 117Q, 121D, 121E, 121L, 121M, 121R, 121S, 121T, 121V, 121W, 121Y, 122P, 123D, 123I, 123L, 123R, 123Y, 124I, 124L, 125C, 125G, 125V, 125W, 126G, 127C, 127R, 128A, 128R, 128S, 129A, 129M, 129P, 129S, 129V, 130F, 130I, 130Y, 134T, 143T, 146N, 149L, 149M, 149T, 149V, 150A, 157N, 158E, 158H, 158K, 158W, 163Q, 164N, 267H, 270M, 270S, 270Y, 345E, 355D, 360G, 360K, 360R, 360S, and 361R.

85. A non-natural alcohol dehydrogenase of embodiment 82 wherein $XR^2$ is selected from the group consisting of 107S, 121D, 123D, 123I, 123L, 123R, 123Y, 129A, 129M, 129P, 129S, 129V, 130F, 130I, 130Y, 143T, 146N, 149L, 149M, 149T, 149V, 158E, 158H, 158K, 158W, 267H, 270M, 270S, 270Y, 355D, 360G, 360K, 360R, and 360S 86. A non-natural alcohol dehydrogenase of embodiment 82 wherein $R^1XR^2$ is selected from the group consisting of (a) S11T, D38N, H42Q, E48D, N53I, E56K, D60E, V61A, I63F, P65Q, D70N, P71I, P71T, P71V, T74S, D81G, K84R, E86K, N87K, I94V, S99P, S99T, A103V, I106L, G107S, L108V, L108W, V109Y, N112K, N112R, R115H, I116F, N117D, N117Q, N117Y, Q120H, Q120R, G121A, G121D, G121E, G121L, G121M, G121R, G121S, G121T, G121V, G121W, G121Y, V122A, V122P, N123D, N123I, N123L, N123R, N123Y, S124I, S124L, S124R, V125C, V125G, V125W, E126G, E126V, K127C, K127R, P128A, P128R, P128S, V129A, V129M, V129P, V129S, V130F, V130I, V130Y, A134T, S143T, T145M, T146N, S147R, L148A, L148F, L148G, L148I, L148T, L148V, L148W, A149L, A149M, A149T, A149V, V150A, V150I, T152M, A155V, K157N, V158E, V158H, V158K, V158W, P161A, P161G, P161Q, P161S, P161V, I163F, I163N, I163Q, I163T, D164G, D164N, E165G, K181R, A184T, L186M, T190A, T190S, I199V, Q217K, L226M, G256C, Q267H, G269S, G270M, G270S, G270Y, T296S, R298H, A300T, I302V, G312V, A316V, I323M, F333L, P336L, S337C, G343D, V344A, V344G, K345E, E350K, K354M, N355D, N355I, N355K, E358G, V360A, V360G, V360K, V360R, V360S, C361N, C361R, Q363K, and K379M; or the group consisting of (b) D38N, D60E, P71I, P71V, N87K, S99T, A103V, G107S, L108V, L108W, V109Y, R115H, I116F, N117D, N117Q, G121D, G121E, G121L, G121M, G121R, G121S, G121T, G121V, G121W, G121Y, V122P, N123D, N123I, N123L, N123R, N123Y, S124I, S124L, V125C, V125G, V125W, E126G, K127C, K127R, P128A, P128R, P128S, V129A, V129M, V129P, V129S, V130F, V130I, V130Y, A134T, S143T, T146N, A149L, A149M, A149T, A149V, V150A, K157N, V158E, V158H, V158K, V158W, I163Q, D164N, Q267H, G270M, G270S, G270Y, K345E, N355D, V360G, V360K, V360R, V360S, and C361R.

87. A non-natural alcohol dehydrogenase of embodiment 82 wherein the non-natural alcohol dehydrogenase has sequence identity of 45% or greater, 55% or greater, 65% or greater, 75% or greater, 85% or greater, 90% or greater, 92.5% or greater, 95% or greater, 96% or greater, 97% or greater, 98% or greater, or 99% or greater to any one of the templates of embodiment 53, and comprises an original amino acid at all positions that are not substituted at amino acid position numbers of group (a) 11, 38, 42, 48, 53, 56, 60, 61, 63, 65, 70, 71, 74, 81, 84, 86, 87, 94, 99, 103, 106, 107, 108, 109, 112, 115, 116, 117, 117, 120, 121, 122, 123, 124, 125, 126, 127, 128, 129, 130, 134, 143, 145, 146, 147, 148, 149, 150, 152, 155, 157, 158, 161, 163, 164, 165, 181, 184, 186, 190, 199, 217, 226, 256, 267, 269, 270, 296, 298, 300, 302, 312, 316, 323, 333, 336, 337, 343, 344, 345, 350, 354, 355, 358, 360, 361, 363 and 379; or of group (b) 38, 60, 71, 87, 99, 103, 107, 108, 109, 115, 116, 117, 121, 122, 123, 124, 125, 126, 127, 128, 129, 130, 134, 143, 146, 149, 150, 157, 158, 163, 164, 267, 270, 345, 355, 360, and 361.

88. A non-natural alcohol dehydrogenase of embodiment 82 wherein the non-natural alcohol dehydrogenase has sequence identity of 45% or greater, 55% or greater, 65% or greater, 75% or greater, 85% or greater, 90% or greater, 92.5% or greater, 95% or greater, 96% or greater, 97% or greater, 98% or greater, or 99% or greater to any one of the templates of embodiment 53, and comprises an original amino acid at all positions that are not amino acid position numbers 107, 121, 123, 129, 130, 143, 146, 149, 158, 267, 270, 355, 360.

89. A non-natural alcohol dehydrogenase of embodiment 82 wherein the non-natural alcohol dehydrogenase comprises two, three, four, five, six, seven, eight, nine, ten, eleven or twelve amino acid substitutions selected from the group consisting of: (a) S11T, D38N, H42Q, E48D, N53I, E56K, D60E, V61A, I63F, P65Q, D70N, P71I, P71T, P71V, T74S, D81G, K84R, E86K, N87K, I94V, S99P, S99T, A103V, I106L, G107S, L108V, L108W, V109Y, N112K, N112R, R115H, I116F, N117D, N117Q, N117Y, Q120H, Q120R, G121A, G121D, G121E, G121L, G121M, G121R, G121S, G121T, G121V, G121W, G121Y, V122A, V122P, N123D, N123I, N123L, N123R, N123Y, S124I, S124L, S124R, V125C, V125G, V125W, E126G, E126V, K127C, K127R, P128A, P128R, P128S, V129A, V129M, V129P, V129S, V130F, V130I, V130Y, A134T, S143T, T145M, T146N, S147R, L148A, L148F, L148G, L148I, L148T, L148V, L148W, A149L, A149M, A149T, A149V, V150A, V150I, T152M, A155V, K157N, V158E, V158H, V158K, V158W, P161A, P161G, P161Q, P161S, P161V, I163F, I163N, I163Q, I163T, D164G, D164N, E165G, K181R, A184T, L186M, T190A, T190S, I199V, Q217K, L226M, G256C, Q267H, G269S, G270M, G270S, G270Y, T296S, R298H, A300T, I302V, G312V, A316V, I323M, F333L, P336L, S337C, G343D, V344A, V344G, K345E, E350K, K354M, N355D, N355I, N355K, E358G, V360A, V360G, V360K, V360R, V360S, C361N, C361R, Q363K, and K379M or the group consisting of (b) D38N, D60E, P71I, P71V, N87K, S99T, A103V, G107S, L108V, L108W, V109Y, R115H, I116F, N117D, N117Q, G121D, G121E, G121L, G121M, G121R, G121S, G121T, G121V, G121W, G121Y, V122P, N123D, N123I, N123L, N123R, N123Y, S124I, S124L, V125C, V125G, V125W, E126G, K127C, K127R, P128A, P128R, P128S, V129A, V129M, V129P, V129S, V130F, V130I, V130Y, A134T, S143T, T146N, A149L, A149M, A149T, A149V, V150A, K157N, V158E, V158H, V158K, V158W, I163Q, D164N, Q267H, G270M, G270S, G270Y, K345E, N355D, V360G, V360K, V360R, V360S and C361R.

90. A non-natural alcohol dehydrogenase of embodiment 82 wherein the non-natural alcohol dehydrogenase comprises a set of amino acid substitutions selected from the group consisting of (a) D70N, L148G, P161G, V360A; (b) D70N, L148G, V360A, C361N; (c) D70N, L148V, V150I, P161A, V360G; (d) D70N, L148V, V360G; (e) D70N, P161A, V360A; (f) D70N, P161V, V360G, C361N; (g) D70N, V150I, P161A, V360A; (h) D70N, V150I, P161V, V360G, C361N; (i) E48D, L148V, P161A, V360A; (j) L148G, P161A, V360A, C361N; (k) L148G, P161A, V360G; (l) L148G, P161A, V360G, C361N; (m) L148G, P161G, V360A; (n) L148G, P161G, V360G, C361N; (o) L148G, V360A, C361N; (p) L148G, V360G, C361N; (q) L148I, P161G, V360G; (r) L148I, P161V, V360G; (s) L148T, V150I, V360A; (t) L148T, V360G; (u) L148V, P161A, V360A; (v) L148V, V150I, P161A, V360A; (w) L148V, V150I, P161A, V360A, C361N; (x) L148V, V150I, P161A, V360G; (y) L148V, V150I, P161A, V360G, C361N; (z) L148V, V150I, P161A, V360G, C361N; (aa) L148V, V150I, P161G, V360A; (ab) L148V, V150I, P161V, V360G, C361N; (ac) L148W, P161A, V360A, C361N; (ad) N112K, S147R, P161A, V360A; (ae) P161A, Q217K, V360A, C361N; (af) P161A, V360A, C361N; (ag) P161A, V360G; (ah) P161V, E358G, V360G; (ai) P161V, V360A, C361N; (aj) L148W, P161A, V360A, C361N; (ak) N112K, S147R, P161A, V360A; (al) P161A, Q217K, V360A, C361N; (am) P161A, V360A, C361N; (an) P161A, V360G; (ao) P161V, E358G, V360G; (ap) P161V, V360A, C361N; (aq) P161V, V360G; (ar) P65Q, L148G, V150I, P161A, V360G, C361N; (as) S147R, L148A, V150I, P161A, V360G; (at) S147R, L148F, V150I, P161G, V360G; (au) S147R, L148V, P161G, V360A; (av) P161V, V360G; (aw) P65Q, L148G, V150I, P161A, V360G, C361N; (ax) S147R, L148A, V150I, P161A, V360G; (ay) S147R, L148F, V150I, P161G, V360G; (az) S147R, L148V, P161G, V360A; (aaa) S147R, L148V, P161V, V360G; (aab) S147R, L148V, V150I, P161A, C361N; (aac) S147R, L148V, V150I, P161G, V360G; (aad) S147R, P161A, V360A; (aae) S147R, P161A, V360A, C361N; (aaf) S147R, P161A, V360G; (aag) S147R, P161V, V360G; (aah) S147R, P161V, V360G, C361N; (aai) S147R, V150I, P161V, V360A; (aaj) S147R, V150I, V360A, C361N; (aak) T145M, L148I, V360G; (aal) V150I, I302V, V360G, C361N; (aam) V150I, P161A, C361N; (aan) V150I, P161G, V360A, C361N; (aao) V150I, P161G, V360G; (aap) V150I, P161G, V360G, C361N; (aaq) V150I, P161V, C361N; (aar) V150I, P161V, K354R, V360A, C361N; (aas) V150I, P161V, V360A, C361N; (aat) V150I, P161V, V360G, C361N; (aau) V150I, V360A, C361N; (aav) V150I, V360G; (aaw) S11T, T74S, G269S, V344A; (aax) K84R, I163T; (aay) V122A, I163N; (aaz) G107S, F333L; (aaaa) V129M, T152M, G343D; (aaab) I63F, N355K; (aaac) G107S, F333L; (aaad) E86K, S99T, A149V; (aaae) N53I, V158E; (aaaf) N355I, K379M; (aaag) H42Q, G107S; (aaah) Q120H, I163N; (aaai) A149V, I323M; (aaaj) G107S, F333L; (aaak) D164G, K181R; (aaal) A155V, R298H, N355D; (aaam) N123D, E165G; (aaan) I163F, L186M; (aaao) G121A, T296S; (aaap) I94V, S99P, N123I; (aaaq) E126V, V129M, V344G; (aaar) Q120R, S143T; (aaas) G256C, A316V; (aaat) P161Q, G312V; (aaau) L226M, A300T, V360A; (aaav) S337C, E350K, N355D, Q363K; (aaaw) D81G, V158E; (aaax) I106L, N117Y, E126V; (aaay) G107S, G121D; (aaaz) V61A, V158E; (aaaaa) N53I, V158E; (aaaab) N117Y, T190S; (aaaac) S124R, I199V; (aaaad) K354M, C361R; (aaaae) A184T, C361R; (aaaag) E56K, Q267H; (aaaag) S124R, E126G; (aaaah) T190A, N355K; (aaaai) P71T, F333L; (aaaaj) G107S, F333L; and (aaaak) N123I, P336L, (aaaal) D38D/A149V, (aaaam) D38N/V163V, (aaaan) D73D/L108V, (aaaao) G121R/P161S, and (aaaap) N112R/P161S.

91. A non-natural alcohol dehydrogenase of embodiment 82 wherein the non-natural alcohol dehydrogenase comprises a sequence motif selected from the group consisting of TNA and VTNAF (SEQ ID NO: 79).

92. A non-natural alcohol dehydrogenase of embodiment 82 wherein the non-natural alcohol dehydrogenase comprises a sequence motif selected from the group consisting of VEV and GVEVA (SEQ ID NO: 80).

93. A non-natural alcohol dehydrogenase of embodiment 82 wherein the non-natural alcohol dehydrogenase comprises a sequence motif selected from the group consisting of DIA, PDIAD (SEQ ID NO: 81), DVA, and PDVAD (SEQ ID NO: 82). 94. A non-natural alcohol dehydrogenase of embodiment 82 wherein the non-natural alcohol dehydrogenase comprises a sequence motif selected from the group consisting of EKC and QEKCD (SEQ ID NO: 83).

95. A non-natural alcohol dehydrogenase of embodiment 82 wherein the non-natural alcohol dehydrogenase comprises a sequence motif selected from the group consisting of STH and GSTHD (SEQ ID NO: 84).

96. A non-natural alcohol dehydrogenase of embodiment 82 wherein the non-natural alcohol dehydrogenase comprises a sequence motif selected from the group consisting of TVK and DTVKA (SEQ ID NO: 85). 97. A non-natural alcohol dehydrogenase of embodiment 82 wherein the non-natural alcohol dehydrogenase comprises a sequence motif selected from the group consisting of SLV, GVV, GWV, GLY, ISLVA (SEQ ID NO: 86), IGVVA (SEQ ID NO: 87), IGWVA (SEQ ID NO: 88), and IGLYA (SEQ ID NO: 89).

98. A non-natural alcohol dehydrogenase of embodiment 82 wherein the non-natural alcohol dehydrogenase comprises a sequence motif selected from the group consisting of HIN, RFN, RID, RIQ, GHIND (SEQ ID NO: 90), GRFND (SEQ ID NO: 91), GRIDD (SEQ ID NO: 92), and GRIQD (SEQ ID NO: 93).

99. A non-natural alcohol dehydrogenase of embodiment 82 wherein the non-natural alcohol dehydrogenase comprises a sequence motif selected from the group consisting of DVNSVEKPVV (SEQ ID NO: 94), EVNSVEKPVV (SEQ ID NO: 95), LVNSVEKPVV (SEQ ID NO: 96), MVNSVEKPVV (SEQ ID NO: 97), RVNSVEKPVV (SEQ ID NO: 98), SVNSVEKPVV (SEQ ID NO: 99), TVNSVEKPVV (SEQ ID NO: 100), VVNSVEKPVV (SEQ ID NO: 101), WVNSVEKPVV (SEQ ID NO: 102), YVNSVEKPVV (SEQ ID NO: 103), GPNSVEKPVV (SEQ ID NO: 104), GVDSVEKPVV (SEQ ID NO: 105), GVISVEKPVV (SEQ ID NO: 106), GVLSVEKPVV (SEQ ID NO: 107), GVRSVEKPVV (SEQ ID NO: 108), GVYSVEKPVV (SEQ ID NO: 109). GVNIVEKPVV (SEQ ID NO: 110), GVNLVEKPVV (SEQ ID NO: 111), GVNSCEKPVV (SEQ ID NO: 112), GVNSGEKPVV (SEQ ID NO: 113), GVNSWEKPVV (SEQ ID NO: 114), GVNSVGKPVV (SEQ ID NO: 115), GVNSVECPVV (SEQ ID NO: 116), GVNSVERPVV (SEQ ID NO: 117), GVNSVEKAVV (SEQ ID NO: 118). GVNSVEKRVV (SEQ ID NO: 119). GVNSVEKSVV (SEQ ID NO: 120). GVNSVEKPAV (SEQ ID NO: 121). GVNSVEKPMV (SEQ ID NO: 122). GVNSVEKPPV (SEQ ID NO: 123). GVNSVEKPSV (SEQ ID NO: 124). GVNSVEKPVF (SEQ ID NO: 125). GVNSVEKPVI (SEQ ID NO: 126), and GVNSVEKPVY (SEQ ID NO: 127).

100. A non-natural alcohol dehydrogenase of embodiment 82 wherein the non-natural alcohol dehydrogenase comprises a sequence motif selected from the group consisting of TETT (SEQ ID NO: 128), SETN (SEQ ID NO: 129), GTETTS (SEQ ID NO: 130), and GSETNS (SEQ ID NO: 131).

101. A non-natural alcohol dehydrogenase of embodiment 82 wherein the non-natural alcohol dehydrogenase comprises a sequence motif selected from the group consisting of LLVI (SEQ ID NO: 132), LMVI (SEQ ID NO: 133), LTVI (SEQ ID NO: 134), LVVI (SEQ ID NO: 135), and LAAI (SEQ ID NO: 136).

102. A non-natural alcohol dehydrogenase of embodiment 82 wherein the non-natural alcohol dehydrogenase comprises a sequence motif selected from the group consisting of NVKMPVID (SEQ ID NO: 137), KEKMPVID (SEQ ID NO: 138), KHKMPVID (SEQ ID NO: 139), KKKMPVID (SEQ ID NO: 140), KWKMPVID (SEQ ID NO: 141), KVKMPVQD (SEQ ID NO: 142), and KVKMPVIN (SEQ ID NO: 143).

103. A non-natural alcohol dehydrogenase of embodiment 82 wherein the non-natural alcohol dehydrogenase comprises a sequence motif selected from the group consisting of HVGG (SEQ ID NO: 144), QVGM (SEQ ID NO: 145), QVGS (SEQ ID NO: 146), and QVGY (SEQ ID NO: 147).

104. A non-natural alcohol dehydrogenase of embodiment 82 wherein the non-natural alcohol dehydrogenase comprises a sequence motif selected from the group consisting of VEE and GVEEE (SEQ ID NO: 148).

105. A non-natural alcohol dehydrogenase of embodiment 82 wherein the non-natural alcohol dehydrogenase comprises a sequence motif selected from the group consisting of DAYEDVC (SEQ ID NO: 149), NAYEDGC (SEQ ID NO: 150), NAYEDKC (SEQ ID NO: 151), and NAYEDRC (SEQ ID NO: 152), and NAYEDSC (SEQ ID NO: 153), and NAYEDVR (SEQ ID NO: 154).

106. A nucleic acid encoding the non-natural alcohol dehydrogenase of any of embodiments 82-105.

107. An expression construct comprising the nucleic acid of 106.

108. An engineered cell comprising the nucleic acid or expression construct of embodiments 106 or 107.

109. The engineered cell of embodiment 108 further comprising one or more alcohol metabolic pathway gene(s) encoding a protein selected from the group consisting of a), a formate dehydrogenase (EM8), a formaldehyde activating enzyme (EM10), a formaldehyde dehydrogenase (EM11), a S-(hydroxymethyl)glutathione synthase (EM12), a glutathione-dependent formaldehyde dehydrogenase (EM13), a S-formylglutathione hydrolase (EM14), a formate hydrogen lyase (EM15), a hydrogenase (EM16).

110. The engineered cell of embodiment 108 further comprising one or more alcohol metabolic pathway gene(s) encoding a protein selected from the group consisting of a succinyl-CoA reductase (aldehyde forming) (EB3), a 4-hydroxybutyrate (4-HB) dehydrogenase (EB4), a 4-HB kinase (EB5), a phosphotrans-4-hydroxybutyrylase (EB6), a 4-hydroxybutyryl-CoA reductase (aldehyde forming) (EB7), a 1,4-butanediol dehydrogenase (EB8); a succinate reductase (EB9), a succinyl-CoA reductase (alcohol forming) (EB10), 4-hydroxybutyryl-CoA transferase (EB11), a 4-hydroxybutyryl-CoA synthetase (EB12), a 4-HB reductase (EB13), and a 4-hydroxybutyryl-CoA reductase (alcohol forming) (EB15), a succinyl-CoA transferase (EB1), and a succinyl-CoA synthetase (EB2A).

111. The engineered cell of embodiment 108-110 which is bacteria.

112. The transgenic bacteria of embodiment 111 which is *Bacillus*.

113. A method for increasing the conversion of a methanol or ethanol to a dehydrogenated product of the alcohol comprising a step of (a) culturing the engineered cell of any of embodiments 108-112 in a culture medium comprising a methanol or ethanol, where in said culturing the cell provides at least two fold greater conversion of the methanol or ethanol to a dehydrogenated product of the alcohol, as compared to an engineered cell expressing a corresponding alcohol dehydrogenase without amino acid substitution.

114. A method for increasing the conversion of a methanol or ethanol to a dehydrogenated product of the alcohol comprising a step of (a) providing a reaction composition having a pH in the range of 6-8, the composition comprising a non-natural alcohol dehydrogenase of any of embodiments 82-105, where in the composition said culturing the cell provides at least two fold greater conversion of the methanol or ethanol to a dehydrogenated product of the alcohol, as compared to an engineered cell expressing a corresponding alcohol dehydrogenase without amino acid substitution.

115. A method of providing a diol comprising culturing the engineered cell of any of embodiments 108-112 in a culture medium comprising a methanol or ethanol to provide the diol.

116. The method of embodiment 115 wherein the diol is 1,4 butanediol.

117. A method of preparing a polymer comprising obtaining a monomer product produced by the engineered cell or method of any of embodiments 108-116 and polymerizing the monomer to provide a polymeric product.

118. A polymer prepared according to the method of embodiment 117.

119. A method of screening for a non-natural alcohol dehydrogenase having increased activity, optionally at least 2 fold, optionally at least 4 fold or greater activity, compared to its unmodified counterpart, comprising (1) creating one or more non-natural alcohol dehydrogenases selected from SEQ ID NO:1 and non-natural alcohol dehydrogenases having a sequence identity of 45% or greater to SEQ ID NO:1 having a substitution at a position other than an amino acid position selected from group (a) 11, 38, 42, 48, 53, 56, 60, 61, 63, 65, 70, 71, 74, 81, 84, 86, 87, 94, 99, 103, 106, 107, 108, 109, 112, 115, 116, 117, 117, 120, 121, 122, 123, 124, 125, 126, 127, 128, 129, 130, 134, 143, 145, 146, 147, 148, 149, 150, 152, 155, 157, 158, 161, 163, 164, 165, 181, 184, 186, 190, 199, 217, 226, 256, 267, 269, 270, 296, 298, 300, 302, 312, 316, 323, 333, 336, 337, 343, 344, 345, 350, 354, 355, 358, 360, 361, 363 and 379; or of group (b) 38, 60, 71, 87, 99, 103, 107, 108, 109, 115, 116, 117, 121, 122, 123, 124, 125, 126, 127, 128, 129, 130, 134, 143, 146, 149, 150, 157, 158, 163, 164, 267, 270, 345, 355, 360, and 361, or a position corresponding thereto, (2) assay the created enzyme for the activity and (3) selecting those having increased activity, optionally at least 2 fold, optionally at least 4 fold, or greater activity compared to the unmodified counterpart.

EXAMPLES

Assay for Testing Activity of Methanol Dehydrogenase In Vitro

A high-throughput screening assay was used to evaluate lysates for methanol dehydrogenase (MeDH) oxidation activity of methanol and other alcohol substrates. Lysates were prepared by a commercial chemical reagent from *Escherichia coli* cells that contained a plasmid harboring a MeDH library variant and an integrated chromosomal copy of the activator protein. An aliquot of the lysate was applied to a 384-well assay plate. To initiate the alcohol oxidation reaction, a substrate-buffer mix (pH 7.6 or pH 8.5) containing 0.5 M methanol or other alcohol, 0.5 mM NAD, 5 mM $MgCl_2$, 10 M 1-methoxy-5-methylphenazinium methylsulfate (1-methoxy PMS), & 1 mM 3-(4,5-dimethylthiazol-2-yl)-2,5-diphenyltetrazolium bromide (MTT) was added. Initial rates were monitored via absorbance at 560 nm. MeDH variants that showed higher activity than the wild-type control were evaluated for further characterization.

Formaldehyde Assay

A strain lacking frmA, frmB, frmR (the genes responsible for formaldehyde utilization in *E. coli*) was created using Lamba Red recombinase technology. Plasmids expressing methanol dehydrogenases were transformed into the strain, then grown to saturation in LB medium+antibiotic at 37° C. with shaking. Cultures were adjusted by OD and then diluted 1:10 into M9 medium+0.5% glucose+antibiotic and cultured at 37° C. with shaking for 6-8 h until late log phase. Methanol was added to 2% v/v and the cultures were further incubated for 30 min with shaking at 37° C. Cultures were spun down and the supernatant was assayed for formaldehyde produced using DetectX Formaldehyde Detection kit from Arbor Assays, MI according to manufacturer's instructions.

Formate Assay

The assay was developed to evaluate in vivo activity of methanol dehydrogenases by measuring the formate production in a host strain containing the first two steps of the MeOH pathway but lacking formate dehydrogenases (hycE, fdnGHI, fdoGHI, fdhF) that convert formate to $CO_2$. Plasmids expressing methanol dehydrogenases were transformed into this strain. Strains were inoculated from colonies or glycerol stocks in LB+antibiotics in 96-deep well plates. The plates were sealed with breathable culture films and shaken at 37° C. at 800 rpm. Overnight cultures were centrifuged at 5250 rpm for 10 minutes to pellet the cells. Cells were resuspended in 1 ml M9 medium in plates that were sealed with breathable culture films and shaken at 37 degree at 800 rpm. Samples were taken for a time course study and formate concentrations were measured using the formate kit based on instructions provided by the manufacturer.

Assay for Purification of Methanol Dehydrogenases and for Characterizing their Activity Cells expressing methanol dehydrogenase are cultured at 37° C. in LB containing 2 mM $MgSO_4$. Once harvested, cells are lysed in BugBuster Protein Extraction Reagent (Novagen) supplemented with 15 kU/mL lysozyme (Novagen), 25 U/mL bezonase (Novagen), 1× Pierce Protease Inhibitors (Thermo Scientific), 0.5 mM tris(2-carboxyethyl) phosphine hydrochloride, and 2 mM MgSO4. Lysates are clarified via centrifugation and purified on a 5 mL StrepTrap HP column (GE Healthcare Life Sciences). The column is prepared in and washed with 100 mM MOPS pH 7.5, 0.2 M NaCl2, 2 mM $MgSO_4$, 0.5 mM TCEP (buffer A). The purified proteins are eluted with buffer A containing 0.3 mg/mL desthiobiotin.

DNA 2.0 Gene Synthesis

Methanol dehydrogenase gene candidates were synthesized after optimizing for codon usage by DNA 2.0 (Welch et al., PloS One 2009, 4(9):e7002, Design parameters to control synthetic gene expression in *Escherichia coli*).

In Vivo Labeled Assay for Conversion of Methanol to $CO_2$

Strains with functional reductive TCA branch and pyruvate formate lyase deletion were grown aerobically in LB medium overnight, followed by inoculation of M9 high-seed media containing IPTG and aerobic growth for 4 hrs. These strains had methanol dehydrogenase/ACT pairs in the presence and absence of formaldehyde dehydrogenase or formate dehydrogenase. At this time, strains were pelleted, resuspended in fresh M9 medium high-seed media containing 2% $^{13}CH_3OH$, and sealed in anaerobic vials. Head space was replaced with nitrogen and strains grown for 40 hours at 37° C. Following growth headspace was analyzed for 13-$CO_2$. Media was examined for residual methanol as well as BDO and byproducts.

All constructs expressing MeDH mutants and MeDH/ACT pairs grew to slightly lower ODs than strains containing empty vector controls. This is likely due to the high expression of these constructs.

Description of the NAD-Dependent Methanol Dehydrogenase/Activator Protein, its Expression and Use Sequence analysis of the NADH-dependent methanol dehydrogenase from *Bacillus methanolicus* places the enzyme in the alcohol dehydrogenase family III. It does not contain any tryptophan residues, resulting in a low extinction coefficient (18,500 $M^{-1}$, $cm^{-1}$) and should be detected on SDS gels by Coomassie staining.

The enzyme has been characterized as a multisubunit complex built from 43 kDa subunits containing one Zn and 1-2 Mg atoms per subunit. Electron microscopy and sedimentation studies determined it to be a decamer, in which two rings with five-fold symmetry are stacked on top of each other (Vonck et al., J. Biol. Chem. 266, p. 3949-3954, 1991). It is described to contain a tightly but not covalently bound cofactor and requires exogenous $NAD^+$ as $e^-$-acceptor to measure activity in vitro. A strong increase (10-40-fold) of in vitro activity was observed in the presence of an activator protein (Act), which is a homodimer (21 kDa subunits) and contains one Zn and one Mg atom per subunit.

The mechanism of the activation was investigated by Kloosterman et al. (J. Biol. Chem. 277, p. 34785-34792, 2002), showing that Act is a Nudix hydrolase and Hektor et al. (J. Biol. Chem. 277, p. 46966-46973, 2002), demonstrating that mutation of residue S97 to G or T in MeDH changes activation characteristics along with the affinity for the cofactor. While mutation of residues G15 and D88 had no significant impact, a role of residue G13 for stability as well as of residues G95, D100, and K103 for the activity is suggested. Both papers together propose a hypothesis in which Act cleaves MeDH-bound $NAD^+$. MeDH retains AMP bound and enters an activated cycle with increased turnover.

The stoichiometric ratio between Act and MeDH is not well defined in the literature. Kloosterman et al. (J. Biol. Chem. 277, p. 34785-34792, 2002) determine the ratio of dimeric Act to decameric MeDH for full in vitro activation to be 10:1. In contrast, Arfman et al. (J. Biol. Chem. 266, 3955-3960, 1991) determined a ratio of 3:1 in vitro for maximum and a 1:6 ratio for significant activation, but observe a high sensitivity to dilution. Based on expression of both proteins in *Bacillus*, the authors estimate the ratio in vivo to be around 1:17.5. In vitro experiments with purified activator protein (2317A) and methanol dehydrogenase (2315A) have showed the ratio of "act" to methanol dehydrogenase to be 10:1. This in vitro test was done with 5 M methanol, 2 mM NAD and 10 uM methanol dehydrogenase 2315A at pH 7.4.

The sequence of the activator protein (SEQ ID NO: 157) from *Bacillus methanolicus* MGA3 (locus tag: MGA3_09170, GI number: 387591061, Accession number: EIJ83380) used in the assays is shown below:

MGKLFEEKTIKTEQIFSGRVVKLQVDDVELPNGQTSKREIVRHPGAVAVIA

ITNENKIVMVEQYRKPLEKSIVEIPAGKLEKGEDPRITALRELEEETGYEC

EQMEWLISFATSPGFADEIIHIYVAKGLSKKENAAGLDEDEFVDLIELTLD

EALQYIKEQRIYDSKTVIAVQYLQLQEALKNK.

2315 Stability Assay and Data

The thermostability of methanol dehydrogenase 2315A and the corresponding activator protein 2317A were assessed and melting temperatures were found to be 62 and 75° C., respectively. The melting temperatures were measured using a Protein thermal shift assay from Applied biosystems. The assay provides relative thermal stabilities (melting temperatures) of purified proteins. It relies on a proprietary fluorescent dye that binds to hydrophobic regions of denatured proteins upon heating in the RT-PCR machine. The relative melting temperature is calculated from the slope of the fluorescence signal peak.

Current Promoter and Plasmid for Overexpression

Methanol dehydrogenase 2315 was expressed with several constitutive and inducible promoters of varying strengths. The figure below shows the expression levels of two MeDH variants when expressed under three promoters: p119, p104 and p107. The two variants that were expressed were 2315L and 2315B. 2315B was a mutant constituted based on a mutation S97G identified from Hektor et al (ibid).

MDH Protein Concentrations

Methanol dehydrogenase is a very soluble protein. SDS-PAGE analysis of soluble proteins from lysates of *E. coli* strains expressing different variants of the WT 2315A are shown. Specifically, the left panel shows the gel run on the lysates and the right panel shows the gel run on supernatant for the WT enzyme 2315A, compared with the variants 2315L and R, a variant from Hektor et al. called 2315B, and an empty vector.

The cells were lysed using Bugbuster as described previously. The amount of protein was quantified using the Image Lab 3.0 software from BioRad. The WT protein was estimated to be ~27% of the total protein.

Background on Plasmids and Promoters

Vector backbones were obtained from Dr. Rolf Lutz of Expressys www.expressys.de). The vectors and strains are based on the pZ Expression System developed by Dr. Rolf Lutz and Prof. Hermann Bujard (Lutz, R. & Bujard, H. Independent and tight regulation of transcriptional units in *Escherichia coli* via the LacR/O, the TetR/O and AraC/I1-I2 regulatory elements. *Nucleic Acids Res* 25, 1203-1210 (1997)). Art available promoters P119, p104, p107, p119 provided varying levels of enzyme expression as desired. Vectors obtained were pZE13luc, pZA33luc, pZS*13luc and pZE22luc and contained the luciferase gene as a stuffer fragment. To replace the luciferase stuffer fragment with a lacZ-alpha fragment flanked by appropriate restriction enzyme sites, the luciferase stuffer fragment was first removed from each vector by digestion with EcoRI and XbaI. The lacZ-alpha fragment was PCR amplified from pUC19 with the following primers:

lacZalpha-RI
(SEQ ID NO: 155)
5'GACGAATTCGCTAGCAAGAGGAGAAGTCGACATGTCCAATTCACTGGCC

GTCGTTTTAC3' lacZalpha 3'BB
(SEQ ID NO: 156)
5'-GACCCTAGGAAGCTTTCTAGAGTCGACCTATGCGGCATCAGAGCAGA-

3'

This generated a fragment with a 5' end of EcoRI site, NheI site, a Ribosomal Binding Site, a SalI site and the start codon. The 3' end of the fragment contained the stop codon, XbaI, HindIII, and AvrII sites. The PCR product was digested with EcoRI and AvrII and ligated into the base vectors digested with EcoRI and XbaI (XbaI and AvrII have compatible ends and generate a non-site). Because NheI and XbaI restriction enzyme sites generate compatible ends that can be ligated together (but generate a site after ligation that is not digested by either enzyme), the genes cloned into the vectors could be "Biobricked" together openwetware.org/wiki/Synthetic_Biology:BioBricks). Briefly, this method enables joining an unlimited number of genes into the vector using the same 2 restriction sites (as long as the sites do not appear internal to the genes), because the sites between the genes are destroyed after each addition. Initially, expression was low from these vectors, and they were subsequently modified using the Phusion® Site-Directed Mutagenesis Kit (NEB, Ipswich, Mass., USA) to insert the spacer sequence AATTAA between the EcoRI and NheI sites. This eliminated a putative stem loop structure in the RNA that bound the RBS and start codon.

All vectors have the pZ designation followed by letters and numbers indicating the origin of replication, antibiotic resistance marker and promoter/regulatory unit. The origin of replication is the second letter and is denoted by E for ColE1, A for p15A and S for pSC101 (as well as a lower copy number version of pSC101 designated S*)-based origins. The first number represents the antibiotic resistance marker (1 for Ampicillin, 2 for Kanamycin, 3 for Chloramphenicol). The final number defines the promoter that regulated the gene of interest (1 for PLtetO-1, 2 for PLlacO-1 and 3 for PA1lacO-1) and each of these promoters became activated by its corresponding inducer molecule (pLtetO can be induced by tetracycline; pLlacO-1 and pA1lacO-1 can be induced by IPTG). Three base vectors, pZS*13S, pZA33S and pZE13S, were then designed and constructed to serve as "inducible" plasmid vectors.

In addition to the "inducible" promoters mentioned above, a set of "constitutive" promoters were sampled from the Registry (partsregistry.org). Each of these "constitutive" promoters was then introduced into the pZS*13S vector backbone to replace the pA1lacO-1 inducible promoter via Sequence and Ligation Independent Cloning (SLIC) method described by Li & Eledge (Nature Methods 2007, 4:251-256). Of these sampled "constitutive" promoters (p100, p104, p105, p107, p108, p111, p115 & p119), experiments were carried out to establish an order of promoter strength that was verified by protein expression levels. For the work discussed here, we employed both "inducible" and "constitutive" plasmid vectors, modified for the biobricks and SLIC insertions as discussed above. To further fine-tune protein expression levels of some overly expressed proteins, ribosomal binding site (RBS) in between promoter and gene coding sequence was modified accordingly using the RBS calculator (salis.psu.edu/software).

Mutagenesis Techniques—Error Prone-PCR

EpPCR (Pritchard et al., *J Theor. Biol.* 234:497-509 (2005)) introduces random point mutations by reducing the fidelity of DNA polymerase in PCR reactions by the addition of $Mn^{2+}$ ions, by biasing dNTP concentrations, or by other conditional variations. The five step cloning process to confine the mutagenesis to the target gene of interest involves: 1) error-prone PCR amplification of the gene of interest; 2) restriction enzyme digestion; 3) gel purification of the desired DNA fragment; 4) ligation into a vector; 5) transformation of the gene variants into a suitable host and screening of the library for improved performance. This method can generate multiple mutations in a single gene simultaneously, which can be useful to screen a larger number of potential variants having a desired activity. A high number of mutants can be generated by EpPCR, so a high-throughput screening assay or a selection method, for example, using robotics, is useful to identify those with desirable characteristics.

Mutagenesis Techniques—Site Saturation Mutagenesis

In Site Saturation Mutagenesis, the starting materials are a supercoiled dsDNA plasmid containing an insert and two primers which are degenerate at the desired site of mutations (Kretz et al., *Methods Enzymol.* 388:3-11 (2004)). Primers carrying the mutation of interest, anneal to the same sequence on opposite strands of DNA. The mutation is typically in the middle of the primer and flanked on each side by approximately 20 nucleotides of correct sequence. The sequence in the primer is NNN or NNK (coding) and MNN (noncoding) (N=all 4, K=G, T, M=A, C). After extension, DpnI is used to digest dam-methylated DNA to eliminate the wild-type template. This technique explores all possible amino acid substitutions at a given locus (that is, one codon). The technique facilitates the generation of all possible replacements at a single-site with no nonsense codons and results in equal to near-equal representation of most possible alleles. This technique does not require prior knowledge of the structure, mechanism, or domains of the target enzyme. If followed by shuffling or Gene Reassembly, this technology creates a diverse library of recombinants containing all possible combinations of single-site up-mutations. The usefulness of this technology combination has been demonstrated for the successful evolution of over 50 different enzymes, and also for more than one property in a given enzyme.

Combinatorial Mutants

MeDH Structure Model and Structures for Comparison

To design a library of mutations for improving the catalytic rates of 2315, genes of several MeDHs as well as various Fe-dependent ADH genes were aligned. The described structure/function relationships for the Fe-dependent ADHs (40-47% sequence identity to MeDHs) were used to identify regions of functional importance within the MeDH sequence. An alignment of the identified regions is presented in FIG. 4.

Blast search using the MeDH sequence against the PDB structure database found several structures of Fe-dependent alcohol dehydrogenases with sequence identities between 40 and 47%.

Similarities are spread out over the whole length of the protein. Given this similarity to known structures, the MeDH sequence was used to generate a 3-dimensional model using the web-based iTasser structure prediction tool (Roy et al, Nature Protocols, 5: 725-738 (2010)). The following three structures were specifically used for alignment and comparison with the MeDH from *Bacillus*:

3OX4: ADH-2 from *Zymomonas mobilis* (sequence identity 47%)

1RRM: Lactaldehyde reductase from *Escherichia coli* (FucO, sequence identity 43%)

3BFJ: 1,3-PDO oxidoreductase from *Klebsiella pneumoniae* (DhaT, sequence identity 47%)

The *Zymomonas* enzyme was crystallized with bound cofactor and the structure was well analyzed including the annotation of certain amino acid residues for metal, cofactor and proposed substrate binding (EtOH modeled into structure, Moon et al., J. Mol. Biol. 407, p 413-424, 2011). Like the Lactaldehyde reductase (Montella et al., J. Bact. 187, p. 4957-4966, 2005) from *E. coli*, the *Zymomonas* ADH is a homodimer. In contrast, the *Klebsiella* enzyme (Marcal et al., J. Bact. 191, p. 1143-1151, 2009) was found to be a decamer with a structure that resembles the MeDH appearance in electron microscopy studies.

Sequence comparison shows that all four coordination residues of the Fe-dependent ADHs are conserved in the MeDH structure. Two of these four residues are in a histidine-rich sequence (residues 258-290) suggested by Hektor et al. (J. Biol. Chem. 277, p. 46966-46973, 2002) as a putative metal binding site. As Fe and Zn share very similar binding characteristics, the same amino acids responsible for the Fe-binding in the ADHs may coordinate the Zn-atom of MeDH. From the alignment, the following four amino acids are likely to constitute the metal binding site in MeDH (numbering transferred to Genomatica gene ID 2315): D193, H197, H262, H276

Amino acids considered important for cofactor binding in the *Zymomonas* ADH are mostly conserved in the MeDH sequence. The respective residues are listed below for Genomatica gene ID 2315. If the respective amino acid differs, the *Zymomonas* ADH residue is noted in parentheses: D38, D70(N), G97, S98, T137, T138, T146, L148(F), L178

To cast a wide net, residues in a distance of 8 Å or less from the C1 atom of propanediol were identified and are listed together with the annotated *Zymomonas* residues below. Residue numbers were transferred to Genomatica gene ID 2315 and the respective amino acids in the original protein are given in parentheses.

From *Zymomonas* ADH-2: L148(F149), V150(I151), P161(A162), F253(F254), L258(L259), H266(H267), D359 (D360), V360(A361), C361(C362)

From *E. coli* FucO (<8 Å distance): T141(T144), G142 (A145), S143(A146), L148(N151), A149(Y152), H266 (H267)

Mapping of the suggested mutagenesis sites onto the structure model of MeDH shows that the residues selected as target sites line the entrance to the active site of the monomer. Positions 253, 258, 266, and 359 were found to be strictly conserved, suggesting that they are more likely to be essential for function and were therefore eliminated from the list of residues identified for mutations.

For the remaining five residues, amino acids for substitution were selected based on their occurrence in related sequences. Only for position 148 which was annotated with having a role in limiting the substrate size as well as positioning the nicotinamide ring in the active site, a full panel of amino acids (NNK) is proposed. Narrowing down the pool of substitutions in the other four positions made it possible to include additional target sites while maintaining a reasonable library size. The following three sites were added based on their proposed function and location in Fe-dependent ADHs: D70, T145, S147.

When comparing the variation for the respective positions in a sequence alignment it was noted that one of the residues is homolog to residue 160 in an in house tested alcohol dehydrogenase. As a P160G mutation increased the activity of this alcohol dehydrogenase, a glycine was added to the list of substitutions in the respective MeDH position. The table below summarizes the final list of targeted residues and substitutions (positions based on gene 2315A):

| Position | amino acids | Variants |
| --- | --- | --- |
| 70 | D, N | 2 |
| 145 | T, M | 2 |
| 147 | S, R | 2 |
| 148 | NNK | 20 |
| 150 | V, I | 2 |
| 161 | P, A, V, G | 4 |
| 360 | V, A, G | 3 |
| 361 | C, N | 2 |
| | Total | 7680 |

TABLE 1

Amino acids mutations with respect to SEQ ID NO: 1, providing greater than two fold activity when present as single mutations:

| Mutation | In Vitro Activity (Secondary Screen; (Average of triplicate assays) | In Vivo Formaldehyde Activity (fold over wild-type) | Wild-type Amino Acid and Position with respect to 2315 | Position and Substitution with respect to 2315 | Position with respect to 2315 | Top Hits (at least 3x in vitro + 2x in vivo) | x = Top 16 for initial combinatorial library |
| --- | --- | --- | --- | --- | --- | --- | --- |
| D60E | 5.8 | 0.6 | D60 | 60E | 60 | | |
| N87K | 3.0 | 0.6 | N87 | 87K | 87 | | |
| S99T | 3.3 | 0.9 | S99 | 99T | 99 | | |
| A103V | 3.1 | 1.9 | A103 | 103V | 103 | | |
| V109Y | 2.0 | 4.3 | V109 | 109Y | 109 | | |
| R115H | 2.6 | 3.9 | R115 | 115H | 115 | | |
| I116F | 3.4 | 1.5 | I116 | 116F | 116 | | |
| N117D | 2.6 | 2.0 | N117 | 117D | 117 | | |
| G121D | 2.7 | 2.0 | G121 | 121D | 121 | | x |
| G121E | 2.5 | 1.6 | G121 | 121E | 121 | | |
| G121L | 2.7 | 1.3 | G121 | 121L | 121 | | |
| G121M | 2.6 | 1.8 | G121 | 121M | 121 | | |
| G121R | 2.8 | 1.7 | G121 | 121R | 121 | | |
| G121S | 2.8 | 2.6 | G121 | 121S | 121 | | x |
| G121T | 2.7 | | G121 | 121T | 121 | | |
| G121V | 3.9 | 1.5 | G121 | 121V | 121 | | |
| G121W | 2.5 | 1.7 | G121 | 121W | 121 | | |
| G121Y | 3.1 | 1.5 | G121 | 121Y | 121 | | |
| V122P | 2.5 | 2.3 | V122 | 122P | 122 | | |
| N123L | 2.7 | 1.8 | N123 | 123L | 123 | | |
| N123R | 2.7 | 1.6 | N123 | 123R | 123 | | |
| N123Y | 3.0 | 1.8 | N123 | 123Y | 123 | | |
| S124I | 3.4 | 0.9 | S124 | 124I | 124 | | |
| S124L | 2.4 | 1.2 | S124 | 124L | 124 | | |
| V125C | 2.6 | 3.2 | V125 | 125C | 125 | | |
| V125G | 2.6 | 3.3 | V125 | 125G | 125 | | |
| V125W | 2.7 | 3.9 | V125 | 125W | 125 | | |
| E126G | 4.0 | 0.6 | E126 | 126G | 126 | | |
| K127C | 2.6 | 3.9 | K127 | 127C | 127 | | |
| K127R | 2.5 | 3.3 | K127 | 127R | 127 | | |
| P128A | 2.3 | 3.0 | P128 | 128A | 128 | | |
| P128R | 2.4 | 3.3 | P128 | 128R | 128 | | |
| V129A | 3.7 | 1.9 | V129 | 129A | 129 | | |
| V129M | 4.7 | 1.4 | V129 | 129M | 129 | | X |
| V129P | 2.8 | 1.3 | V129 | 129P | 129 | | |
| V129S | 3.0 | 1.5 | V129 | 129S | 129 | | |
| V130F | 2.1 | 1.4 | V130 | 130F | 130 | | |
| V130Y | 2.0 | 2.0 | V130 | 130Y | 130 | | |
| A134T | 4.4 | 0.0 | A134 | 134T | 134 | | |
| A149T | 5.9 | 0.8 | A149 | 149T | 149 | | |
| V150A | 3.0 | 1.2 | V150 | 150A | 150 | | |
| K157N | 3.6 | 0.8 | K157 | 157N | 157 | | |
| V158E | 2.6 | 4.3 | V158 | 158E | 158 | | x |
| V158H | 2.2 | 2.8 | V158 | 158H | 158 | | |
| V158K | 2.0 | 2.6 | V158 | 158K | 158 | | |
| V158W | 2.5 | 4.0 | V158 | 158W | 158 | | |
| D164N | 3.7 | 0.7 | D164 | 164N | 164 | | |
| G270S | 2.8 | 2.9 | G270 | 270S | 270 | | x |
| K345E | 4.1 | 0.6 | K345 | 345E | 345 | | |
| N355D | 3.3 | 1.7 | N355 | 355D | 355 | | x |
| C361R | 3.0 | 0.8 | C361 | 361R | 361 | | |
| D38N | 5.4 | 7.3 | D38 | 38N | 38 | + | |
| P71I | 7.6 | 2.5 | P71 | 71I | 71 | + | |
| P71V | 6.8 | 3.5 | P71 | 71V | 71 | + | |
| G107S | 5.1 | 2.5 | G107 | 107S | 107 | + | x |
| L108V | 6.4 | 3.9 | L108 | 108V | 108 | + | |
| L108W | 7.4 | 4.8 | L108 | 108W | 108 | + | |

TABLE 1-continued

Amino acids mutations with respect to SEQ ID NO: 1, providing greater than two fold activity when present as single mutations:

| Mutation | In Vitro Activity (Secondary Screen; (Average of triplicate assays) | In Vivo Formaldehyde Activity (fold over wild-type) | Wild-type Amino Acid and Position with respect to 2315 | Position and Substitution with respect to 2315 | Position with respect to 2315 | Top Hits (at least 3x in vitro + 2x in vivo) | x = Top 16 for initial combinatorial library |
|---|---|---|---|---|---|---|---|
| N117Q | 3.3 | 4.3 | N117 | 117Q | 117 | + | |
| N123D | 3.0 | 2.0 | N123 | 123D | 123 | + | x |
| N123I | 3.1 | 2.5 | N123 | 123I | 123 | + | X |
| P128S | 3.1 | 3.7 | P128 | 128S | 128 | + | |
| V130I | 3.4 | 2.3 | V130 | 130I | 130 | + | X |
| S143T | 3.8 | 2.4 | S143 | 143T | 143 | + | X |
| T146N | 3.4 | 2.0 | T146 | 146N | 146 | + | x |
| A149L | 4.8 | 3.0 | A149 | 149L | 149 | + | |
| A149M | 4.6 | 2.7 | A149 | 149M | 149 | + | |
| A149V | 4.9 | 2.9 | A149 | 149V | 149 | + | x |
| I163Q | 4.4 | 2.1 | I163 | 163Q | 163 | + | |
| Q267H | 6.3 | 4.3 | Q267 | 267H | 267 | + | X |
| G270M | 4.3 | 4.2 | G270 | 270M | 270 | + | |
| G270Y | 4.2 | 4.2 | G270 | 270Y | 270 | + | |
| V360G | 4.9 | 2.1 | V360 | 360G | 360 | + | x |
| V360K | 4.6 | 2.6 | V360 | 360K | 360 | + | |
| V360R | 4.6 | 3.4 | V360 | 360R | 360 | + | x |
| V360S | 4.5 | 3.5 | V360 | 360S | 360 | + | |

TABLE 2

Additional combination mutations with respect to SEQ ID NO: 1 (generated from rationale design)

| Mutations | In Vitro Activity (fald generation; average of triplicates) | In Vivo Activity (formaldehyde generation) |
|---|---|---|
| D70N, L148G, P161G, V360A | 6.2 | 2.92 |
| D70N, L148G, V360A, C361N | 6.9 | 3.02 |
| D70N, L148V, V150I, P161A, V360G | 6.3 | 3.91 |
| D70N, L148V, V360G | 6.6 | 3.95 |
| D70N, P161A, V360A | 6.2 | 3.93 |
| D70N, P161V, V360G, C361N | 5.6 | 3.95 |
| D70N, V150I, P161A, V360A | 6.1 | 3.69 |
| D70N, V150I, P161V, V360G, C361N | 6.0 | 3.35 |
| E48D, L148V, P161A, V360A | 7.7 | 5.79 |
| L148G, P161A, V360A, C361N | 5.7 | 2.42 |
| L148G, P161A, V360G | 5.6 | 3.0 |
| L148G, P161A, V360G, C361N | 6.1 | 3.00 |
| L148G, P161G, V360A | 7.4 | 3.0 |
| L148G, P161G, V360G, C361N | 6.8 | 2.50 |
| L148G, V360A, C361N | 6.3 | 3.80 |
| L148G, V360G, C361N | 6.6 | 3.67 |
| L148I, P161G, V360G | 5.5 | 3.89 |
| L148I, P161V, V360G | 7.1 | 5.51 |
| L148T, V150I, V360A | 5.7 | 6.92 |
| L148T, V360G | 5.6 | 6.26 |
| L148V, P161A, V360A | 7.5 | 5.7 |
| L148V, V150I, P161A, V360A | 6.4 | 5.7 |
| L148V, V150I, P161A, V360A, C361N | 6.1 | 1.97 |
| L148V, V150I, P161A, V360G | 8.2 | 5.27 |
| L148V, V150I, P161A, V360G, C361N | 6.6 | 4.23 |
| L148V, V150I, P161A, V360G, C361N | 5.9 | 3.80 |
| L148V, V150I, P161G, V360A | 6.6 | 5.14 |
| L148V, V150I, P161V, V360G, C361N | 7.3 | 4.07 |
| L148W, P161A, V360A, C361N | 5.7 | 1.06 |
| N112K, S147R, P161A, V360A | 9.7 | 5.40 |
| P161A, Q217K, V360A, C361N | 6.7 | 4.15 |
| P161A, V360A, C361N | 8.0 | 3.58 |
| P161A, V360G | 7.4 | 4.8 |
| P161V, E358G, V360G | 6.0 | 4.96 |
| P161V, V360A, C361N | 9.7 | 5.2 |
| P161V, V360G | 6.4 | 4.0 |
| P65Q, L148G, V150I, P161A, V360G, C361N | 5.5 | 2.32 |
| S147R, L148A, V150I, P161A, V360G | 5.6 | 4.07 |
| S147R, L148F, V150I, P161G, V360G | 6.7 | 6.0 |
| S147R, L148V, P161G, V360A | 6.3 | 4.4 |
| S147R, L148V, P161V, V360G | 8.9 | 6.15 |
| S147R, L148V, V150I, P161A, C361N | 5.8 | 3.10 |
| S147R, L148V, V150I, P161G, V360G | 6.7 | 4.17 |
| S147R, P161A, V360A | 6.3 | 5.53 |
| S147R, P161A, V360A, C361N | 6.6 | 3.6 |
| S147R, P161A, V360G | 5.7 | 5.22 |
| S147R, P161V, V360G | 10.0 | 5.84 |
| S147R, P161V, V360G, C361N | 5.7 | 2.11 |
| S147R, V150I, P161V, V360A | 5.7 | 5.13 |
| S147R, V150I, V360A, C361N | 5.6 | 4.66 |
| T145M, L148I, V360G | 8.0 | 3.48 |
| V150I, I302V, V360G, C361N | 7.8 | 4.01 |
| V150I, P161A, C361N | 5.8 | 3.42 |
| V150I, P161G, V360A, C361N | 5.6 | 2.88 |
| V150I, P161G, V360G | 5.6 | 4.28 |
| V150I, P161G, V360G, C361N | 7.1 | 3.26 |
| V150I, P161V, C361N | 5.7 | 3.9 |
| V150I, P161V, K354R, V360A, C361N | 8.8 | 4.24 |
| V150I, P161V, V360A, C361N | 6.0 | 5.04 |
| V150I, P161V, V360G, C361N | 5.6 | 4.9 |
| V150I, V360A, C361N | 6.4 | 4.43 |
| V150I, V360G | 6.8 | 6.79 |

TABLE 3

Additional combination mutations with respect to SEQ ID NO: 1 (generated from epPCR)

| Mutations | In Vitro Assay-Average of Triplicates |
|---|---|
| S11T, T74S, G269S, V344A | 5.75 |
| K84R, I163T | 5.38 |
| V122A, I163N | 5.01 |
| G107S, F333L | 4.55 |
| V129M, T152M, G343D | 4.45 |
| I63F, N355K | 4.44 |
| G107S, F333L | 4.42 |
| E86K, S99T, A149V | 4.41 |
| N53I, V158E | 4.38 |
| N355I, K379M | 4.30 |
| H42Q, G107S | 4.08 |
| Q120H, I163N | 4.06 |
| A149V, I323M | 4.04 |
| G107S, F333L | 3.69 |
| D164G, K181R | 3.68 |
| A155V, R298H, N355D | 3.66 |
| N123D, E165G | 3.65 |
| I163F, L186M | 3.65 |
| G121A, T296S | 3.63 |
| I94V, S99P, N123I | 3.62 |
| E126V, V129M, V344G | 3.60 |
| Q120R, S143T | 3.58 |
| G256C, A316V | 3.56 |
| P161Q, G312V | 3.52 |
| L226M, A300T, V360A | 3.49 |
| S337C, E350K, N355D, Q363K | 3.43 |
| D81G, V158E | 3.42 |
| I106L, N117Y, E126V | 3.40 |
| G107S, G121D | 3.36 |
| V61A, V158E | 3.31 |
| N53I, V158E | 3.28 |
| N117Y, T190S | 3.16 |
| S124R, I199V | 3.13 |
| K354M, C361R | 2.97 |
| A184T, C361R | 2.86 |
| E56K, Q267H | 2.85 |
| S124R, E126G | 2.79 |
| T190A, N355K | 2.77 |
| P71T, F333L | 2.75 |
| G107S, F333L | 2.74 |
| N123I, P336L | 2.71 |

TABLE 4

Additional combination mutations with respect to SEQ ID NO: 1:

| Mutation | Average Secondary | in vivo Formaldehyde assay |
|---|---|---|
| D38D/A149V | 5.1 | 3.0 |
| D38N/V163V | 6.6 | 9.9 |
| D73D/L108V | 6.8 | 3.9 |
| G121R/P161S | 4.4 | 2.8 |
| G121R/P161S | 3.9 | 2.8 |
| G121R/P161S | 4.1 | 2.9 |
| N112R/P161S | 7.8 | 3.2 |

TABLE 5

Putative motifs and roles of the amino acid positions with respect to SEQ ID NO: 1.

| Wild-type Sequence | From | To | Length | Rationale |
|---|---|---|---|---|
| DAF | 38 | 40 | 3 | NADH binding |
| D | 70 | 70 | 1 | NADH binding |
| G | 95 | 95 | 1 | Activation |
| GS | 97 | 98 | 2 | NADH & Activation |
| TT | 137 | 138 | 2 | NADH binding |
| TGS | 141 | 143 | 3 | NADH binding |
| TTSLAV | 145 | 150 | 6 | NADH & Substrate binding |
| PVI | 161 | 163 | 3 | Substrate & NADH (956 Gtp) |
| L | 178 | 178 | 1 | NADH binding |
| A | 201 | 201 | 1 | 956 gTp |
| F | 253 | 253 | 1 | Substrate binding |
| L | 258 | 258 | 1 | Substrate binding |
| H | 266 | 266 | 1 | Substrate binding |
| G | 270 | 270 | 1 | 956 gtP |
| DVC | 359 | 361 | 3 | Substrate binding |
| | | | 30 | Total |

TABLE 6

In vivo assays showing formaldehyde (HCHO) production by various NNOMO comprising a plasmid expressing a methanol dehydrogenase

| Accession number | HCHO (μM) |
|---|---|
| Experiment 1 | |
| EIJ77596.1 | >50 |
| EIJ83020.1 | >20 |
| EIJ80770.1 | >50 |
| ZP_10132907.1 | >20 |
| ZP_10132325.1 | >20 |
| ZP_10131932.1 | >50 |
| ZP_07048751.1 | >50 |
| YP_001699778.1 | >50 |
| YP_004681552.1 | >10 |
| ZP_10819291.1 | <1 |
| Empty vector | 2.33 |
| Experiment 2 | |
| EIJ77596.1 | >50 |
| NP_00659.2 | >50 |
| YP_004758576.1 | >20 |
| ZP_09352758.1 | >50 |
| ZP_10129817.1 | >20 |
| YP_001139613.1 | >20 |
| NP_014555.1 | >10 |
| WP_007139094.1 | >10 |
| NP_343875.1 | >1 |
| YP_006863258 | >1 |
| NP_394301.1 | >1 |
| ZP_10750164.1 | >1 |
| YP_023929.1 | >1 |
| ZP_08977641.1 | <1 |
| ZP_10117398.1 | <1 |
| YP_004108045.1 | <1 |
| ZP_09753449.1 | <1 |
| Empty vector | 0.17 |
| Experiment 3 | |
| EIJ77596.1 | >50 |
| NP_561852 | >50 |
| YP_002138168 | >50 |
| YP_026233.1 | >50 |
| YP_001447544 | >50 |
| Metalibrary | >50 |
| YP_359772 | >50 |
| ZP_01220157.1 | >50 |
| ZP_07335453.1 | >20 |
| YP_001337153 | >20 |

TABLE 6-continued

In vivo assays showing formaldehyde (HCHO) production by various NNOMO comprising a plasmid expressing a methanol dehydrogenase

| Accession number | HCHO (μM) |
|---|---|
| YP_694908 | >20 |
| NP_717107 | >20 |
| AAC45651 | >10 |
| ZP_11313277.1 | >10 |
| ZP_16224338.1 | >10 |
| YP_001113612 | >10 |
| YP_004860127 | >10 |
| YP_003310546 | >10 |
| YP_001343716 | >10 |
| NP_717107 | >10 |
| YP_002434746 | >10 |
| Empty vector | 0.11 |
| Experiment 4 | |
| EIJ77596.1 | >50 |
| ZP_10241531.1 | >50 |
| YP_005052855 | >50 |
| ZP_10132907.1 | >50 |
| NP_617528 | >50 |
| NP_617528 | >50 |
| ZP_08977641.1 | >20 |
| YP_237055 | >20 |
| Empty vector | <20 |

TABLE 7

Wild-type enzymology

| | Methanol | | | Ethanol | | | EtOH/MeOH | |
|---|---|---|---|---|---|---|---|---|
| | $k_{cat}$ ($s^{-1}$) | $K_M$ (mM) | $k_{cat}/K_M$ ($s^{-1}$ mM$^{-1}$) | $k_{cat}$ ($s^{-1}$) | $K_M$ (mM) | $k_{cat}/K_M$ ($s^{-1}$ mM$^{-1}$) | $k_{cat}$ ($s^{-1}$) | $k_{cat}/K_M$ ($s^{-1}$ mM$^{-1}$) |
| MeDH *B. methanolicus* (2315A + 2317A) | 0.03 | 70 | $4.3 \times 10^{-4}$ | 0.16 | 209 | $7.7 \times 10^{-4}$ | 5.3 | 1.7 |
| Human ADHB1 (2479B) | 0.27 | 290 | $9.3 \times 10^{-4}$ | 2.85 | 1 | 2.85 | 11 | 3061 |
| *Corynebacterium glutamicum* (2496B) | 0.7 | 3 | 0.23 | 4.8 | 6.8 | 0.71 | 7 | 3 |
| *Geobacillus stearothermophilus* (2480B) | 0.06 | 20 | 0.003 | 1.3 | 82 | 0.016 | 22 | 5 |
| *Saccharomyces cerevisiae* (2497B) | Not available | | | 340 | 17 | 20 | N a | N a |
| *Flavobacterium frigidimaris* (2499B) | Not available | | | 27 | 0.17 | 158 | N a | N a |
| *Escherichia coli* (58) | 0.047 | 2500 | $1.9 \times 10^{-5}$ | 1.5 | 115 | 0.013 | 32 | 699 |
| *Clostridium perfringens* (2430) | 0.009 | 84 | $1.1 \times 10^{-4}$ | 0.73 | 33 | 0.022 | 91 | 232 |
| *Geobacter bemijiensis* (2449) | 0.022 | 88 | $2.5 \times 10^{-4}$ | 0.95 | 72 | 0.013 | 43 | 53 |

TABLE 8

Wild type and variant enzymology

| Variant | $k_{cat}$, min$^{-1}$ | $K_M$, mM | $k_{cat}/K_M$, M$^{-1}$ min$^{-1}$ |
|---|---|---|---|
| Wild-type | 4.9 | 95 | 53 |
| V360R | 12 | 280 | 43 |
| V360G | 22 | 130 | 170 |
| S147R, L148F, V150I, P161G, V360G | 4.4 | 370 | 12 |
| P161V, V360A, C361N | 12 | 180 | 70 |
| S147R, P161A, V360G | 9.9 | 180 | 55 |
| S147R, P161V, V360G | 8.7 | 190 | 47 |
| N112K, S147R, P161A, V360A | 4.2 | 210 | 20 |
| A149V | 7.2 | 410 | 18 |

Activity using methanol was determined.
[a] Assays were performed at pH 7.6, 37° C. in the presence of 2 mM NAD.

TABLE 9

Wild type and variant enzymology

| Variant | $k_{cat}$, min$^{-1}$ | $K_M$, mM | $k_{cat}/K_M$, M$^{-1}$ min$^{-1}$ |
|---|---|---|---|
| Wild-type | 3.8 | 310 | 13 |
| V360R | 3.7 | 210 | 18 |
| V360G | 3.2 | 280 | 12 |
| S147R, L148F, V150I, P161G, V360G | 5.3 | 240 | 23 |
| P161V, V360A, C361N | 52 | 110 | 500 |
| S147R, P161A, V360G | 15 | 190 | 76 |
| S147R, P161V, V360G | 15 | 280 | 55 |
| N112K, S147R, P161A, V360A | 7.8 | 120 | 66 |
| A149V | 2.8 | 460 | 62 |

1,4-Butanediol-dependent steady-state kinetic parameters for wild-type and variant methanol dehydrogenase.[a]
[a] Assays were performed at pH 7.6, 37° C. in the presence of 2 mM NAD.

TABLE 10

Substitution templates

| Tested Activity | AA/NA SEQ ID NO: | GenBankID | GI No. | Organism | AA length | % Identity (global) | % Similarity | # gap |
|---|---|---|---|---|---|---|---|---|
| +++ | 1/2 | EIJ77596.1 | 387585261 | *Bacillus methanolicus* MGA3 | 382 | 100 | 100 | 0 |
| n.d | 3/4 | AAA22593.1 | 143175 | *Bacillus methanolicus* C1 | 381 | 97 | 99 | 0 |
| + | 5/6 | EIJ77618.1 | 387585284 | *Bacillus methanolicus* PB1 | 383 | 93 | 96 | 0 |
| + | 7/8 | EIJ78790.1 | 387586466 | *Bacillus methanolicus* PB1 | 383 | 90 | 93 | 0 |
| + | 9/10 | EIJ80770.1 | 387588449 | *Bacillus methanolicus* MGA3 | 385 | 62 | 79 | 1 |
| ++ | 11/12 | EIJ78397.1 | 387586073 | *Bacillus methanolicus* PB1 | 385 | 61 | 78 | 1 |
| + | 13/14 | EIJ83020.1 | 387590701 | *Bacillus methanolicus* MGA3 | 385 | 61 | 79 | 1 |
| ++ | 15/16 | EFI69743.1 | 298729190 | *Lysinibacillus fusiformis* | 401 | 56 | 74 | 5 |
| + | 17/18 | YP_004860127.1 | 347752562 | *Bacillus coagulans* 36D1 | 386 | 56 | 76 | 1 |
| ++ | 19/20 | YP_001699778.1 | 169829620 | *Lysinibacillus sphaericus* | 402 | 54 | 73 | 5 |
| + | 21/22 | ZP_11313277.1 | 410459529 | *Bacillus azotoformans* LMG 9581 | 386 | 54 | 73 | 1 |
| n.d | 23/24 | ZP_05587334.1 | 257139072 | *Burkholderia thailandensis* E264 | 390 | 54 | 70 | 2 |
| + | 25/26 | YP_004681552.1 | 339322658 | *Cupriavidus necator* N-1 | 390 | 53 | 70 | 2 |
| n.d | 27/28 | AGF87161 | 451936849 | uncultured organism | 393 | 53 | 71 | 3 |
| ++ | 29/30 | YP_002138168.1 | 197117741 | *Geobacter bemidjiensis* Bem | 387 | 52 | 71 | 1 |
| ++ | 31/32 | YP_359772.1 | 78043360 | *Carboxydothermus hydrogenoformans* Z-2901 | 383 | 52 | 72 | 0 |
| + | 33/34 | YP_001343716.1 | 152978087 | *Actinobacillus succinogenes* 130Z | 385 | 51 | 71 | 1 |
| + | 35/36 | ZP_16224338.1 | 421788018 | *Acinetobacter baumannii* Naval-82 | 390 | 51 | 70 | 2 |
| + | 37/38 | AAC45651.1 | 2393887 | *Clostridium pasteurianum* DSM 525 | 385 | 51 | 69 | 1 |
| n.d | 39/40 | YP_007491369.1 | 452211255 | *Methanosarcina mazei* Tuc01 | 386 | 51 | 71 | 1 |
| n.d | 41/42 | YP_002434746 | 218885425 | *Desulfovibrio vulgaris* str. 'Miyazaki F' | 393 | 50 | 70 | 3 |
| ++ | 43/44 | YP_005052855 | 374301216 | *Desulfovibrio africanus* str. Walvis Bay | 393 | 49 | 70 | 3 |
| ++ | 45/46 | NP_561852.1 | 18309918 | *Clostridium perfringens* str. 13 | 385 | 49 | 68 | 1 |
| ++ | 47/48 | YP_001447544 | 156976638 | *Vibrio campbellii* ATCC BAA-1116 | 382 | 49 | 69 | 0 |
| + | 49/50 | YP_001113612.1 | 134300116 | *Desulfotomaculum reducens* MI-1 | 388 | 49 | 70 | 2 |
| n.d | 51/52 | YP_011618 | 46580810 | *Desulfovibrio vulgaris* str. Hildenborough | 393 | 49 | 70 | 3 |

TABLE 10-continued

Substitution templates

| Tested Activity | AA/NA SEQ ID NO: | GenBankID | GI No. | Organism | AA length | % Identity (global) | % Similarity | # gap |
|---|---|---|---|---|---|---|---|---|
| ++ | 53/54 | ZP_01220157.1 | 90412151 | *Photobacterium profundum* 3TCK | 382 | 48 | 69 | 0 |
| ++ | 55/56 | YP_003990729.1 | 312112413 | *Geobacillus* sp. Y4.1MC1 | 384 | 48 | 67 | 1 |
| + | 57/58 | ZP_07335453.1 | 303249216 | *Desulfovibrio fructosovorans* JJ | 393 | 48 | 69 | 3 |
| + | 59/60 | NP_717107 | 24373064 | *Shewanella oneidensis* MR-1 | 382 | 48 | 66 | 0 |
| + | 61/62 | YP_003310546.1 | 269122369 | *Sebaldella termitidis* ATCC 33386 | 384 | 48 | 68 | 1 |
| ++ | 63/64 | ZP_10241531.1 | 390456003 | *Paenibacillus peoriae* KCTC 3763 | 384 | 47 | 67 | 1 |
| + | 65/66 | YP_001337153.1 | 152972007 | *Klebsiella pneumoniae* subsp. *pneumoniae* MGH 78578 | 387 | 47 | 67 | 1 |
| ++ | 67/68 | YP_026233.1 | 49176377 | *Escherichia coli* | 383 | 46 | 64 | 0 |
| + | 69/70 | YP_694908 | 110799824 | *Clostridium perfringens* ATCC 13124 | 382 | 46 | 69 | 0 |
| n.d | 71/72 | YP_725376.1 | 113866887 | *Ralstonia eutropha* H16 | 366 | 46 | 60 | 15 |
| n.d | 73/74 | YP_001663549 | 167040564 | *Thermoanaerobacter* sp. X514 | 389 | 45 | 68 | 2 |
| n.d | 75/76 | EKC54576 | 406526935 | human gut metagenome | 384 | 37 | 55 | 3 |
| n.d | 77/78 | YP_001126968.1 | 138896515 | *Geobacillus themodenitrificans* NG80-2 | 387 | 27 | 44 | 7 |

Percent identity is given based on global alignment to SEQ ID NO: 1.

TABLE 11

Template Polypeptides
Sequences of Template Polypeptides indicating exemplary substitutions, their
positions and their corresponding positions in other template sequences:

```
SEQ
ID
NO:    GI No.     Protein Sequence 1   387585261  MTTNFFIPPASVIGRGAVKEVGTRLKQIGAKKALIVTDAFLHSTG
                 LSEEVAKNIREAGVDVAIFPKAQPDPADTQVHEGVDVFKQENC
                 DSLVSIGGGSSHDTAKAIGLVAANGGRINDYQGVNSVEKPVVP
                 VVAITTTAGTGSETTSLAVITDSARKVKMPVIDEKITPTVAIVDPE
                 LMVKKPAGLTIATGMDALSHAIEAYVAKGATPVTDAFAIQAMK
                 LINEYLPKAVANGEDIEAREKMAYAQYMAGVAFNNGGLGLVH
                 SISHQVGGVYKLQHGICNSVNMPHVCAFNLIAKTERFAHIAELL
                 GENVAGLSTAAAAERAIVALERINKSFGIPSGYAEMGVKEEDIEL
                 LAKNAYEDVCTQSNPRVPTVQDIAQIIKNAM 3     143175   MTNFFIPPASVIGRGAVKEVGTRLKQIGAKKALIVTDAFLHSTGL
                 SEEVAKNIREAGLDVAIFPKAQPDPADTQVHEGVDVFKQENCD
                 ALVSIGGGSSHDTAKAIGLVAANGGRINDYQGVNSVEKPVVPV
                 VAITTTAGTGSETTSLAVITDSARKVKMPVIDEKITPTVAIVDPEL
                 MVKKPAGLTIATGMDALSHAIEAYVAKGATPVTDAFAIQAMKL
                 INEYLPKAVANGEDIEAREAMAYAQYMAGVAFNNGGLGLVHSI
                 SHQVGGVYKLQHGICNSVNMPHVCAFNLIAKTERFAHIAELLGE
                 NVSGLSTAAAAERAIVALERYNKNFGIPSGYAEMGVKEEDIELL
                 AKNAFEDVCTQSNPRVATVQDIAQIIKNAL 5   387585284  MTQRNFFIPPASVIGRGAVKEVGTRLKQIGATKALIVTDAFLHGT
                 GLSEEVAKNIREAGLDAVIFPKAQPDPADTQVHEGVDIFKQEKC
                 DALVSIGGGSSHDTAKAIGLVAANGGRINDYQGVNSVEKPVVP
```

TABLE 11-continued

Template Polypeptides
Sequences of Template Polypeptides indicating exemplary substitutions, their
positions and their corresponding positions in other template sequences:

| SEQ ID NO: | GI No. | Protein Sequence |
|---|---|---|
|  |  | VVAITTTAGTGSETTSLAVITDSARKVKMPVIDEKITPTVAIVDPE LMVKKPAGLTIATGMDALSHAIEAYVAKRATPVTDAFAIQAMK LINEYLPRAVANGEDIEAREAMAYAQYMAGVAFNNGGLGLVHS ISHQVGGVYKLQHGICNSVNMPHVCQFNLIARTERFAHIAELLG ENVSGLSTASAAERAIVALQRYNKNFGIPSGYAEMGVKEEDIEL LANNAYQDVCTLDNPRVPTVQDIAQIIKNAL |
| 7 | 387586466 | MTKTKFFIPSSTVFGRGAVKEVGARLKAIGATKALIVTDAFLHST GLSEEVAKNIREAGLDVVIFPKAQPDPADTQVHEGVEVFKQEKC DALVSIGGGSSHDTAKGIGLVAANGGRINDYQGVNSVEKQVVP QIAITTTAGTGSETTSLAVITDSARKVKMPVIDEKITPTVAIVDPE LMVKKPAGLTIATGMDALSHAIEAYVAKRATPVTDAFAIQAMK LINEYLPKAVANGEDIEAREAMAYAQYMAGVAFNNGGLGLVH SISHQVGGVYKLQHGICNSVVMPHVCQFNLIARTERFAHIAELL GENVSGLSTASAAERTIAALERYNRNFGIPSGYKAMGVKEEDIE LLANNAMQDVCTLDNPRVPTVQDIQQIIKNAL |
| 9 | 387588449 | MKNTQSAFYMPSVNLFGAGSVNEVGTRLAGLGVKKALLVTDA GLHSLGLSEKIAGIIREAGVEVAIFPKAEPNPTDKNVAEGLEAYN AENCDSIVTLGGGSSHDAGKAIALVAANGGTIHDYEGVDVSKK PMVPLIAINTTAGTGSELTKFTIITDTERKVKMAIVDKHVTPTLSI NDPELMVGMPPSLTAATGLDALTHAIEAYVSTGATPITDALAIQ AIKIISKYLPRAVANGKDIEAREQMAFAQSLAGMAFNNAGLGYV HAIAHQLGGFYNFPHGVCNAILLPHVCRFNLISKVERYAEIAAFL GENVDGLSTYEAAEKAIKAIERMARDLNIPKGFKELGAKEEDIET LAKNAMNDACALTNPRKPKLEEVIQIIKNAM |
| 11 | 387586073 | MTNTQSIFYIPSVNLFGPGSVNEVGTRLAGLGVKKALLVTDAGL HGLGLSEKIASIIREAGVEVLIFPKAEPNPTDKNVAEGLEVYNAE NCDSIVTLGGGSSHDAGKGIALVAANGGTIYDYEGVDKSKKP MVPLIAINTTAGTGSELTRFTIITDTERKVKMAIVDKHVTPTLSIN DPELMVGMPPSLTAATGLDALTHAIEAYVSTAATPITDALAIQAI KIISKYLPRAFANGKDMEAREQMAFAQSLAGMAFNNASLGYVH AIAHQFGGFYNFPHGVCNAILLPHVCRFNLISKVERFAEIAALLG ENVAGLSTREAAEKGIKAIERMAKDLNIPRGFKELGAKEEDIVTL AENAMKDATALTNPRKPKLEEVIQIIKNAM |
| 13 | 387590701 | MTNTQSAFFMPSVNLFGAGSVNEVGTRLADLGVKKALLVTDAG LHGLGLSEKISSIIRAAGVEVSIFPKAEPNPTDKNVAEGLEAYNA ENCDSIVTLGGGSSHDAGKAIALVAANGGKIHDYEGVDVSKEP MVPLIAINTTAGTGSELTKFTIITDTERKVKMAIVDKHVTPTLSIN DPELMVGMPPSLTAATGLDALTHAIEAYVSTGATPITDALAIQA KIISKYLPRAVANGKDIEAREQMAFAQSLAGMAFNNAGLGYVH AIAHQLGGFYNFPHGVCNAVLLPYVCRFNLISKVERYAEIAAFL GENVDGLSTYDAAEKAIKAIERMAKDLNIPKGFKELGAKEEDIE TLAKNAMKDACALTNPRKPKLEEVIQIIKNAM |
| 15 | 298729190 | MSDVLKQFVMPKTNLFGPGAIQEVGKRLNDLEVKKTLIVTDEGL HKLGLSEQIANIITAAGIDVAIFPKAEPNPTDQNIEDGISVYHAEN CDSIVSLGGGSAHDAAKGIGLIASNGGRIHDYEGVDKSQNPLVP LIAINTTAGTASEMTRFTIITDTARKVKMAIVDKHVTPLLSINDPE LMIGLPPALTAATGVDALTHAIESFVSTNATPITDACAEKVLQLIP EYLPRAYANGADIEAREQMVYAQFLAGMAFNNASLGYVHAIA HQLGGFYNLPHGVCNAILLPHVCRFNVTARTERFARIAELLGEN VEGLSKRDAAEKAITAIEKLSQDLNIPSGFRELGAKDEDIEILAKN ALLDVCAETNPRKATLEDIKQIITNAMGPIVKKEESLEAVALS |
| 17 | 347752562 | MLTGLRTDFQMPSVNLFGQGTAEEIGNRLKNLGCRRPLIVTDEG LHQLGYSEKIAAYIKEAGLEVAIYPKAEPNPTDKNVEDGLKTYH EENCDSIVSLGGGSAHDCAKGIGLVAANGGKIHDYEGLDRSEK PMVPLVAINTTAGTASEMTKFTIITDTSRKVKMAIVDKHVTPVL SINDPLLMVGMPPSLTAATGLDALTHAVEAYVSTAATPVTDAC AIKAIQIIPQYLPKAVANGNDMEAREQMVYAQYLAGMAFNNAS LGYVHAIAHQFGGFYNLPHGVCNAILLPHVCRFNLIARKERFAEI AVALGEKTDSLSVDEAAEKAITAIERLAAQLNIPKGFKELGAKEE DIEILAQHAMQDACAATNPRKPTQKEVEAIIKAAM |
| 19 | 169829620 | MSDVLKQFVMPKKNLFGPGAIQEVGKHLNDLEVKKTLIVTDEG LHKLGLSEQIANIITAAGIDVAIFPKAEPNPTDQNIEDGIADYHAE SCDSIVSLGGGSAHDAAKGIGLIASNGGRIQDYEGVDKSQNPLV PLIAINTTAGTASEMTRFTIITDTARKVKMAIVDKHVTPLLSINDS ELMIGLPPALTAATGVDALTHAIESFVSTNATPITDACAEKVLQL |

TABLE 11-continued

Template Polypeptides
Sequences of Template Polypeptides indicating exemplary substitutions, their
positions and their corresponding positions in other template sequences:

| SEQ ID NO: | GI No. | Protein Sequence |
|---|---|---|
| | | VPEFLPRAYANGADLEAREQMVYAQFLAGMAFNNASLGYVHAI AHQLGGYYNLPHGVCNAILLPHVCRFNVTARTERFARIAELLGE NVTGLSKRDAAEKAISAIEKLSKDLNIPSGFRELGAKDEDIEILAK NAMLDVCAETNPRKATLDDIKQIITNAMGPIVKKEESLEAVAAL S |
| 21 | 410459529 | MANQKVYGFFMPTVNLMGVGAVNEAGPRIKALGCNKSLLVTD KGLSKMGVAEEIANIIGQAGVEVSIFDGAEPNPTDLNVEAGLKQ YRELGCDSIISLGGGSSHDCAKGIGLVASNGGTIHDYEGVDMSK EPMIPLVAINTTAGTASEMTRFCIITDTSRKIKMAIVDKHTTPLIS INDPILTVKMPAGLTAATGMDALTHAIEAYVSTDATPITDACAL QTIRLVSQNLRAAVANGEDIDARNNMCYAQFLGGMAFNNASLG YVHAIAHQLGGFYNLPHGVCNAVLLPHVERFNLIAKPERFVDIAI ALGENVSGLPTRAAAEIALTAIETLAKDVGIPGSLTELGVKEEDIP LLAENAMRDACSFTNPRKATLDDVQGMIRAAL |
| 23 | 257139072 | MSYLNIAQRTDSFFIPCVTLIGPGCARETGVRAKSLGAKKALIVT DAGLHKMGLSEIVAGHIRDAGLQAVIFAGAEPNPTDVNVHDGV ERFQREGCDFIVSLGGGSSHDCAKGIGLVTAGGGHIRDYEGIDK STVPMTPLISINTTAGTAAEMTRFCIITNSSNHVKMAIVDWRCTP LIAIDDPCLMVAMPPALTAATGMDALTHAVEAYVSTAATPITDA CAEKAIALIGEWLPKAVANGESMEARAAMCYAQYLAGMAFNN ASLGYVHAMAHQLGGFYNLPHGVCNAILLPHVCEFNLIAAPERF ATIASLLGVNTAGSSTVDAARAGHAAIPRLSASIGIPAGLAALGV RVEDHEVMASNAQKDACMLTNPRKATLAQVIAIFAAAM |
| 25 | 339322658 | MTHLNIANRVDSFFIPCVTLFGPGCARETGARARSLGARKALIVT DAGLHKMGLSEVVAGHIREAGLQAVIFPGAEPNPTDVNVHDGV KLFEREECDFIVSLGGGSSHDCAKGIGLVTAGGGHIRDYEGIDK STVPMTPLISINTTAGTAAEMTRFCIITNSSNHVKMAIVDWRCTP LIAIDDPSLMVAMPPALTAATGMDALTHAIEAYVSTAATPITDA CAEKAIVLIAEWLPKAVANGDSMEARAAMCYAQYLAGMAFNN ASLGYVHAMAHQLGGFYNLPHGVCNAILLPHVSEFNLIAAPERY ARIAELLGENIGGLSAHDAAKAAVSAIRTLSTSIGIPAGLAGLGV KADDHEVMASNAQKDACMLTNPRKATLAQVMAIFAAAM |
| 27 | 451936849 | MSLVNYLQLADRTDGFFIPSVTLVGPGCVKEVGPRAKMLGAKR ALIVTDAGLHKMGLSQEIADLLRSEGIDSVIFAGAEPNPTDINVH DGVKVYQKEKCDFIVSLGGGSSHDCAKGIGLVTAGGGHIRDYE GVDKSKVPMTPLIAINTTAGTASEMTRFCIITNTDTHVKMAIVD WRCTPLVAIDDPRLMVKMPPALTAATGMDALTHAVEAYVSTA ATPITDTCAEKAIELIGQWLPKAVANGDWMEARAAMCYAQYL AGMAFNNASLGYVHAMAHQLGGFYNLPHGVCNAILLPHVCQF NLIAATERYARIAALLGVDTSGMETREAALAAIAAIKELSSSIGIP RGLSELGVKAADHKVMAENAQKDACMLTNPRKATLEQVIGIFE AAM |
| 29 | 197117741 | MALGEQTYGFYIPTVSLMGIGSAKETGGQIKALGASKALIVTDK GLSAMGVADKIKSQVEEAGVSAVIFDGAEPNPTDINVHDGVKV YQDNGCDAIISLGGGSSHDCAKGIGMVIGNGGHIRDLEGVNKT TKPMPAFVAINTTAGTASEMTRFCIITNTDTHVKMAIVDWRCTP NVAINDPLLMVGKPAALTAATGMDALTHAVEAYVSTIATPITDA CAIKAIELIAEFLSKAVANGEDLEARDKMAYAEYLAGMAFNNA SLGYVHSMAHQLGGFYNLPHGVCNAILLPAVSQYNLIACPKRFA DIAKALGENIDGLSVTEAGQKAIDRIRTLSASIGIPTGLKALNVKE ADLTIMAENAKKDACQFTNPRKATLEQVVQIFKDAM |
| 31 | 78043360 | MKTYRFYMPPVSLMGIGCLKEAGEEIKKLGFKKALIVTDKVLVK IGLVNKLTEILDNEGIEYVIFDETKPNPTVKNVEDGLKMLKENNC DFLISFGGGSPHDCAKGIGLVATNGGSIKDYEGVNKSAKPMLP LVAVNTTAGTASEMTRFSIITDEDRHVKMAIVDWHVTPIMAVN DPELMVEMPKALTAATGMDALTHAIEAYVSIDATPVTDAAALK AIELIFKYLKRAVENGKDIEARDKMAYAEYLAGVAFNNAGLGY VHAMAHQLGGFYDLPHGVCNAVLLPHVQAYNLQVVPERFIDIA KAMGINVENLTAKEAGEKVLEAIKNLSREIGIPSGLKELGVKEED LKTLAENALKDACGFTNPKQASLDDIIRIFKEAM |
| 33 | 152978087 | MSTYYFLPTRNVFGENAVEEVGTLMKSLGGNNPLIVTDAFLAK NGMADQLAAVLSNAGLKPVIFGGAEPNPTDKNVEEGIVFYNEH GCDSIISLGGGSSHDCAKGIGLIASNGGRIQDYEGVDRSHNAMV PLMAVNTTAGTASEITRFCIITDTARKVKMAIVDWRITPQIAVND PLLMKGMPPSLTAATGMDALTHAIEAYVSTAANPLTDAAALMA |

TABLE 11-continued

Template Polypeptides
Sequences of Template Polypeptides indicating exemplary substitutions, their
positions and their corresponding positions in other template sequences:

| SEQ ID NO: | GI No. | Protein Sequence |
|---|---|---|
| | | ITMIQQYLPKAVANGDYMKARDKMAYAQYLAGIAFNNASLGY VHAMAHQLGGFYNLPHGVCNAILLPYVEEFNLIGNLNRFRDIAK AMGENIDGLCTDDAALKAIGAIRRLSKQVGIPANLQLLGVKPED FDVMAENAMKDVCMLTNPRKATKQQVIEIFQRAYDGD |
| 35 | 421788018 | MAFKNIADQTNGFYIPCVSLFGPGCAKEIGTKAQNLGAKKALIV TDEGLFKFGVADLIASYLTEAGVASHIFPGAEPNPTDINVHNGVN AYNENGCDFIVSLGGGSSHDCAKGIGLVTAGGGHIRDYEGIDK SKVPMTPLIAVNTTAGTASEMTRFCIITNTDTHVKMAIVDWRCT PLIAIDDPKLMIAKPAGLTAATGMDALTHAVEAYVSTAANPITD ACAEKAITMISQWLQPAVANGENIEARDAMSYAQYLAGMAFN NASLGYVHAMAHQLGGFYNLPHGVCNAILLPHVCEFNLIACPD RYAKIAELMGVNTHGLTVTEAAYAAIDAIRKLSSLIGIPSGLTEL GVKTEDLAVMAENAQKDACMLTNPRKANHAQVVEIFKAAL |
| 37 | 2393887 | MRMYDFLAPNVNFMGAGAIKLVGERCKILGGKKALIVTDKFLR NMEDGAVAQTVKYIKEAGIDVAFYDDVEPNPKDTNVRDGLKV YRKENCDLIVTVGGGSSHDCGKGIGIAATHEGDLYDYAGIETL TNPLPPIVAVNTTAGTGSEVTRHCVITNTKTKIKFVIVSWRNLPL VSINDPILMIKKPAGLTAATGMDALTHAIESYVSKDANPVTDAL AIQAIKLIANNLRQAVALGENLEARENMAYASLLAGMAFNNAN LGYVHAMAHQLGGLYDMAHGVANAMLLPHVERYNLISNPKKF ADIAEFMGENIEGLSVMEAAEKAIDAMFRLSKDVGIPASLKEMG VNEGDFEYMAKMALKDGNAFSNPRKGNEKDIVKIFREAF |
| 39 | 452211255 | MIEKMTYTYLNPKIALMGPGCVNGIGTHAKDLGGTKALIVSGKS RHGKELAADIRRILERAGIEAAIFPGADPNPTDTSVMEGADIYRK ENCNMIVAVGGGSPMDCAKAIGIVVYNGGRINDYEGVGKVTR GIPPLITVNTTAGTASEMTSFTIITDTERHIKMAIVDPRITPDVAV NDPELMVSMPPALTAATGMDALTHAVEAYVSTMATPTTDAAAI KAIELISKYLPEAVLHGEDIRARDMMAHAEYLAGIAFNNASLGY VHSMAHQLGGFYDLPHGVCNAILLPYVEMYNKQVCPERFADIA KAMGEKVEGLSPEEAADKAIEAIKKLAAEIGIPSGLKELGAREED LELLAENAMQDVCRLTNPRELSKEDIIEIYRKAL |
| 41 | 218885425 | MAVQEQVYGFFIPSVTLIGIGASKAIPEKIKALGGSKPLIVTDMGI VKAGILKQITDLLDAAKMAYSVYDETIPNPTDDNVHKGVEVYK KNKCDSLITLGGGSSHDCGKGIGLVIANGGKIHDFEGVDKSFKP MPPYVAVNTTAGTASEMTRFCIITDT SRKVKMAIVDWRVTPSIA LDDDPLLMMGMPPALTAATGMDALTHAVEAYVSTIATPMTDAC AEQAITLIATFLRRAVANGRDIEARERMCFAQYLAGMAFNNASL GHVHAMAHQLGGFYDLPHGECNAILLPHVSQFNLIAKLDRFARI AELMGENISGLSVRDAAEKAICAIKRLSADVGIPAGLVALGKRY GKDVKAKDIAIMTKNAQKDACGLTNPRCPTDADVAAIYEAAM |
| 43 | 374301216 | MAVREQVYGFFIPSVTLIGIGASKEIPNKIRDLGGKKPLIVTDQGI VKAGILKMITDHMDKAGMQYSVYDKTIPNPTDNNVAEGVEVY KKEGCDSLITLGGGSSHDCGKGVGLVVSNGGKIHDYEGVDKST KPLPPYVAVNTTAGTASEMTRFCIITDTSRKVKMAIVDWRVTP GIALDDPLLMVGMPPALTAATGMDALTHAVEAYVSTIATPMTD ACAEKAISLIFTFLRRATANGQDIEAREGMCFAQYLAGMAFNNA SLGHVHAMAHQLGGFYDLPHGECNAILLPHVEKYNLIAKVERF GKMAEIMGENIQGMSPRAAAEKCLDAIRQLSQDVGIPSGLIELG KRYGKNVKKEDIDTMTGNAQKDACGFTNPRCPSDKDVKAIYEA AL |
| 45 | 18309918 | MRMYDYLVPSVNFMGANSISVVGERCKILGGKKALIVTDKFLR GLKGGAVELTEKYLKEAGIEVAYYDGVEPNPKDTNVKDGLKIF QDENCDMIVTVGGGSSHDCGKGIGIAATHEGDLYDYAGIETLT NPLPPIVAVNTTAGTASEVTRHCVITNTKTKVKFVIVSWRNLPL VSINDPMLVGKPAGLTAATGMDALTHAVEAYVSKDANPVTD AAAIQAIKLISSNLRQAVALGENLVARENMAYGSLLAGMAFNN ANLGYVHAMAHQLGGLYDMPHGVANAMLLPHVCKYNLISNP QKFADIAEFMGENIEGLSVMDAAQKAIDAMFRLSTDIGIPAKLR DMGVKEEDFGYMAEMALKDGNAFSNPRKGNERDIVEIFKAAF |
| 47 | 156976638 | MTSAFFIPTVNLMGAGCLKDATDSIQSQGFKKGLIVTDKILNQIG VVKQVQDLLAERDVETVVFDGTQPNPTISNVNDGLALLTDNEC DFVISLGGGSPHDCAKGIALVASNGGKIADYEGVDQSAKPMMP LIAINTTAGTASEMTRFCIITDEERHIKMAIVDKHTTPLISVNDPE LMLAKPASLTAATGMDALTHAIEAYVSIAATPITDAVAIKAIELI QAYLRTAVKNGEDLEAREQMAYAQFMAGMAFNNASLGYVHA |

TABLE 11-continued

Template Polypeptides
Sequences of Template Polypeptides indicating exemplary substitutions, their
positions and their corresponding positions in other template sequences:

| SEQ ID NO: | GI No. | Protein Sequence |
|---|---|---|
| | | MAHQLGGFYDLPHGVCNAILLPHVQRYNAQVCPERLRDVAKA MGVNVEDMSAEAGAAAAIDAIVTLAKDVGIPAGIKELGAKLEDI PTLADNALKDACGFTNPKQATHEEISKIFEEAM |
| 49 | 134300116 | MTVGEQVFGYFIPTVNLMGVGAHKEIPDQVKVLGGSNVLIVTD AFLGRPGGMADDIKGMLEAENIKVTIYAGAEPNPTDVNVHDGL KVYQECGADMILSLGGGSHDCAKGIGIVATNGGNIRDYEGIN KSSKAMPPFIAVNTTAGTASEMTRFCIITNTSNHVKMAIVDWRC TPNIAINDPLLMAGMPPALTAATGMDALTHAIEAYVSVAATPVT DSAALMAIKLISQYLRAAVANGENMEARDKMAYAEFLGGMAF NNASLGYVHAMAHQLGGFYNLPHGVCNAILLPHVEAFNLIACP ERFVDIAVAMGENVEGLSVRDAADKALSAIRKLSADVGIPAGLT ELGVKEEDLKTMAENAMKDAC**ALTNPRKATLNDIVGIYKTAL |
| 51 | 46580810 | MAVQEQVYGFFIPRVTLIGIGASKAIPEKIKALGGSKPLIVTDMGI VKAGILKQITDLLDAAKMAYSVYDETIPNPTDDNVHKGVDVYK KNKCDSLITLGGGSHDCGKGIGLVVANGGKIHDFEGVDKSTQ RMPPYLAVNTTAGTASEMTRFCIITDTSRKVKMAIVDWRVTPNI ALDDPLLMLGMPPALTAATGMDALTHAVEAYVSTIATPMTDAC AEQAITLIATFLRRAVANGQDLEARERMCFAQYLAGMAFNNAS LGHVHAMAHQLGGFYDLPHGECNAILLPHVSKFNLIAKLDRYA RIAQLMGENIAGLSTREAAERAISAIKCLSTDVGIPAGLVALGKR YGKDVKAADIAIMTKNAQKDAC**GLTNPRCPTDADVAAIYEAAL |
| 53 | 90412151 | MSSAFFIPSVNLMGAGCLTEAADAVKAHGFKKALIVTDKVLNQI GVVKQVVDLLAERNVEAVVFDGTQPNPTMGNVEAGLALLKAN ECDFVISLGGGSPHDCAKGIALVASNGGSISDYEGVDVSAKPQL PLVAINTTAGTASEMTRFCIITDEARHIKMAIVDKNTTPLMSVND PELMLAKPASLTAATGMDALTHAIEAYVSTAATPITDAVAIKAM ELIQAHLRTAVNDGQNLEAREQMAYAQFMAGMAFNNASLGYV HAMAHQLGGFYDLPHGVCNAVLLPHVQRYNAKVCPERLRDVA KAMGVNVEAMTADQGADAALEAIQVLSKDVGIPAGLKDLGAK NEDISILADNALKDAC**GFTNPKQATHEEISEIFAAAM |
| 55 | 312112413 | M NAHVFYVPSTNLMGRGCLAKVGPFIKEFGEKKALVVTDKFL HKSGIAGKVLAVLDEIGVNYVVYDDVKPNPTTKNVYAGADLFK KNECDFLVSVGGGSPQDTAKAIGLYVTNGGDIRDYEGVNKTK NKSVPIVAVNTTAGTSSEFTINYVITDEERNVKMVMVDKNSLVT ISVNDPELMVDKPAALTAATGMDALTHAIEAVVTPGSYTVTDA TALAAIEIIFNYLPRAVKNGHDIEAREQMAYAMELVGIAFNNAG LGMVHAMAHQLGGMYDLPHGVCNAMLLPIVERENAKRDPRKF RAIAKAAGIDVTGKTDEQCAEEVIEAIKALSREIGIPSKLSELGVD EVDLEKLANNALKDACAPGNPFQPTKEEVISMFKEIL |
| 57 | 303249216 | MAVREQVYGFFIPSVTLIGIGAAKQIPEKIKALGGTKPLIVTDKGV VKVGVCKMITDLLDAAGMKYHIYDETIPNPTDENVHKGVEVYK KEGCDSLITLGGGSHDCGKGIGLVISNGGKIHDYEGVDKSSKP FMPYLAVNTTAGTASEMTRFCIITDLSRHVKMAIVDWRVTPHIA IDDPVLMVGMPPALTASTGMDALTHAEAFVSTIANPMTDACAI EAIKLIFKYLRKAVANGQDMEAREGMCFAEYLAGMAFNNASLG HVHAMAHQLGGFYDLPHGECNAILLPHVESYNLIAKVEKFAEM AKIMGENIEGMAPRDAAELCLKAIRQLSVDVGIPAGLVELGKRY GKDVKAADIPTMTGNAQKDAC**GLTNPRCPTDKDVAAIYTAAL |
| 59 | 24373064 | MAAKFFIPSVNVLGKGAVDDAIGDIKTLGFKRALIVTDKPLVNIG LVGEVAEKLGQNGITSTVFDGVQPNPTVGNVEAGLALLKANQC DFVISLGGGSPHDCAKGIALVATNGGSIKDYEGLDKSTKPQLPL VAINTTAGTASEMTRFCIITDEARHIKMAIVDKHTTPILSVNDPE LMLKKPASLTAATGMDALTHAVEAYVSIAANPITDACAIKAIELI QGNLVNAVKQGQDIEAREQMAYAQFLAGMAFNNASLGYVHA MAHQLGGFYDLPHGVCNALLLPHVQEYNAKVVPHRLKDIAKA MGVDVAKMTDEQGAAAAITAIKTLSVAVNIPENLTLLGVKAEDI PTLADNALKDAC**GFTNPKQATHAEICQIFTNAL |
| 61 | 269122369 | MKVSRRIYWPAVTLIGPGCVKEIGGDIKDLGLKKALVVTDNVLV KIGVVKKVTDVLDESGINYVVVDDIQPNPTMKNIHDGLNTYKSE NCDFVISIGGGSPQDAGKAIGLLATNGGEIKDYEGINMSKHHS VPIIAINTTAGTASEVTINYVITNEDTHIKMVMVDKNCLASIAVS DPELMTGKPADLTAATGMDALTHAIEAYVSTGAYELTDVLALE AVKLIGESLEDAVKDGNNIEARSKMAYASYIAGMSFNNAGLGY VHSMAHQLGG**FYNLPHGVCNAILLPHVEKFNSANTGDKLRKVA |

TABLE 11-continued

Template Polypeptides
Sequences of Template Polypeptides indicating exemplary substitutions, their
positions and their corresponding positions in other template sequences:

| SEQ ID NO: | GI No. | Protein Sequence |
|---|---|---|
| | | EILGENVEGLSVEEANAKAIEAIMKLSERVGIPKGLKELGVKEED FKVMAENALKDVCAGTNPREVTLEDTIALYKEAL |
| 63 | 390456003 | MTGTSKFMMPGMSLMGSGALADAGTEIGKLGYTNALIVTDKPL VDIGIVKKVTSVLESINVKSVVYSGTQPNPTVTNVNEGLELLSQS KCDFIISLGGGSPHDCAKGIALLASNGGQIGDYEGVDKSTKPSF PLIAINTTAGTASEMTMFCIITDEERHIKMAIVDNHTTPLIAVNDP DLMMAMPKSLTAATGMDALTHSIEAYVSTNATPITDACAIKAIE LIRDNLARAVDDGNDVEARSQMAYAEFLAGMAENNAGLGFVH AMAHQLGGFYNLPHGVCNAILLPHVERYNAKASAERLTDIARA LGENTDGVTPEQGANLALQAIEKLAKRVNIPSGLEELGVKREDF TVLAANALKDACGVTNPVQPTQQEVIAIFEQAM |
| 65 | 152972007 | MSYRMFDYLVPNVNFFGPNAISVVGERCQLLGGKKALLVTDKG LRAIKDGAVDKTLHYLREAGIEVAIFDGVEPNPKDTNVRDGLAV FRREQCDIIVTVGGGSPHDCGKGIGIAATHEGDLYQYAGIETLT NPLPPIVAVNTTAGTASEVTRHCVLTNTETKVKFVIVSWRNLPS VSINDPLLMIGKPAALTAATGMDALTHAVEAYISKDANPVTDAA AMQAIRLIARNLRQAVALGSNLQARENMAYASLLAGMAFNNA NLGYVHAMAHQLGGLYDMPHGVANAVLLPHVARYNLIANPEK FADIAELMGENITGLSTLDAAEKAIAAITRLSMDIGIPQHLRDLGV KEADFPYMAEMALKDGNAFSNPRKGNEQEIAAIFRQAF |
| 67 | 49176377 | MAASTFFIPSVNVIGADSLTDAMNMMADYGFTRTLIVTDNMLT KLGMAGDVQKALEERNIFSVIYDGTQPNPTTENVAAGLKLLKE NNCDSVISLGGGSPHDCAKGIALVAANGGDIRDYEGVDRSAKP QLPMIAINTTAGTASEMTRECIITDEARHIKMAIVDKHVTPLLSV NDSSLMIGMPKSLTAATGMDALTHAIEAYVSIAATPITDACALK AVTMIAENLPLAVEDGSNAKAREAMAYAQFLAGMAFNNASLG YVHAMAHQLGGFYNLPHGVCNAVLLPHVQVFNSKVAAARLRD CAAAMGVNVTGKNDAEGAEACINAIRELAKKVDIPAGLRDLNV KEEDFAVLATNALKDAC**GFTNPIQATHEEIVAIYRAAM |
| 69 | 110799824 | MSYKFFMPAISLMGADCLKDAGDQVGELGEKKALIVTDKVLGQ IGIVKKVTDVLDNKNIEYAIYDETKPNPTVKNVNDGLALLKEKE CDFVISLGGGSAHDCAKGIALLATNGGEIKDYEGVDKSKKPQL PMVGINTTAGTGSEMTLFAIITDEERHIKMALVDKHLTPIIAVND PILMLAMPKSLTAATGMDALTHAIEAYVSTAATPITDACAEKAIE LISNYLVNAVENGQDVEARDMMAYAEYLAGMAFNNASLGYVH AMAHQLGGFYNLPHGVCNAILLPHVQEYNKSTSASRLAKIAKI MGGNIEGLTDEQGADLCIDMIKSLSQTIGIPEGLGVLGVKESDFE TLATNALNDACSLTNPRKGNLEEVIAIFKKAM |
| 71 | 113866887 | MRARPARAPKRKAQERPSSSRMPACTRWGYPKPSRGTSARQGF RPLIFPGAEPNPTDVNVHDGVKLFEQEGCDFIVSLGGGSSHDCA KGIGLVTAGGGHIRDYEGIDKSTVPMTPLISINTTAGTAAEMTR FCIITNSSNHVKMAIVDWRCTPLIADDPRLMVAMPPALTAATG MDALTHAVEAYVSTAATPITDACAEKAIALIGEWLPKAVANGN SLEARAAMCYAQYLAGMAFNNASLGYVHAMAHQLGGLYNLP HGVCNAILLPHVSEFNLIAAPERFAKIAELLGENVASLSTSDAAK AAISAIRALAASIGIPAGLASLGVKAEDHEVMAHNAQKDAC**MLT NPRRATTAQVIAIFAAAM |
| 73 | 167040564 | MKIFKFHMPPINLIGVGCLKDVGREIKKLGFKKGIIVTDKVLVRA GLVNNVISVLEEEGIEYVVFDETKPNPTIKNVTNGLKLLIENKCD FIISCGGGSAHDCAKGIGLIAKEKNFIDEVERLDKVKCGGWNSA LLLPLVAINTTAGTGSEVTKFAIITDEEKRIKMPIVDWRITPLIAV NDPLLMIGMPKSLTAASGMDALTHAIEAYISIDANPFTDALALK AIEIIFNYLKRAVENGNDIEAREKMAYAEFLAGIAFNNAGLGYV HAMAHQLGGFYDLPHGVCNAVLLPHVLEYNLEAVQNKLIYIAK AMGIDVDKLTTKEIGGKIIESINQLSQEIGIPSRLKELGVKEEDIKE LSQNALKDVCGFTNPKKATLEDIINIFKSAM |
| 75 | 406526935 | MGNRIILNGTSYFGRGARENVITELRNRNFTKALVVTDKNLLDA HVTNLVTDVLDKNDFSYQIYSDIKPNPTTLNVQEGVTFCRNSKA DVIIAVGGGSAIDTAKAISIIMTNPEHFDVISLDGAVETKNAGMP IIALPTTAGTAAEVTINYVITNPVGPKKMVCVDPHDIPIVAIIDQD LMEKMPKSLAASTGMDALTHAMEGYTTKAAWLMTDMFHLNA MALIYKNLEKAVNLKDRDAIDNVGYGQYIAGMGFSNVGLGIVH SMAHSLGAFFDTPHGLANALLLPHVLKFNGKICPDLFRNMGRA MGLDMDNLTDDEAVDKVVDAVRSLAIKIGIPQTLKEIGIKKEDL PMLAHQAIDDVCTAGNPRNVTEQDILALYQEAYE |

TABLE 11-continued

Template Polypeptides
Sequences of Template Polypeptides indicating exemplary substitutions, their
positions and their corresponding positions in other template sequences:

| SEQ ID NO: | GI No. | Protein Sequence |
|---|---|---|

77  138896515  MQNFTFRNPTKLIFGRGQIEQLKEEVPKYGKKVLLVYGGGSIKR
NGLYDEVMSLLTDIGAEVVELPGVEPNPRLSTVKKGVDICRREG
IEFLLAVGGSVIDCTKAIAAGAKFDGDPWEFITKKATVTEALP
FGTVLTLAATGSEMNAGSVITNWETKEKYGWGSPVTFPQFSILD
PTYTMTVPKDH

Val Val Pro Val Val Ala Ile Thr Thr Thr Ala Gly Thr Gly Ser Glu
    130                 135                 140

Thr Thr Ser Leu Ala Val Ile Thr Asp Ser Ala Arg Lys Val Lys Met
145                 150                 155                 160

Pro Val Ile Asp Glu Lys Ile Thr Pro Thr Val Ala Ile Val Asp Pro
                165                 170                 175

Glu Leu Met Val Lys Lys Pro Ala Gly Leu Thr Ile Ala Thr Gly Met
                180                 185                 190

Asp Ala Leu Ser His Ala Ile Glu Ala Tyr Val Ala Lys Gly Ala Thr
            195                 200                 205

Pro Val Thr Asp Ala Phe Ala Ile Gln Ala Met Lys Leu Ile Asn Glu
    210                 215                 220

Tyr Leu Pro Lys Ala Val Ala Asn Gly Glu Asp Ile Glu Ala Arg Glu
225                 230                 235                 240

Lys Met Ala Tyr Ala Gln Tyr Met Ala Gly Val Ala Phe Asn Asn Gly
                245                 250                 255

Gly Leu Gly Leu Val His Ser Ile Ser His Gln Val Gly Gly Val Tyr
                260                 265                 270

Lys Leu Gln His Gly Ile Cys Asn Ser Val Asn Met Pro His Val Cys
            275                 280                 285

Ala Phe Asn Leu Ile Ala Lys Thr Glu Arg Phe Ala His Ile Ala Glu
    290                 295                 300

Leu Leu Gly Glu Asn Val Ala Gly Leu Ser Thr Ala Ala Ala Ala Glu
305                 310                 315                 320

Arg Ala Ile Val Ala Leu Glu Arg Ile Asn Lys Ser Phe Gly Ile Pro
                325                 330                 335

Ser Gly Tyr Ala Glu Met Gly Val Lys Glu Glu Asp Ile Glu Leu Leu
                340                 345                 350

Ala Lys Asn Ala Tyr Glu Asp Val Cys Thr Gln Ser Asn Pro Arg Val
            355                 360                 365

Pro Thr Val Gln Asp Ile Ala Gln Ile Ile Lys Asn Ala Met
    370                 375                 380

<210> SEQ ID NO 2
<211> LENGTH: 1149
<212> TYPE: DNA
<213> ORGANISM: Bacillus methanolicus MGA3

<400> SEQUENCE: 2
atgacaacaa actttttcat tccaccagcc agcgtaattg acgcggtgc agtaaaggaa      60 gtaggaacaa gacttaagca aattggagct aagaaagcgc ttatcgttac agatgcattc    120
cttcacagca caggtttatc tgaagaagtt gctaaaaaca ttcgtgaagc tggcgttgat    180
gttgcgattt tcccaaaagc tcaaccagat ccagcagata cacaagttca tgaaggtgta    240
gatgtattca acaagaaaaa ctgtgattca cttgtttcta tcggtggagg tagctctcac    300
gatacagcta aagcaatcgg tttagttgca gcaaacggcg aagaatcaa tgactatcaa     360 ggtgtaaaca gcgtagaaaa accagtcgtt ccagtagttg caatcactac aacagctggt    420
actggtagtg aaacaacatc tcttgcggtt attacagact ctgcacgtaa agtaaaaatg    480
cctgttattg atgagaaaat tactccaact gtagcaattg ttgacccaga attaatggtg    540
aaaaaaccag ctggattaac aatcgcaact ggtatggatg cattgtccca tgcaattgaa    600
gcatatgttg caaaaggtgc tacaccagtt actgatgcat tgctattca gcaatgaaa     660 cttatcaatg aatacttacc aaaagcggtt gcgaacggag aagacatcga agcacgtgaa    720

```
aaaatggctt atgcacaata catggcagga gtggcattta acaacggtgg tttaggacta      780
gttcactcta tttctcacca agtaggtgga gtttacaaat tacaacacgg aatctgtaac      840
tcagttaata tgccacacgt ttgcgcattc aacctaattg ctaaaactga gcgcttcgca      900
cacattgctg agcttttagg tgagaatgtt gctggcttaa gcactgcagc agctgctgag      960
agagcaattg tagctcttga aagaatcaac aaatccttcg gtatcccatc tggctatgca     1020
gaaatgggcg tgaaagaaga ggatatcgaa ttattagcga aaaacgcata cgaagacgta     1080
tgtactcaaa gcaacccacg cgttcctact gttcaagaca ttgcacaaat catcaaaaac     1140
gctatgtaa                                                             1149
```

<210> SEQ ID NO 3
<211> LENGTH: 381
<212> TYPE: PRT
<213> ORGANISM: Bacillus methanolicus C1

<400> SEQUENCE: 3

```
Met Thr Asn Phe Phe Ile Pro Pro Ala Ser Val Ile Gly Arg Gly Ala
1               5                   10                  15

Val Lys Glu Val Gly Thr Arg Leu Lys Gln Ile Gly Ala Lys Lys Ala
            20                  25                  30

Leu Ile Val Thr Asp Ala Phe Leu His Ser Thr Gly Leu Ser Glu Glu
        35                  40                  45

Val Ala Lys Asn Ile Arg Glu Ala Gly Leu Asp Val Ala Ile Phe Pro
    50                  55                  60

Lys Ala Gln Pro Asp Pro Ala Asp Thr Gln Val His Glu Gly Val Asp
65                  70                  75                  80

Val Phe Lys Gln Glu Asn Cys Asp Ala Leu Val Ser Ile Gly Gly Gly
                85                  90                  95

Ser Ser His Asp Thr Ala Lys Ala Ile Gly Leu Val Ala Ala Asn Gly
            100                 105                 110

Gly Arg Ile Asn Asp Tyr Gln Gly Val Asn Ser Val Glu Lys Pro Val
        115                 120                 125

Val Pro Val Val Ala Ile Thr Thr Thr Ala Gly Thr Gly Ser Glu Thr
    130                 135                 140

Thr Ser Leu Ala Val Ile Thr Asp Ser Ala Arg Lys Val Lys Met Pro
145                 150                 155                 160

Val Ile Asp Glu Lys Ile Thr Pro Thr Val Ala Ile Val Asp Pro Glu
                165                 170                 175

Leu Met Val Lys Lys Pro Ala Gly Leu Thr Ile Ala Thr Gly Met Asp
            180                 185                 190

Ala Leu Ser His Ala Ile Glu Ala Tyr Val Ala Lys Gly Ala Thr Pro
        195                 200                 205

Val Thr Asp Ala Phe Ala Ile Gln Ala Met Lys Leu Ile Asn Glu Tyr
    210                 215                 220

Leu Pro Lys Ala Val Ala Asn Gly Glu Asp Ile Glu Ala Arg Glu Ala
225                 230                 235                 240

Met Ala Tyr Ala Gln Tyr Met Ala Gly Val Ala Phe Asn Asn Gly Gly
                245                 250                 255

Leu Gly Leu Val His Ser Ile Ser His Gln Val Gly Gly Val Tyr Lys
            260                 265                 270

Leu Gln His Gly Ile Cys Asn Ser Val Asn Met Pro His Val Cys Ala
        275                 280                 285
```

Phe Asn Leu Ile Ala Lys Thr Glu Arg Phe Ala His Ile Ala Glu Leu
            290                 295                 300

Leu Gly Glu Asn Val Ser Gly Leu Ser Thr Ala Ala Ala Glu Arg
305                 310                 315                 320

Ala Ile Val Ala Leu Glu Arg Tyr Asn Lys Asn Phe Gly Ile Pro Ser
                325                 330                 335

Gly Tyr Ala Glu Met Gly Val Lys Glu Asp Ile Glu Leu Leu Ala
            340                 345                 350

Lys Asn Ala Phe Glu Asp Val Cys Thr Gln Ser Asn Pro Arg Val Ala
                355                 360                 365

Thr Val Gln Asp Ile Ala Gln Ile Ile Lys Asn Ala Leu
            370                 375                 380

<210> SEQ ID NO 4
<211> LENGTH: 1120
<212> TYPE: DNA
<213> ORGANISM: Bacillus methanolicus C1

<400> SEQUENCE: 4

```
atgacaaact ttttcattcc accagccagc gtaattggac gaggtgcagt aaaggaagta    60
ggaacaagac ttaagcaaat tggagctaag aaagcgctta tcgttacaga tgcatttctt   120
catagcacag gtttatctga agaagttgct aaaaacattc gtgaagctgg ccttgatgtt   180
gcgattttcc caaagctca accagatcca gcagatacac aagttcatga aggtgtagat   240
gtattcaaac aagaaaactg tgatgcactt gtttctatcg gtggaggtag ctctcacgat   300
acagctaaag caatcggttt agttgcagca acggcggaa gaatcaatga ctatcaaggt   360
gtaaacagtg tagaaaaacc agtcgttcca gtagttgcaa tcactacaac agctggtact   420
ggtagtgaaa caacatctct tgcagttatt acagactctg cacgtaaagt aaaaatgcct   480
gttattgatg agaaaattac tccaactgta gcaattgttg acccagaatt aatggtgaaa   540
aaaccagctg gattaacaat cgcaactggt atggacgcat atcacacgc aattgaagca   600
tatgttgcaa aggtgctac accagttact gatgcatttg caattcaagc aatgaaactc   660
atcaatgaat acttaccaaa agcggtggca acggagaag acatcgaagc acgtgaagca   720
atggcttatg cacaatacat ggcaggagtg gcatttaaca cggtggttt aggattagta   780
cactctattt ctcaccaagt aggtggagtt acaaaattac aacacggaat ctgtaactca   840
gttaatatgc cacacgtttg cgcattcaac ctaattgcta aaactgagcg cttcgcacac   900
attgctgagc ttttaggcga gaatgtttct ggcttaagca ctgcagcagc tgctgagaga   960
gcaattgtag cgcttgaacg ctataacaaa aacttcggta tcccatctgg ctatgcagaa  1020
atgggcgtga agaagagga tatcgaatta ttagcgaaaa acgcattcga agacgtatgt  1080
actcaaagca acccacgtgt tgctacagtt caagacattg                        1120
```

<210> SEQ ID NO 5
<211> LENGTH: 383
<212> TYPE: PRT
<213> ORGANISM: Bacillus methanolicus PB1

<400> SEQUENCE: 5

Met Thr Gln Arg Asn Phe Phe Ile Pro Pro Ala Ser Val Ile Gly Arg
1               5                   10                  15

Gly Ala Val Lys Glu Val Gly Thr Arg Leu Lys Gln Ile Gly Ala Thr
            20                  25                  30

```
Lys Ala Leu Ile Val Thr Asp Ala Phe Leu His Gly Thr Gly Leu Ser
         35                  40                  45

Glu Glu Val Ala Lys Asn Ile Arg Glu Ala Gly Leu Asp Ala Val Ile
 50                  55                  60

Phe Pro Lys Ala Gln Pro Asp Pro Ala Asp Thr Gln Val His Glu Gly
 65                  70                  75                  80

Val Asp Ile Phe Lys Gln Glu Lys Cys Asp Ala Leu Val Ser Ile Gly
                 85                  90                  95

Gly Gly Ser Ser His Asp Thr Ala Lys Ala Ile Gly Leu Val Ala Ala
             100                 105                 110

Asn Gly Gly Arg Ile Asn Asp Tyr Gln Gly Val Asn Ser Val Glu Lys
         115                 120                 125

Pro Val Val Pro Val Val Ala Ile Thr Thr Thr Ala Gly Thr Gly Ser
130                 135                 140

Glu Thr Thr Ser Leu Ala Val Ile Thr Asp Ser Ala Arg Lys Val Lys
145                 150                 155                 160

Met Pro Val Ile Asp Glu Lys Ile Thr Pro Thr Val Ala Ile Val Asp
                 165                 170                 175

Pro Glu Leu Met Val Lys Lys Pro Ala Gly Leu Thr Ile Ala Thr Gly
             180                 185                 190

Met Asp Ala Leu Ser His Ala Ile Glu Ala Tyr Val Ala Lys Arg Ala
         195                 200                 205

Thr Pro Val Thr Asp Ala Phe Ala Ile Gln Ala Met Lys Leu Ile Asn
    210                 215                 220

Glu Tyr Leu Pro Arg Ala Val Ala Asn Gly Glu Asp Ile Glu Ala Arg
225                 230                 235                 240

Glu Ala Met Ala Tyr Ala Gln Tyr Met Ala Gly Val Ala Phe Asn Asn
                 245                 250                 255

Gly Gly Leu Gly Leu Val His Ser Ile Ser His Gln Val Gly Gly Val
             260                 265                 270

Tyr Lys Leu Gln His Gly Ile Cys Asn Ser Val Asn Met Pro His Val
         275                 280                 285

Cys Gln Phe Asn Leu Ile Ala Arg Thr Glu Arg Phe Ala His Ile Ala
    290                 295                 300

Glu Leu Leu Gly Glu Asn Val Ser Gly Leu Ser Thr Ala Ser Ala Ala
305                 310                 315                 320

Glu Arg Ala Ile Val Ala Leu Gln Arg Tyr Asn Lys Asn Phe Gly Ile
                 325                 330                 335

Pro Ser Gly Tyr Ala Glu Met Gly Val Lys Glu Asp Ile Glu Leu
             340                 345                 350

Leu Ala Asn Asn Ala Tyr Gln Asp Val Cys Thr Leu Asp Asn Pro Arg
         355                 360                 365

Val Pro Thr Val Gln Asp Ile Ala Gln Ile Ile Lys Asn Ala Leu
370                 375                 380

<210> SEQ ID NO 6
<211> LENGTH: 1152
<212> TYPE: DNA
<213> ORGANISM: Bacillus methanolicus PB1

<400> SEQUENCE: 6
atgacgcaaa gaaactttt cattccacca gctagcgtaa ttggacgcgg cgctgtaaaa    60
gaagtaggaa caagacttaa gcaaattgga gctacaaaag cacttatcgt tacagatgca   120
```

```
tttcttcatg gcacaggttt gtcagaagaa gttgctaaaa acattcgtga agctggcctt      180
gatgctgtaa ttttcccaaa agctcaacca gatccagcag atacacaagt tcatgaaggc      240
gtagatatat tcaaacaaga aaaatgtgat gcacttgttt ctatcggtgg aggtagctct      300
cacgatacag caaaagcaat cggtttagtt gcagcaaacg gcggaagaat caacgactat      360
caaggtgtaa acagtgtaga aaaccggtt gttccagtag ttgcaatcac tacaacagct      420
```

```
ggtactggta gtgaaacaac atctcttgcg gttattacag attctgcacg taaagtaaaa      480
atgccagtta tcgatgagaa aattacacca actgtagcaa ttgttgaccc agaattaatg      540
gtgaaaaaac cagctggatt aacaattgca actggtatgg atgcattatc ccatgcaatt      600
gaagcatatg ttgcaaaacg tgctacacca gttactgatg cgtttgcaat tcaagcaatg      660
aaactcatta atgaatactt accacgtgcg gttgcaaatg gagaagacat cgaagcacgt      720
gaagcaatgg cttatgcaca atacatggca ggagtggcat taacaacgg aggtttagga      780 ttagtacact ctatttctca ccaagtaggt ggagtttaca agttacaaca cggaatctgt      840
aactcagtta atatgccaca cgtttgccaa ttcaacttaa ttgctcgtac tgaacgcttc      900
gcacacattg ctgagctttt aggcgagaat gtttctggct taagcactgc atctgctgct      960
gagagagcaa ttgtagcgct tcaacgctat aacaaaaact tcggtatccc atctggctat     1020
gcagaaatgg gcgtaaaaga agaggatatc gaattattag cgaacaacgc gtaccaagac     1080
gtatgtactc tagataaccc acgtgttcct actgttcaag acattgcaca aatcatcaaa     1140
aacgctctgt aa                                                         1152
```

<210> SEQ ID NO 7
<211> LENGTH: 383
<212> TYPE: PRT
<213> ORGANISM: Bacillus methanolicus PB1

<400> SEQUENCE: 7

Met Thr Lys Thr Lys Phe Phe Ile Pro Ser Ser Thr Val Phe Gly Arg
1               5                   10                  15

Gly Ala Val Lys Glu Val Gly Ala Arg Leu Lys Ala Ile Gly Ala Thr
                20                  25                  30

Lys Ala Leu Ile Val Thr Asp Ala Phe Leu His Ser Thr Gly Leu Ser
            35                  40                  45

Glu Glu Val Ala Lys Asn Ile Arg Glu Ala Gly Leu Asp Val Val Ile
        50                  55                  60

Phe Pro Lys Ala Gln Pro Asp Pro Ala Asp Thr Gln Val His Glu Gly
65                  70                  75                  80

Val Glu Val Phe Lys Gln Glu Lys Cys Asp Ala Leu Val Ser Ile Gly
                85                  90                  95

Gly Gly Ser Ser His Asp Thr Ala Lys Gly Ile Gly Leu Val Ala Ala
            100                 105                 110

Asn Gly Gly Arg Ile Asn Asp Tyr Gln Gly Val Asn Ser Val Glu Lys
        115                 120                 125

Gln Val Val Pro Gln Ile Ala Ile Thr Thr Thr Ala Gly Thr Gly Ser
    130                 135                 140

Glu Thr Thr Ser Leu Ala Val Ile Thr Asp Ser Ala Arg Lys Val Lys
145                 150                 155                 160

Met Pro Val Ile Asp Glu Lys Ile Thr Pro Thr Val Ala Ile Val Asp
                165                 170                 175

Pro Glu Leu Met Val Lys Lys Pro Ala Gly Leu Thr Ile Ala Thr Gly
            180                 185                 190

```
Met Asp Ala Leu Ser His Ala Ile Glu Ala Tyr Val Ala Lys Arg Ala
            195                 200                 205

Thr Pro Val Thr Asp Ala Phe Ala Ile Gln Ala Met Lys Leu Ile Asn
    210                 215                 220

Glu Tyr Leu Pro Lys Ala Val Ala Asn Gly Glu Asp Ile Glu Ala Arg
225                 230                 235                 240

Glu Ala Met Ala Tyr Ala Gln Tyr Met Ala Gly Val Ala Phe Asn Asn
                245                 250                 255

Gly Gly Leu Gly Leu Val His Ser Ile Ser His Gln Val Gly Gly Val
                260                 265                 270

Tyr Lys Leu Gln His Gly Ile Cys Asn Ser Val Val Met Pro His Val
            275                 280                 285

Cys Gln Phe Asn Leu Ile Ala Arg Thr Glu Arg Phe Ala His Ile Ala
    290                 295                 300

Glu Leu Leu Gly Glu Asn Val Ser Gly Leu Ser Thr Ala Ser Ala Ala
305                 310                 315                 320

Glu Arg Thr Ile Ala Ala Leu Glu Arg Tyr Asn Arg Asn Phe Gly Ile
                325                 330                 335

Pro Ser Gly Tyr Lys Ala Met Gly Val Lys Glu Glu Asp Ile Glu Leu
                340                 345                 350

Leu Ala Asn Asn Ala Met Gln Asp Val Cys Thr Leu Asp Asn Pro Arg
            355                 360                 365

Val Pro Thr Val Gln Asp Ile Gln Gln Ile Ile Lys Asn Ala Leu
    370                 375                 380

<210> SEQ ID NO 8
<211> LENGTH: 1152
<212> TYPE: DNA
<213> ORGANISM: Bacillus methanolicus PB1

<400> SEQUENCE: 8
atgactaaaa caaaattttt cattccatca tccactgtat ttggacgagg cgctgtaaag    60
gaagtaggtg caagactaaa agctattgga gctacgaaag cacttatcgt tacagacgca   120
ttccttcaca gcacaggttt gtcagaagaa gttgctaaaa acattcgtga agctggcctt   180
gatgttgtaa ttttttcctaa agctcaacca gatccagcag atacacaagt tcatgaaggc   240
gtagaggtat tcaaacaaga aaaatgtgat gcacttgttt ctatcggtgg gggcagctct   300
cacgatacag caaaggaat cggcttagtt gcagcaaacg gcggaagaat caacgactat   360
caaggtgtaa atagtgtaga aaaacaagtc gttccacaga ttgcaatcac tacaacagct   420
ggtactggaa gtgaaacaac atctcttgcg ttattacag actctgcacg taaagtaaaa   480
atgccggtta ttgatgaaaa aattacacca actgtagcaa ttgttgaccc agaattaatg   540
gtgaaaaaac cagctggatt aacaatagca actggtatgg atgcattatc ccatgcaatt   600
gaagcatatg ttgcaaaacg tgctacacca gttactgatg catttgcgat tcaagcaatg   660
aaactcatta tgaatactt accaaaagcg gttgcaaatg gagaagacat cgaagcacgt   720
gaagcaatgg cttatgcaca atacatggca ggagtggcat ttaataacgg aggtttagga   780
ttagtacact ctatttctca ccaagtaggt ggagtttaca attacaaca cggaatctgt   840 aactcagttg taatgccaca tgtttgccaa ttcaacttaa ttgctcgtac tgaacgcttc   900
gcacacattg ctgagctttt aggcgagaat gtttctggct taagcactgc atctgctgca   960
gaaagaacaa ttgcagcgct tgaacgctac aacagaaact tcggtattcc atcaggctat  1020
```

```
aaagcaatgg gcgtaaaaga agaagatatc gaattattag caaacaacgc aatgcaagat    1080
gtatgtactc tagacaaccc tcgtgtccct acggttcaag acattcaaca aatcatcaaa    1140
aacgctctgt aa                                                       1152
```

<210> SEQ ID NO 9
<211> LENGTH: 385
<212> TYPE: PRT
<213> ORGANISM: Bacillus methanolicus MGA3

<400> SEQUENCE: 9

```
Met Lys Asn Thr Gln Ser Ala Phe Tyr Met Pro Ser Val Asn Leu Phe
1               5                   10                  15

Gly Ala Gly Ser Val Asn Glu Val Gly Thr Arg Leu Ala Gly Leu Gly
            20                  25                  30

Val Lys Lys Ala Leu Leu Val Thr Asp Ala Gly Leu His Ser Leu Gly
        35                  40                  45

Leu Ser Glu Lys Ile Ala Gly Ile Ile Arg Glu Ala Gly Val Glu Val
    50                  55                  60

Ala Ile Phe Pro Lys Ala Glu Pro Asn Pro Thr Asp Lys Asn Val Ala
65                  70                  75                  80

Glu Gly Leu Glu Ala Tyr Asn Ala Glu Asn Cys Asp Ser Ile Val Thr
                85                  90                  95

Leu Gly Gly Gly Ser Ser His Asp Ala Gly Lys Ala Ile Ala Leu Val
            100                 105                 110

Ala Ala Asn Gly Gly Thr Ile His Asp Tyr Glu Gly Val Asp Val Ser
        115                 120                 125

Lys Lys Pro Met Val Pro Leu Ile Ala Ile Asn Thr Thr Ala Gly Thr
    130                 135                 140

Gly Ser Glu Leu Thr Lys Phe Thr Ile Ile Thr Asp Thr Glu Arg Lys
145                 150                 155                 160

Val Lys Met Ala Ile Val Asp Lys His Val Thr Pro Thr Leu Ser Ile
                165                 170                 175

Asn Asp Pro Glu Leu Met Val Gly Met Pro Pro Ser Leu Thr Ala Ala
            180                 185                 190

Thr Gly Leu Asp Ala Leu Thr His Ala Ile Glu Ala Tyr Val Ser Thr
        195                 200                 205

Gly Ala Thr Pro Ile Thr Asp Ala Leu Ala Ile Gln Ala Ile Lys Ile
    210                 215                 220

Ile Ser Lys Tyr Leu Pro Arg Ala Val Ala Asn Gly Lys Asp Ile Glu
225                 230                 235                 240

Ala Arg Glu Gln Met Ala Phe Ala Gln Ser Leu Ala Gly Met Ala Phe
                245                 250                 255

Asn Asn Ala Gly Leu Gly Tyr Val His Ala Ile Ala His Gln Leu Gly
            260                 265                 270

Gly Phe Tyr Asn Phe Pro His Gly Val Cys Asn Ala Ile Leu Leu Pro
        275                 280                 285

His Val Cys Arg Phe Asn Leu Ile Ser Lys Val Glu Arg Tyr Ala Glu
    290                 295                 300

Ile Ala Ala Phe Leu Gly Glu Asn Val Asp Gly Leu Ser Thr Tyr Glu
305                 310                 315                 320

Ala Ala Glu Lys Ala Ile Lys Ala Ile Glu Arg Met Ala Arg Asp Leu
                325                 330                 335

Asn Ile Pro Lys Gly Phe Lys Glu Leu Gly Ala Lys Glu Glu Asp Ile
            340                 345                 350
```

-continued

```
Glu Thr Leu Ala Lys Asn Ala Met Asn Asp Ala Cys Ala Leu Thr Asn
        355                 360                 365

Pro Arg Lys Pro Lys Leu Glu Glu Val Ile Gln Ile Ile Lys Asn Ala
        370                 375                 380

Met
385

<210> SEQ ID NO 10
<211> LENGTH: 1158
<212> TYPE: DNA
<213> ORGANISM: Bacillus methanolicus MGA3

<400> SEQUENCE: 10
atgaaaaaca ctcaaagtgc attttacatg ccttcagtca atctatttgg tgcaggctct      60
gttaatgagg ttggaactcg attagctggt cttggtgtga aaaaagcttt attagttaca     120
gatgctggtc ttcacagttt aggcctttct gaaaaaattg ccggtatcat tcgtgaagct     180
ggtgtggaag tagctatttt tccaaaagcc gaaccaaatc aactgataaa aacgtcgca     240 gaaggtttag aagcgtataa cgctgaaaac tgtgacagca ttgtcactct ggcggcgga     300 agctcacatg atgctggaaa agccattgca ttagtagctg ctaacggtgg aacaattcac     360
gattatgaag gtgtcgatgt atcaaaaaaa ccaatggtcc ctctaattgc gattaataca     420
acagctggta caggcagtga attaactaaa ttcacaatca tcacagatac tgaacgcaaa     480
gtgaaaatgg ccattgttga taaacatgta acacctacac tttcaatcaa tgacccagag     540
ctaatggttg gaatgcctcc gtccttaaca gctgctactg gattagatgc attaactcat     600
gcgattgaag catatgtttc aactggtgct actccaatta cagatgcact tgcaattcag     660
gcgatcaaaa ttatttctaa atacttgccg cgtgcagttg caaatggaaa agacattgaa     720
gcacgtgaac aaatggcctt cgcacaatca ttagctggca tggcattcaa taacgcgggt     780
ttaggctatg ttcatgcgat tgcacaccaa ttaggaggat tctacaactt ccctcatggc     840
gtttgcaatg cgatccttct gccgcatgtt tgtcgtttca acttaatttc taaagtggaa     900
cgttatgcag aaatcgctgc ttttcttggt gaaaatgtcg acggcctaag cacctacgaa     960
gcagctgaaa aagctattaa agcgatcgaa agaatggcta gagaccttaa cattccaaaa    1020
ggctttaaag aactaggtgc taagaagaa gatattgaga ctttagctaa aaatgcgatg    1080
aatgatgcat gtgcattaac aaatcctcgt aaacctaagt tagaagaagt catccaaatt    1140
attaaaaatg ctatgtaa                                                 1158

<210> SEQ ID NO 11
<211> LENGTH: 385
<212> TYPE: PRT
<213> ORGANISM: Bacillus methanolicus PB1

<400> SEQUENCE: 11

Met Thr Asn Thr Gln Ser Ile Phe Tyr Ile Pro Ser Val Asn Leu Phe
1               5                   10                  15

Gly Pro Gly Ser Val Asn Glu Val Gly Thr Arg Leu Ala Gly Leu Gly
            20                  25                  30

Val Lys Lys Ala Leu Leu Val Thr Asp Ala Gly Leu His Gly Leu Gly
        35                  40                  45

Leu Ser Glu Lys Ile Ala Ser Ile Ile Arg Glu Ala Gly Val Glu Val
    50                  55                  60
```

Leu Ile Phe Pro Lys Ala Glu Pro Asn Pro Thr Asp Lys Asn Val Ala
65                  70                  75                  80

Glu Gly Leu Glu Val Tyr Asn Ala Glu Asn Cys Asp Ser Ile Val Thr
                85                  90                  95

Leu Gly Gly Gly Ser Ser His Asp Ala Gly Lys Gly Ile Ala Leu Val
            100                 105                 110

Ala Ala Asn Gly Gly Thr Ile Tyr Asp Tyr Glu Gly Val Asp Lys Ser
            115                 120                 125

Lys Lys Pro Met Val Pro Leu Ile Ala Ile Asn Thr Thr Ala Gly Thr
130                 135                 140

Gly Ser Glu Leu Thr Arg Phe Thr Ile Ile Thr Asp Thr Glu Arg Lys
145                 150                 155                 160

Val Lys Met Ala Ile Val Asp Lys His Val Thr Pro Thr Leu Ser Ile
                165                 170                 175

Asn Asp Pro Glu Leu Met Val Gly Met Pro Pro Ser Leu Thr Ala Ala
            180                 185                 190

Thr Gly Leu Asp Ala Leu Thr His Ala Ile Glu Ala Tyr Val Ser Thr
            195                 200                 205

Ala Ala Thr Pro Ile Thr Asp Ala Leu Ala Ile Gln Ala Ile Lys Ile
210                 215                 220

Ile Ser Lys Tyr Leu Pro Arg Ala Phe Ala Asn Gly Lys Asp Met Glu
225                 230                 235                 240

Ala Arg Glu Gln Met Ala Phe Ala Gln Ser Leu Ala Gly Met Ala Phe
                245                 250                 255

Asn Asn Ala Ser Leu Gly Tyr Val His Ala Ile Ala His Gln Phe Gly
            260                 265                 270

Gly Phe Tyr Asn Phe Pro His Gly Val Cys Asn Ala Ile Leu Leu Pro
            275                 280                 285

His Val Cys Arg Phe Asn Leu Ile Ser Lys Val Glu Arg Phe Ala Glu
290                 295                 300

Ile Ala Ala Leu Leu Gly Glu Asn Val Ala Gly Leu Ser Thr Arg Glu
305                 310                 315                 320

Ala Ala Glu Lys Gly Ile Lys Ala Ile Glu Arg Met Ala Lys Asp Leu
                325                 330                 335

Asn Ile Pro Arg Gly Phe Lys Glu Leu Gly Ala Lys Glu Glu Asp Ile
            340                 345                 350

Val Thr Leu Ala Glu Asn Ala Met Lys Asp Ala Thr Ala Leu Thr Asn
            355                 360                 365

Pro Arg Lys Pro Lys Leu Glu Glu Val Ile Gln Ile Ile Lys Asn Ala
370                 375                 380

Met
385

<210> SEQ ID NO 12
<211> LENGTH: 1158
<212> TYPE: DNA
<213> ORGANISM: Bacillus methanolicus PB1

<400> SEQUENCE: 12
atgacaaaca ctcaaagtat attttacata ccttcagtca atttgtttgg tccaggatct    60
gttaatgagg ttggaactcg attagctggc cttggcgtga aaaaagcttt attagttaca   120
gatgctggtc ttcacggctt aggtctttct gaaaaaattg ccagtatcat tcgtgaagct   180
ggtgtggaag tattaatttt tccaaaagcc gaaccaaatc caactgataa aaacgtcgca   240

```
gaaggtttgg aagtgtataa cgctgaaaac tgtgacagca ttgtcacttt gggcggcgga    300
agctcgcatg atgctggaaa aggcattgca ttagtagctg ctaacggtgg aacaatttac    360
gattatgaag gtgtcgataa atcaaaaaaa ccaatggtcc cgctcattgc gattaataca    420
acagctggta caggcagtga attaactaga tttacaatca tcacagatac tgaacgtaaa    480
gtgaaaatgg cgattgttga taaacatgta acacctacac tttcaatcaa cgacccagaa    540
ctaatggtcg gaatgcctcc gtctttaaca gctgctactg gattagatgc attaactcat    600
gcaattgaag cttatgtttc aacggctgct actccaatta cagatgcact tgccattcag    660
gcgatcaaaa tcatttctaa atacttgcca cgtgcatttg caaatggcaa agatatggaa    720
gcacgtgagc aaatggcctt cgctcaatca ttagctggta tggcatttaa taacgcttct    780
ttaggctatg ttcatgcaat tgcacaccaa tttggcggat tctacaactt ccctcatggc    840
gtttgcaatg cgatccttct gccacatgta tgccgattta atttaatttc taaagtggaa    900
cgttttgcag aaattgctgc tctcctaggt gaaaatgtcg ccggcctaag tactcgcgaa    960
gcagctgaaa aaggtattaa agcgatcgaa agaatggcta agaccttaa cattccaaga    1020 ggctttaaag aactgggtgc taagaagaa gacattgtga ctttagctga aaatgcgatg    1080
aaagatgcaa cggcattaac aaatcctcgt aaacctaagt tggaagaagt tatacaaatt    1140
attaaaaatg ctatgtaa                                                  1158

<210> SEQ ID NO 13
<211> LENGTH: 385
<212> TYPE: PRT
<213> ORGANISM: Bacillus methanolicus MGA3

<400> SEQUENCE: 13

Met Thr Asn Thr Gln Ser Ala Phe Phe Met Pro Ser Val Asn Leu Phe
1               5                   10                  15

Gly Ala Gly Ser Val Asn Glu Val Gly Thr Arg Leu Ala Asp Leu Gly
            20                  25                  30

Val Lys Lys Ala Leu Leu Val Thr Asp Ala Gly Leu His Gly Leu Gly
        35                  40                  45

Leu Ser Glu Lys Ile Ser Ser Ile Ile Arg Ala Ala Gly Val Glu Val
    50                  55                  60

Ser Ile Phe Pro Lys Ala Glu Pro Asn Pro Thr Asp Lys Asn Val Ala
65                  70                  75                  80

Glu Gly Leu Glu Ala Tyr Asn Ala Glu Asn Cys Asp Ser Ile Val Thr
                85                  90                  95

Leu Gly Gly Gly Ser Ser His Asp Ala Gly Lys Ala Ile Ala Leu Val
            100                 105                 110

Ala Ala Asn Gly Gly Lys Ile His Asp Tyr Glu Gly Val Asp Val Ser
        115                 120                 125

Lys Glu Pro Met Val Pro Leu Ile Ala Ile Asn Thr Thr Ala Gly Thr
    130                 135                 140

Gly Ser Glu Leu Thr Lys Phe Thr Ile Ile Thr Asp Thr Glu Arg Lys
145                 150                 155                 160

Val Lys Met Ala Ile Val Asp Lys His Val Thr Pro Thr Leu Ser Ile
                165                 170                 175

Asn Asp Pro Glu Leu Met Val Gly Met Pro Pro Ser Leu Thr Ala Ala
            180                 185                 190

Thr Gly Leu Asp Ala Leu Thr His Ala Ile Glu Ala Tyr Val Ser Thr
        195                 200                 205
```

```
Gly Ala Thr Pro Ile Thr Asp Ala Leu Ala Ile Gln Ala Ile Lys Ile
    210                 215                 220
Ile Ser Lys Tyr Leu Pro Arg Ala Val Ala Asn Gly Lys Asp Ile Glu
225                 230                 235                 240
Ala Arg Glu Gln Met Ala Phe Ala Gln Ser Leu Ala Gly Met Ala Phe
                245                 250                 255
Asn Asn Ala Gly Leu Gly Tyr Val His Ala Ile Ala His Gln Leu Gly
                260                 265                 270
Gly Phe Tyr Asn Phe Pro His Gly Val Cys Asn Ala Val Leu Leu Pro
            275                 280                 285
Tyr Val Cys Arg Phe Asn Leu Ile Ser Lys Val Glu Arg Tyr Ala Glu
            290                 295                 300
Ile Ala Ala Phe Leu Gly Glu Asn Val Asp Gly Leu Ser Thr Tyr Asp
305                 310                 315                 320
Ala Ala Glu Lys Ala Ile Lys Ala Ile Glu Arg Met Ala Lys Asp Leu
                325                 330                 335
Asn Ile Pro Lys Gly Phe Lys Glu Leu Gly Ala Lys Glu Glu Asp Ile
                340                 345                 350
Glu Thr Leu Ala Lys Asn Ala Met Lys Asp Ala Cys Ala Leu Thr Asn
            355                 360                 365
Pro Arg Lys Pro Lys Leu Glu Glu Val Ile Gln Ile Ile Lys Asn Ala
        370                 375                 380
Met
385

<210> SEQ ID NO 14
<211> LENGTH: 1158
<212> TYPE: DNA
<213> ORGANISM: Bacillus methanolicus MGA3

<400> SEQUENCE: 14
atgacaaaca ctcaaagtgc atttttatg ccttcagtca atctatttgg tgcaggatca      60
gttaatgagg ttggaactcg attagctgat cttggtgtga aaaaagcttt attagttaca     120
gatgctggtc ttcacggttt aggtctttct gaaaaatttt ccagtattat tcgtgcagct     180
ggtgtggaag tatccatttt tccaaaagcc gaaccaaatc aaccgataa aaacgtcgca      240 gaaggtttag aagcgtataa cgctgaaaac tgtgacagca ttgtcactct gggcggcgga     300
agttcacatg atgccggaaa agccattgca ttagtagctg ctaatggtgg aaaaattcac     360
gattatgaag tgtcgatgt atcaaaagaa ccaatggtcc cgctaattgc gattaataca     420
acagctggta caggcagtga attaactaaa ttcacaatca tcacagatac tgaacgcaaa     480
gtgaaaatgg ccattgtgga taaacatgta cacctacac tttcaatcaa cgacccagag     540
ctaatggttg aatgcctcc gtccttaact gctgctactg gattagatgc attaactcat     600
gcaattgaag catatgtttc aactggtgct actccaatta cagatgcact tgcaattcag     660
gcgatcaaaa tcatttctaa atacttgccg cgtgcagttg caaatggaaa agacattgaa     720
gcacgtgaac aaatggcctt cgctcaatca ttagctggca tggcattcaa taacgcgggt     780
ttaggctatg ttcatgcgat tgcacaccaa ttaggaggat tctacaactt ccctcatggc     840
gtttgcaatg cggtccttct gccatatgta tgtcgattta acttaatttc taaagtggaa     900
cgttatgcag aaatcgctgc ttttcttggt gaaaatgtcg acggtctaag tacgtacgat     960
gcagctgaaa agctattaa agcgatcgaa agaatggcta aagaccttaa cattccaaaa    1020
```
ggctttaaag aactaggtgc taaagaagaa gacattgaga ctttagctaa gaatgcgatg   1080
aaagatgcat gtgcattaac aaatcctcgt aaacctaagt tagaagaagt catccaaatt   1140
attaaaaatg cgatgtaa   1158

<210> SEQ ID NO 15
<211> LENGTH: 401
<212> TYPE: PRT
<213> ORGANISM: Lysinibacillus fusiformis

<400> SEQUENCE: 15

Met Ser Asp Val Leu Lys Gln Phe Val Met Pro Lys Thr Asn Leu Phe
1               5                   10                  15

Gly Pro Gly Ala Ile Gln Glu Val Gly Lys Arg Leu Asn Asp Leu Glu
            20                  25                  30

Val

Glu Ile Leu Ala Lys Asn Ala Leu Leu Asp Val Cys Ala Glu Thr Asn
         355                 360                 365

Pro Arg Lys Ala Thr Leu Glu Asp Ile Lys Gln Ile Ile Thr Asn Ala
     370                 375                 380

Met Gly Pro Ile Val Lys Lys Glu Glu Ser Leu Glu Ala Val Ala Leu
385                 390                 395                 400

Ser

<210> SEQ ID NO 16
<211> LENGTH: 1206
<212> TYPE: DNA
<213> ORGANISM: Lysinibacillus fusiformis

<400> SEQUENCE: 16

| | | | | | |
|---|---|---|---|---|---|
| atgtcagacg | ttctaaagca | atttgttatg | ccgaaaacaa | acttatttgg | acctggagca | 60 |
| attcaagaag | ttggtaaacg | cttaaatgat | ttagaagtga | aaagacatt | aatcgtaaca | 120 |
| gatgagggcc | tacacaaatt | aggtctctca | gaacaaattg | caaacatcat | tacagctgct | 180 |
| ggaattgatg | tagcaatttt | ccctaaagca | gaaccaaatc | aacagatca | aaacattgaa | 240 |
| gatggtattt | ccgtgtatca | tgcggaaaac | tgcgattcta | ttgtttctct | tggaggaggc | 300 |
| agcgcacacg | atgcagcaaa | aggtatcgga | cttattgctt | cgaatggtgg | acgcattcat | 360 |
| gattatgaag | gcgttgacaa | atcacaaaat | ccacttgtgc | cattaattgc | aattaataca | 420 |
| actgctggta | ctgccagtga | aatgactcgt | tcactatta | tcacggatac | agcacgcaaa | 480 |
| gtaaaaatgg | ccattgttga | taagcacgtg | acaccgttac | tttctataaa | cgatcctgaa | 540 |
| ttaatgattg | gtttacctcc | tgctcttacg | gcagctactg | gggttgatgc | actaacacat | 600 |
| gctattgaat | cattcgtttc | tacgaatgct | acaccaatca | cggacgcatg | tgctgaaaag | 660 |
| gtccttcaac | taatccctga | atatttacct | cgtgcctatg | caaatggagc | tgatatagaa | 720 |
| gctcgtgaac | aaatggtata | tgcacaattt | ttagcgggaa | tggcctttaa | taatgcatca | 780 |
| cttggctatg | ttcatgcaat | tgctcatcaa | ttgggtggtt | tctataaccct | accgcatggc | 840 |
| gtgtgcaacg | caattttatt | accacacgtt | tgtcgattta | atgtcacagc | acgtacagag | 900 |
| cgctttgctc | gtatcgctga | gttattagga | gaaaatgtag | aaggtttaag | taagcgcgac | 960 |
| gccgctgaaa | aggctattac | agctattgag | aagttatcac | aagatttaaa | tattcctagc | 1020 |
| ggcttccgtg | aattaggtgc | aaaagatgag | gatattgaga | tcttagcaaa | aaatgcattg | 1080 |
| ttagatgtgt | gtgctgagac | gaatcctcgt | aaagcaacac | tagaggatat | caaacaaatc | 1140 |
| atcacaaatg | caatgggtcc | tattgtgaaa | aagaagagt | cactcgaggc | agttgccctc | 1200 |
| tcttaa | | | | | | 1206 |

<210> SEQ ID NO 17
<211> LENGTH: 386
<212> TYPE: PRT
<213> ORGANISM: Bacillus coagulans 36D1

<400> SEQUENCE: 17

Met Leu Thr Gly Leu Arg Thr Asp Phe Gln Met Pro Ser Val Asn Leu
1               5                   10                  15

Phe Gly Gln Gly Thr Ala Glu Glu Ile Gly Asn Arg Leu Lys Asn Leu
                20                  25                  30

Gly Cys Arg Arg Pro Leu Ile Val Thr Asp Glu Gly Leu His Gln Leu
            35                  40                  45

Gly Tyr Ser Glu Lys Ile Ala Ala Tyr Ile Lys Glu Ala Gly Leu Glu
    50                  55                  60

Val Ala Ile Tyr Pro Lys Ala Glu Pro Asn Pro Thr Asp Lys Asn Val
 65                  70                  75                  80

Glu Asp Gly Leu Lys Thr Tyr His Glu Asn Cys Asp Ser Ile Val
                85                  90                  95

Ser Leu Gly Gly Gly Ser Ala His Asp Cys Ala Lys Gly Ile Gly Leu
            100                 105                 110

Val Ala Ala Asn Gly Gly Lys Ile His Asp Tyr Glu Gly Leu Asp Arg
            115                 120                 125

Ser Glu Lys Pro Met Val Pro Leu Val Ala Ile Asn Thr Thr Ala Gly
            130                 135                 140

Thr Ala Ser Glu Met Thr Lys Phe Thr Ile Ile Thr Asp Thr Ser Arg
145                 150                 155                 160

Lys Val Lys Met Ala Ile Val Asp Lys His Val Thr Pro Val Leu Ser
                165                 170                 175

Ile Asn Asp Pro Leu Leu Met Val Gly Met Pro Pro Ser Leu Thr Ala
                180                 185                 190

Ala Thr Gly Leu Asp Ala Leu Thr His Ala Val Glu Ala Tyr Val Ser
            195                 200                 205

Thr Ala Ala Thr Pro Val Thr Asp Ala Cys Ala Ile Lys Ala Ile Gln
210                 215                 220

Ile Ile Pro Gln Tyr Leu Pro Lys Ala Val Ala Asn Gly Asn Asp Met
225                 230                 235                 240

Glu Ala Arg Glu Gln Met Val Tyr Ala Gln Tyr Leu Ala Gly Met Ala
                245                 250                 255

Phe Asn Asn Ala Ser Leu Gly Tyr Val His Ala Ile Ala His Gln Phe
            260                 265                 270

Gly Gly Phe Tyr Asn Leu Pro His Gly Val Cys Asn Ala Ile Leu Leu
            275                 280                 285

Pro His Val Cys Arg Phe Asn Leu Ile Ala Arg Lys Glu Arg Phe Ala
            290                 295                 300

Glu Ile Ala Val Ala Leu Gly Glu Lys Thr Asp Ser Leu Ser Val Asp
305                 310                 315                 320

Glu Ala Ala Glu Lys Ala Ile Thr Ala Ile Glu Arg Leu Ala Ala Gln
                325                 330                 335

Leu Asn Ile Pro Lys Gly Phe Lys Glu Leu Gly Ala Lys Glu Glu Asp
            340                 345                 350

Ile Glu Ile Leu Ala Gln His Ala Met Gln Asp Ala Cys Ala Ala Thr
            355                 360                 365

Asn Pro Arg Lys Pro Thr Gln Lys Glu Val Glu Ala Ile Ile Lys Ala
370                 375                 380

Ala Met
385

<210> SEQ ID NO 18
<211> LENGTH: 1161
<212> TYPE: DNA
<213> ORGANISM: Bacillus coagulans 36D1

<400> SEQUENCE: 18
atgttaacag gattacgtac tgattttcaa atgccttccg taaacttgtt tggacagggg     60
acggcagaag aaattggaaa caggctgaaa atcttgggt gtcgcagacc gctgattgta    120
accgatgaag ggctccacca actgggggtat tccgaaaaaa ttgcagccta tataaagaa    180

```
gccggcctgg aagtggcgat ctatccgaag gctgaaccaa atccgacaga caaaaatgtg    240
gaagacgggt taaaaaccta tcatgaagaa aattgcgatt caatcgtttc acttggcggc    300
gggagcgcgc atgactgtgc aaaagggatc gggctcgttg cggccaatgg gggcaaaatc    360
catgattatg aagggctgga ccgttctgaa aaaccaatgg tgccgctcgt tgcaattaat    420
acaacagccg ggactgccag cgaaatgaca aaatttacga ttattaccga tacgagtcgg    480
aaagtgaaaa tggcgattgt agataaacat gtgacaccgg ttttgtccat taatgatcca    540
ttattaatgg tcgggatgcc gccgtcttta actgcggcaa cggggcttga cgctttgacc    600
catgcagtgg aagcatatgt ttcaactgcg gccacaccgg taacggatgc atgcgccatt    660
aaagcgattc aaattattcc gcaatatttg ccaaaggctg ttgcaaacgg caatgatatg    720
gaagcgcgtg aacaaatggt atatgcgcag tatttggcag gcatggcgtt taataatgca    780
tctttgggct atgtccacgc gattgcgcac cagttcggcg gtttctataa cttgccgcac    840
ggcgtttgca atgcgatttt gctcccgcat gtgtgccgtt tcaatctgat tgcgcggaaa    900
gaaagatttg cagaaattgc cgttgcactg ggtgagaaga cggatagcct gagcgtcgac    960
gaagcggcgg aaaaagccat tacagcaatt gaaaggctgg cagcacagct gaacattccg   1020
aaaggcttta aagaactcgg ggctaaagaa gaagatatcg aaatcctcgc ccagcatgca   1080
atgcaggatg cgtgcgcagc cacaaacccg cgcaaaccaa cacaaaaaga agtggaagcg   1140
attataaaag cagcgatgta a                                             1161
```

<210> SEQ ID NO 19
<211> LENGTH: 402
<212> TYPE: PRT
<213> ORGANISM: Lysinibacillus sphaericus

<400> SEQUENCE: 19

```
Met Ser Asp Val Leu Lys Gln Phe Val Met Pro Lys Lys Asn Leu Phe
1               5                   10                  15

Gly Pro Gly Ala Ile Gln Glu Val Gly Lys His Leu Asn Asp Leu Glu
            20                  25                  30

Val Lys Lys Thr Leu Ile Val Thr Asp Glu Gly Leu His Lys Leu Gly
        35                  40                  45

Leu Ser Glu Gln Ile Ala Asn Ile Ile Thr Ala Ala Gly Ile Asp Val
    50                  55                  60

Ala Ile Phe Pro Lys Ala Glu Pro Asn Pro Thr Asp Gln Asn Ile Glu
65                  70                  75                  80

Asp Gly Ile Ala Asp Tyr His Ala Glu Ser Cys Asp Ser Ile Val Ser
                85                  90                  95

Leu Gly Gly Gly Ser Ala His Asp Ala Ala Lys Gly Ile Gly Leu Ile
            100                 105                 110

Ala Ser Asn Gly Gly Arg Ile Gln Asp Tyr Glu Gly Val Asp Lys Ser
        115                 120                 125

Gln Asn Pro Leu Val Pro Leu Ile Ala Ile Asn Thr Thr Ala Gly Thr
    130                 135                 140

Ala Ser Glu Met Thr Arg Phe Thr Ile Ile Thr Asp Thr Ala Arg Lys
145                 150                 155                 160

Val Lys Met Ala Ile Val Asp Lys His Val Thr Pro Leu Leu Ser Ile
                165                 170                 175

Asn Asp Ser Glu Leu Met Ile Gly Leu Pro Pro Ala Leu Thr Ala Ala
            180                 185                 190
```

```
Thr Gly Val Asp Ala Leu Thr His Ala Ile Glu Ser Phe Val Ser Thr
        195                 200                 205

Asn Ala Thr Pro Ile Thr Asp Ala Cys Ala Glu Lys Val Leu Gln Leu
    210                 215                 220

Val Pro Glu Phe Leu Pro Arg Ala Tyr Ala Asn Gly Ala Asp Leu Glu
225                 230                 235                 240

Ala Arg Glu Gln Met Val Tyr Ala Gln Phe Leu Ala Gly Met Ala Phe
                245                 250                 255

Asn Asn Ala Ser Leu Gly Tyr Val His Ala Ile Ala His Gln Leu Gly
            260                 265                 270

Gly Tyr Tyr Asn Leu Pro His Gly Val Cys Asn Ala Ile Leu Leu Pro
        275                 280                 285

His Val Cys Arg Phe Asn Val Thr Ala Arg Thr Glu Arg Phe Ala Arg
    290                 295                 300

Ile Ala Glu Leu Leu Gly Glu Asn Val Thr Gly Leu Ser Lys Arg Asp
305                 310                 315                 320

Ala Ala Glu Lys Ala Ile Ser Ala Ile Glu Lys Leu Ser Lys Asp Leu
                325                 330                 335

Asn Ile Pro Ser Gly Phe Arg Glu Leu Gly Ala Lys Asp Glu Asp Ile
            340                 345                 350

Glu Ile Leu Ala Lys Asn Ala Met Leu Asp Val Cys Ala Glu Thr Asn
        355                 360                 365

Pro Arg Lys Ala Thr Leu Asp Asp Ile Lys Gln Ile Ile Thr Asn Ala
    370                 375                 380

Met Gly Pro Ile Val Lys Lys Glu Glu Ser Leu Glu Ala Val Ala Ala
385                 390                 395                 400

Leu Ser

<210> SEQ ID NO 20
<211> LENGTH: 1209
<212> TYPE: DNA
<213> ORGANISM: Lysinibacillus sphaericus

<400> SEQUENCE: 20
atgtcagacg ttctaaagca atttgttatg ccgaaaaaaa acttatttgg acctggagca      60
attcaagaag ttggtaaaca cttaaatgat ttagaagtga agaagacatt aatcgtaaca     120
gatgagggct tacacaaatt aggtctctct gaacaaattg caaacatcat tacagctgct     180
ggaattgatg tagcaatttt ccctaaagca gaaccaaatc caacagatca aaatattgaa     240
gatggcatag cagattacca tgctgaaagc tgtgattcaa tcgtttctct tggaggaggg     300
agcgctcatg atgcagcaaa aggtatcgga cttattgctt cgaatggtgg acgcattcaa     360
gattatgaag gcgttgataa atcacaaaat ccacttgtgc cattaattgc tattaataca     420
acggctggta ctgctagtga aatgactcgt ttcacgatta ttacagatac agcacgtaaa     480
gtaaaaatgg ccattgttga taaacatgtg accccgttac tttcgattaa tgattccgaa     540
ctgatgattg ggttacctcc tgctctaaca gctgctactg gtgttgatgc attgacacat     600
gctattgaat catttgtttc gacaaatgca acaccaatta cagacgcttg tgctgagaag     660
gtacttcaac tagttcctga atttttacca cgtgcctatg caaatggagc tgatttagaa     720
gcacgtgaac aaatggtata tgcacaattt ttagctggta tggcttttaa taatgcttca     780
ctaggctatg tccatgcgat tgctcatcag ttaggtggct attataatct acctcatggc     840
gtatgtaatg ccattttatt accacatgtt tgccgcttca atgtaacagc acgtactgag     900
```

-continued

```
cgttttgctc gcattgctga attattaggt gaaaatgtga caggattaag taagcgtgat    960
gctgctgaaa aagctatttc agctattgaa aagctatcaa aggatttaaa tattcctagt   1020
ggcttccgcg aactaggtgc aaaagatgag gatattgaaa ttttagcaaa aaatgcgatg   1080
ttagatgttt gcgctgagac aaatcctcgt aaagcaacat tagatgatat taaacaaatt   1140
attacaaatg caatgggccc tatcgtgaaa aaagaggaat cgcttgaagc agttgctgct   1200
ctttcataa                                                           1209
```

<210> SEQ ID NO 21
<211> LENGTH: 386
<212> TYPE: PRT
<213> ORGANISM: Bacillus azotoformans LMG 9581

<400> SEQUENCE: 21

```
Met Ala Asn Gln Lys Val Tyr Gly Phe Phe Met Pro Thr Val Asn Leu
 1               5                  10                  15

Met Gly Val Gly Ala Val Asn Glu Ala Gly Pro Arg Ile Lys Ala Leu
            20                  25                  30

Gly Cys Asn Lys Ser Leu Leu Val Thr Asp Lys Gly Leu Ser Lys Met
        35                  40                  45

Gly Val Ala Glu Glu Ile Ala Asn Ile Ile Gly Gln Ala Gly Val Glu
    50                  55                  60

Val Ser Ile Phe Asp Gly Ala Glu Pro Asn Pro Thr Asp Leu Asn Val
65                  70                  75                  80

Glu Ala Gly Leu Lys Gln Tyr Arg Glu Leu Gly Cys Asp Ser Ile Ile
                85                  90                  95

Ser Leu Gly Gly Gly Ser Ser His Asp Cys Ala Lys Gly Ile Gly Leu
            100                 105                 110

Val Ala Ser Asn Gly Gly Thr Ile His Asp Tyr Glu Gly Val Asp Met
        115                 120                 125

Ser Lys Glu Pro Met Ile Pro Leu Val Ala Ile Asn Thr Thr Ala Gly
    130                 135                 140

Thr Ala Ser Glu Met Thr Arg Phe Cys Ile Ile Thr Asp Thr Ser Arg
145                 150                 155                 160

Lys Ile Lys Met Ala Ile Val Asp Lys His Thr Thr Pro Leu Ile Ser
                165                 170                 175

Ile Asn Asp Pro Ile Leu Thr Val Lys Met Pro Ala Gly Leu Thr Ala
            180                 185                 190

Ala Thr Gly Met Asp Ala Leu Thr His Ala Ile Glu Ala Tyr Val Ser
        195                 200                 205

Thr Asp Ala Thr Pro Ile Thr Asp Ala Cys Ala Leu Gln Thr Ile Arg
    210                 215                 220

Leu Val Ser Gln Asn Leu Arg Ala Ala Val Ala Asn Gly Glu Asp Ile
225                 230                 235                 240

Asp Ala Arg Asn Asn Met Cys Tyr Ala Gln Phe Leu Gly Gly Met Ala
                245                 250                 255

Phe Asn Asn Ala Ser Leu Gly Tyr Val His Ala Ile Ala His Gln Leu
            260                 265                 270

Gly Gly Phe Tyr Asn Leu Pro His Gly Val Cys Asn Ala Val Leu Leu
        275                 280                 285

Pro His Val Glu Arg Phe Asn Leu Ile Ala Lys Pro Glu Arg Phe Val
    290                 295                 300

Asp Ile Ala Ile Ala Leu Gly Glu Asn Val Ser Gly Leu Pro Thr Arg
305                 310                 315                 320
```

Ala Ala Ala Glu Ile Ala Leu Thr Ala Ile Glu Thr Leu Ala Lys Asp
            325                 330                 335

Val Gly Ile Pro Gly Ser Leu Thr Glu Leu Gly Val Lys Glu Glu Asp
        340                 345                 350

Ile Pro Leu Leu Ala Glu Asn Ala Met Arg Asp Ala Cys Ser Phe Thr
    355                 360                 365

Asn Pro Arg Lys Ala Thr Leu Asp Asp Val Gln Gly Met Ile Arg Ala
370                 375                 380

Ala Leu
385

<210> SEQ ID NO 22
<211> LENGTH: 1161
<212> TYPE: DNA
<213> ORGANISM: Bacillus azotoformans LMG 9581

<400> SEQUENCE: 22
atggcaaatc aaaaggttta tggtttcttt atgccaacag tcaatttaat gggagttggt      60
gcagtaaatg aagctggtcc aagaatcaaa gcactaggtt gtaacaaatc tttacttgtt     120
actgacaaag gcttaagcaa aatgggtgta gcagaagaaa ttgcaaacat tattggtcaa     180
gcaggggttg aagtttctat atttgatggc gcagagccca acccaaccga tttaaatgtg     240
gaagctgggt aaaacaata ccgcgaacta ggttgcgatt ctattatttc tctaggagga     300
ggaagttctc atgattgcgc taaggggatt ggacttgttg catcaaatgg tggaacaatt     360
catgactatg agggagttga catgtcaaaa gaaccaatga ttccacttgt tgcgattaat     420
acaacagcag gtacagctag tgaaatgact cgtttctgta ttattacgga tacctctaga     480
aaaatcaaaa tggccatcgt tgataaacat acaacaccat tgatttcaat taatgatcca     540
atcctcaccg ttaagatgcc agcaggatta acagctgcaa caggaatgga tgcgttaact     600
catgcaattg aagcttatgt ttctacagat gcaacaccga ttacagatgc ctgcgccctg     660
caaacgatcc gtctagtaag ccaaaaccct cgagctgcag ttgcgaatgg tgaagatatc     720
gatgccagaa acaatatgtg ctatgctcag ttttttaggcg gaatggcatt taataatgct     780
tccttaggtt atgttcatgc aatcgcccat cagttaggtg attttataa tttaccacat     840 ggtgtatgta atgctgttct tctaccacac gttgaacgat tcaatttaat tgcgaaaccg     900
gagcgatttg ttgatatcgc catcgcttta ggagaaaatg taagcggttt accaacaaga     960
gcagctgcag aaatagcact aacagcaatc gaaacacttg ctaaggatgt tgggattcca    1020
ggaagcttaa cagaacttgg ggtaaaagaa gaagatatcc cacttttagc agaaaacgcg    1080
atgagggatg catgctcgtt cacaaatcct cgtaaagcaa ctttagatga tgtacaaggc    1140
atgattcgtg cagcactgta a                                             1161

<210> SEQ ID NO 23
<211> LENGTH: 386
<212> TYPE: PRT
<213> ORGANISM: Burkholderia thailandensis E264

<400> SEQUENCE: 23

Met Ala Asn Gln Lys Val Tyr Gly Phe Phe Met Pro Thr Val Asn Leu
1               5                   10                  15

Met Gly Val Gly Ala Val Asn Glu Ala Gly Pro Arg Ile Lys Ala Leu
20 25 30

Gly Cys Asn Lys Ser Leu Leu Val Thr Asp Lys Gly Leu Ser Lys Met
            35                  40                  45

Gly Val Ala Glu Glu Ile Ala Asn Ile Ile Gly Gln Ala Gly Val Glu
 50                  55                  60

Val Ser Ile Phe Asp Gly Ala Glu Pro Asn Pro Thr Asp Leu Asn Val
 65                  70                  75                  80

Glu Ala Gly Leu Lys Gln Tyr Arg Glu Leu Gly Cys Asp Ser Ile Ile
                85                  90                  95

Ser Leu Gly Gly Gly Ser Ser His Asp Cys Ala Lys Gly Ile Gly Leu
                100                 105                 110

Val Ala Ser Asn Gly Gly Thr Ile His Asp Tyr Glu Gly Val Asp Met
            115                 120                 125

Ser Lys Glu Pro Met Ile Pro Leu Val Ala Ile Asn Thr Thr Ala Gly
130                 135                 140

Thr Ala Ser Glu Met Thr Arg Phe Cys Ile Ile Thr Asp Thr Ser Arg
145                 150                 155                 160

Lys Ile Lys Met Ala Ile Val Asp Lys His Thr Thr Pro Leu Ile Ser
                165                 170                 175

Ile Asn Asp Pro Ile Leu Thr Val Lys Met Pro Ala Gly Leu Thr Ala
                180                 185                 190

Ala Thr Gly Met Asp Ala Leu Thr His Ala Ile Glu Ala Tyr Val Ser
            195                 200                 205

Thr Asp Ala Thr Pro Ile Thr Asp Ala Cys Ala Leu Gln Thr Ile Arg
210                 215                 220

Leu Val Ser Gln Asn Leu Arg Ala Val Ala Asn Gly Glu Asp Ile
225                 230                 235                 240

Asp Ala Arg Asn Asn Met Cys Tyr Ala Gln Phe Leu Gly Gly Met Ala
                245                 250                 255

Phe Asn Asn Ala Ser Leu Gly Tyr Val His Ala Ile Ala His Gln Leu
                260                 265                 270

Gly Gly Phe Tyr Asn Leu Pro His Gly Val Cys Asn Ala Val Leu Leu
            275                 280                 285

Pro His Val Glu Arg Phe Asn Leu Ile Ala Lys Pro Glu Arg Phe Val
290                 295                 300

Asp Ile Ala Ile Ala Leu Gly Glu Asn Val Ser Gly Leu Pro Thr Arg
305                 310                 315                 320

Ala Ala Ala Glu Ile Ala Leu Thr Ala Ile Glu Thr Leu Ala Lys Asp
                325                 330                 335

Val Gly Ile Pro Gly Ser Leu Thr Glu Leu Gly Val Lys Glu Glu Asp
                340                 345                 350

Ile Pro Leu Leu Ala Glu Asn Ala Met Arg Asp Ala Cys Ser Phe Thr
            355                 360                 365

Asn Pro Arg Lys Ala Thr Leu Asp Asp Val Gln Gly Met Ile Arg Ala
370                 375                 380

Ala Leu
385

<210> SEQ ID NO 24
<211> LENGTH: 1173
<212> TYPE: DNA
<213> ORGANISM: Burkholderia thailandensis E264

<400> SEQUENCE: 24

```
atgagctatc tgaacatcgc gcagcgcacc gacagtttct tcattccctg cgtgaccttg      60
atcggcccgg gctgcgcgcg agagacgggc gtgcgcgcca atcgctggg cgcgaaaaag     120
gcgctgatcg tgaccgacgc ggggctgcac aagatgggc tgtccgagat cgtcgcgggc     180
catatccgcg acgcggggct tcaggccgtg atcttcgcgg gcgcggagcc caacccgacc     240
gacgtcaacg tgcacgacgg cgtcgagcgc tttcagcgcg agggatgcga cttcatcgta     300
tcgctcggcg gtgggtcgtc gcacgactgc gcgaaaggca tcgggctcgt cacggccgga     360
ggcgggcata tccgcgacta tgaagggatc gacaaatcga cggtgccgat gacgccgttg     420
atttcgatca acacgacggc gggcacggcc gcggagatga cgcgattctg catcatcacg     480
aactccagca atcacgtcaa aatggcgatc gtcgactggc gctgcacgcc gctcatcgcg     540
atcgacgatc cgtgcctgat ggtggcgatg ccgcccgcgc tgacggccgc gacaggcatg     600
gacgcgctca cccacgcggt ggaggcctac gtttccaccg ccgcgacgcc gatcaccgac     660
gcctgcgccg aaaaggccat cgcgctgatc ggcgaatggc tgccgaaggc cgtcgcgaac     720
ggcgaatcga tggaggcgcg cgcggccatg tgctacgcgc agtacctcgc cgggatggcg     780
ttcaacaacg cgtcgctcgg ctacgtgcat gcgatggcgc accagctcgg cgggttctac     840
aacctgccgc acgggtctg caacgcgatc ctgctgccgc acgtgtgcga gttcaacctg     900
attgccgcgc ccgaacggtt cgccaccatc gcgtcgctcc tcggcgtcaa tacgccgga     960
tcgagcaccg tcgacgccgc ccgggcgggc catgcggcga tcccgcggct cagcgcctcg    1020
atcggcatcc ccgccggcct ggccgcgctg gcgtcaggg tcgaagatca cgaggtgatg    1080
gcgagcaacg cgcagaagga cgcgtgcatg ctgaccaatc cgcgcaaggc gacgctcgcg    1140
caggtcatcg cgatcttcgc ggcggcgatg tga                                 1173
```

<210> SEQ ID NO 25
<211> LENGTH: 390
<212> TYPE: PRT
<213> ORGANISM: Cupriavidus necator N-1

<400> SEQUENCE: 25

```
Met Thr His Leu Asn Ile Ala Asn Arg Val Asp Ser Phe Phe Ile Pro
1               5                   10                  15

Cys Val Thr Leu Phe Gly Pro Gly Cys Ala Arg Glu Thr Gly Ala Arg
            20                  25                  30

Ala Arg Ser Leu Gly Ala Arg Lys Ala Leu Ile Val Thr Asp Ala Gly
        35                  40                  45

Leu His Lys Met Gly Leu Ser Glu Val Val Ala Gly His Ile Arg Glu
    50                  55                  60

Ala Gly Leu Gln Ala Val Ile Phe Pro Gly Ala Glu Pro Asn Pro Thr
65                  70                  75                  80

Asp Val Asn Val His Asp Gly Val Lys Leu Phe Glu Arg Glu Glu Cys
                85                  90                  95

Asp Phe Ile Val Ser Leu Gly Gly Gly Ser His Asp Cys Ala Lys
            100                 105                 110

Gly Ile Gly Leu Val Thr Ala Gly Gly His Ile Arg Asp Tyr Glu
        115                 120                 125

Gly Ile Asp Lys Ser Thr Val Pro Met Thr Pro Leu Ile Ser Ile Asn
    130                 135                 140
```

```
Thr Thr Ala Gly Thr Ala Glu Met Thr Arg Phe Cys Ile Ile Thr
145                 150                 155                 160

Asn Ser Ser Asn His Val Lys Met Ala Ile Val Asp Trp Arg Cys Thr
            165                 170                 175

Pro Leu Ile Ala Ile Asp Asp Pro Ser Leu Met Val Ala Met Pro Pro
        180                 185                 190

Ala Leu Thr Ala Ala Thr Gly Met Asp Ala Leu Thr His Ala Ile Glu
    195                 200                 205

Ala Tyr Val Ser Thr Ala Ala Thr Pro Ile Thr Asp Ala Cys Ala Glu
210                 215                 220

Lys Ala Ile Val Leu Ile Ala Glu Trp Leu Pro Lys Ala Val Ala Asn
225                 230                 235                 240

Gly Asp Ser Met Glu Ala Arg Ala Ala Met Cys Tyr Ala Gln Tyr Leu
                245                 250                 255

Ala Gly Met Ala Phe Asn Asn Ala Ser Leu Gly Tyr Val His Ala Met
            260                 265                 270

Ala His Gln Leu Gly Gly Phe Tyr Asn Leu Pro His Gly Val Cys Asn
        275                 280                 285

Ala Ile Leu Leu Pro His Val Ser Glu Phe Asn Leu Ile Ala Ala Pro
    290                 295                 300

Glu Arg Tyr Ala Arg Ile Ala Glu Leu Leu Gly Glu Asn Ile Gly Gly
305                 310                 315                 320

Leu Ser Ala His Asp Ala Ala Lys Ala Ala Val Ser Ala Ile Arg Thr
                325                 330                 335

Leu Ser Thr Ser Ile Gly Ile Pro Ala Gly Leu Ala Gly Leu Gly Val
            340                 345                 350

Lys Ala Asp Asp His Glu Val Met Ala Ser Asn Ala Gln Lys Asp Ala
        355                 360                 365

Cys Met Leu Thr Asn Pro Arg Lys Ala Thr Leu Ala Gln Val Met Ala
    370                 375                 380

Ile Phe Ala Ala Ala Met
385                 390
```

<210> SEQ ID NO 26
<211> LENGTH: 1173
<212> TYPE: DNA
<213> ORGANISM: Cupriavidus necator N-1

<400> SEQUENCE: 26

```
atgacccacc tgaacatcgc taatcgcgtc gacagcttct tcattccctg cgtgaccctc    60
ttcggtccgg gctgcgcgcg cgaaacgggc gctcgcgcca gatcactcgg ggccaggaag   120
gctctcatcg tcacggatgc aggcttgcac aagatgggc tctccgaagt cgtcgcgggg   180
cacattgccg aagccgggct ccaggccgtc atctttccgg gtgccgagcc caatcccacc   240
gacgttaacg ttcacgacgg cgtcaagttg ttcgagcggg aagaatgcga cttcatcgtt   300
tcgctcggcg gcggctcatc gcacgactgc gcgaaaggca tcggcctcgt taccgccgga   360
ggcggacata tccgcgacta cgaaggcatc gacaaatcaa cggtgccaat gacgccgctg   420
atttcgatca acacgaccgc tggcactgct gcggaaatga cacgcttttg catcatcact   480
aattcgagca atcatgtgaa gatggcaatc gtcgactggc gttgcacgcc attaatcgcc   540
atcgacgatc cgagcctgat ggtcgcgatg ccgcccgcct tgacggcggc gaccggcatg   600
gacgcgttga ctcacgccat cgaggcatac gtttccaccg ccgccacgcc aattaccgat   660
```

-continued

```
gcctgtgcgg agaaggcgat cgtgctgatc gccgaatggc tgcccaaagc tgtcgcgaac    720
ggggactcga tggaagcacg cgcggccatg tgctacgccc aataccttgc cggcatggcc    780
ttcaacaacg catcactcgg ttacgtgcac gcgatggccc atcaactcgg cggcttctac    840
aatttgcccc acggcgtgtg caacgcgatc ctgctgccgc acgtgtcgga attcaacctc    900
attgccgcgc cggagcgcta cgcgagaatc gccgaactgc taggcgagaa cattgggggc    960
ttgagcgcgc atgacgccgc caaagctgcc gtctcggcga tccggaccct ttccacgtcg   1020
attggcattc cggcgggtct ggcgggcctg ggcgtcaagg cggacgacca tgaagtgatg   1080
gcaagcaatg cgcaaaagga tgcttgcatg ctgacgaatc gcgcaaggc cacgctggcg   1140 caagtcatgg caatcttcgc tgcggcgatg taa                                1173
```

<210> SEQ ID NO 27
<211> LENGTH: 393
<212> TYPE: PRT
<213> ORGANISM: uncultured organism

<400> SEQUENCE: 27

```
Met Ser Leu Val Asn Tyr Leu Gln Leu Ala Asp Arg Thr Asp Gly Phe
1               5                   10                  15

Phe Ile Pro Ser Val Thr Leu Val Gly Pro Gly Cys Val Lys Glu Val
                20                  25                  30

Gly Pro Arg Ala Lys Met Leu Gly Ala Lys Arg Ala Leu Ile Val Thr
            35                  40                  45

Asp Ala Gly Leu His Lys Met Gly Leu Ser Gln Glu Ile Ala Asp Leu
        50                  55                  60

Leu Arg Ser Glu Gly Ile Asp Ser Val Ile Phe Ala Gly Ala Glu Pro
65                  70                  75                  80

Asn Pro Thr Asp Ile Asn Val His Asp Gly Val Lys Val Tyr Gln Lys
                85                  90                  95

Glu Lys Cys Asp Phe Ile Val Ser Leu Gly Gly Gly Ser Ser His Asp
            100                 105                 110

Cys Ala Lys Gly Ile Gly Leu Val Thr Ala Gly Gly His Ile Arg
        115                 120                 125

Asp Tyr Glu Gly Val Asp Lys Ser Lys Val Pro Met Thr Pro Leu Ile
130                 135                 140

Ala Ile Asn Thr Thr Ala Gly Thr Ala Ser Glu Met Thr Arg Phe Cys
145                 150                 155                 160

Ile Ile Thr Asn Thr Asp Thr His Val Lys Met Ala Ile Val Asp Trp
                165                 170                 175

Arg Cys Thr Pro Leu Val Ala Ile Asp Asp Pro Arg Leu Met Val Lys
            180                 185                 190

Met Pro Pro Ala Leu Thr Ala Thr Gly Met Asp Ala Leu Thr His
        195                 200                 205

Ala Val Glu Ala Tyr Val Ser Thr Ala Ala Thr Pro Ile Thr Asp Thr
    210                 215                 220

Cys Ala Glu Lys Ala Ile Glu Leu Ile Gly Gln Trp Leu Pro Lys Ala
225                 230                 235                 240

Val Ala Asn Gly Asp Trp Met Glu Ala Arg Ala Ala Met Cys Tyr Ala
                245                 250                 255

Gln Tyr Leu Ala Gly Met Ala Phe Asn Asn Ala Ser Leu Gly Tyr Val
            260                 265                 270

His Ala Met Ala His Gln Leu Gly Gly Phe Tyr Asn Leu Pro His Gly
        275                 280                 285
```

Val Cys Asn Ala Ile Leu Leu Pro His Val Cys Gln Phe Asn Leu Ile
            290                 295                 300

Ala Ala Thr Glu Arg Tyr Ala Arg Ile Ala Ala Leu Leu Gly Val Asp
305                 310                 315                 320

Thr Ser Gly Met Glu Thr Arg Glu Ala Ala Leu Ala Ala Ile Ala Ala
                325                 330                 335

Ile Lys Glu Leu Ser Ser Ser Ile Gly Ile Pro Arg Gly Leu Ser Glu
            340                 345                 350

Leu Gly Val Lys Ala Ala Asp His Lys Val Met Ala Glu Asn Ala Gln
        355                 360                 365

Lys Asp Ala Cys Met Leu Thr Asn Pro Arg Lys Ala Thr Leu Glu Gln
370                 375                 380

Val Ile Gly Ile Phe Glu Ala Ala Met
385                 390

<210> SEQ ID NO 28
<211> LENGTH: 1182
<212> TYPE: DNA
<213> ORGANISM: uncultured organism

<400> SEQUENCE: 28
atgagtttgg tgaattatct tcaactggcc gaccgcaccg atggtttctt catcccttca      60
gtgaccctcg ttggccctgg atgtgtcaaa gaagttgggc cacgggccaa gatgctgggc     120
gcgaaacggg cgttgatcgt caccgacgct gggttgcaca agatgggggtt gtcgcaggaa    180 attgccgacc tactgcgcag cgagggcatt gacagtgtaa ttttcgctgg tgccgaaccc     240
aatccaaccg acatcaatgt tcatgatggt gtaaaagttt atcagaaaga gaagtgcgat     300
ttcatcgttt ccttgggtgg cggatcctcg cacgactgtg ccaaaggtat cggtctggtc     360
accgcggggg gggggcatat ccgcgactac gaaggagtcg acaagtccaa ggtgccgatg     420
acgccgctga tcgccatcaa caccactgcc ggtaccgcct cggaaatgac cgctttgc      480 atcatcacca ataccgatac ccacgtgaaa atggccatcg tcgactggcg ctgtaccccg     540
ttggtagcga tcgatgatcc tcgcttgatg gtgaagatgc cgcctgcgct taccgccgcc     600
acgggtatgg acgctttgac gcacgcggtc gaggcttatg tttccaccgc cgccaccccc     660
atcaccgata cttgtgccga aaaggccatc gaactcatcg tcaatggct ccccaaagcg      720 gtggccaacg tgattggat ggaagcgcgc gccgccatgt gctatgccca gtatcttgcc      780
ggcatggcgt tcaacaatgc ctcgctcggt tacgtccatg ccatggcgca ccagctcggc     840
ggtttctata atctgccgca tggtgtgtgc aatgccatcc tactgccgca cgtctgccag     900
ttcaatctca tcgcagccac tgaacgctat gcccggattg ccgccttgct gggtgtagac     960
acttcaggca tggagacgcg agaggctgcc ttggcggcga tcgctgccat caaggagctt    1020
tcttcatcca ttggcattcc ccgtggtctg agtgagctgg gtgtgaaggc ggccgatcac    1080
aaggtaatgg ccgaaaacgc ccagaaggat gcctgcatgc tcaccaatcc gcgcaaagct    1140
acgttggaac aggtgatcgg catcttcgag gcggccatgt ga                       1182

<210> SEQ ID NO 29
<211> LENGTH: 387
<212> TYPE: PRT
<213> ORGANISM: Geobacter bemidjiensis Bem

<400> SEQUENCE: 29

Met Ala Leu Gly Glu Gln Thr Tyr Gly Phe Tyr Ile Pro Thr Val Ser
1               5                   10                  15

Leu Met Gly Ile Gly Ser Ala Lys Glu Thr Gly Gly Gln Ile Lys Ala
            20                  25                  30

Leu Gly Ala Ser Lys Ala Leu Ile Val Thr Asp Lys Gly Leu Ser Ala
        35                  40                  45

Met Gly Val Ala Asp Lys Ile Lys Ser Gln Val Glu Glu Ala Gly Val
    50                  55                  60

Ser Ala Val Ile Phe Asp Gly Ala Glu Pro Asn Pro Thr Asp Ile Asn
65                  70                  75                  80

Val His Asp Gly Val Lys Val Tyr Gln Asp Asn Gly Cys Asp Ala Ile
                85                  90                  95

Ile Ser Leu Gly Gly Gly Ser Ser His Asp Cys Ala Lys Gly Ile Gly
            100                 105                 110

Met Val Ile Gly Asn Gly Gly His Ile Arg Asp Leu Glu Gly Val Asn
            115                 120                 125

Lys Thr Thr Lys Pro Met Pro Ala Phe Val Ala Ile Asn Thr Thr Ala
130                 135                 140

Gly Thr Ala Ser Glu Met Thr Arg Phe Cys Ile Ile Thr Asn Thr Asp
145                 150                 155                 160

Thr His Val Lys Met Ala Ile Val Asp Trp Arg Cys Thr Pro Asn Val
                165                 170                 175

Ala Ile Asn Asp Pro Leu Leu Met Val Gly Lys Pro Ala Ala Leu Thr
            180                 185                 190

Ala Ala Thr Gly Met Asp Ala Leu Thr His Ala Val Glu Ala Tyr Val
            195                 200                 205

Ser Thr Ile Ala Thr Pro Ile Thr Asp Ala Cys Ala Ile Lys Ala Ile
210                 215                 220

Glu Leu Ile Ala Glu Phe Leu Ser Lys Ala Val Ala Asn Gly Glu Asp
225                 230                 235                 240

Leu Glu Ala Arg Asp Lys Met Ala Tyr Ala Glu Tyr Leu Ala Gly Met
                245                 250                 255

Ala Phe Asn Asn Ala Ser Leu Gly Tyr Val His Ser Met Ala His Gln
            260                 265                 270

Leu Gly Gly Phe Tyr Asn Leu Pro His Gly Val Cys Asn Ala Ile Leu
            275                 280                 285

Leu Pro Ala Val Ser Gln Tyr Asn Leu Ile Ala Cys Pro Lys Arg Phe
290                 295                 300

Ala Asp Ile Ala Lys Ala Leu Gly Glu Asn Ile Asp Gly Leu Ser Val
305                 310                 315                 320

Thr Glu Ala Gly Gln Lys Ala Ile Asp Arg Ile Arg Thr Leu Ser Ala
                325                 330                 335

Ser Ile Gly Ile Pro Thr Gly Leu Lys Ala Leu Asn Val Lys Glu Ala
            340                 345                 350

Asp Leu Thr Ile Met Ala Glu Asn Ala Lys Lys Asp Ala Cys Gln Phe
            355                 360                 365

Thr Asn Pro Arg Lys Ala Thr Leu Glu Gln Val Val Gln Ile Phe Lys
            370                 375                 380

Asp Ala Met
385

-continued

<210> SEQ ID NO 30
<211> LENGTH: 1164
<212> TYPE: DNA
<213> ORGANISM: Geobacter bemidjiensis Bem

<400> SEQUENCE: 30

```
atggcattag agagcagac gtacggtttc tacattccga cagtatcact gatgggtatt       60
ggttccgcta aagagaccgg tggccagatc aaggcactgg gcgcatccaa ggcgctgatc      120
gttaccgaca aaggcctctc ggccatgggc gttgccgaca agatcaaatc ccaggttgaa      180
gaggccggtg tttccgcagt catcttcgac ggcgcagagc ccaacccgac cgacatcaac      240
gtgcacgacg gcgtgaaggt gtaccaggac aacggctgtg acgcgatcat ctccctgggc      300
ggcggttcct cccatgactg cgctaaaggc atcggcatgg tcatcggcaa cggcggccac      360
atccgcgatc tcgaaggcgt gaacaagacc accaagccga tgccggcatt cgtggccatc      420
aacaccaccg caggcaccgc gtccgaaatg acccgtttct gcatcatcac caacaccgac      480
acccacgtga agatggcgat cgtcgactgg cgctgcaccc cgaacgtcgc gatcaacgac      540
ccgctgctca tggtcggcaa gccggcggca ctgaccgcgg caaccggcat ggacgcactg      600
acccacgccg tcgaggcgta cgtgtccacc atcgctaccc cgatcaccga cgcttgcgcc      660
atcaaggcaa tcgagctgat cgccgagttc ctctccaagg cagttgccaa cggcgaagac      720
ctcgaggcgc gcgacaagat ggcttacgcc gagtacctgg ccggcatggc gttcaacaac      780
gcatcgcttg gctacgttca ctccatggct caccagctgg gcggcttcta caacctgccg      840
cacggcgtct gcaacgccat cctgctcccg gccgtcagcc agtacaacct gatcgcttgc      900
ccgaagcgtt tcgccgacat cgcgaaagcc ctcggcgaga catcgacgg cctctccgtg      960
accgaagcag gccagaaggc aatcgacagg atccgcaccc tctccgcttc catcggcatc      1020
ccgaccggcc tcaaggccct caacgtcaag gaagccgacc tcaccatcat ggctgagaac      1080
gcgaagaagg acgcttgcca gttcaccaac ccgcgcaagg caacccttga gcaggtcgtc      1140
cagatcttca aggacgcaat gtaa                                              1164
```

<210> SEQ ID NO 31
<211> LENGTH: 383
<212> TYPE: PRT
<213> ORGANISM: Carboxydothermus hydrogenoformans Z-2901

<400> SEQUENCE: 31

```
Met Lys Thr Tyr Arg Phe Tyr Met Pro Pro Val Ser Leu Met Gly Ile
1               5                   10                  15

Gly Cys Leu Lys Glu Ala Gly Glu Glu Ile Lys Lys Leu Gly Phe Lys
            20                  25                  30

Lys Ala Leu Ile Val Thr Asp Lys Val Leu Val Lys Ile Gly Leu Val
        35                  40                  45

Asn Lys Leu Thr Glu Ile Leu Asp Asn Glu Gly Ile Glu Tyr Val Ile
    50                  55                  60

Phe Asp Glu Thr Lys Pro Asn Pro Thr Val Lys Asn Val Glu Asp Gly
65                  70                  75                  80

Leu Lys Met Leu Lys Glu Asn Asn Cys Asp Phe Leu Ile Ser Phe Gly
            85                  90                  95

Gly Gly Ser Pro His Asp Cys Ala Lys Gly Ile Gly Leu Val Ala Thr
            100                 105                 110

Asn Gly Gly Ser Ile Lys Asp Tyr Glu Gly Val Asn Lys Ser Ala Lys
            115                 120                 125
```

```
Pro Met Leu Pro Leu Val Ala Val Asn Thr Thr Ala Gly Thr Ala Ser
        130                 135                 140

Glu Met Thr Arg Phe Ser Ile Ile Thr Asp Glu Asp Arg His Val Lys
145                 150                 155                 160

Met Ala Ile Val Asp Trp His Val Thr Pro Ile Met Ala Val Asn Asp
                165                 170                 175

Pro Glu Leu Met Val Glu Met Pro Lys Ala Leu Thr Ala Ala Thr Gly
            180                 185                 190

Met Asp Ala Leu Thr His Ala Ile Glu Ala Tyr Val Ser Ile Asp Ala
        195                 200                 205

Thr Pro Val Thr Asp Ala Ala Leu Lys Ala Ile Glu Leu Ile Phe
    210                 215                 220

Lys Tyr Leu Lys Arg Ala Val Glu Asn Gly Lys Asp Ile Glu Ala Arg
225                 230                 235                 240

Asp Lys Met Ala Tyr Ala Glu Tyr Leu Ala Gly Val Ala Phe Asn Asn
                245                 250                 255

Ala Gly Leu Gly Tyr Val His Ala Met Ala His Gln Leu Gly Gly Phe
            260                 265                 270

Tyr Asp Leu Pro His Gly Val Cys Asn Ala Val Leu Leu Pro His Val
        275                 280                 285

Gln Ala Tyr Asn Leu Gln Val Val Pro Glu Arg Phe Ile Asp Ile Ala
    290                 295                 300

Lys Ala Met Gly Ile Asn Val Glu Asn Leu Thr Ala Lys Glu Ala Gly
305                 310                 315                 320

Glu Lys Val Leu Glu Ala Ile Lys Asn Leu Ser Arg Glu Ile Gly Ile
                325                 330                 335

Pro Ser Gly Leu Lys Glu Leu Gly Val Lys Glu Glu Asp Leu Lys Thr
            340                 345                 350

Leu Ala Glu Asn Ala Leu Lys Asp Ala Cys Gly Phe Thr Asn Pro Lys
        355                 360                 365

Gln Ala Ser Leu Asp Asp Ile Ile Arg Ile Phe Lys Glu Ala Met
    370                 375                 380
```

<210> SEQ ID NO 32
<211> LENGTH: 1152
<212> TYPE: DNA
<213> ORGANISM: Carboxydothermus hydrogenoformans Z-2901

<400> SEQUENCE: 32

```
atgaagacgt accgttttta catgccgccg gttagcctaa tgggtattgg ctgcctgaaa      60
gaggccggcg aggaaattaa aaagctcggt tttaaaaaag ctcttattgt aaccgataag     120
gtactggtta agattggtct tgttaataag ttaaccgaaa tcctggacaa cgaaggaatc     180
gagtacgtta tttttgatga aactaaacca atcctacgg ttaaaaatgt tgaagatggt      240
cttaaaatgt taaagagaa caactgtgat tttttaattt cctttggtgg aggttcgcct      300
catgactgtg ccaaaggcat tgggctggtg caactaatg tgggctccat caagattat       360
gaaggggtaa ataagtcggc taaacccatg ttacctctgg tggcggtaaa cactactgct     420
ggtaccgcaa gtgaaatgac gagattttca ataataaccg acgaggatag acacgtaaag     480
atggccattg tcgactggca tgtaactccg ataatggctg ttaacgatcc cgaattaatg     540
gtagagatgc caaaagcttt aactgccgca acgggtatgg atgccttaac ccatgctatt     600
gaagcttacg tatctattga tgcaactccg gttaccgacg cggcagcttt aaaggcaatc     660
gagcttattt ttaaatacct gaaacgggca gtagaaaatg gaaaggatat tgaggcaagg     720
```

-continued

```
gataaaatgg cttatgcgga gtatttagcc ggggtagcct ttaacaatgc aggcttagga       780
tatgtacacg cgatggccca ccagctggga gggttttacg atcttcctca tggtgtgtgt       840
aatgctgtat tgctacctca tgtgcaggcc tataatctgc aggttgtacc cgaaaggttt       900
attgatatag ctaaggcaat gggaataaat gtagaaaact aacggcaaa agaagctgga        960 gaaaaggtac ttgaagcaat taaaaatctt tcgcgggaaa ttggcatacc atcgggtctt      1020
aaggaattag gagttaagga agaggatctt aagactttag ccgaaaatgc cctgaaagat      1080
gcttgcggat ttaccaatcc aaagcaggcg agcttagatg atattatacg gatatttaaa      1140
gaagcaatgt aa                                                          1152
```

<210> SEQ ID NO 33
<211> LENGTH: 385
<212> TYPE: PRT
<213> ORGANISM: Actinobacillus succinogenes 130Z

<400> SEQUENCE: 33

```
Met Ser Thr Tyr Tyr Phe Leu Pro Thr Arg Asn Val Phe Gly Glu Asn
1               5                   10                  15

Ala Val Glu Glu Val Gly Thr Leu Met Lys Ser Leu Gly Gly Asn Asn
            20                  25                  30

Pro Leu Ile Val Thr Asp Ala Phe Leu Ala Lys Asn Gly Met Ala Asp
        35                  40                  45

Gln Leu Ala Ala Val Leu Ser Asn Ala Gly Leu Lys Pro Val Ile Phe
    50                  55                  60

Gly Gly Ala Glu Pro Asn Pro Thr Asp Lys Asn Val Glu Glu Gly Ile
65                  70                  75                  80

Val Phe Tyr Asn Glu His Gly Cys Asp Ser Ile Ile Ser Leu Gly Gly
                85                  90                  95

Gly Ser Ser His Asp Cys Ala Lys Gly Ile Gly Leu Ile Ala Ser Asn
            100                 105                 110

Gly Gly Arg Ile Gln Asp Tyr Glu Gly Val Asp Arg Ser His Asn Ala
        115                 120                 125

Met Val Pro Leu Met Ala Val Asn Thr Thr Ala Gly Thr Ala Ser Glu
    130                 135                 140

Ile Thr Arg Phe Cys Ile Ile Thr Asp Thr Ala Arg Lys Val Lys Met
145                 150                 155                 160

Ala Ile Val Asp Trp Arg Ile Thr Pro Gln Ile Ala Val Asn Asp Pro
                165                 170                 175

Leu Leu Met Lys Gly Met Pro Pro Ser Leu Thr Ala Ala Thr Gly Met
            180                 185                 190

Asp Ala Leu Thr His Ala Ile Glu Ala Tyr Val Ser Thr Ala Ala Asn
        195                 200                 205

Pro Leu Thr Asp Ala Ala Ala Leu Met Ala Ile Thr Met Ile Gln Gln
    210                 215                 220

Tyr Leu Pro Lys Ala Val Ala Asn Gly Asp Tyr Met Lys Ala Arg Asp
225                 230                 235                 240

Lys Met Ala Tyr Ala Gln Tyr Leu Ala Gly Ile Ala Phe Asn Asn Ala
                245                 250                 255

Ser Leu Gly Tyr Val His Ala Met Ala His Gln Leu Gly Gly Phe Tyr
            260                 265                 270

Asn Leu Pro His Gly Val Cys Asn Ala Ile Leu Leu Pro Tyr Val Glu
        275                 280                 285
```

```
Glu Phe Asn Leu Ile Gly Asn Leu Asn Arg Phe Arg Asp Ile Ala Lys
        290                 295                 300

Ala Met Gly Glu Asn Ile Asp Gly Leu Cys Thr Asp Ala Ala Leu
305                 310                 315                 320

Lys Ala Ile Gly Ala Ile Arg Arg Leu Ser Lys Gln Val Gly Ile Pro
                325                 330                 335

Ala Asn Leu Gln Leu Leu Gly Val Lys Pro Glu Asp Phe Asp Val Met
                340                 345                 350

Ala Glu Asn Ala Met Lys Asp Val Cys Met Leu Thr Asn Pro Arg Lys
            355                 360                 365

Ala Thr Lys Gln Gln Val Ile Glu Ile Phe Gln Arg Ala Tyr Asp Gly
        370                 375                 380

Asp
385

<210> SEQ ID NO 34
<211> LENGTH: 1158
<212> TYPE: DNA
<213> ORGANISM: Actinobacillus succinogenes 130Z

<400> SEQUENCE: 34
atgtcaacat attattttt accaaccaga atgtattcg gcgaaaatgc agttgaagaa       60
gtcggcacat taatgaaaag tttaggcggc aacaatcctc tgattgttac cgatgctttc      120
ctcgccaaaa acggtatggc ggatcaatta gccgccgtat taagtaacgc aggtttaaaa      180
ccggtgattt tcggcggtgc cgaaccgaat ccgacagaca aaaacgtaga agagggtatt      240
gtgttttata cgaacacggg ttgcgattcc atcatttctt gggcggtgg ttcctcccac       300 gactgtgcca aggtatcgg tttaatcgcc agtaacggcg gacgcattca ggattacgaa       360
ggcgtcgatc gttcccacaa tgcgatggta ccgctgatgg cggtcaacac cacggcggga      420
acggcgtctg aaatcacccg gttctgtatt attaccgaca cggcgcggaa agtgaaaatg      480
gcgattgtag actggcgcat cactccgcaa atcgcggtga cgatccatt gttgatgaaa       540 ggcatgccgc caagcctgac cgcagcaacc ggtatggacg ccctgacgca cgcaatcgaa      600
gcctacgtat ccactgccgc caacccgctc acggatgccg cagcgctgat ggcgatcacc      660
atgattcagc aatacctgcc gaaagcggta gcgaacggcg actatatgaa agcccgcgat      720
aaaatggcat atgcgcaata tttggcaggt atcgcttca ataatgcctc tctcggctat       780
gttcatgcga tggcacacca actgggcggt ttctacaacc tgccgcacgg tgtgtgtaac      840
gcgattctgt tgcctatgt ggaagaattc aacctcatcg gtaatctcaa ccgtttccgc       900
gacatcgcca agctatggg tgaaaatatc gacggtttat gcacggacga tgcggcactg      960
aaagccattg gcgcgattcg ccgtttaagc aaacaagtgg gaatcccggc aaatctgcaa     1020
ctgctcggcg tgaaaccgga agatttcgac gtgatggcgg aaaatgcgat gaaagacgtg     1080
tgtatgctca ccaatccgcg caaagccacc aaacagcaag tcatcgaaat tttccaacgg     1140
gcttatgacg gcgattaa                                                    1158

<210> SEQ ID NO 35
<211> LENGTH: 390
<212> TYPE: PRT
<213> ORGANISM: Acinetobacter baumannii Naval-82

<400> SEQUENCE: 35

Met Ala Phe Lys Asn Ile Ala Asp Gln Thr Asn Gly Phe Tyr Ile Pro
1               5                   10                  15
```

Cys Val Ser Leu Phe Gly Pro Gly Cys Ala Lys Glu Ile Gly Thr Lys
            20                  25                  30

Ala Gln Asn Leu Gly Ala Lys Lys Ala Leu Ile Val Thr Asp Glu Gly
            35                  40                  45

Leu Phe Lys Phe Gly Val Ala Asp Leu Ile Ala Ser Tyr Leu Thr Glu
 50                  55                  60

Ala Gly Val Ala Ser His Ile Phe Pro Gly Ala Glu Pro Asn Pro Thr
 65                  70                  75                  80

Asp Ile Asn Val His Asn Gly Val Asn Ala Tyr Asn Glu Asn Gly Cys
                85                  90                  95

Asp Phe Ile Val Ser Leu Gly Gly Ser Ser His Asp Cys Ala Lys
            100                 105                 110

Gly Ile Gly Leu Val Thr Ala Gly Gly His Ile Arg Asp Tyr Glu
            115                 120                 125

Gly Ile Asp Lys Ser Lys Val Pro Met Thr Pro Leu Ile Ala Val Asn
130                 135                 140

Thr Thr Ala Gly Thr Ala Ser Glu Met Thr Arg Phe Cys Ile Ile Thr
145                 150                 155                 160

Asn Thr Asp Thr His Val Lys Met Ala Ile Val Asp Trp Arg Cys Thr
                165                 170                 175

Pro Leu Ile Ala Ile Asp Asp Pro Lys Leu Met Ile Ala Lys Pro Ala
            180                 185                 190

Gly Leu Thr Ala Ala Thr Gly Met Asp Ala Leu Thr His Ala Val Glu
            195                 200                 205

Ala Tyr Val Ser Thr Ala Ala Asn Pro Ile Thr Asp Ala Cys Ala Glu
 210                 215                 220

Lys Ala Ile Thr Met Ile Ser Gln Trp Leu Gln Pro Ala Val Ala Asn
225                 230                 235                 240

Gly Glu Asn Ile Glu Ala Arg Asp Ala Met Ser Tyr Ala Gln Tyr Leu
            245                 250                 255

Ala Gly Met Ala Phe Asn Asn Ala Ser Leu Gly Tyr Val His Ala Met
            260                 265                 270

Ala His Gln Leu Gly Gly Phe Tyr Asn Leu Pro His Gly Val Cys Asn
            275                 280                 285

Ala Ile Leu Leu Pro His Val Cys Glu Phe Asn Leu Ile Ala Cys Pro
 290                 295                 300

Asp Arg Tyr Ala Lys Ile Ala Glu Leu Met Gly Val Asn Thr His Gly
305                 310                 315                 320

Leu Thr Val Thr Glu Ala Ala Tyr Ala Ile Asp Ala Ile Arg Lys
            325                 330                 335

Leu Ser Ser Leu Ile Gly Ile Pro Ser Gly Leu Thr Glu Leu Gly Val
            340                 345                 350

Lys Thr Glu Asp Leu Ala Val Met Ala Glu Asn Ala Gln Lys Asp Ala
            355                 360                 365

Cys Met Leu Thr Asn Pro Arg Lys Ala Asn His Ala Gln Val Val Glu
            370                 375                 380

Ile Phe Lys Ala Ala Leu
385                 390

<210> SEQ ID NO 36
<211> LENGTH: 1173
<212> TYPE: DNA
<213> ORGANISM: Acinetobacter baumannii Naval-82

<400> SEQUENCE: 36

```
atggcttta aaaatattgc agatcaaaca aacggttttt atattccttg cgtatcactc    60
tttggaccag gatgtgccaa agaaattgga acaaaggcgc agaacctcgg cgcaaaaaaa   120
gcattaattg tgaccgatga agggctattt aaatttggcg ttgcagatct tatcgcaagc   180
tatttaaccg aagcaggcgt agcgagccat attttcccgg gcgcggaacc taacccaacc   240
gatattaatg tccacaacgg tgtgaatgcc tataacgaaa atggctgtga ctttattgtg   300
tcgttaggcg gcggctcatc tcatgactgt gcaaagggga ttggcttagt gactgcgggt   360
ggtggtcata ttcgtgacta cgaaggcatc gataaaagta aagtcccaat gacgccatta   420
attgcagtga atacaacggc tggtacggca tctgaaatga cccgtttctg tattattacc   480
aatacagata ctcatgtaaa aatggctatt gtggactggc gttgtactcc acttattgcg   540
attgatgacc cgaaacttat gattgcaaaa ccagcaggtt taacggctgc aacaggtatg   600
gatgcattaa cccatgcagt tgaagcatat gtatctacgg cagcaaaccc aattaccgat   660
gcttgtgcag aaaaagccat caccatgatt agtcaatggt acaacccgc tgtcgcaaat   720
ggcgaaaaca tcgaagctcg tgatgctatg agctatgcgc agtacttggc tggtatggca   780
tttaacaatg catctttagg ttatgttcat gcaatggcac accagttggg cgggttctac   840
aacctacctc atggtgtatg taacgcaatc ttgctaccac atgtttgtga atttaactta   900
attgcttgtc cagatcgtta tgcaaaaatc gcagaattaa tgggtgtaaa tacccacggt   960
ctcaccgtaa cagaagctgc gtatgctgca attgatgcca ttcgtaaact gtcttcttta  1020
attggtatcc catctggcct aacagaactg ggcgtaaaaa ccgaagacct cgcggttatg  1080
gccgaaaatg ctcaaaaaga tgcatgtatg ctcaccaacc ctcgtaaagc aaaccatgca  1140
caagttgtgg agattttcaa agcagcactt taa                              1173
```

<210> SEQ ID NO 37
<211> LENGTH: 385
<212> TYPE: PRT
<213> ORGANISM: Clostridium pasteurianum DSM 525

<400> SEQUENCE: 37

```
Met Arg Met Tyr Asp Phe Leu Ala Pro Asn Val Asn Phe Met Gly Ala
1               5                   10                  15

Gly Ala Ile Lys Leu Val Gly Glu Arg Cys Lys Ile Leu Gly Gly Lys
            20                  25                  30

Lys Ala Leu Ile Val Thr Asp Lys Phe Leu Arg Asn Met Glu Asp Gly
        35                  40                  45

Ala Val Ala Gln Thr Val Lys Tyr Ile Lys Glu Ala Gly Ile Asp Val
    50                  55                  60

Ala Phe Tyr Asp Asp Val Glu Pro Asn Pro Lys Asp Thr Asn Val Arg
65                  70                  75                  80

Asp Gly Leu Lys Val Tyr Arg Lys Glu Asn Cys Asp Leu Ile Val Thr
                85                  90                  95

Val Gly Gly Gly Ser Ser His Asp Cys Gly Lys Gly Ile Gly Ile Ala
            100                 105                 110

Ala Thr His Glu Gly Asp Leu Tyr Asp Tyr Ala Gly Ile Glu Thr Leu
        115                 120                 125

Thr Asn Pro Leu Pro Pro Ile Val Ala Val Asn Thr Thr Ala Gly Thr
    130                 135                 140

Gly Ser Glu Val Thr Arg His Cys Val Ile Thr Asn Thr Lys Thr Lys
145                 150                 155                 160
```

Ile Lys Phe Val Ile Val Ser Trp Arg Asn Leu Pro Leu Val Ser Ile
            165                 170                 175

Asn Asp Pro Ile Leu Met Ile Lys Lys Pro Ala Gly Leu Thr Ala Ala
        180                 185                 190

Thr Gly Met Asp Ala Leu Thr His Ala Ile Glu Ser Tyr Val Ser Lys
    195                 200                 205

Asp Ala Asn Pro Val Thr Asp Ala Leu Ala Ile Gln Ala Ile Lys Leu
210                 215                 220

Ile Ala Asn Asn Leu Arg Gln Ala Val Ala Leu Gly Glu Asn Leu Glu
225                 230                 235                 240

Ala Arg Glu Asn Met Ala Tyr Ala Ser Leu Leu Ala Gly Met Ala Phe
                245                 250                 255

Asn Asn Ala Asn Leu Gly Tyr Val His Ala Met Ala His Gln Leu Gly
            260                 265                 270

Gly Leu Tyr Asp Met Ala His Gly Val Ala Asn Ala Met Leu Leu Pro
        275                 280                 285

His Val Glu Arg Tyr Asn Leu Ile Ser Asn Pro Lys Lys Phe Ala Asp
290                 295                 300

Ile Ala Glu Phe Met Gly Glu Asn Ile Glu Gly Leu Ser Val Met Glu
305                 310                 315                 320

Ala Ala Glu Lys Ala Ile Asp Ala Met Phe Arg Leu Ser Lys Asp Val
                325                 330                 335

Gly Ile Pro Ala Ser Leu Lys Glu Met Gly Val Asn Glu Gly Asp Phe
            340                 345                 350

Glu Tyr Met Ala Lys Met Ala Leu Lys Asp Gly Asn Ala Phe Ser Asn
        355                 360                 365

Pro Arg Lys Gly Asn Glu Lys Asp Ile Val Lys Ile Phe Arg Glu Ala
    370                 375                 380

Phe
385

<210> SEQ ID NO 38
<211> LENGTH: 1158
<212> TYPE: DNA
<213> ORGANISM: Clostridium pasteurianum DSM 525

<400> SEQUENCE: 38
atgagaatgt atgattttt agcaccaaat gtaaacttta tgggagcagg tgcaataaaa      60
ttagtgggag aaagatgtaa aatattaggc ggaaagaaag ctttaatagt tacagataaa     120
ttcttgagaa atatggaaga tggagctgta gctcaaacgg ttaaatatat taagaagca     180 ggaatagatt tgcttttta tgatgatgta gagcctaatc ctaaggatac taatgttaga     240
gatggattaa aagtatatag aaaagaaaac tgtgatttaa tagttactgt aggaggagga     300
agttctcatg actgtggaaa gggaataggt attgcagcta cacgcgaggg agatctttat     360
gactatgctg gtatagaaac ccttactaat ccattgcctc cgatagtagc tgtaaataca     420
acagctggaa caggcagcga ggttactcgt cattgtgtta tcacaaacac aaaaacaaag     480
attaaatttg ttattgtaag ctggagaaat ctgccgttag tatccattaa tgatccaata     540
cttatgatta aaaagcctgc aggattaaca gcagctacag aatggatgc cttaactcat     600 gccatagagt cctatgtttc taaagatgca aacccagtaa cagatgcctt agctatacaa     660
gcaataaaat taatagctaa caatctgcgt caggcagtag ccctttggaga aaatctggaa     720 gctagagaaa atatggccta cgcatcactt ctggcaggaa tggcatttaa taatgcaaat     780

-continued

```
ttaggatatg tacatgctat ggcacatcaa ttaggaggcc tgtatgatat ggcacatggt    840
gttgccaatg ccatgttatt accacatgta gaacgctata atcttatatc aaatcctaag    900
aaatttgcag atatagcaga attcatggga gagaatattg aaggactttc agtaatggaa    960
gcagcagaaa aagctataga tgctatgttt agactttcaa aggatgttgg gataccagca   1020
agtcttaaag aaatgggagt taatgaagga gattttgaat atatggcaaa aatggcattg   1080
aaagatggaa atgcattcag taatccaaga aaggtaatg aaaagatat agttaaaata    1140 tttagagaag cattttaa                                                 1158
```

<210> SEQ ID NO 39
<211> LENGTH: 386
<212> TYPE: PRT
<213> ORGANISM: Methanosarcina mazei Tuc01

<400> SEQUENCE: 39

```
Met Ile Glu Lys Met Thr Tyr Thr Tyr Leu Asn Pro Lys Ile Ala Leu
1               5                   10                  15

Met Gly Pro Gly Cys Val Asn Gly Ile Gly Thr His Ala Lys Asp Leu
            20                  25                  30

Gly Gly Thr Lys Ala Leu Ile Val Ser Gly Lys Ser Arg His Gly Lys
        35                  40                  45

Glu Leu Ala Ala Asp Ile Arg Arg Ile Leu Glu Arg Ala Gly Ile Glu
    50                  55                  60

Ala Ala Ile Phe Pro Gly Ala Asp Pro Asn Pro Thr Asp Thr Ser Val
65                  70                  75                  80

Met Glu Gly Ala Asp Ile Tyr Arg Lys Glu Asn Cys Asn Met Ile Val
                85                  90                  95

Ala Val Gly Gly Gly Ser Pro Met Asp Cys Ala Lys Ala Ile Gly Ile
            100                 105                 110

Val Val Tyr Asn Gly Gly Arg Ile Asn Asp Tyr Glu Gly Val Gly Lys
        115                 120                 125

Val Thr Arg Gly Ile Pro Pro Leu Ile Thr Val Asn Thr Thr Ala Gly
    130                 135                 140

Thr Ala Ser Glu Met Thr Ser Phe Thr Ile Ile Thr Asp Thr Glu Arg
145                 150                 155                 160

His Ile Lys Met Ala Ile Val Asp Pro Arg Ile Thr Pro Asp Val Ala
                165                 170                 175

Val Asn Asp Pro Glu Leu Met Val Ser Met Pro Ala Leu Thr Ala
            180                 185                 190

Ala Thr Gly Met Asp Ala Leu Thr His Ala Val Glu Ala Tyr Val Ser
        195                 200                 205

Thr Met Ala Thr Pro Thr Thr Asp Ala Ala Ala Ile Lys Ala Ile Glu
    210                 215                 220

Leu Ile Ser Lys Tyr Leu Pro Glu Ala Val Leu His Gly Glu Asp Ile
225                 230                 235                 240

Arg Ala Arg Asp Met Met Ala His Ala Glu Tyr Leu Ala Gly Ile Ala
                245                 250                 255

Phe Asn Asn Ala Ser Leu Gly Tyr Val His Ser Met Ala His Gln Leu
            260                 265                 270

Gly Gly Phe Tyr Asp Leu Pro His Gly Val Cys Asn Ala Ile Leu Leu
        275                 280                 285

Pro Tyr Val Glu Met Tyr Asn Lys Gln Val Cys Pro Glu Arg Phe Ala
    290                 295                 300
```

Asp Ile Ala Lys Ala Met Gly Glu Lys Val Glu Gly Leu Ser Pro Glu
305                 310                 315                 320

Glu Ala Ala Asp Lys Ala Ile Glu Ala Ile Lys Lys Leu Ala Ala Glu
                325                 330                 335

Ile Gly Ile Pro Ser Gly Leu Lys Glu Leu Gly Ala Arg Glu Glu Asp
            340                 345                 350

Leu Glu Leu Leu Ala Glu Asn Ala Met Gln Asp Val Cys Arg Leu Thr
        355                 360                 365

Asn Pro Arg Glu Leu Ser Lys Glu Asp Ile Ile Glu Ile Tyr Arg Lys
    370                 375                 380

Ala Leu
385

<210> SEQ ID NO 40
<211> LENGTH: 1161
<212> TYPE: DNA
<213> ORGANISM: Methanosarcina mazei Tuc01

<400> SEQUENCE: 40
atgatagaaa agatgacata cacttacctg aacccaaaga tagccctgat gggacctgga      60
tgtgtaaacg ggatcggcac gcatgcaaaa gacctggggg gtacgaaagc cctgatagtt     120
tcaggcaaga gcaggcatgg gaaagagctt gcagcggata ttcgcagaat tcttgaacgt     180
gcggggatag aagcagcaat ctttccggga gcagacccga accctaccga tacttcagtt     240
atggaagggg cagacattta caggaaagaa aactgtaaca tgatagttgc tgtcggaggc     300
gggagcccta tggactgtgc aaaggcaatc ggcattgtgg tatataatgg gggaaggata     360
aatgattacg aaggagtggg taaagttacc agaggaattc cccctcttat cacggtaaac     420
acgacagcgg gcactgcgag cgagatgacc agtttttacaa ttattactga tactgaaagg     480
cacatcaaaa tggctatcgt cgacccccgg atcacacctg atgtggcggt taacgacccc     540
gaactgatgg tcagcatgcc gccagcactt acggctgcaa cagggatgga tgctctgacc     600
catgctgtgg aagcttatgt ttctaccatg gctaccccga ctaccgatgc ggctgccata     660
aaagcaatag agcttatatc aaaatacctg cccgaagccg tcctccacgg ggaagatata     720
cgggccaggg acatgatggc acacgcagaa tatcttgcag gcattgcttt caacaatgca     780
agtcttgggt atgttcattc catggctcat cagctcggag gctttatga cctcccgcat     840 ggggtctgca atgccatcct cctgccttat gtggagatgt ataacaagca ggtttgccct     900
gaacgttttg cagacatcgc aaaggcaatg ggagaaaaag ttgagggatt gagccccgaa     960
gaagcagcgg ataaagcaat agaagcgatc aaaaagcttg cagcagaaat cggaattcct    1020
tcaggtctga agagctcgg ggcaagggaa gaagaccttg aacttctggc tgagaatgcc    1080
atgcaggacg tttgccgcct tacaaatcca agagaactct caaaagaaga tatcatcgag    1140
atttacagaa aagccctgtg a                                              1161

<210> SEQ ID NO 41
<211> LENGTH: 393
<212> TYPE: PRT
<213> ORGANISM: Desulfovibrio vulgaris str. 'Miyazaki F'

<400> SEQUENCE: 41

Met Ala Val Gln Glu Gln Val Tyr Gly Phe Phe Ile Pro Ser Val Thr
1               5                   10                  15

Leu Ile Gly Ile Gly Ala Ser Lys Ala Ile Pro Glu Lys Ile Lys Ala
         20                  25                  30

Leu Gly Gly Ser Lys Pro Leu Ile Val Thr Asp Met Gly Ile Val Lys
         35                  40                  45

Ala Gly Ile Leu Lys Gln Ile Thr Asp Leu Leu Asp Ala Ala Lys Met
 50                  55                  60

Ala Tyr Ser Val Tyr Asp Glu Thr Ile Pro Asn Pro Thr Asp Asp Asn
 65                  70                  75                  80

Val His Lys Gly Val Glu Val Tyr Lys Lys Asn Lys Cys Asp Ser Leu
                 85                  90                  95

Ile Thr Leu Gly Gly Ser Ser His Asp Cys Gly Lys Gly Ile Gly
                100                 105                 110

Leu Val Ile Ala Asn Gly Gly Lys Ile His Asp Phe Glu Gly Val Asp
             115                 120                 125

Lys Ser Phe Lys Pro Met Pro Pro Tyr Val Ala Val Asn Thr Thr Ala
130                 135                 140

Gly Thr Ala Ser Glu Met Thr Arg Phe Cys Ile Ile Thr Asp Thr Ser
145                 150                 155                 160

Arg Lys Val Lys Met Ala Ile Val Asp Trp Arg Val Thr Pro Ser Ile
                165                 170                 175

Ala Leu Asp Asp Pro Leu Leu Met Met Gly Met Pro Pro Ala Leu Thr
            180                 185                 190

Ala Ala Thr Gly Met Asp Ala Leu Thr His Ala Val Glu Ala Tyr Val
            195                 200                 205

Ser Thr Ile Ala Thr Pro Met Thr Asp Ala Cys Ala Glu Gln Ala Ile
        210                 215                 220

Thr Leu Ile Ala Thr Phe Leu Arg Arg Ala Val Ala Asn Gly Arg Asp
225                 230                 235                 240

Ile Glu Ala Arg Glu Arg Met Cys Phe Ala Gln Tyr Leu Ala Gly Met
                245                 250                 255

Ala Phe Asn Asn Ala Ser Leu Gly His Val His Ala Met Ala His Gln
            260                 265                 270

Leu Gly Gly Phe Tyr Asp Leu Pro His Gly Glu Cys Asn Ala Ile Leu
        275                 280                 285

Leu Pro His Val Ser Gln Phe Asn Leu Ile Ala Lys Leu Asp Arg Phe
290                 295                 300

Ala Arg Ile Ala Glu Leu Met Gly Glu Asn Ile Ser Gly Leu Ser Val
305                 310                 315                 320

Arg Asp Ala Ala Glu Lys Ala Ile Cys Ala Ile Lys Arg Leu Ser Ala
                325                 330                 335

Asp Val Gly Ile Pro Ala Gly Leu Val Ala Leu Gly Lys Arg Tyr Gly
            340                 345                 350

Lys Asp Val Lys Ala Lys Asp Ile Ala Ile Met Thr Lys Asn Ala Gln
        355                 360                 365

Lys Asp Ala Cys Gly Leu Thr Asn Pro Arg Cys Pro Thr Asp Ala Asp
370                 375                 380

Val Ala Ala Ile Tyr Glu Ala Ala Met
385                 390

<210> SEQ ID NO 42
<211> LENGTH: 1182
<212> TYPE: DNA
<213> ORGANISM: Desulfovibrio vulgaris str. 'Miyazaki F'

<400> SEQUENCE: 42

```
atggcagtgc aggaacaggt ctacggggttc ttcattccca gcgttaccct gataggcatc    60
ggtgcttcca aggccatccc cgagaaaatc aaggcgctcg gcgggtccaa gccgctcatc   120
gtcaccgaca tgggcatcgt caaggcgggc atcctgaagc agatcaccga cctgctggac   180
gccgccaaga tggcctactc cgtatacgac gagaccatcc ccaaccccac cgacgacaac   240
gtccacaagg gcgtggaagt ctacaagaag aacaagtgcg acagcctgat taccctgggt   300
ggcggcagct cgcacgactg cggcaagggc atcggcctcg tcatcgccaa cggcggcaag   360
attcacgact cgaaggcgt ggacaagtcg ttcaagccca tgccgcctta cgtggccgtg    420
aacaccacgg cgggcaccgc ctctgaaatg acccgcttct gcatcatcac cgacaccagt   480
cgcaaggtga agatggccat cgttgactgg cgcgtgaccc ccagcatcgc cctggacgac   540
ccgctgctga tgatgggcat gccccggcg ctgaccgccg ccaccggcat ggacgccctg    600
acccacgccg tggaagccta cgtttccacc atcgccaccc ccatgaccga tgcctgtgcc   660
gaacaggcca tcacgctcat cgccaccttc ctgcgccgcg ccgtgccaa cgggcgcgac    720
atcgaggccc gcgagcggat gtgcttcgcc cagtacctgg cgggcatggc cttcaacaac   780
gccagccttg ccacgtgca cgccatggcc accagcttg gcggcttcta cgacctgccg    840
catggcgaat gcaacgccat cctgctgccc cacgtctcgc agttcaacct catcgccaag   900
ctggaccgct tgcccgcat cgcggaactg atgggcgaga acatcagcgg cctttcggtg    960
cgcgacgcgg cggaaaaggc catctgcgcc atcaagcgcc tgtcggcgga cgtgggcatt  1020
cccgccggtc tggtggccct tggcaagcgc tacggcaagg acgtgaaggc caaggacatc  1080
gccatcatga ccaagaacgc ccagaaggac gcctgcggcc tgaccaatcc gcgctgtccc  1140
accgatgctg atgtcgcggc catttacgaa gcggccatgt aa                    1182
```

<210> SEQ ID NO 43
<211> LENGTH: 393
<212> TYPE: PRT
<213> ORGANISM: Desulfovibrio africanus str. Walvis Bay

<400> SEQUENCE: 43

```
Met Ala Val Arg Glu Gln Val Tyr Gly Phe Phe Ile Pro Ser Val Thr
1               5                   10                  15

Leu Ile Gly Ile Gly Ala Ser Lys Glu Ile Pro Asn Lys Ile Arg Asp
            20                  25                  30

Leu Gly Gly Lys Lys Pro Leu Ile Val Thr Asp Gln Gly Ile Val Lys
        35                  40                  45

Ala Gly Ile Leu Lys Met Ile Thr Asp His Met Asp Lys Ala Gly Met
    50                  55                  60

Gln Tyr Ser Val Tyr Asp Lys Thr Ile Pro Asn Pro Thr Asp Asn Asn
65                  70                  75                  80

Val Ala Glu Gly Val Glu Val Tyr Lys Lys Glu Gly Cys Asp Ser Leu
                85                  90                  95

Ile Thr Leu Gly Gly Gly Ser Ser His Asp Cys Gly Lys Gly Val Gly
            100                 105                 110

Leu Val Val Ser Asn Gly Gly Lys Ile His Asp Tyr Glu Gly Val Asp
        115                 120                 125

Lys Ser Thr Lys Pro Leu Pro Pro Tyr Val Ala Val Asn Thr Thr Ala
    130                 135                 140

Gly Thr Ala Ser Glu Met Thr Arg Phe Cys Ile Ile Thr Asp Thr Ser
145                 150                 155                 160
```

```
Arg Lys Val Lys Met Ala Ile Val Asp Trp Arg Val Thr Pro Gly Ile
                165                 170                 175

Ala Leu Asp Asp Pro Leu Leu Met Val Gly Met Pro Pro Ala Leu Thr
            180                 185                 190

Ala Ala Thr Gly Met Asp Ala Leu Thr His Ala Val Glu Ala Tyr Val
        195                 200                 205

Ser Thr Ile Ala Thr Pro Met Thr Asp Ala Cys Ala Glu Lys Ala Ile
    210                 215                 220

Ser Leu Ile Phe Thr Phe Leu Arg Arg Ala Thr Ala Asn Gly Gln Asp
225                 230                 235                 240

Ile Glu Ala Arg Glu Gly Met Cys Phe Ala Gln Tyr Leu Ala Gly Met
                245                 250                 255

Ala Phe Asn Asn Ala Ser Leu Gly His Val His Ala Met Ala His Gln
            260                 265                 270

Leu Gly Gly Phe Tyr Asp Leu Pro His Gly Glu Cys Asn Ala Ile Leu
        275                 280                 285

Leu Pro His Val Glu Lys Tyr Asn Leu Ile Ala Lys Val Glu Arg Phe
    290                 295                 300

Gly Lys Met Ala Glu Ile Met Gly Glu Asn Ile Gln Gly Met Ser Pro
305                 310                 315                 320

Arg Ala Ala Ala Glu Lys Cys Leu Asp Ala Ile Arg Gln Leu Ser Gln
                325                 330                 335

Asp Val Gly Ile Pro Ser Gly Leu Ile Glu Leu Gly Lys Arg Tyr Gly
            340                 345                 350

Lys Asn Val Lys Lys Glu Asp Ile Asp Thr Met Thr Gly Asn Ala Gln
        355                 360                 365

Lys Asp Ala Cys Gly Phe Thr Asn Pro Arg Cys Pro Ser Asp Lys Asp
370                 375                 380

Val Lys Ala Ile Tyr Glu Ala Ala Leu
385                 390

<210> SEQ ID NO 44
<211> LENGTH: 1182
<212> TYPE: DNA
<213> ORGANISM: Desulfovibrio africanus str. Walvis Bay

<400> SEQUENCE: 44
atggcagtac gtgagcaggt ctacggattc ttcattccca gcgtcaccct tatcggcatc      60
ggtgcttcca aggaaattcc caacaaaatc cgtgatctcg gcggcaagaa acctctcatc     120
gtgaccgacc agggcatcgt caaggccggc atcctcaaga tgatcaccga ccacatggac     180
aaggccggga tgcagtacag cgtctatgac aagaccattc ccaacccaac cgacaacaac     240
gtggccgagg gcgtcgaagt ctataagaag gaaggctgtg acagcctgat taccctgggt     300
ggcggctcct cccacgactg cggcaagggc gtcggcctcg tcgtctccaa cggcggcaag     360
attcacgact acgaaggcgt ggacaagtcc accaagcccc tgcccccta tgtggccgtg     420 aacaccaccg ccggcaccgc ttccgagatg acccgcttct gcatcatcac ggacacctcg     480
cgcaaggtta aaatggctat cgtcgactgg cgcgtgaccc cgggtatcgc ccttgacgac     540
cccttgctca tggtcggcat gccccctgct ttgaccgccg ctaccggcat ggacgctctg     600
acccacgccg tcgaggccta tgtctcgacc atcgccacgc ccatgactga tgcttgcgct     660
gagaaggcca tctcccttat cttcacattc ctgcgccgcg ccacggctaa cggtcaggac     720
atagaggccc gtgaaggcat gtgcttcgcc cagtacttgg ccggcatggc cttcaacaac     780
```

-continued

```
gcctcgcttg gccacgtgca cgccatggct caccagttgg gcggcttcta cgacctgccg      840
cacggcgagt gcaatgccat cctgctgccg cacgtcgaga agtacaacct gattgccaag      900
gtcgagcgct tcggtaaaat ggccgaaatc atgggcgaga acatccaggg catgtccccg      960
cgcgccgcgg ccgagaagtg ccttgatgcc attcgccagt tgtctcagga cgtcggcatc      1020
ccgtccggcc tgatcgaact cggcaagcgc tacggcaaga acgtgaagaa ggaagacatt      1080
gataccatga ccggcaacgc tcagaaggat gcgtgcggtt tcaccaaccc cgctgcccg      1140 agcgacaagg acgtcaaggc catctacgag ccgcgctgt aa                         1182
```

<210> SEQ ID NO 45
<211> LENGTH: 385
<212> TYPE: PRT
<213> ORGANISM: Clostridium perfringens str. 13

<400> SEQUENCE: 45

```
Met Arg Met Tyr Asp Tyr Leu Val Pro Ser Val Asn Phe Met Gly Ala
1               5                   10                  15

Asn Ser Ile Ser Val Val Gly Glu Arg Cys Lys Ile Leu Gly Gly Lys
                20                  25                  30

Lys Ala Leu Ile Val Thr Asp Lys Phe Leu Arg Gly Leu Lys Gly Gly
            35                  40                  45

Ala Val Glu Leu Thr Glu Lys Tyr Leu Lys Glu Ala Gly Ile Glu Val
        50                  55                  60

Ala Tyr Tyr Asp Gly Val Glu Pro Asn Pro Lys Asp Thr Asn Val Lys
65                  70                  75                  80

Asp Gly Leu Lys Ile Phe Gln Asp Glu Asn Cys Asp Met Ile Val Thr
                85                  90                  95

Val Gly Gly Gly Ser Ser His Asp Cys Gly Lys Gly Ile Gly Ile Ala
            100                 105                 110

Ala Thr His Glu Gly Asp Leu Tyr Asp Tyr Ala Gly Ile Glu Thr Leu
        115                 120                 125

Thr Asn Pro Leu Pro Pro Ile Val Ala Val Asn Thr Thr Ala Gly Thr
130                 135                 140

Ala Ser Glu Val Thr Arg His Cys Val Ile Thr Asn Thr Lys Thr Lys
145                 150                 155                 160

Val Lys Phe Val Ile Val Ser Trp Arg Asn Leu Pro Leu Val Ser Ile
                165                 170                 175

Asn Asp Pro Met Leu Met Val Gly Lys Pro Ala Gly Leu Thr Ala Ala
            180                 185                 190

Thr Gly Met Asp Ala Leu Thr His Ala Val Glu Ala Tyr Val Ser Lys
        195                 200                 205

Asp Ala Asn Pro Val Thr Asp Ala Ala Ile Gln Ala Ile Lys Leu
    210                 215                 220

Ile Ser Ser Asn Leu Arg Gln Ala Val Ala Leu Gly Glu Asn Leu Val
225                 230                 235                 240

Ala Arg Glu Asn Met Ala Tyr Gly Ser Leu Leu Ala Gly Met Ala Phe
                245                 250                 255

Asn Asn Ala Asn Leu Gly Tyr Val His Ala Met Ala His Gln Leu Gly
            260                 265                 270

Gly Leu Tyr Asp Met Pro His Gly Val Ala Asn Ala Met Leu Leu Pro
        275                 280                 285

His Val Cys Lys Tyr Asn Leu Ile Ser Asn Pro Gln Lys Phe Ala Asp
    290                 295                 300
```

```
Ile Ala Glu Phe Met Gly Glu Asn Ile Glu Gly Leu Ser Val Met Asp
305                 310                 315                 320

Ala Ala Gln Lys Ala Ile Asp Ala Met Phe Arg Leu Ser Thr Asp Ile
                325                 330                 335

Gly Ile Pro Ala Lys Leu Arg Asp Met Gly Val Lys Glu Glu Asp Phe
            340                 345                 350

Gly Tyr Met Ala Glu Met Ala Leu Lys Asp Gly Asn Ala Phe Ser Asn
        355                 360                 365

Pro Arg Lys Gly Asn Glu Arg Asp Ile Val Glu Ile Phe Lys Ala Ala
    370                 375                 380

Phe
385

<210> SEQ ID NO 46
<211> LENGTH: 1158
<212> TYPE: DNA
<213> ORGANISM: Clostridium perfringens str. 13

<400> SEQUENCE: 46
atgagaatgt acgattattt agtaccaagt gtaaacttta tgggagctaa ctcaatatca      60
gtagttggtg aaagatgtaa aatattaggt ggaaagaaag ctttaatagt tacagataaa     120
ttcttaagag gattaaaagg tggagcagtt gaattaactg aaaaatacct aaaagaagca     180
ggaatcgaag ttgcttatta tgatggagtt gaaccaaacc caaaagatac aaacgttaaa     240
gatggtttaa aaatattcca agacgaaaac tgtgatatga tcgttacagt tggtggagga     300
agctcacatg actgtggtaa aggaataggt atagctgcaa ctcacgaagg agatctttat     360
gactatgctg gaatagaaac tttaacaaat ccacttcctc caatagtagc agtaaacact     420
acagctggaa ctgcaagtga agtaactaga cactgtgtta taacaaacac taaaactaaa     480
gttaaattcg ttatagtaag ctggagaaac ttacctttag tttcaatcaa tgacccaatg     540
ttaatggttg gaaaaccagc aggattaaca gctgcaacag gaatggacgc tttaactcat     600
gctgtagaag catacgtatc aaaagatgct aaccctgtaa cagatgctgc tgcaatacaa     660
gctataaaat taatatcaag caatttaaga caagctgttg ctttaggaga aaacttagta     720
gctagagaaa acatggctta cggttcatta ttagctggta tggcattcaa caatgctaac     780
ttaggatatg tacatgctat ggctcaccaa ttaggcggat tatatgatat gcctcatgga     840
gtagctaacg ctatgttatt accacacgta tgtaaatata acttaatatc taacccacaa     900
aaattcgctg atatagctga atttatggga gaaaacatag aaggattatc agtaatggac     960
gctgctcaaa aagctataga tgcaatgttc agattatcaa ctgatatcgg aataccagca    1020
aaattaagag acatgggagt aaaagaagaa gacttcggat acatggctga aatggctctt    1080
aaagatggta atgcattcag taacccaaga aaaggtaacg aaagagacat cgttgaaata    1140
ttcaaagctg cattctaa                                                  1158

<210> SEQ ID NO 47
<211> LENGTH: 382
<212> TYPE: PRT
<213> ORGANISM: Vibrio campbellii ATCC BAA-1116

<400> SEQUENCE: 47

Met Thr Ser Ala Phe Phe Ile Pro Thr Val Asn Leu Met Gly Ala Gly
1               5                   10                  15
```

Cys Leu Lys Asp Ala Thr Asp Ser Ile Gln Ser Gln Gly Phe Lys Lys
              20                  25                  30

Gly Leu Ile Val Thr Asp Lys Ile Leu Asn Gln Ile Gly Val Val Lys
             35                  40                  45

Gln Val Gln Asp Leu Leu Ala Glu Arg Asp Val Glu Thr Val Val Phe
 50                  55                  60

Asp Gly Thr Gln Pro Asn Pro Thr Ile Ser Val Asn Asp Gly Leu
 65                  70                  75                  80

Ala Leu Leu Thr Asp Asn Glu Cys Asp Phe Val Ile Ser Leu Gly Gly
                 85                  90                  95

Gly Ser Pro His Asp Cys Ala Lys Gly Ile Ala Leu Val Ala Ser Asn
                100                 105                 110

Gly Gly Lys Ile Ala Asp Tyr Glu Gly Val Asp Gln Ser Ala Lys Pro
            115                 120                 125

Met Met Pro Leu Ile Ala Ile Asn Thr Thr Ala Gly Thr Ala Ser Glu
130                 135                 140

Met Thr Arg Phe Cys Ile Ile Thr Asp Glu Arg His Ile Lys Met
145                 150                 155                 160

Ala Ile Val Asp Lys His Thr Thr Pro Leu Ile Ser Val Asn Asp Pro
                165                 170                 175

Glu Leu Met Leu Ala Lys Pro Ala Ser Leu Thr Ala Ala Thr Gly Met
                180                 185                 190

Asp Ala Leu Thr His Ala Ile Glu Ala Tyr Val Ser Ile Ala Ala Thr
            195                 200                 205

Pro Ile Thr Asp Ala Val Ala Ile Lys Ala Ile Glu Leu Ile Gln Ala
210                 215                 220

Tyr Leu Arg Thr Ala Val Lys Asn Gly Glu Asp Leu Glu Ala Arg Glu
225                 230                 235                 240

Gln Met Ala Tyr Ala Gln Phe Met Ala Gly Met Ala Phe Asn Asn Ala
                245                 250                 255

Ser Leu Gly Tyr Val His Ala Met Ala His Gln Leu Gly Gly Phe Tyr
            260                 265                 270

Asp Leu Pro His Gly Val Cys Asn Ala Ile Leu Leu Pro His Val Gln
            275                 280                 285

Arg Tyr Asn Ala Gln Val Cys Pro Glu Arg Leu Arg Asp Val Ala Lys
            290                 295                 300

Ala Met Gly Val Asn Val Glu Asp Met Ser Ala Glu Ala Gly Ala Ala
305                 310                 315                 320

Ala Ala Ile Asp Ala Ile Val Thr Leu Ala Lys Asp Val Gly Ile Pro
                325                 330                 335

Ala Gly Ile Lys Glu Leu Gly Ala Lys Leu Glu Asp Ile Pro Thr Leu
            340                 345                 350

Ala Asp Asn Ala Leu Lys Asp Ala Cys Gly Phe Thr Asn Pro Lys Gln
            355                 360                 365

Ala Thr His Glu Glu Ile Ser Lys Ile Phe Glu Glu Ala Met
            370                 375                 380

<210> SEQ ID NO 48
<211> LENGTH: 1149
<212> TYPE: DNA
<213> ORGANISM: Vibrio campbellii ATCC BAA-1116

-continued

<400> SEQUENCE: 48

```
atgacaagtg catttttat ccctaccgta aacctaatgg gcgctggttg tttgaaagac      60
gccacagaca gcatccaatc tcaaggcttt aaaaaggtt tgattgttac ggataagatt     120
cttaaccaaa tcggtgtagt aaagcaggtt caagatctac tggcagaacg cgacgtggaa     180
accgttgtat cgatggcac tcaaccaaac cctactatca gcaacgttaa tgacggctta     240
gcacttctta ctgataacga atgtgacttc gttatctctc taggcggtgg ttcaccacac     300
gactgtgcga aggtatcgc acttgttgct tctaacggcg gcaaaatcgc agattacgaa     360
ggcgtagacc agtctgcaaa accaatgatg ccacttatcg caatcaacac gactgcgggt     420
actgcatctg aaatgacgcg tttctgcatc atcactgacg aagagcgtca catcaagatg     480
gctatcgttg ataagcacac aacaccgctt atctcagtaa acgatccaga gctaatgcta     540
gctaagcctg cttcgctaac cgcggcaaca ggtatggatg ccctaactca cgcgattgaa     600
gcttacgtgt ctatcgcagc aacaccaatc actgatgcgg tagcaatcaa agcaattgaa     660
cttatccaag cgtacctacg cacagcagtg aaaaatggtg aagatctaga agctcgtgag     720
caaatggcat acgcacagtt catggcgggt atggcgttca acaacgcgtc tctaggttac     780
gtgcacgcaa tggcacacca actaggtggt ttctacgacc ttccacacgg tgtttgtaac     840
gcgattcttc tacctcacgt acagcgttac aacgcgcaag tatgtccaga gcgcctacgt     900
gatgtagcga aagcaatggg cgtaaacgta aagacatgt ctgctgaagc aggtgcagcg     960
gcagcaatcg atgctatcgt aactctagcg aaagatgtag gcattcctgc aggtatcaag    1020
gagcttggtg cgaagctaga agacatccca acactagcag acaacgcact gaaagacgct    1080
tgtggtttca ctaaccctaa acaagcaact cacgaagaaa tctctaagat cttcgaagaa    1140
gcgatgtaa                                                              1149
```

<210> SEQ ID NO 49
<211> LENGTH: 388
<212> TYPE: PRT
<213> ORGANISM: Desulfotomaculum reducens MI-1

<400> SEQUENCE: 49

```
Met Thr Val Gly Glu Gln Val Phe Gly Tyr Phe Ile Pro Thr Val Asn
1               5                   10                  15

Leu Met Gly Val Gly Ala His Lys Glu Ile Pro Asp Gln Val Lys Val
            20                  25                  30

Leu Gly Gly Ser Asn Val Leu Ile Val Thr Asp Ala Phe Leu Gly Arg
        35                  40                  45

Pro Gly Gly Met Ala Asp Asp Ile Lys Gly Met Leu Glu Ala Glu Asn
    50                  55                  60

Ile Lys Val Thr Ile Tyr Ala Gly Ala Glu Pro Asn Pro Thr Asp Val
65                  70                  75                  80

Asn Val His Asp Gly Leu Lys Val Tyr Gln Glu Cys Gly Ala Asp Met
                85                  90                  95

Ile Leu Ser Leu Gly Gly Gly Ser Ser His Asp Cys Ala Lys Gly Ile
            100                 105                 110

Gly Ile Val Ala Thr Asn Gly Gly Asn Ile Arg Asp Tyr Glu Gly Ile
        115                 120                 125

Asn Lys Ser Ser Lys Ala Met Pro Pro Phe Ile Ala Val Asn Thr Thr
    130                 135                 140
```

| | | | | | | | | | | | | |
|---|---|---|---|---|---|---|---|---|---|---|---|---|
|Ala|Gly|Thr|Ala|Ser|Glu|Met|Thr|Arg|Phe|Cys|Ile|Ile|Thr|Asn|Thr|
|145| | | | |150| | | | |155| | | | |160|

Ala Gly Thr Ala Ser Glu Met Thr Arg Phe Cys Ile Ile Thr Asn Thr
145                 150                 155                 160

Ser Asn His Val Lys Met Ala Ile Val Asp Trp Arg Cys Thr Pro Asn
                165                 170                 175

Ile Ala Ile Asn Asp Pro Leu Leu Met Ala Gly Met Pro Pro Ala Leu
            180                 185                 190

Thr Ala Ala Thr Gly Met Asp Ala Leu Thr His Ala Ile Glu Ala Tyr
        195                 200                 205

Val Ser Val Ala Ala Thr Pro Val Thr Asp Ser Ala Ala Leu Met Ala
    210                 215                 220

Ile Lys Leu Ile Ser Gln Tyr Leu Arg Ala Ala Val Ala Asn Gly Glu
225                 230                 235                 240

Asn Met Glu Ala Arg Asp Lys Met Ala Tyr Ala Glu Phe Leu Gly Gly
                245                 250                 255

Met Ala Phe Asn Asn Ala Ser Leu Gly Tyr Val His Ala Met Ala His
            260                 265                 270

Gln Leu Gly Gly Phe Tyr Asn Leu Pro His Gly Val Cys Asn Ala Ile
        275                 280                 285

Leu Leu Pro His Val Glu Ala Phe Asn Leu Ile Ala Cys Pro Glu Arg
    290                 295                 300

Phe Val Asp Ile Ala Val Ala Met Gly Glu Asn Val Glu Gly Leu Ser
305                 310                 315                 320

Val Arg Asp Ala Ala Asp Lys Ala Leu Ser Ala Ile Arg Lys Leu Ser
                325                 330                 335

Ala Asp Val Gly Ile Pro Ala Gly Leu Thr Glu Leu Gly Val Lys Glu
            340                 345                 350

Glu Asp Leu Lys Thr Met Ala Glu Asn Ala Met Lys Asp Ala Cys Ala
        355                 360                 365

Leu Thr Asn Pro Arg Lys Ala Thr Leu Asn Asp Ile Val Gly Ile Tyr
    370                 375                 380

Lys Thr Ala Leu
385

<210> SEQ ID NO 50
<211> LENGTH: 1167
<212> TYPE: DNA
<213> ORGANISM: Desulfotomaculum reducens MI-1

<400> SEQUENCE: 50

```
atgacagttg gagaacaagt atttggctat tttattccta cagtaaacct gatgggtgta      60
ggtgcacaca aggagattcc cgatcaagtt aaagtattag gaggttccaa tgttttaatt     120
gtaactgatg ctttccttgg acgtcctggc ggtatggcgg atgacattaa agggatgttg     180
gaagctgaga atattaaagt gaccatttat gccggtgcag aacctaatcc cacagatgtt     240
aacgttcatg atggcctgaa agtttatcag gagtgcggtg ctgacatgat cctttccttg     300
ggcggcggta gttcccacga ctgtgccaag ggcattggca tagttgctac caatggtggt     360
aacattcgcg actatgaagg cattaacaag agcagcaagg cgatgcctcc ctttattgct     420
gtaaacacca ccgctggtac cgcttctgaa atgacccgtt tctgcattat taccaatacc     480
agcaaccatg ttaaaatggc gattgttgat tggcgttgca cccccaacat tgccattaat     540 gacccttttgt taatggctgg gatgcctcca gcattaactg ctgccacagg tatggatgct     600
ctgacccacg ccattgaagc ttacgtatcc gtcgctgcaa ctccagtcac cgattctgcg     660
```

```
gccctaatgg ctattaagtt aatttcacaa tatctgcggg ctgcagttgc caacggagag    720
aatatggaag cccgtgacaa gatggcttat gctgagtttt taggtggtat ggcctttaat    780
aatgcttctt tgggttacgt acacgcaatg gctcaccagt tgggtggatt ttacaatctg    840
cctcacggtg tttgcaacgc tattctgcta ccccatgtgg aagccttcaa cttgattgcc    900
tgccccgagc gttttgttga tattgctgtc gcaatgggtg agaacgtgga aggattgtct    960
gttcgtgatg ctgcggacaa ggcgctatct gccattagaa agctatcggc cgatgttgga   1020
attcctgcag gtttaactga actgggtgtt aaggaagaag acctgaagac catggcagaa   1080
aacgctatga aggatgcttg cgccttaacc aacccgagaa agctactct gaatgatatt    1140 gttggaatct acaagactgc cctataa                                        1167
```

<210> SEQ ID NO 51
<211> LENGTH: 393
<212> TYPE: PRT
<213> ORGANISM: Desulfovibrio vulgaris str. Hildenborough

<400> SEQUENCE: 51

```
Met Ala Val Gln Glu Gln Val Tyr Gly Phe Phe Ile Pro Arg Val Thr
1               5                   10                  15

Leu Ile Gly Ile Gly Ala Ser Lys Ala Ile Pro Glu Lys Ile Lys Ala
            20                  25                  30

Leu Gly Gly Ser Lys Pro Leu Ile Val Thr Asp Met Gly Ile Val Lys
        35                  40                  45

Ala Gly Ile Leu Lys Gln Ile Thr Asp Leu Leu Asp Ala Ala Lys Met
    50                  55                  60

Ala Tyr Ser Val Tyr Asp Glu Thr Ile Pro Asn Pro Thr Asp Asp Asn
65                  70                  75                  80

Val His Lys Gly Val Asp Val Tyr Lys Lys Asn Lys Cys Asp Ser Leu
                85                  90                  95

Ile Thr Leu Gly Gly Gly Ser Ser His Asp Cys Gly Lys Gly Ile Gly
            100                 105                 110

Leu Val Val Ala Asn Gly Gly Lys Ile His Asp Phe Glu Gly Val Asp
        115                 120                 125

Lys Ser Thr Gln Arg Met Pro Pro Tyr Leu Ala Val Asn Thr Thr Ala
    130                 135                 140

Gly Thr Ala Ser Glu Met Thr Arg Phe Cys Ile Ile Thr Asp Thr Ser
145                 150                 155                 160

Arg Lys Val Lys Met Ala Ile Val Asp Trp Arg Val Thr Pro Asn Ile
                165                 170                 175

Ala Leu Asp Asp Pro Leu Leu Met Leu Gly Met Pro Pro Ala Leu Thr
            180                 185                 190

Ala Ala Thr Gly Met Asp Ala Leu Thr His Ala Val Glu Ala Tyr Val
        195                 200                 205

Ser Thr Ile Ala Thr Pro Met Thr Asp Ala Cys Ala Glu Gln Ala Ile
    210                 215                 220

Thr Leu Ile Ala Thr Phe Leu Arg Arg Ala Val Ala Asn Gly Gln Asp
225                 230                 235                 240

Leu Glu Ala Arg Glu Arg Met Cys Phe Ala Gln Tyr Leu Ala Gly Met
                245                 250                 255

Ala Phe Asn Asn Ala Ser Leu Gly His Val His Ala Met Ala His Gln
            260                 265                 270

Leu Gly Gly Phe Tyr Asp Leu Pro His Gly Glu Cys Asn Ala Ile Leu
        275                 280                 285
```

Leu Pro His Val Ser Lys Phe Asn Leu Ile Ala Lys Leu Asp Arg Tyr
        290                 295                 300

Ala Arg Ile Ala Gln Leu Met Gly Glu Asn Ile Ala Gly Leu Ser Thr
305                 310                 315                 320

Arg Glu Ala Ala Glu Arg Ala Ile Ser Ala Ile Lys Cys Leu Ser Thr
                325                 330                 335

Asp Val Gly Ile Pro Ala Gly Leu Val Ala Leu Gly Lys Arg Tyr Gly
                340                 345                 350

Lys Asp Val Lys Ala Asp Ile Ala Ile Met Thr Lys Asn Ala Gln
            355                 360                 365

Lys Asp Ala Cys Gly Leu Thr Asn Pro Arg Cys Pro Thr Asp Ala Asp
        370                 375                 380

Val Ala Ala Ile Tyr Glu Ala Ala Leu
385                 390

<210> SEQ ID NO 52
<211> LENGTH: 1182
<212> TYPE: DNA
<213> ORGANISM: Desulfovibrio vulgaris str. Hildenborough

<400> SEQUENCE: 52
atggcagtac aggaacaggt ctacggtttc ttcattcccc gggtgaccct catcggcatc        60
ggtgcctcca aggccattcc tgaaaagatc aaggcgcttg gcgggtcgaa gccgctcatc       120
gtcaccgaca tgggcatcgt caaggctggc atcctgaagc agataaccga ccttctcgac       180
gccgcgaaga tggcctacag cgtgtatgac gagaccatcc ccaaccccac ggacgacaac       240
gtccacaagg gtgtcgacgt ctacaagaag aacaagtgcg acagcctcat caccctcggt       300
ggcggcagct cgcacgactg tggcaagggc atcggcctcg tcgtcgccaa cggcggcaag       360
attcacgact tcgaaggcgt ggacaagtcg acccagcgca tgccccccta ccttgcggtc       420
aacaccacgg caggcaccgc ttcggagatg acccgcttct gcatcatcac cgacaccagc       480
cgcaaggtga agatggccat cgtcgactgg cgcgtgaccc cgaacatcgc cctcgacgac       540
cccctgctga tgctcggaat gccccccgca ctcaccgcgg ccaccggcat ggacgccctg       600
acccacgccg tggaagccta cgtctccacc atcgccaccc ccatgaccga cgcctgcgca       660
gaacaggcca tcacgctcat cgccaccttc ctgcgccgtg ccgttgccaa cggtcaggac       720
ctcgaggccc gcgaacgcat gtgcttcgcg cagtaccttg ccggcatggc cttcaacaat       780
gccagcctcg gccatgtcca tgccatggcg caccagcttg gcggtttcta cgacctgccg       840
cacggcgagt gcaacgccat cctgctgccc cacgtctcca agttcaacct catcgccaag       900
cttgaccgct acgcccgcat cgcacagctg atgggcgaga catcgccgg tctgtccacg       960 cgtgaagccg ccgaaagggc catcagcgcc atcaagtgcc tgtccaccga tgtgggcatc      1020
cccgccggtc tggtggcgct tggcaagcgt tacggcaagg acgtcaaggc cgccgacatc      1080
gccatcatga ccaagaacgc gcagaaggac gcctgcggcc tgaccaatcc gcgttgtccg      1140
acggatgctg acgtcgcagc catttacgaa gcggccctgt aa                        1182

<210> SEQ ID NO 53
<211> LENGTH: 382
<212> TYPE: PRT
<213> ORGANISM: Photobacterium profundum 3TCK

<400> SEQUENCE: 53

| | | | | | | | | | | | | | | |
|---|---|---|---|---|---|---|---|---|---|---|---|---|---|---|
|Met|Ser|Ser|Ala|Phe|Phe|Ile|Pro|Ser|Val|Asn|Leu|Met|Gly|Ala|Gly
|1| | | |5| | | | |10| | | | |15|

Cys Leu Thr Glu Ala Ala Asp Ala Val Lys Ala His Gly Phe Lys Lys
            20                  25                  30

Ala Leu Ile Val Thr Asp Lys Val Leu Asn Gln Ile Gly Val Val Lys
                35                  40                  45

Gln Val Val Asp Leu Leu Ala Glu Arg Asn Val Ala Val Val Phe
 50                  55                  60

Asp Gly Thr Gln Pro Asn Pro Thr Met Gly Asn Val Glu Ala Gly Leu
65                  70                  75                  80

Ala Leu Leu Lys Ala Asn Glu Cys Asp Phe Val Ile Ser Leu Gly Gly
                85                  90                  95

Gly Ser Pro His Asp Cys Ala Lys Gly Ile Ala Leu Val Ala Ser Asn
            100                 105                 110

Gly Gly Ser Ile Ser Asp Tyr Glu Gly Val Asp Val Ser Ala Lys Pro
            115                 120                 125

Gln Leu Pro Leu Val Ala Ile Asn Thr Thr Ala Gly Thr Ala Ser Glu
130                 135                 140

Met Thr Arg Phe Cys Ile Ile Thr Asp Glu Ala Arg His Ile Lys Met
145                 150                 155                 160

Ala Ile Val Asp Lys Asn Thr Thr Pro Leu Met Ser Val Asn Asp Pro
                165                 170                 175

Glu Leu Met Leu Ala Lys Pro Ala Ser Leu Thr Ala Ala Thr Gly Met
            180                 185                 190

Asp Ala Leu Thr His Ala Ile Glu Ala Tyr Val Ser Thr Ala Ala Thr
            195                 200                 205

Pro Ile Thr Asp Ala Val Ala Ile Lys Ala Met Glu Leu Ile Gln Ala
210                 215                 220

His Leu Arg Thr Ala Val Asn Asp Gly Gln Asn Leu Glu Ala Arg Glu
225                 230                 235                 240

Gln Met Ala Tyr Ala Gln Phe Met Ala Gly Met Ala Phe Asn Asn Ala
                245                 250                 255

Ser Leu Gly Tyr Val His Ala Met Ala His Gln Leu Gly Gly Phe Tyr
            260                 265                 270

Asp Leu Pro His Gly Val Cys Asn Ala Val Leu Leu Pro His Val Gln
            275                 280                 285

Arg Tyr Asn Ala Lys Val Cys Pro Glu Arg Leu Arg Asp Val Ala Lys
290                 295                 300

Ala Met Gly Val Asn Val Glu Ala Met Thr Ala Asp Gln Gly Ala Asp
305                 310                 315                 320

Ala Ala Leu Glu Ala Ile Gln Val Leu Ser Lys Asp Val Gly Ile Pro
                325                 330                 335

Ala Gly Leu Lys Asp Leu Gly Ala Lys Asn Glu Asp Ile Ser Ile Leu
            340                 345                 350

Ala Asp Asn Ala Leu Lys Asp Ala Cys Gly Phe Thr Asn Pro Lys Gln
            355                 360                 365

Ala Thr His Glu Glu Ile Ser Glu Ile Phe Ala Ala Ala Met
370                 375                 380

<210> SEQ ID NO 54
<211> LENGTH: 1149
<212> TYPE: DNA

<213> ORGANISM: Photobacterium profundum 3TCK

<400> SEQUENCE: 54

```
atgagcagtg cattttttat cccctcggta aacttaatgg gcgctggttg tttaactgag      60
gcggcagatg cggttaaagc acatggcttc aaaaaagcat taatcgtaac tgataaagta     120
ttgaaccaaa ttggcgtggt taagcaagtg gtcgatctgc tggctgaacg caacgtagaa     180
gcagttgttt ttgatggcac acaacctaac ccaacaatgg gtaatgttga agcaggttta     240
gcgctattaa aagccaatga gtgtgatttt gttatctcat taggtggtgg ctcgccgcac     300
gattgtgcga aggtattgc acttgttgct tcaaatggcg gttcaatttc tgattatgaa     360
gggggttgatg taagtgctaa acctcagtta ccacttgttg cgattaatac gacagctggt     420
acagcatcag agatgacacg cttctgtatt attactgatg aagcgcgtca cattaaaatg     480
gcaattgttg ataaaaatac aacgccatta atgtcagtta atgatcctga attgatgtta     540
gcaaagccag catcattaac cgcagcaacc ggtatggatg cgctaacaca cgctattgaa     600
gcttacgttt caactgcagc aacaccaatt acagatgctg tagcaattaa agctatggag     660
cttattcagg cgcacttacg tactgctgta aatgatggtc aaaaccttga agcgcgtgaa     720
caaatggcgt acgcacaatt catggcaggt atggcattta caatgcatc tttaggttac     780
gtacacgcaa tggcgcacca gttaggtggt ttttacgact tgccacacgg tgtgtgtaat     840
gcggttcttt tacctcatgt tcagcgctat aacgctaaag tatgtcctga gcgtttacgt     900
gatgtggcaa aagctatggg tgtgaatgtt gaagctatga cagcagatca aggtgcagat     960
gctgcattag aagccattca agtgctatcg aaagatgtag gtattccagc gggtcttaaa    1020
gaccttggtg caaagaatga agatatttca attcttgctg ataatgcgtt gaaagatgca    1080
tgtggcttta ctaatcccaa acaagcaact catgaagaaa tttctgagat ttttgcggct    1140
gcaatgtaa                                                            1149
```

<210> SEQ ID NO 55
<211> LENGTH: 384
<212> TYPE: PRT
<213> ORGANISM: Geobacillus sp. Y4.1MC1

<400> SEQUENCE: 55

```
Met Ser Asn Ala His Val Phe Tyr Val Pro Ser Thr Asn Leu Met Gly
 1               5                  10                  15

Arg Gly Cys Leu Ala Lys Val Gly Pro Phe Ile Lys Glu Phe Gly Phe
                20                  25                  30

Lys Lys Ala Leu Val Val Thr Asp Lys Phe Leu His Lys Ser Gly Ile
            35                  40                  45

Ala Gly Lys Val Leu Ala Val Leu Asp Glu Ile Gly Val Asn Tyr Val
        50                  55                  60

Val Tyr Asp Asp Val Lys Pro Asn Pro Thr Thr Lys Asn Val Tyr Ala
 65                  70                  75                  80

Gly Ala Asp Leu Phe Lys Lys Asn Glu Cys Asp Phe Leu Val Ser Val
                85                  90                  95

Gly Gly Gly Ser Pro Gln Asp Thr Ala Lys Ala Ile Gly Leu Tyr Val
            100                 105                 110

Thr Asn Gly Gly Asp Ile Arg Asp Tyr Glu Gly Val Asn Lys Thr Lys
        115                 120                 125

Asn Lys Ser Val Pro Ile Val Ala Val Asn Thr Thr Ala Gly Thr Ser
    130                 135                 140
```

```
Ser Glu Phe Thr Ile Asn Tyr Val Ile Thr Asp Glu Glu Arg Asn Val
145                 150                 155                 160

Lys Met Val Met Val Asp Lys Asn Ser Leu Val Thr Ile Ser Val Asn
                165                 170                 175

Asp Pro Glu Leu Met Val Asp Lys Pro Ala Ala Leu Thr Ala Ala Thr
            180                 185                 190

Gly Met Asp Ala Leu Thr His Ala Ile Glu Ala Val Val Thr Pro Gly
        195                 200                 205

Ser Tyr Thr Val Thr Asp Ala Thr Ala Leu Ala Ala Ile Glu Ile Ile
    210                 215                 220

Phe Asn Tyr Leu Pro Arg Ala Val Lys Asn Gly His Asp Ile Glu Ala
225                 230                 235                 240

Arg Glu Gln Met Ala Tyr Ala Met Phe Leu Val Gly Ile Ala Phe Asn
                245                 250                 255

Asn Ala Gly Leu Gly Met Val His Ala Met Ala His Gln Leu Gly Gly
            260                 265                 270

Met Tyr Asp Leu Pro His Gly Val Cys Asn Ala Met Leu Leu Pro Ile
        275                 280                 285

Val Glu Arg Glu Asn Ala Lys Arg Asp Pro Arg Lys Phe Arg Ala Ile
    290                 295                 300

Ala Lys Ala Ala Gly Ile Asp Val Thr Gly Lys Thr Asp Glu Gln Cys
305                 310                 315                 320

Ala Glu Glu Val Ile Glu Ala Ile Lys Ala Leu Ser Arg Glu Ile Gly
                325                 330                 335

Ile Pro Ser Lys Leu Ser Glu Leu Gly Val Asp Glu Val Asp Leu Glu
            340                 345                 350

Lys Leu Ala Asn Asn Ala Leu Lys Asp Ala Cys Ala Pro Gly Asn Pro
        355                 360                 365

Phe Gln Pro Thr Lys Glu Glu Val Ile Ser Met Phe Lys Glu Ile Leu
    370                 375                 380

<210> SEQ ID NO 56
<211> LENGTH: 1155
<212> TYPE: DNA
<213> ORGANISM: Geobacillus sp. Y4.1MC1

<400> SEQUENCE: 56
atgagcaatg cgcatgtttt ttatgtgcca agcacgaatt tgatgggaag agggtgtttg      60
gcgaaagttg gtccgtttat taaagagttt ggttttaaaa aagcgttggt tgtaaccgat     120
aaatttctgc ataaaagcgg tattgctgga aaggtattag cggtattgga tgaaataggt     180
gttaactacg ttgtttatga tgatgtgaaa ccaaatccaa ctacgaaaaa cgtatatgct     240
ggtgcagatc ttttaaaaa gaatgaatgt gatttttag tatccgttgg aggtggctcg     300
ccacaggata cagcgaaagc gattggactt tatgtaacaa acggcggcga tatccgcgat     360
tatgaaggtg taaacaaaac aaaaaataaa tcggttccga ttgtagcggt aaatacaaca     420
gctggaacat ccagtgaatt tacaatcaac tatgttataa cagatgaaga acgtaatgta     480
aaaatggtta tggtagataa gaatagttta gtgaccattt ctgtcaatga tcccgaatta     540
atggtagata aacctgctgc tttaactgca gcgacaggta tggatgcgct gacacatgca     600
atagaagcgg ttgtaactcc aggttcatat acagttaccg atgcgacagc gcttgcagca     660
atagaaatta ttttaattaa cctccctaga gccgtaaaaa atggtcacga cattgaagcg     720
cgtgaacaaa tggcatacgc catgtttcta gttggaattg cctttaacaa tgcaggcctc     780
```

-continued

```
ggtatggttc atgctatggc ccatcagctt ggaggaatgt acgatttgcc ccacggtgta    840
tgcaacgcaa tgcttctgcc gattgtagag cgggaaaatg caaagcggga tccaagaaaa    900
ttccgtgcga ttgcaaaggc agcaggaatt gacgtaacag gaaaaacaga tgaacaatgt    960
gcagaagaag tcattgaagc gattaaagca ttatcgagag aaataggtat tccaagcaaa   1020 cttcagagc ttggcgttga tgaagtggat ttggaaaaat tagcaaataa tgctcttaaa   1080
gatgcgtgtg caccaggtaa tccatttcaa cctacgaaag aggaagtaat ttctatgttt   1140
aaagaaattt tataa                                                    1155
```

<210> SEQ ID NO 57
<211> LENGTH: 393
<212> TYPE: PRT
<213> ORGANISM: Desulfovibrio fructosovorans JJ

<400> SEQUENCE: 57

```
Met Ala Val Arg Glu Gln Val Tyr Gly Phe Phe Ile Pro Ser Val Thr
1               5                   10                  15

Leu Ile Gly Ile Gly Ala Ala Lys Gln Ile Pro Glu Lys Ile Lys Ala
            20                  25                  30

Leu Gly Gly Thr Lys Pro Leu Ile Val Thr Asp Lys Gly Val Val Lys
        35                  40                  45

Val Gly Val Cys Lys Met Ile Thr Asp Leu Leu Asp Ala Ala Gly Met
    50                  55                  60

Lys Tyr His Ile Tyr Asp Glu Thr Ile Pro Asn Pro Thr Asp Glu Asn
65                  70                  75                  80

Val His Lys Gly Val Glu Val Tyr Lys Lys Gly Cys Asp Ser Leu
            85                  90                  95

Ile Thr Leu Gly Gly Gly Ser Ser His Asp Cys Gly Lys Gly Ile Gly
            100                 105                 110

Leu Val Ile Ser Asn Gly Gly Lys Ile His Asp Tyr Glu Gly Val Asp
        115                 120                 125

Lys Ser Ser Lys Pro Phe Met Pro Tyr Leu Ala Val Asn Thr Thr Ala
130                 135                 140

Gly Thr Ala Ser Glu Met Thr Arg Phe Cys Ile Ile Thr Asp Leu Ser
145                 150                 155                 160

Arg His Val Lys Met Ala Ile Val Asp Trp Arg Val Thr Pro His Ile
                165                 170                 175

Ala Ile Asp Asp Pro Val Leu Met Val Gly Met Pro Pro Ala Leu Thr
            180                 185                 190

Ala Ser Thr Gly Met Asp Ala Leu Thr His Ala Val Glu Ala Phe Val
        195                 200                 205

Ser Thr Ile Ala Asn Pro Met Thr Asp Ala Cys Ala Ile Glu Ala Ile
    210                 215                 220

Lys Leu Ile Phe Lys Tyr Leu Arg Lys Ala Val Ala Asn Gly Gln Asp
225                 230                 235                 240

Met Glu Ala Arg Glu Gly Met Cys Phe Ala Glu Tyr Leu Ala Gly Met
                245                 250                 255

Ala Phe Asn Asn Ala Ser Leu Gly His Val His Ala Met Ala His Gln
            260                 265                 270

Leu Gly Gly Phe Tyr Asp Leu Pro His Gly Glu Cys Asn Ala Ile Leu
        275                 280                 285

Leu Pro His Val Glu Ser Tyr Asn Leu Ile Ala Lys Val Glu Lys Phe
    290                 295                 300
```

```
Ala Glu Met Ala Lys Ile Met Gly Glu Asn Ile Glu Gly Met Ala Pro
305                 310                 315                 320

Arg Asp Ala Ala Glu Leu Cys Leu Lys Ala Ile Arg Gln Leu Ser Val
            325                 330                 335

Asp Val Gly Ile Pro Ala Gly Leu Val Glu Leu Gly Lys Arg Tyr Gly
        340                 345                 350

Lys Asp Val Lys Ala Ala Asp Ile Pro Thr Met Thr Gly Asn Ala Gln
        355                 360                 365

Lys Asp Ala Cys Gly Leu Thr Asn Pro Arg Cys Pro Thr Asp Lys Asp
    370                 375                 380

Val Ala Ala Ile Tyr Thr Ala Ala Leu
385                 390

<210> SEQ ID NO 58
<211> LENGTH: 1182
<212> TYPE: DNA
<213> ORGANISM: Desulfovibrio fructosovorans JJ

<400> SEQUENCE: 58
atggcagttc gcgagcaagt ttacggtttc ttcattccca gcgtgaccct catcggcatc      60
ggcgccgcca agcagatccc tgagaagatc aaggctctgg cggtaccaa gccgcttatc     120
gtcacggaca agggcgtggt caaagtcggt gtctgcaaga tgatcaccga tctgcttgat     180
gccgccggca tgaagtacca catctatgac gagaccatcc ccaacccac cgacgaaaac     240
gtccacaagg gcgtggaagt ctacaagaaa gagggttgcg acagcctcat cactctgggc     300
ggcggttcct cccacgactg cggcaagggc atcggcctcg tcatctccaa cggcggcaag     360
atccacgact acgaaggcgt ggacaagtcc tccaagccct tcatgccgta tctggccgtc     420
aacaccacgg ccggcaccgc ttcggaaatg acccgcttct gcatcatcac cgacctgtcc     480
cgccacgtga agatggccat cgttgactgg cgcgtcaccc cgcacatcgc catcgacgac     540
ccggtcctca tggtcggcat gccccggcc ctgaccgcct ccaccggcat ggacgccctg     600
acccacgccg tcgaggcctt cgtgtccacc atcgccaacc cgatgaccga cgcctgcgcc     660
atcgaagcca tcaagctgat cttcaagtac ctgcgcaagg ccgtggccaa cggtcaggac     720
atggaagccc gcgaaggcat gtgcttcgcc gagtacctgg ccggcatggc gttcaacaac     780
gcctccctcg tcacgtcca cgccatggcc caccagctgg cgggcttcta tgacctgccg     840
cacggcgaat gcaacgccat cctgcttccc cacgtcgaga gctacaacct gatcgccaag     900
gtcgagaagt cgccgaaat ggccaagatc atgggcgaga catcgaagg catggccccg     960
cgcgacgccg ccgaactgtg cctcaaggcc atccgccagc tgtccgtcga cgtcggcatc    1020
ccggccggcc tggtcgagct tggcaagcgt tatggcaagg acgtcaaggc tgccgacatc    1080
ccgaccatga ccggcaacgc tcagaaggac gcctgcggtc tgaccaaccc cgctgcccg    1140
accgacaagg acgtggccgc catctacacg gccgccctgt aa                       1182

<210> SEQ ID NO 59
<211> LENGTH: 382
<212> TYPE: PRT
<213> ORGANISM: Shewanella oneidensis MR-1

<400> SEQUENCE: 59

Met Ala Ala Lys Phe Phe Ile Pro Ser Val Asn Val Leu Gly Lys Gly
1               5                  10                  15

Ala Val Asp Asp Ala Ile Gly Asp Ile Lys Thr Leu Gly Phe Lys Arg
            20                  25                  30
```

Ala Leu Ile Val Thr Asp Lys Pro Leu Val Asn Ile Gly Leu Val Gly
         35                  40                  45

Glu Val Ala Glu Lys Leu Gly Gln Asn Gly Ile Thr Ser Thr Val Phe
 50                  55                  60

Asp Gly Val Gln Pro Asn Pro Thr Val Gly Asn Val Glu Ala Gly Leu
 65                  70                  75                  80

Ala Leu Leu Lys Ala Asn Gln Cys Asp Phe Val Ile Ser Leu Gly Gly
             85                  90                  95

Gly Ser Pro His Asp Cys Ala Lys Gly Ile Ala Leu Val Ala Thr Asn
            100                 105                 110

Gly Gly Ser Ile Lys Asp Tyr Glu Gly Leu Asp Lys Ser Thr Lys Pro
            115                 120                 125

Gln Leu Pro Leu Val Ala Ile Asn Thr Thr Ala Gly Thr Ala Ser Glu
        130                 135                 140

Met Thr Arg Phe Cys Ile Ile Thr Asp Glu Ala Arg His Ile Lys Met
145                 150                 155                 160

Ala Ile Val Asp Lys His Thr Thr Pro Ile Leu Ser Val Asn Asp Pro
                165                 170                 175

Glu Leu Met Leu Lys Lys Pro Ala Ser Leu Thr Ala Ala Thr Gly Met
        180                 185                 190

Asp Ala Leu Thr His Ala Val Glu Ala Tyr Val Ser Ile Ala Ala Asn
        195                 200                 205

Pro Ile Thr Asp Ala Cys Ala Ile Lys Ala Ile Glu Leu Ile Gln Gly
        210                 215                 220

Asn Leu Val Asn Ala Val Lys Gln Gly Gln Asp Ile Glu Ala Arg Glu
225                 230                 235                 240

Gln Met Ala Tyr Ala Gln Phe Leu Ala Gly Met Ala Phe Asn Asn Ala
                245                 250                 255

Ser Leu Gly Tyr Val His Ala Met Ala His Gln Leu Gly Gly Phe Tyr
            260                 265                 270

Asp Leu Pro His Gly Val Cys Asn Ala Leu Leu Leu Pro His Val Gln
        275                 280                 285

Glu Tyr Asn Ala Lys Val Val Pro His Arg Leu Lys Asp Ile Ala Lys
        290                 295                 300

Ala Met Gly Val Asp Val Ala Lys Met Thr Asp Glu Gln Gly Ala Ala
305                 310                 315                 320

Ala Ala Ile Thr Ala Ile Lys Thr Leu Ser Val Ala Val Asn Ile Pro
                325                 330                 335

Glu Asn Leu Thr Leu Leu Gly Val Lys Ala Glu Asp Ile Pro Thr Leu
            340                 345                 350

Ala Asp Asn Ala Leu Lys Asp Ala Cys Gly Phe Thr Asn Pro Lys Gln
        355                 360                 365

Ala Thr His Ala Glu Ile Cys Gln Ile Phe Thr Asn Ala Leu
        370                 375                 380

<210> SEQ ID NO 60
<211> LENGTH: 1149
<212> TYPE: DNA
<213> ORGANISM: Shewanella oneidensis MR-1

<400> SEQUENCE: 60
atggctgcta aattttttat tccttccgtc aacgtactag gcaaaggcgc tgtagatgat      60
gctattggtg atatcaaaac cttaggcttt aagcgcgcgc ttatcgtaac ggataaacct     120

```
ttagtcaata ttggtctggt cggtgaagtg gccgaaaaac tcggccagaa tggcattaca    180
tcaaccgtat ttgatggcgt acaacctaac ccaacggttg gtaacgttga agcaggtctt    240
gcgctgttaa aagccaatca atgtgatttc gtgatttcat taggtggtgg ctcgccccac    300
gattgcgcta aaggtatcgc cctggtggca actaacggcg gtagcattaa agactacgaa    360
ggcttagaca aatccactaa gccacaactg ccgttagtgg caatcaacac gaccgctggt    420
actgccagtg agatgacacg tttctgtatc atcaccgacg aagctcgcca tatcaaaatg    480
gcaattgtcg ataaacacac cacgccaata ctttcagtaa atgatccaga gttgatgctg    540
aaaaagcctg caagtctcac agcagcaacg ggcatggatg cgctcaccca tgcggttgaa    600
gcctatgtgt ctattgccgc gaatcccatt actgatgcct gtgcaattaa ggcgattgaa    660
ctcattcaag caacttagt gaatgcggta aacaaggcc aagatattga agcccgtgag    720
caaatggctt atgcgcaatt cttagcgggt atggccttta caacgccag cttaggttat    780 gtgcacgcca tggcgcacca attaggcggt ttctacgatc taccccatgg tgtgtgtaac    840
gccctattat taccccatgt tcaagaatac aacgctaaag tggtgccaca tcgcctaaaa    900
gatattgcca aagcgatggg tgtagatgtg gcgaagatga ccgatgagca aggtgcagct    960
gcagctatca ccgccattaa aaccttatcc gttgcggtta tatccctga aaatctgaca    1020 ttactcggcg tgaaagcaga agatattcca acgttggctg acaacgcatt gaaggatgcc    1080
tgtggtttca caaaccctaa acaggcaacc catgcagaga tctgtcagat ctttactaac    1140
gcgttataa                                                          1149
```

<210> SEQ ID NO 61
<211> LENGTH: 384
<212> TYPE: PRT
<213> ORGANISM: Sebaldella termitidis ATCC 33386

<400> SEQUENCE: 61

```
Met Lys Val Ser Arg Arg Ile Tyr Trp Pro Ala Val Thr Leu Ile Gly
1               5                   10                  15

Pro Gly Cys Val Lys Glu Ile Gly Gly Asp Ile Lys Asp Leu Gly Leu
                20                  25                  30

Lys Lys Ala Leu Val Val Thr Asp Asn Val Leu Val Lys Ile Gly Val
            35                  40                  45

Val Lys Lys Val Thr Asp Val Leu Asp Glu Ser Gly Ile Asn Tyr Val
        50                  55                  60

Val Val Asp Asp Ile Gln Pro Asn Pro Thr Met Lys Asn Ile His Asp
65                  70                  75                  80

Gly Leu Asn Thr Tyr Lys Ser Glu Asn Cys Asp Phe Val Ile Ser Ile
                85                  90                  95

Gly Gly Gly Ser Pro Gln Asp Ala Gly Lys Ala Ile Gly Leu Leu Ala
                100                 105                 110

Thr Asn Gly Gly Glu Ile Lys Asp Tyr Glu Gly Ile Asn Met Ser Lys
            115                 120                 125

His Lys Ser Val Pro Ile Ile Ala Ile Asn Thr Thr Ala Gly Thr Ala
        130                 135                 140

Ser Glu Val Thr Ile Asn Tyr Val Ile Thr Asn Glu Asp Thr His Ile
145                 150                 155                 160

Lys Met Val Met Val Asp Lys Asn Cys Leu Ala Ser Ile Ala Val Ser
                165                 170                 175

Asp Pro Glu Leu Met Thr Gly Lys Pro Ala Asp Leu Thr Ala Ala Thr
                180                 185                 190
```

Gly Met Asp Ala Leu Thr His Ala Ile Glu Ala Tyr Val Ser Thr Gly
        195                 200                 205

Ala Tyr Glu Leu Thr Asp Val Leu Ala Leu Glu Ala Val Lys Leu Ile
    210                 215                 220

Gly Glu Ser Leu Glu Asp Ala Val Lys Asp Gly Asn Asn Ile Glu Ala
225                 230                 235                 240

Arg Ser Lys Met Ala Tyr Ala Ser Tyr Ile Ala Gly Met Ser Phe Asn
                245                 250                 255

Asn Ala Gly Leu Gly Tyr Val His Ser Met Ala His Gln Leu Gly Gly
            260                 265                 270

Phe Tyr Asn Leu Pro His Gly Val Cys Asn Ala Ile Leu Leu Pro His
        275                 280                 285

Val Glu Lys Phe Asn Ser Ala Asn Thr Gly Asp Lys Leu Arg Lys Val
    290                 295                 300

Ala Glu Ile Leu Gly Glu Asn Val Gly Leu Ser Val Glu Glu Ala
305                 310                 315                 320

Asn Ala Lys Ala Ile Glu Ala Ile Met Lys Leu Ser Glu Arg Val Gly
                325                 330                 335

Ile Pro Lys Gly Leu Lys Glu Leu Gly Val Lys Glu Glu Asp Phe Lys
            340                 345                 350

Val Met Ala Glu Asn Ala Leu Lys Asp Val Cys Ala Gly Thr Asn Pro
        355                 360                 365

Arg Glu Val Thr Leu Glu Asp Thr Ile Ala Leu Tyr Lys Glu Ala Leu
    370                 375                 380

<210> SEQ ID NO 62
<211> LENGTH: 1155
<212> TYPE: DNA
<213> ORGANISM: Sebaldella termitidis ATCC 33386

<400> SEQUENCE: 62
atgaaagtaa gcagaaggat ttactggcct gcagtcactc tgatagggcc tgggtgtgta      60
aaagaaatag gaggagatat taaggactta ggtttgaaaa aagctctggt agtaacagat     120
aatgttcttg ttaagatcgg agtagtgaaa aaagtaactg atgtactgga tgaaagcggt     180
ataaattacg ttgtagtaga tgatatacag cctaatccta caatgaaaaa tattcatgac     240
ggtctgaaca cttacaaatc tgaaaattgt gatttcgtaa tatcaatcgg aggtggttca     300
cctcaggatg caggtaaggc aataggtctt ctggctacaa acggcggtga atcaaggat     360 tacgaaggaa taaacatgtc aaaacacaaa tctgtaccta taattgcaat caatactaca     420
gccggtactg caagcgaggt tactataaac tatgttataa caaatgaaga tacacatata     480
aaaatggtta tggttgataa aaactgtctt gcaagtatag ctgtaagcga tcctgagctg     540
atgacgggaa aacctgctga tcttactgcg gctacaggaa tggatgcgct gacacacgct     600
atagaagcat atgtttctac aggcgcatac gagcttacag atgttcttgc actggaagct     660
gtaaagctga taggcgaatc tcttgaggat gccgtaaaag acgggaataa tatagaggca     720
agatcaaaga tggcatatgc ttcttatata gcaggaatgt cttttaacaa tgcaggactg     780
ggatatgtgc attcgatggc acatcagctc ggcggtttct ataatcttcc gcatggtgta     840
tgtaatgcaa tacttcttcc tcatgtggaa aaatttaatt ccgcaaatac aggtgataaa     900
ctgagaaaag tagcggaaat actcggagaa aatgtagagg gactgtctgt ggaagaagca     960
aatgcaaagg ctatagaagc tataatgaag ctgtctgaaa gagtgggaat acctaagggg    1020

```
ctgaaagaac tcggggtaaa agaagaggac tttaaggtaa tggcagaaaa tgcactgaaa        1080
gatgtgtgtg ccgggacaaa tccaagagag gttactctgg aagatacaat agctctgtat        1140
aaagaggcac tttaa                                                          1155
```

<210> SEQ ID NO 63
<211> LENGTH: 384
<212> TYPE: PRT
<213> ORGANISM: Paenibacillus peoriae KCTC 3763

<400> SEQUENCE: 63

```
Met Thr Gly Thr Ser Lys Phe Met Met Pro Gly Met Ser Leu Met Gly
1               5                   10                  15

Ser Gly Ala Leu Ala Asp Ala Gly Thr Glu Ile Gly Lys Leu Gly Tyr
            20                  25                  30

Thr Asn Ala Leu Ile Val Thr Asp Lys Pro Leu Val Asp Ile Gly Ile
        35                  40                  45

Val Lys Lys Val Thr Ser Val Leu Glu Ser Ile Asn Val Lys Ser Val
50                  55                  60

Val Tyr Ser Gly Thr Gln Pro Asn Pro Thr Val Thr Asn Val Asn Glu
65                  70                  75                  80

Gly Leu Glu Leu Leu Ser Gln Ser Lys Cys Asp Phe Ile Ile Ser Leu
                85                  90                  95

Gly Gly Gly Ser Pro His Asp Cys Ala Lys Gly Ile Ala Leu Leu Ala
            100                 105                 110

Ser Asn Gly Gly Gln Ile Gly Asp Tyr Glu Gly Val Asp Lys Ser Thr
        115                 120                 125

Lys Pro Ser Phe Pro Leu Ile Ala Ile Asn Thr Thr Ala Gly Thr Ala
130                 135                 140

Ser Glu Met Thr Met Phe Cys Ile Ile Thr Asp Glu Glu Arg His Ile
145                 150                 155                 160

Lys Met Ala Ile Val Asp Asn His Thr Thr Pro Leu Ile Ala Val Asn
                165                 170                 175

Asp Pro Asp Leu Met Met Ala Met Pro Lys Ser Leu Thr Ala Ala Thr
            180                 185                 190

Gly Met Asp Ala Leu Thr His Ser Ile Glu Ala Tyr Val Ser Thr Asn
        195                 200                 205

Ala Thr Pro Ile Thr Asp Ala Cys Ala Ile Lys Ala Ile Glu Leu Ile
210                 215                 220

Arg Asp Asn Leu Ala Arg Ala Val Asp Asp Gly Asn Asp Val Glu Ala
225                 230                 235                 240

Arg Ser Gln Met Ala Tyr Ala Glu Phe Leu Ala Gly Met Ala Phe Asn
                245                 250                 255

Asn Ala Gly Leu Gly Phe Val His Ala Met Ala His Gln Leu Gly Gly
            260                 265                 270

Phe Tyr Asn Leu Pro His Gly Val Cys Asn Ala Ile Leu Leu Pro His
        275                 280                 285

Val Glu Arg Tyr Asn Ala Lys Ala Ser Ala Glu Arg Leu Thr Asp Ile
290                 295                 300

Ala Arg Ala Leu Gly Glu Asn Thr Asp Gly Val Thr Pro Glu Gln Gly
305                 310                 315                 320

Ala Asn Leu Ala Leu Gln Ala Ile Glu Lys Leu Ala Lys Arg Val Asn
                325                 330                 335

Ile Pro Ser Gly Leu Glu Glu Leu Gly Val Lys Arg Glu Asp Phe Thr
            340                 345                 350
```

Val Leu Ala Ala Asn Ala Leu Lys Asp Ala Cys Gly Val Thr Asn Pro
            355                 360                 365

Val Gln Pro Thr Gln Gln Glu Val Ile Ala Ile Phe Glu Gln Ala Met
        370                 375                 380

<210> SEQ ID NO 64
<211> LENGTH: 1155
<212> TYPE: DNA
<213> ORGANISM: Paenibacillus peoriae KCTC 3763

<400> SEQUENCE: 64

| | |
|---|---|
| atgacaggaa cttcaaaatt catgatgccg ggtatgagtc ttatgggctc aggcgcactg | 60 |
| gcggatgcag gtacagagat tgggaagctg ggctatacaa atgcattgat cgtaaccgat | 120 |
| aaacctttag ttgatatcgg tattgtgaaa aaagtaacaa gcgtgttgga agtataaac | 180 |
| gtaaaatccg tcgtatacag tggtacacag ccgaatccta cagttacaaa tgtgaacgag | 240 |
| ggcctggagc tgctgagtca atccaaatgc gatttcatta tttcgctcgg aggtgggtca | 300 |
| ccgcatgact gtgccaaggg catcgcactg ttggcttcca atggcggtca aattggcgac | 360 |
| tacgaaggcg tggataaatc cacgaagccc tccttccctc tgattgccat taacacaacg | 420 |
| gcaggaacgg ctagcgaaat gaccatgttt tgtattatta cggacgaaga gcgccatatc | 480 |
| aaaatggcga ttgtcgacaa tcacacgaca ccgctcattg ctgtcaatga tcctgatctg | 540 |
| atgatggcta tgcccaaatc attaactgct gcaacaggaa tggatgcgct cacccattct | 600 |
| attgaagctt atgtttccac caatgctaca cccattacag atgcgtgtgc gatcaaagca | 660 |
| attgagctga ttcgagacaa tttggccaga gccgtcgatg acggtaacga cgtagaggct | 720 |
| cgcagccaaa tggcctacgc tgaatttctg gcaggcatgg cattcaataa cgccggatta | 780 |
| ggctttgttc acgccatggc acatcagctt ggcggcttct ataatctgcc acacggcgtt | 840 |
| tgcaacgcca ttttgctgcc gcatgtagag cgctataacg ccaaggcatc cgccgaacga | 900 |
| ctcactgata tcgcacgtgc tcttggcgag aatacagacg gcgttacacc ggaacaaggt | 960 |
| gccaacctcg ctctgcaggc tatcgagaag ctggctaaac gggtcaacat cccgtccggt | 1020 |
| ctggaagagc ttggtgtcaa acgcgaagat ttcaccgtac tcgcagcgaa tgcgcttaaa | 1080 |
| gatgcctgcg gcgtaaccaa tccggttcag cctacgcagc aagaagtcat cgccattttt | 1140 |
| gaacaggcca tgtaa | 1155 |

<210> SEQ ID NO 65
<211> LENGTH: 387
<212> TYPE: PRT
<213> ORGANISM: Klebsiella pneumoniae subsp. pneumoniae MGH 78578

<400> SEQUENCE: 65

Met Ser Tyr Arg Met Phe Asp Tyr Leu Val Pro Asn Val Asn Phe Phe
1               5                   10                  15

Gly Pro Asn Ala Ile Ser Val Val Gly Glu Arg Cys Gln Leu Leu Gly
            20                  25                  30

Gly Lys Lys Ala Leu Leu Val Thr Asp Lys Gly Leu Arg Ala Ile Lys
        35                  40                  45

Asp Gly Ala Val Asp Lys Thr Leu His Tyr Leu Arg Glu Ala Gly Ile
    50                  55                  60

Glu Val Ala Ile Phe Asp Gly Val Glu Pro Asn Pro Lys Asp Thr Asn
65                  70                  75                  80

Val Arg Asp Gly Leu Ala Val Phe Arg Arg Glu Gln Cys Asp Ile Ile
             85                  90                  95

Val Thr Val Gly Gly Ser Pro His Asp Cys Gly Lys Gly Ile Gly
        100                 105                 110

Ile Ala Ala Thr His Glu Gly Asp Leu Tyr Gln Tyr Ala Gly Ile Glu
            115                 120                 125

Thr Leu Thr Asn Pro Leu Pro Pro Ile Val Ala Val Asn Thr Thr Ala
        130                 135                 140

Gly Thr Ala Ser Glu Val Thr Arg His Cys Val Leu Thr Asn Thr Glu
145                 150                 155                 160

Thr Lys Val Lys Phe Val Ile Val Ser Trp Arg Asn Leu Pro Ser Val
                165                 170                 175

Ser Ile Asn Asp Pro Leu Leu Met Ile Gly Lys Pro Ala Ala Leu Thr
            180                 185                 190

Ala Ala Thr Gly Met Asp Ala Leu Thr His Ala Val Glu Ala Tyr Ile
        195                 200                 205

Ser Lys Asp Ala Asn Pro Val Thr Asp Ala Ala Met Gln Ala Ile
        210                 215                 220

Arg Leu Ile Ala Arg Asn Leu Arg Gln Ala Val Ala Leu Gly Ser Asn
225                 230                 235                 240

Leu Gln Ala Arg Glu Asn Met Ala Tyr Ala Ser Leu Leu Ala Gly Met
                245                 250                 255

Ala Phe Asn Asn Ala Asn Leu Gly Tyr Val His Ala Met Ala His Gln
            260                 265                 270

Leu Gly Gly Leu Tyr Asp Met Pro His Gly Val Ala Asn Ala Val Leu
        275                 280                 285

Leu Pro His Val Ala Arg Tyr Asn Leu Ile Ala Asn Pro Glu Lys Phe
        290                 295                 300

Ala Asp Ile Ala Glu Leu Met Gly Glu Asn Ile Thr Gly Leu Ser Thr
305                 310                 315                 320

Leu Asp Ala Ala Glu Lys Ala Ile Ala Ala Ile Thr Arg Leu Ser Met
                325                 330                 335

Asp Ile Gly Ile Pro Gln His Leu Arg Asp Leu Gly Val Lys Glu Ala
            340                 345                 350

Asp Phe Pro Tyr Met Ala Glu Met Ala Leu Lys Asp Gly Asn Ala Phe
        355                 360                 365

Ser Asn Pro Arg Lys Gly Asn Glu Gln Glu Ile Ala Ala Ile Phe Arg
370                 375                 380

Gln Ala Phe
385

<210> SEQ ID NO 66
<211> LENGTH: 1164
<212> TYPE: DNA
<213> ORGANISM: Klebsiella pneumoniae subsp. pneumoniae MGH 78578

<400> SEQUENCE: 66
atgagctatc gtatgtttga ttatctggtg ccaaacgtta acttttttgg ccccaacgcc      60
atttccgtag tcggcgaacg ctgccagctg ctgggggga aaaagccct gctggtcacc      120 gacaaaggcc tgcgggcaat taagatggc gcggtggaca aaaccctgca ttatctgcgg      180
gaggccggga tcgaggtggc gatctttgac ggcgtcgagc cgaacccgaa agacaccaac      240
gtgcgcgacg gcctcgccgt gtttcgccgc gaacagtgcg acatcatcgt caccgtgggc      300

```
ggcggcagcc cgcacgattg cggcaaaggc atcggcatcg ccgccaccca tgagggcgat      360
ctgtaccagt atgccggaat cgagaccctg accaacccgc tgccgcctat cgtcgcggtc      420
aataccaccg ccggcaccgc cagcgaggtc acccgccact gcgtcctgac caacaccgaa      480
accaaagtga agtttgtgat cgtcagctgg cgcaacctgc cgtcggtctc tatcaacgat      540
ccactgctga tgatcggtaa accggccgcc ctgaccgcgg cgaccgggat ggatgccctg      600
acccacgccg tagaggccta tatctccaaa gacgctaacc cggtgacgga cgccgccgcc      660
atgcaggcga tccgcctcat cgcccgcaac ctgcgccagg ccgtggccct cggcagcaat      720
ctgcaggcgc gggaaaacat ggcctatgct tctctgctgg ccgggatggc tttcaataac      780
gccaacctcg gctacgtgca cgccatggcg caccagctgg gcggcctgta cgacatgccg      840
cacggcgtgg ccaacgctgt cctgctgccg catgtggcgc gctacaacct gatcgccaac      900
ccggagaaat cgccgatat tgctgaactg atgggcgaaa atatcaccgg actgtccact      960
ctcgacgcgg cggaaaaagc catcgccgct atcacgcgtc tgtcgatgga tatcggtatt     1020
ccgcagcatc tgcgcgatct gggggtaaaa gaggccgact tcccctacat ggcggagatg     1080
gctctgaaag acggcaatgc gttctcgaac ccgcgtaaag caacgagca ggagattgcc      1140 gcgattttcc gccaggcatt ctga                                            1164
```

<210> SEQ ID NO 67
<211> LENGTH: 383
<212> TYPE: PRT
<213> ORGANISM: Escherichia coli

<400> SEQUENCE: 67

```
Met Ala Ala Ser Thr Phe Phe Ile Pro Ser Val Asn Val Ile Gly Ala
1               5                   10                  15

Asp Ser Leu Thr Asp Ala Met Asn Met Met Ala Asp Tyr Gly Phe Thr
            20                  25                  30

Arg Thr Leu Ile Val Thr Asp Asn Met Leu Thr Lys Leu Gly Met Ala
        35                  40                  45

Gly Asp Val Gln Lys Ala Leu Glu Glu Arg Asn Ile Phe Ser Val Ile
    50                  55                  60

Tyr Asp Gly Thr Gln Pro Asn Pro Thr Thr Glu Asn Val Ala Ala Gly
65                  70                  75                  80

Leu Lys Leu Leu Lys Glu Asn Asn Cys Asp Ser Val Ile Ser Leu Gly
                85                  90                  95

Gly Gly Ser Pro His Asp Cys Ala Lys Gly Ile Ala Leu Val Ala Ala
            100                 105                 110

Asn Gly Gly Asp Ile Arg Asp Tyr Glu Gly Val Asp Arg Ser Ala Lys
        115                 120                 125

Pro Gln Leu Pro Met Ile Ala Ile Asn Thr Thr Ala Gly Thr Ala Ser
    130                 135                 140

Glu Met Thr Arg Phe Cys Ile Ile Thr Asp Glu Ala Arg His Ile Lys
145                 150                 155                 160

Met Ala Ile Val Asp Lys His Val Thr Pro Leu Leu Ser Val Asn Asp
                165                 170                 175

Ser Ser Leu Met Ile Gly Met Pro Lys Ser Leu Thr Ala Ala Thr Gly
            180                 185                 190

Met Asp Ala Leu Thr His Ala Ile Glu Ala Tyr Val Ser Ile Ala Ala
        195                 200                 205

Thr Pro Ile Thr Asp Ala Cys Ala Leu Lys Ala Val Thr Met Ile Ala
    210                 215                 220
```

Glu Asn Leu Pro Leu Ala Val Glu Asp Gly Ser Asn Ala Lys Ala Arg
225                 230                 235                 240

Glu Ala Met Ala Tyr Ala Gln Phe Leu Ala Gly Met Ala Phe Asn Asn
            245                 250                 255

Ala Ser Leu Gly Tyr Val His Ala Met Ala His Gln Leu Gly Gly Phe
        260                 265                 270

Tyr Asn Leu Pro His Gly Val Cys Asn Ala Val Leu Leu Pro His Val
    275                 280                 285

Gln Val Phe Asn Ser Lys Val Ala Ala Arg Leu Arg Asp Cys Ala
290                 295                 300

Ala Ala Met Gly Val Asn Val Thr Gly Lys Asn Asp Ala Glu Gly Ala
305                 310                 315                 320

Glu Ala Cys Ile Asn Ala Ile Arg Glu Leu Ala Lys Lys Val Asp Ile
            325                 330                 335

Pro Ala Gly Leu Arg Asp Leu Asn Val Lys Glu Glu Asp Phe Ala Val
        340                 345                 350

Leu Ala Thr Asn Ala Leu Lys Asp Ala Cys Gly Phe Thr Asn Pro Ile
    355                 360                 365

Gln Ala Thr His Glu Glu Ile Val Ala Ile Tyr Arg Ala Ala Met
370                 375                 380

<210> SEQ ID NO 68
<211> LENGTH: 1152
<212> TYPE: DNA
<213> ORGANISM: Escherichia coli

<400> SEQUENCE: 68
atggcagctt caacgttctt tattccttct gtgaatgtca tcggcgctga ttcattgact      60
gatgcaatga atatgatggc agattatgga tttacccgta ccttaattgt cactgacaat     120
atgttaacga aattaggtat ggcgggcgat gtgcaaaaag cactggaaga acgcaatatt     180
tttagcgtta tttatgatgg cacccaacct aaccccacca cggaaaacgt cgccgcaggt     240
ttgaaattac ttaaagagaa taattgcgat agcgtgatct ccttaggcgg tggttctcca     300
cacgactgcg caaaaggtat tgcgctggtg cagccaatgc gggcgatat cgcgattac     360 gaaggcgttg accgctctgc aaaaccgcag ctgccgatga tcgccatcaa taccacggcg     420
ggtacggcct ctgaaatgac ccgtttctgc atcatcactg acgaagcgcg tcatatcaaa     480
atggcgattg ttgataaaca tgtcactccg ctgctttctg tcaatgactc ctctctgatg     540
attggtatgc cgaagtcact gaccgccgca acgggtatgg atgccttaac gcacgctatc     600
gaagcatatg tttctattgc cgccacgccg atcactgacg cttgtgcact gaaagccgtg     660
accatgattg ccgaaaacct gccgttagcc gttgaagatg gcagtaatgc gaaagcgcgt     720
gaagcaatgg cttatgccca gttcctcgcc ggtatggcgt tcaataatgc ttctctgggt     780
tatgttcatg cgatggcgca ccagctgggc ggtttctaca acctgccaca cggtgtatgt     840
aacgccgttt tgctgccgca cgttcaggta ttcaacagca agtcgccgc tgcacgtctg     900 cgtgactgtg ccgctgcaat gggcgtgaac gtgacaggta aaaacgacgc ggaaggtgct     960
gaagcctgca ttaacgccat ccgtgaactg gcgaagaaag tggatatccc ggcaggccta    1020
cgcgacctga acgtgaaaga agaagatttc gcggtattgg cgactaatgc cctgaaagat    1080
gcctgtggct ttactaaccc gatccaggca actcacgaag aaattgtggc gatttatcgc    1140
gcagcgatgt aa                                                         1152

<210> SEQ ID NO 69
<211> LENGTH: 382
<212> TYPE: PRT
<213> ORGANISM: Clostridium perfringens ATCC 13124

<400> SEQUENCE: 69

Met Ser Tyr Lys Phe Phe Met Pro Ala Ile Ser Leu Met Gly Ala Asp
1               5                   10                  15

Cys Leu Lys Asp Ala Gly Asp Gln Val Gly Glu Leu Gly Phe Lys Lys
            20                  25                  30

Ala Leu Ile Val Thr Asp Lys Val Leu Gly Gln Ile Gly Ile Val Lys
        35                  40                  45

Lys Val Thr Asp Val Leu Asp Asn Lys Asn Ile Glu Tyr Ala Ile Tyr
50                  55                  60

Asp Glu Thr Lys Pro Asn Pro Thr Val Lys Asn Val Asn Asp Gly Leu
65                  70                  75                  80

Ala Leu Leu Lys Glu Lys Glu Cys Asp Phe Val Ile Ser Leu Gly Gly
            85                  90                  95

Gly Ser Ala His Asp Cys Ala Lys Gly Ile Ala Leu Leu Ala Thr Asn
            100                 105                 110

Gly Gly Glu Ile Lys Asp Tyr Glu Gly Val Asp Lys Ser Lys Lys Pro
        115                 120                 125

Gln Leu Pro Met Val Gly Ile Asn Thr Thr Ala Gly Thr Gly Ser Glu
    130                 135                 140

Met Thr Leu Phe Ala Ile Ile Thr Asp Glu Glu Arg His Ile Lys Met
145                 150                 155                 160

Ala Leu Val Asp Lys His Leu Thr Pro Ile Ile Ala Val Asn Asp Pro
            165                 170                 175

Ile Leu Met Leu Ala Met Pro Lys Ser Leu Thr Ala Ala Thr Gly Met
            180                 185                 190

Asp Ala Leu Thr His Ala Ile Glu Ala Tyr Val Ser Thr Ala Ala Thr
        195                 200                 205

Pro Ile Thr Asp Ala Cys Ala Glu Lys Ala Ile Glu Leu Ile Ser Asn
210                 215                 220

Tyr Leu Val Asn Ala Val Glu Asn Gly Gln Asp Val Glu Ala Arg Asp
225                 230                 235                 240

Met Met Ala Tyr Ala Glu Tyr Leu Ala Gly Met Ala Phe Asn Asn Ala
            245                 250                 255

Ser Leu Gly Tyr Val His Ala Met Ala His Gln Leu Gly Gly Phe Tyr
            260                 265                 270

Asn Leu Pro His Gly Val Cys Asn Ala Ile Leu Leu Pro His Val Gln
        275                 280                 285

Glu Tyr Asn Lys Ser Thr Ser Ala Ser Arg Leu Ala Lys Ile Ala Lys
    290                 295                 300

Ile Met Gly Gly Asn Ile Glu Gly Leu Thr Asp Glu Gln Gly Ala Asp
305                 310                 315                 320

Leu Cys Ile Asp Met Ile Lys Ser Leu Ser Gln Thr Ile Gly Ile Pro
            325                 330                 335

Glu Gly Leu Gly Val Leu Gly Val Lys Glu Ser Asp Phe Glu Thr Leu
            340                 345                 350

Ala Thr Asn Ala Leu Asn Asp Ala Cys Ser Leu Thr Asn Pro Arg Lys
        355                 360                 365

Gly Asn Leu Glu Glu Val Ile Ala Ile Phe Lys Lys Ala Met
    370                 375                 380

<210> SEQ ID NO 70
<211> LENGTH: 1149
<212> TYPE: DNA
<213> ORGANISM: Clostridium perfringens ATCC 13124

<400> SEQUENCE: 70
atgagttata aattttttat gccagcaata agtttaatgg gagcagattg cttaaaagac 60
gctggtgatc aagttggaga attaggattt aaaaaagctt taatagtaac agataaagtt 120
ttaggtcaaa taggaatagt taaaaaagta acagatgttt tagataataa gaatatagaa 180
tatgcaatat atgatgaaac taaaccaaac ccaacagtta aaaatgttaa tgatggttta 240
gcattattaa aagaaaaaga atgtgatttt gttatttcat taggtggagg ctcagctcat 300
gactgtgcta aaggaatagc tttattagct actaatggcg gagaaataaa agattatgag 360
ggagtagata aatctaaaaa acctcaatta ccaatggtag gtataaatac aactgctggt 420
actggtagtg aaatgacttt attcgctatt ataactgatg aagaaagaca tataaaaatg 480
gctttagtag ataagcattt aacaccaata atagcggtta atgatcctat tttaatgctt 540
gctatgccaa aatcattaac agcggctact ggtatggatg ccttaacaca cgctatagag 600
gcttatgttt caactgctgc tacaccaata acagatgctt gtgcagagaa agctatagaa 660
cttataagta attatttagt gaatgctgtt gaaaatggac aagatgtgga agctagagat 720
atgatggctt atgctgaata cttagcagga atggcattta acaatgctag tttaggatat 780
gttcacgcta tggctcacca attaggtgga ttctacaact tacctcatgg ggtatgtaat 840
gcaatattat tacctcatgt tcaagaatat aacaaatcta caagtgcttc aagattagct 900
aaaattgcta aaataatggg tggaaacata gaaggattaa ctgatgagca aggagcagat 960
ctttgcatag atatgataaa atcattatca caaactatag gaattccaga gggacttgga 1020
gtattaggag taaaagaaag tgattttgaa actttagcta ctaatgcttt aaatgatgct 1080
tgttcattaa caaatccaag aaaaggaaac ttagaagaag taatagctat attcaaaaaa 1140
gcaatgtag 1149

<210> SEQ ID NO 71
<211> LENGTH: 366
<212> TYPE: PRT
<213> ORGANISM: Ralstonia eutropha H16

<400> SEQUENCE: 71

Met Arg Ala Arg Pro Ala Arg Ala Pro Lys Arg Lys Ala Gln Glu Arg
1 5 10 15

Pro Ser Ser Ser Arg Met Pro Ala Cys Thr Arg Trp Gly Tyr Pro Lys
20 25 30

Pro Ser Arg Gly Thr Ser Ala Arg Gln Gly Phe Arg Pro Leu Ile Phe
35 40 45

Pro Gly Ala Glu Pro Asn Pro Thr Asp Val Asn Val His Asp Gly Val
50 55 60

Lys Leu Phe Glu Gln Glu Gly Cys Asp Phe Ile Val Ser Leu Gly Gly
65 70 75 80

Gly Ser Ser His Asp Cys Ala Lys Gly Ile Gly Leu Val Thr Ala Gly
85 90 95

Gly Gly His Ile Arg Asp Tyr Glu Gly Ile Asp Lys Ser Thr Val Pro
100 105 110

Met Thr Pro Leu Ile Ser Ile Asn Thr Thr Ala Gly Thr Ala Ala Glu
        115                 120                 125

Met Thr Arg Phe Cys Ile Ile Thr Asn Ser Ser Asn His Val Lys Met
130                 135                 140

Ala Ile Val Asp Trp Arg Cys Thr Pro Leu Ile Ala Ile Asp Asp Pro
145                 150                 155                 160

Arg Leu Met Val Ala Met Pro Pro Ala Leu Thr Ala Ala Thr Gly Met
                165                 170                 175

Asp Ala Leu Thr His Ala Val Glu Ala Tyr Val Ser Thr Ala Ala Thr
            180                 185                 190

Pro Ile Thr Asp Ala Cys Ala Glu Lys Ala Ile Ala Leu Ile Gly Glu
        195                 200                 205

Trp Leu Pro Lys Ala Val Ala Asn Gly Asn Ser Leu Glu Ala Arg Ala
    210                 215                 220

Ala Met Cys Tyr Ala Gln Tyr Leu Ala Gly Met Ala Phe Asn Asn Ala
225                 230                 235                 240

Ser Leu Gly Tyr Val His Ala Met Ala His Gln Leu Gly Gly Leu Tyr
                245                 250                 255

Asn Leu Pro His Gly Val Cys Asn Ala Ile Leu Leu Pro His Val Ser
            260                 265                 270

Glu Phe Asn Leu Ile Ala Ala Pro Glu Arg Phe Ala Lys Ile Ala Glu
        275                 280                 285

Leu Leu Gly Glu Asn Val Ala Ser Leu Ser Thr Ser Asp Ala Ala Lys
    290                 295                 300

Ala Ala Ile Ser Ala Ile Arg Ala Leu Ala Ala Ser Ile Gly Ile Pro
305                 310                 315                 320

Ala Gly Leu Ala Ser Leu Gly Val Lys Ala Glu Asp His Glu Val Met
                325                 330                 335

Ala His Asn Ala Gln Lys Asp Ala Cys Met Leu Thr Asn Pro Arg Arg
            340                 345                 350

Ala Thr Thr Ala Gln Val Ile Ala Ile Phe Ala Ala Ala Met
        355                 360                 365

<210> SEQ ID NO 72
<211> LENGTH: 1101
<212> TYPE: DNA
<213> ORGANISM: Ralstonia eutropha H16

<400> SEQUENCE: 72
atgcgcgcga gaccggcacg cgcgccaaag cgcaaggcgc aagaaaggcc ctcatcgtca    60
cggatgccgg cctgcacaag atggggctat ccgaaaccat cgcggggtac atccgcgagg   120
cagggcttca ggccactcat ttttccaggg gccgaaccca atccaaccga cgtcaatgtt   180
catgacggcg tcaagctgtt cgagcaggag ggatgcgact cattgtctc gctgggcggc   240 ggctcctcgc acgactgcgc gaaaggaatc ggcctcgtta ccgccggagg cggacatatc   300
cgcgactacg agggcatcga caaatcgacg gtgccaatga cgccgctcat ttccatcaat   360
acgaccgccg gcaccgctgc ggagatgact cgcttttgca tcatcaccaa ttcgagcaat   420
cacgtgaaga tggccatcgt cgattggcgc tgcacaccgc tgatcgcaat cgacgatccc   480
cggctgatgg tcgcaatgcc gcccgcattg actgccgcga ccggcatgga tgcgctcacg   540
cacgccgtcg aagcatacgt tccaccgcg gccacgccaa ttaccgatgc atgcgcggaa   600
aaagcgattg cgttgatcgg cgagtggctg cccaaggccg tagccaatgg caattcgctg   660

```
gaagcgcgtg ccgcgatgtg ctacgcgcaa taccttgctg gcatggcctt caacaatgcg    720
tcgctcggct atgtgcacgc aatggcccat caacttggcg gcctctacaa cctgccacat    780
ggtgtgtgca acgcgatctt gctgccccat gtatcggaat tcaaccttat tgccgcgcct    840
gaacgcttcg cgaagatcgc agaactgctc ggcgaaaacg ttgcgagcct cagtaccagt    900
gacgcggcca aggctgcgat ctcggcgatc cgggctctcg ccgcttcgat cggcattcct    960
gccggcctgg ccagcctggg cgtcaaggcg gaagaccatg aggtgatggc gcacaacgca   1020 caaaagatg catgcatgct gacgaatcca cgcagggcca ccacggcgca agtcatcgct   1080
atcttcgctg cagcgatgta a                                              1101
```

<210> SEQ ID NO 73
<211> LENGTH: 389
<212> TYPE: PRT
<213> ORGANISM: Thermoanaerobacter sp. X514

<400> SEQUENCE: 73

```
Met Lys Ile Phe Lys Phe His Met Pro Pro Ile Asn Leu Ile Gly Val
1               5                   10                  15

Gly Cys Leu Lys Asp Val Gly Arg Glu Ile Lys Lys Leu Gly Phe Lys
            20                  25                  30

Lys Gly Ile Ile Val Thr Asp Lys Val Leu Val Arg Ala Gly Leu Val
        35                  40                  45

Asn Asn Val Ile Ser Val Leu Glu Glu Gly Ile Glu Tyr Val Val
    50                  55                  60

Phe Asp Glu Thr Lys Pro Asn Pro Thr Ile Lys Asn Val Thr Asn Gly
65                  70                  75                  80

Leu Lys Leu Leu Ile Glu Asn Lys Cys Asp Phe Ile Ile Ser Cys Gly
                85                  90                  95

Gly Gly Ser Ala His Asp Cys Ala Lys Gly Ile Gly Leu Ile Ala Lys
            100                 105                 110

Glu Lys Asn Phe Ile Asp Glu Val Glu Arg Leu Asp Lys Val Lys Cys
        115                 120                 125

Gly Gly Trp Asn Ser Ala Leu Leu Leu Pro Leu Val Ala Ile Asn Thr
    130                 135                 140

Thr Ala Gly Thr Gly Ser Glu Val Thr Lys Phe Ala Ile Ile Thr Asp
145                 150                 155                 160

Glu Glu Lys Arg Ile Lys Met Pro Ile Val Asp Trp Arg Ile Thr Pro
                165                 170                 175

Leu Ile Ala Val Asn Asp Pro Leu Leu Met Ile Gly Met Pro Lys Ser
            180                 185                 190

Leu Thr Ala Ala Ser Gly Met Asp Ala Leu Thr His Ala Ile Glu Ala
        195                 200                 205

Tyr Ile Ser Ile Asp Ala Asn Pro Phe Thr Asp Ala Leu Ala Leu Lys
    210                 215                 220

Ala Ile Glu Ile Ile Phe Asn Tyr Leu Lys Arg Ala Val Glu Asn Gly
225                 230                 235                 240

Asn Asp Ile Glu Ala Arg Glu Lys Met Ala Tyr Ala Glu Phe Leu Ala
                245                 250                 255

Gly Ile Ala Phe Asn Asn Ala Gly Leu Gly Tyr Val His Ala Met Ala
            260                 265                 270

His Gln Leu Gly Gly Phe Tyr Asp Leu Pro His Gly Val Cys Asn Ala
        275                 280                 285
```

Val Leu Leu Pro His Val Leu Glu Tyr Asn Leu Glu Ala Val Gln Asn
            290                 295                 300

Lys Leu Ile Tyr Ile Ala Lys Ala Met Gly Ile Asp Val Asp Lys Leu
305                 310                 315                 320

Thr Thr Lys Glu Ile Gly Gly Lys Ile Ile Glu Ser Ile Asn Gln Leu
                325                 330                 335

Ser Gln Glu Ile Gly Ile Pro Ser Arg Leu Lys Glu Leu Gly Val Lys
            340                 345                 350

Glu Glu Asp Ile Lys Glu Leu Ser Gln Asn Ala Leu Lys Asp Val Cys
            355                 360                 365

Gly Phe Thr Asn Pro Lys Lys Ala Thr Leu Glu Asp Ile Ile Asn Ile
370                 375                 380

Phe Lys Ser Ala Met
385

<210> SEQ ID NO 74
<211> LENGTH: 1170
<212> TYPE: DNA
<213> ORGANISM: Thermoanaerobacter sp. X514

<400> SEQUENCE: 74
atgaaaatat ttaaattcca tatgcccct ataaatttaa taggtgtggg atgtttaaaa      60
gatgtgggaa gggagatcaa aaaattaggt tttaaaaaag gaattattgt tacagataaa     120
gtacttgtca gagctgggct tgtgaataat gtaattagtg ttttagaaga agaaggaata     180
gaatatgttg tctttgatga acaaaaccc aaccctacaa ttaaaaatgt aacaaatgga      240
cttaagcttt tgatagagaa taagtgtgat tttattattt cgtgcggcgg aggatcagct     300
catgactgcg caaagggat aggcctcatt gctaaagaga gaatttcat tgatgaggta      360 gagcgtctag acaaagtaaa gtgtggtggt tggaatagtg cattattact gcccctagtt     420
gctataaata ccacggctgg aacaggtagt gaagttacta aatttgctat aattacagat     480
gaagaaaaac gtattaaaat gccaattgtg gattggcgca ttacacctct aatagcagta     540
aatgatcctc tcttgatgat aggtatgcca aaatctctaa cagctgcaag tggcatggat     600
gcactaactc acgctattga agcttacatt tcgattgatg caaatccatt tacagatgca     660
cttgctttga agctattga attatattc aactaccta aaagagcggt agaaaatgga       720
aatgatattg aagcaagaga aaagatggca tatgcagagt tcttggcggg gattgctttt     780
aataacgcag gtttaggtta tgtccatgct atggctcatc aattaggagg attttacgat     840
cttcctcatg gtgtatgtaa tgccgtatta ttacctcatg ttttggaata taatcttgag     900
gcagttcaaa ataaacttat atatatagcg aaagcgatgg gtatagatgt agataaatta     960
acaacaaaag aaataggagg caaaattatt gaaagcataa accagctctc tcaagagatt    1020
ggtataccat cgaggttaaa agaactgggg gtaaaagaag aagacattaa agagttatcg    1080
caaaatgcat taaagatgt atgtggtttt acaaatccta aaaaggcaac attagaagat    1140
attattaata ttttcaagtc tgcaatgtaa                                     1170

<210> SEQ ID NO 75
<211> LENGTH: 384
<212> TYPE: PRT
<213> ORGANISM: human gut metagenome

<400> SEQUENCE: 75

```
Met Gly Asn Arg Ile Ile Leu Asn Gly Thr Ser Tyr Phe Gly Arg Gly
1               5                   10                  15

Ala Arg Glu Asn Val Ile Thr Glu Leu Arg Asn Arg Asn Phe Thr Lys
            20                  25                  30

Ala Leu Val Val Thr Asp Lys Asn Leu Leu Asp Ala His Val Thr Asn
        35                  40                  45

Leu Val Thr Asp Val Leu Asp Lys Asn Asp Phe Ser Tyr Gln Ile Tyr
    50                  55                  60

Ser Asp Ile Lys Pro Asn Pro Thr Thr Leu Asn Val Gln Gly Val
65                  70                  75                  80

Thr Phe Cys Arg Asn Ser Lys Ala Asp Val Ile Ala Val Gly Gly
                85                  90                  95

Gly Ser Ala Ile Asp Thr Ala Lys Ala Ile Ser Ile Ile Met Thr Asn
                100                 105                 110

Pro Glu His Phe Asp Val Ile Ser Leu Asp Gly Ala Val Glu Thr Lys
            115                 120                 125

Asn Ala Gly Met Pro Ile Ile Ala Leu Pro Thr Thr Ala Gly Thr Ala
130                 135                 140

Ala Glu Val Thr Ile Asn Tyr Val Ile Thr Asn Pro Val Gly Pro Lys
145                 150                 155                 160

Lys Met Val Cys Val Asp Pro His Asp Ile Pro Ile Val Ala Ile Ile
                165                 170                 175

Asp Gln Asp Leu Met Glu Lys Met Pro Lys Ser Leu Ala Ala Ser Thr
            180                 185                 190

Gly Met Asp Ala Leu Thr His Ala Met Glu Gly Tyr Thr Thr Lys Ala
        195                 200                 205

Ala Trp Leu Met Thr Asp Met Phe His Leu Asn Ala Met Ala Leu Ile
    210                 215                 220

Tyr Lys Asn Leu Glu Lys Ala Val Asn Leu Lys Asp Arg Asp Ala Ile
225                 230                 235                 240

Asp Asn Val Gly Tyr Gly Gln Tyr Ile Ala Gly Met Gly Phe Ser Asn
                245                 250                 255

Val Gly Leu Gly Ile Val His Ser Met Ala His Ser Leu Gly Ala Phe
            260                 265                 270

Phe Asp Thr Pro His Gly Leu Ala Asn Ala Leu Leu Leu Pro His Val
        275                 280                 285

Leu Lys Phe Asn Gly Lys Ile Cys Pro Asp Leu Phe Arg Asn Met Gly
    290                 295                 300

Arg Ala Met Gly Leu Asp Met Asp Asn Leu Thr Asp Asp Glu Ala Val
305                 310                 315                 320

Asp Lys Val Val Asp Ala Val Arg Ser Leu Ala Ile Lys Ile Gly Ile
                325                 330                 335

Pro Gln Thr Leu Lys Glu Ile Gly Ile Lys Lys Glu Asp Leu Pro Met
            340                 345                 350

Leu Ala His Gln Ala Ile Asp Asp Val Cys Thr Ala Gly Asn Pro Arg
        355                 360                 365

Asn Val Thr Glu Gln Asp Ile Leu Ala Leu Tyr Gln Glu Ala Tyr Glu
    370                 375                 380
```

<210> SEQ ID NO 76
<211> LENGTH: 1155
<212> TYPE: DNA

<213> ORGANISM: human gut metagenome

<400> SEQUENCE: 76

```
atgggaaata gaattattct gaatggaact tcttattttg gtcgtggtgc tagagagaat      60
gttattactg agttaagaaa tagaaatttc actaaagctt tagttgtaac tgataaaaat     120
ttacttgatg cacatgtgac taatttagtt acagatgttc ttgataaaaa tgattttca     180
tatcagattt attctgatat aaagcctaat ccaactactc ttaatgttca agaaggagtt     240
actttctgtc gtaatagtaa ggctgatgtt attattgcgg taggtggcgg aagtgctata     300
gatactgcaa aggcaattag tattattatg actaatcctg aacattttga tgttatttcg     360
ttggatgggg ctgttgaaac aaaaaatgct ggtatgccta ttatagcttt accaacaacg     420
gctggtactg cagcagaggt aacaataaat tatgttatta ctaatcctgt aggaccaaag     480
aaaatggtgt gtgttgatcc acatgatatt ccaatagtgg ctattattga tcaggacttg     540
atggaaaaaa tgccaaaaag tttagctgcg tctaccggaa tggatgcttt aactcatgct     600
atggaaggat atacaactaa agcagcgtgg ttaatgactg atatgttcca tttgaatgcc     660
atggcgctta tttataaaaa tttggaaaag gcagttaatt tgaaagatag agatgctatt     720
gataatgttg gatatggtca atatatagct ggtatggat tttccaatgt aggtttaggt      780
attgttcatt caatggctca ttcacttggg gcattctttg atactccaca cggtttggct     840
aatgctttat tactacctca tgttttaaaa tttaatggaa aaatatgtcc ggatttattt     900
agaaatatgg gtagagcaat ggggctagat atggataatt taactgatga tgaagcagtt     960
gataaagtgg tagatgctgt tagaagttta gctataaaga ttggaattcc tcaaacatta    1020
aaagaaattg aataaaaaa ggaagattta ccaatgcttg cgcatcaagc aattgatgat    1080
gtgtgtacag ctggtaatcc acgtaatgta actgaacaag atatattagc cctatatcaa    1140
gaggcttatg aataa                                                    1155
```

<210> SEQ ID NO 77
<211> LENGTH: 387
<212> TYPE: PRT
<213> ORGANISM: Geobacillus themodenitrificans NG80-2

<400> SEQUENCE: 77

```
Met Gln Asn Phe Thr Phe Arg Asn Pro Thr Lys Leu Ile Phe Gly Arg
1               5                   10                  15

Gly Gln Ile Glu Gln Leu Lys Glu Glu Val Pro Lys Tyr Gly Lys Lys
            20                  25                  30

Val Leu Leu Val Tyr Gly Gly Gly Ser Ile Lys Arg Asn Gly Leu Tyr
        35                  40                  45

Asp Glu Val Met Ser Leu Leu Thr Asp Ile Gly Ala Glu Val Val Glu
    50                  55                  60

Leu Pro Gly Val Glu Pro Asn Pro Arg Leu Ser Thr Val Lys Lys Gly
65                  70                  75                  80

Val Asp Ile Cys Arg Arg Glu Gly Ile Glu Phe Leu Leu Ala Val Gly
                85                  90                  95

Gly Gly Ser Val Ile Asp Cys Thr Lys Ala Ile Ala Ala Gly Ala Lys
            100                 105                 110

Phe Asp Gly Asp Pro Trp Glu Phe Ile Thr Lys Lys Ala Thr Val Thr
        115                 120                 125

Glu Ala Leu Pro Phe Gly Thr Val Leu Thr Leu Ala Ala Thr Gly Ser
    130                 135                 140
```

Glu Met Asn Ala Gly Ser Val Ile Thr Asn Trp Glu Thr Lys Glu Lys
145                 150                 155                 160

Tyr Gly Trp Gly Ser Pro Val Thr Phe Pro Gln Phe Ser Ile Leu Asp
            165                 170                 175

Pro Thr Tyr Thr Met Thr Val Pro Lys Asp His Thr Val Tyr Gly Ile
        180                 185                 190

Val Asp Met Met Ser His Val Phe Glu Gln Tyr Phe His His Thr Pro
    195                 200                 205

Asn Thr Pro Leu Gln Asp Arg Met Cys Glu Ala Val Leu Lys Thr Val
        210                 215                 220

Ile Glu Ala Ala Pro Lys Leu Val Asp Asp Leu Glu Asn Tyr Glu Leu
225                 230                 235                 240

Arg Glu Thr Ile Met Tyr Ser Gly Thr Ile Ala Leu Asn Gly Phe Leu
                245                 250                 255

Gln Met Gly Val Arg Gly Asp Trp Ala Thr His Asp Ile Glu His Ala
            260                 265                 270

Val Ser Ala Val Tyr Asp Ile Pro His Ala Gly Gly Leu Ala Ile Leu
        275                 280                 285

Phe Pro Asn Trp Met Lys His Val Leu Asp Glu Asn Val Ser Arg Phe
290                 295                 300

Ala Gln Leu Ala Val Arg Val Phe Asp Val Asp Pro Thr Gly Lys Thr
305                 310                 315                 320

Glu Arg Asp Val Ala Leu Glu Gly Ile Glu Arg Leu Arg Ala Phe Trp
                325                 330                 335

Ser Ser Leu Gly Ala Pro Ser Arg Leu Ala Asp Tyr Gly Ile Gly Glu
            340                 345                 350

Glu Asn Leu Glu Leu Met Ala Asp Lys Ala Met Ala Phe Gly Glu Phe
        355                 360                 365

Gly Arg Phe Lys Thr Leu Asn Arg Asp Asp Val Leu Ala Ile Leu Arg
    370                 375                 380

Ala Ser Leu
385

<210> SEQ ID NO 78
<211> LENGTH: 1164
<212> TYPE: DNA
<213> ORGANISM: Geobacillus themodenitrificans NG80-2

<400> SEQUENCE: 78
atgcaaaatt ttacgtttcg caatccgacc aaactcattt ttggggagagg acaaattgag    60 cagctcaaag aagaagtgcc gaaatatggc aaaaaagtgc tgcttgtcta tgggggcggc   120
agcattaaac gaaacggact atatgatgaa gtcatgagcc tattgacgga cattggcgcc   180
gaagtcgttg aactgccagg cgtcgaaccg aacccgcgcc tttcgaccgt caaaaaaggg   240
gtagacattt gcagacggga aggaattgaa ttttttgcttg ccgttggcgg cggcagtgtg   300
atcgactgta cgaaagcgat tgcagccggc gcgaagtttg atggcgatcc gtgggagttc   360
attacgaaaa aagcgactgt cactgaggcg ttgccgtttg gacggtcct gacgctggca   420 gcgaccggct cggaaatgaa cgccggatcg gtgatcacca ttgggagac gaaagaaaaa   480 tacggctggg gcagcccggt gacattcccg caattttcga ttttggatcc gacgtacacg   540
atgacggtgc cgaaagacca taccgtttac ggcatcgtcg atatgatgtc ccatgtgttt   600
gagcaatatt tccatcatac gccgaacacg ccgctgcaag accggatgtg cgaggcagtg   660
ttaaaaacgg tcattgaggc ggcgccaaaa ttggttgacg acttagagaa ctacgagctg   720

```
cgcgagacga tcatgtactc gggcacgatc gccttaaacg gcttttgca aatgggcgtg    780 cgcggtgatt gggcgacgca tgatatcgag catgcggtct ctgctgtata cgatatcccg    840
cacgccgggg gattggccat tttgttcccg aattggatga acatgtgct tgatgaaaat    900 gtcagccgtt tcgcccaact ggcggtgcgc gtctttgacg tcgatccgac gggcaaaacg    960
gagcgcgacg tggcgcttga gggcatcgag cggttgcgcg cgttttggtc gagcctcggg   1020
gcgccgtctc gattggctga ttatggcatc ggcgaggaaa atctcgagct gatggcggat   1080
aaagcgatgg cgtttggtga gtttggccgt ttcaaaacgt taaatcgtga tgatgtgctc   1140
gccattttgc gtgcgtcttt ataa                                          1164
```

<210> SEQ ID NO 79
<211> LENGTH: 5
<212> TYPE: PRT
<213> ORGANISM: Artificial Sequence
<220> FEATURE:
<223> OTHER INFORMATION: peptide motif

<400> SEQUENCE: 79

Val Thr Asn Ala Phe
1               5

<210> SEQ ID NO 80
<211> LENGTH: 5
<212> TYPE: PRT
<213> ORGANISM: Artificial Sequence
<220> FEATURE:
<223> OTHER INFORMATION: peptide motif

<400> SEQUENCE: 80

Gly Val Glu Val Ala
1               5

<210> SEQ ID NO 81
<211> LENGTH: 5
<212> TYPE: PRT
<213> ORGANISM: Artificial Sequence
<220> FEATURE:
<223> OTHER INFORMATION: peptide motif

<400> SEQUENCE: 81

Pro Asp Ile Ala Asp
1               5

<210> SEQ ID NO 82
<211> LENGTH: 5
<212> TYPE: PRT
<213> ORGANISM: Artificial Sequence
<220> FEATURE:
<223> OTHER INFORMATION: peptide motif

<400> SEQUENCE: 82

Pro Asp Val Ala Asp
1               5

<210> SEQ ID NO 83
<211> LENGTH: 5
<212> TYPE: PRT
<213> ORGANISM: Artificial Sequence
<220> FEATURE:
<223> OTHER INFORMATION: peptide motif

<400> SEQUENCE: 83

Gln Glu Lys Cys Asp
1               5

<210> SEQ ID NO 84
<211> LENGTH: 5
<212> TYPE: PRT
<213> ORGANISM: Artificial Sequence
<220> FEATURE:
<223> OTHER INFORMATION: peptide motif

<400> SEQUENCE: 84

Gly Ser Thr His Asp
1               5

<210> SEQ ID NO 85
<211> LENGTH: 5
<212> TYPE: PRT
<213> ORGANISM: Artificial Sequence
<220> FEATURE:
<223> OTHER INFORMATION: peptide motif

<400> SEQUENCE: 85

Asp Thr Val Lys Ala
1               5

<210> SEQ ID NO 86
<211> LENGTH: 5
<212> TYPE: PRT
<213> ORGANISM: Artificial Sequence
<220> FEATURE:
<223> OTHER INFORMATION: peptide motif

<400> SEQUENCE: 86

Ile Ser Leu Val Ala
1               5

<210> SEQ ID NO 87
<211> LENGTH: 5
<212> TYPE: PRT
<213> ORGANISM: Artificial Sequence
<220> FEATURE:
<223> OTHER INFORMATION: peptide motif

<400> SEQUENCE: 87

Ile Gly Val Val Ala
1               5

<210> SEQ ID NO 88
<211> LENGTH: 5
<212> TYPE: PRT
<213> ORGANISM: Artificial Sequence
<220> FEATURE:
<223> OTHER INFORMATION: peptide motif

<400> SEQUENCE: 88

Ile Gly Trp Val Ala
1               5

<210> SEQ ID NO 89
<211> LENGTH: 5
<212> TYPE: PRT
<213> ORGANISM: Artificial Sequence
<220> FEATURE:
<223> OTHER INFORMATION: peptide motif

```
<400> SEQUENCE: 89

Ile Gly Leu Tyr Ala
1               5

<210> SEQ ID NO 90
<211> LENGTH: 5
<212> TYPE: PRT
<213> ORGANISM: Artificial Sequence
<220> FEATURE:
<223> OTHER INFORMATION: peptide motif

<400> SEQUENCE: 90

Gly His Ile Asn Asp
1               5

<210> SEQ ID NO 91
<211> LENGTH: 5
<212> TYPE: PRT
<213> ORGANISM: Artificial Sequence
<220> FEATURE:
<223> OTHER INFORMATION: peptide motif

<400> SEQUENCE: 91

Gly Arg Phe Asn Asp
1               5

<210> SEQ ID NO 92
<211> LENGTH: 5
<212> TYPE: PRT
<213> ORGANISM: Artificial Sequence
<220> FEATURE:
<223> OTHER INFORMATION: peptide motif

<400> SEQUENCE: 92

Gly Arg Ile Asp Asp
1               5

<210> SEQ ID NO 93
<211> LENGTH: 5
<212> TYPE: PRT
<213> ORGANISM: Artificial Sequence
<220> FEATURE:
<223> OTHER INFORMATION: peptide motif

<400> SEQUENCE: 93

Gly Arg Ile Gln Asp
1               5

<210> SEQ ID NO 94
<211> LENGTH: 10
<212> TYPE: PRT
<213> ORGANISM: Artificial Sequence
<220> FEATURE:
<223> OTHER INFORMATION: peptide motif

<400> SEQUENCE: 94

Asp Val Asn Ser Val Glu Lys Pro Val Val
1               5                   10

<210> SEQ ID NO 95
<211> LENGTH: 10
<212> TYPE: PRT
<213> ORGANISM: Artificial Sequence
<220> FEATURE:
<223> OTHER INFORMATION: peptide motif
```

<400> SEQUENCE: 95

Glu Val Asn Ser Val Glu Lys Pro Val Val
1               5                   10

<210> SEQ ID NO 96
<211> LENGTH: 10
<212> TYPE: PRT
<213> ORGANISM: Artificial Sequence
<220> FEATURE:
<223> OTHER INFORMATION: peptide motif

<400> SEQUENCE: 96

Leu Val Asn Ser Val Glu Lys Pro Val Val
1               5                   10

<210> SEQ ID NO 97
<211> LENGTH: 10
<212> TYPE: PRT
<213> ORGANISM: Artificial Sequence
<220> FEATURE:
<223> OTHER INFORMATION: peptide motif

<400> SEQUENCE: 97

Met Val Asn Ser Val Glu Lys Pro Val Val
1               5                   10

<210> SEQ ID NO 98
<211> LENGTH: 10
<212> TYPE: PRT
<213> ORGANISM: Artificial Sequence
<220> FEATURE:
<223> OTHER INFORMATION: peptide motif

<400> SEQUENCE: 98

Arg Val Asn Ser Val Glu Lys Pro Val Val
1               5                   10

<210> SEQ ID NO 99
<211> LENGTH: 10
<212> TYPE: PRT
<213> ORGANISM: Artificial Sequence
<220> FEATURE:
<223> OTHER INFORMATION: peptide motif

<400> SEQUENCE: 99

Ser Val Asn Ser Val Glu Lys Pro Val Val
1               5                   10

<210> SEQ ID NO 100
<211> LENGTH: 10
<212> TYPE: PRT
<213> ORGANISM: Artificial Sequence
<220> FEATURE:
<223> OTHER INFORMATION: peptide motif

<400> SEQUENCE: 100

Thr Val Asn Ser Val Glu Lys Pro Val Val
1               5                   10

<210> SEQ ID NO 101
<211> LENGTH: 10
<212> TYPE: PRT
<213> ORGANISM: Artificial Sequence
<220> FEATURE:
<223> OTHER INFORMATION: peptide motif

```
<400> SEQUENCE: 101

Val Val Asn Ser Val Glu Lys Pro Val Val
1               5                   10

<210> SEQ ID NO 102
<211> LENGTH: 10
<212> TYPE: PRT
<213> ORGANISM: Artificial Sequence
<220> FEATURE:
<223> OTHER INFORMATION: peptide motif

<400> SEQUENCE: 102

Trp Val Asn Ser Val Glu Lys Pro Val Val
1               5                   10

<210> SEQ ID NO 103
<211> LENGTH: 10
<212> TYPE: PRT
<213> ORGANISM: Artificial Sequence
<220> FEATURE:
<223> OTHER INFORMATION: peptide motif

<400> SEQUENCE: 103

Tyr Val Asn Ser Val Glu Lys Pro Val Val
1               5                   10

<210> SEQ ID NO 104
<211> LENGTH: 10
<212> TYPE: PRT
<213> ORGANISM: Artificial Sequence
<220> FEATURE:
<223> OTHER INFORMATION: peptide motif

<400> SEQUENCE: 104

Gly Pro Asn Ser Val Glu Lys Pro Val Val
1               5                   10

<210> SEQ ID NO 105
<211> LENGTH: 10
<212> TYPE: PRT
<213> ORGANISM: Artificial Sequence
<220> FEATURE:
<223> OTHER INFORMATION: peptide motif

<400> SEQUENCE: 105

Gly Val Asp Ser Val Glu Lys Pro Val Val
1               5                   10

<210> SEQ ID NO 106
<211> LENGTH: 10
<212> TYPE: PRT
<213> ORGANISM: Artificial Sequence
<220> FEATURE:
<223> OTHER INFORMATION: peptide motif

<400> SEQUENCE: 106

Gly Val Ile Ser Val Glu Lys Pro Val Val
1               5                   10

<210> SEQ ID NO 107
<211> LENGTH: 10
<212> TYPE: PRT
<213> ORGANISM: Artificial Sequence
<220> FEATURE:
<223> OTHER INFORMATION: peptide motif
```

```
<400> SEQUENCE: 107

Gly Val Leu Ser Val Glu Lys Pro Val Val
1               5                   10

<210> SEQ ID NO 108
<211> LENGTH: 10
<212> TYPE: PRT
<213> ORGANISM: Artificial Sequence
<220> FEATURE:
<223> OTHER INFORMATION: peptide motif

<400> SEQUENCE: 108

Gly Val Arg Ser Val Glu Lys Pro Val Val
1               5                   10

<210> SEQ ID NO 109
<211> LENGTH: 10
<212> TYPE: PRT
<213> ORGANISM: Artificial Sequence
<220> FEATURE:
<223> OTHER INFORMATION: peptide motif

<400> SEQUENCE: 109

Gly Val Tyr Ser Val Glu Lys Pro Val Val
1               5                   10

<210> SEQ ID NO 110
<211> LENGTH: 10
<212> TYPE: PRT
<213> ORGANISM: Artificial Sequence
<220> FEATURE:
<223> OTHER INFORMATION: peptide motif

<400> SEQUENCE: 110

Gly Val Asn Ile Val Glu Lys Pro Val Val
1               5                   10

<210> SEQ ID NO 111
<211> LENGTH: 10
<212> TYPE: PRT
<213> ORGANISM: Artificial Sequence
<220> FEATURE:
<223> OTHER INFORMATION: peptide motif

<400> SEQUENCE: 111

Gly Val Asn Leu Val Glu Lys Pro Val Val
1               5                   10

<210> SEQ ID NO 112
<211> LENGTH: 10
<212> TYPE: PRT
<213> ORGANISM: Artificial Sequence
<220> FEATURE:
<223> OTHER INFORMATION: peptide motif

<400> SEQUENCE: 112

Gly Val Asn Ser Cys Glu Lys Pro Val Val
1               5                   10

<210> SEQ ID NO 113
<211> LENGTH: 10
<212> TYPE: PRT
<213> ORGANISM: Artificial Sequence
<220> FEATURE:
<223> OTHER INFORMATION: peptide motif
```

```
<400> SEQUENCE: 113

Gly Val Asn Ser Gly Glu Lys Pro Val Val
1               5                   10

<210> SEQ ID NO 114
<211> LENGTH: 10
<212> TYPE: PRT
<213> ORGANISM: Artificial Sequence
<220> FEATURE:
<223> OTHER INFORMATION: peptide motif

<400> SEQUENCE: 114

Gly Val Asn Ser Trp Glu Lys Pro Val Val
1               5                   10

<210> SEQ ID NO 115
<211> LENGTH: 10
<212> TYPE: PRT
<213> ORGANISM: Artificial Sequence
<220> FEATURE:
<223> OTHER INFORMATION: peptide motif

<400> SEQUENCE: 115

Gly Val Asn Ser Val Gly Lys Pro Val Val
1               5                   10

<210> SEQ ID NO 116
<211> LENGTH: 10
<212> TYPE: PRT
<213> ORGANISM: Artificial Sequence
<220> FEATURE:
<223> OTHER INFORMATION: peptide sequence

<400> SEQUENCE: 116

Gly Val Asn Ser Val Glu Cys Pro Val Val
1               5                   10

<210> SEQ ID NO 117
<211> LENGTH: 10
<212> TYPE: PRT
<213> ORGANISM: Artificial Sequence
<220> FEATURE:
<223> OTHER INFORMATION: peptide motif

<400> SEQUENCE: 117

Gly Val Asn Ser Val Glu Arg Pro Val Val
1               5                   10

<210> SEQ ID NO 118
<211> LENGTH: 10
<212> TYPE: PRT
<213> ORGANISM: Artificial Sequence
<220> FEATURE:
<223> OTHER INFORMATION: peptide motif

<400> SEQUENCE: 118

Gly Val Asn Ser Val Glu Lys Ala Val Val
1               5                   10

<210> SEQ ID NO 119
<211> LENGTH: 10
<212> TYPE: PRT
<213> ORGANISM: Artificial Sequence
<220> FEATURE:
<223> OTHER INFORMATION: peptide motif
```

```
<400> SEQUENCE: 119

Gly Val Asn Ser Val Glu Lys Arg Val Val
1               5                   10

<210> SEQ ID NO 120
<211> LENGTH: 10
<212> TYPE: PRT
<213> ORGANISM: Artificial Sequence
<220> FEATURE:
<223> OTHER INFORMATION: peptide motif

<400> SEQUENCE: 120

Gly Val Asn Ser Val Glu Lys Ser Val Val
1               5                   10

<210> SEQ ID NO 121
<211> LENGTH: 10
<212> TYPE: PRT
<213> ORGANISM: Artificial Sequence
<220> FEATURE:
<223> OTHER INFORMATION: peptide motif

<400> SEQUENCE: 121

Gly Val Asn Ser Val Glu Lys Pro Ala Val
1               5                   10

<210> SEQ ID NO 122
<211> LENGTH: 10
<212> TYPE: PRT
<213> ORGANISM: Artificial Sequence
<220> FEATURE:
<223> OTHER INFORMATION: peptide motif

<400> SEQUENCE: 122

Gly Val Asn Ser Val Glu Lys Pro Met Val
1               5                   10

<210> SEQ ID NO 123
<211> LENGTH: 10
<212> TYPE: PRT
<213> ORGANISM: Artificial Sequence
<220> FEATURE:
<223> OTHER INFORMATION: peptide motif

<400> SEQUENCE: 123

Gly Val Asn Ser Val Glu Lys Pro Pro Val
1               5                   10

<210> SEQ ID NO 124
<211> LENGTH: 10
<212> TYPE: PRT
<213> ORGANISM: Artificial Sequence
<220> FEATURE:
<223> OTHER INFORMATION: peptide motif

<400> SEQUENCE: 124

Gly Val Asn Ser Val Glu Lys Pro Ser Val
1               5                   10

<210> SEQ ID NO 125
<211> LENGTH: 10
<212> TYPE: PRT
<213> ORGANISM: Artificial Sequence
<220> FEATURE:
<223> OTHER INFORMATION: peptide motif
```

```
<400> SEQUENCE: 125

Gly Val Asn Ser Val Glu Lys Pro Val Phe
1               5                   10

<210> SEQ ID NO 126
<211> LENGTH: 10
<212> TYPE: PRT
<213> ORGANISM: Artificial Sequence
<220> FEATURE:
<223> OTHER INFORMATION: peptide motif

<400> SEQUENCE: 126

Gly Val Asn Ser Val Glu Lys Pro Val Ile
1               5                   10

<210> SEQ ID NO 127
<211> LENGTH: 10
<212> TYPE: PRT
<213> ORGANISM: Artificial Sequence
<220> FEATURE:
<223> OTHER INFORMATION: peptide motif

<400> SEQUENCE: 127

Gly Val Asn Ser Val Glu Lys Pro Val Tyr
1               5                   10

<210> SEQ ID NO 128
<211> LENGTH: 4
<212> TYPE: PRT
<213> ORGANISM: Artificial Sequence
<220> FEATURE:
<223> OTHER INFORMATION: peptide motif

<400> SEQUENCE: 128

Thr Glu Thr Thr
1

<210> SEQ ID NO 129
<211> LENGTH: 4
<212> TYPE: PRT
<213> ORGANISM: Artificial Sequence
<220> FEATURE:
<223> OTHER INFORMATION: peptide motif

<400> SEQUENCE: 129

Ser Glu Thr Asn
1

<210> SEQ ID NO 130
<211> LENGTH: 6
<212> TYPE: PRT
<213> ORGANISM: Artificial Sequence
<220> FEATURE:
<223> OTHER INFORMATION: peptide motif

<400> SEQUENCE: 130

Gly Thr Glu Thr Thr Ser
1               5

<210> SEQ ID NO 131
<211> LENGTH: 6
<212> TYPE: PRT
<213> ORGANISM: Artificial Sequence
<220> FEATURE:
<223> OTHER INFORMATION: peptide motif
```

<400> SEQUENCE: 131

Gly Ser Glu Thr Asn Ser
1               5

<210> SEQ ID NO 132
<211> LENGTH: 4
<212> TYPE: PRT
<213> ORGANISM: Artificial Sequence
<220> FEATURE:
<223> OTHER INFORMATION: peptide motif

<400> SEQUENCE: 132

Leu Leu Val Ile
1

<210> SEQ ID NO 133
<211> LENGTH: 4
<212> TYPE: PRT
<213> ORGANISM: Artificial Sequence
<220> FEATURE:
<223> OTHER INFORMATION: peptide motif

<400> SEQUENCE: 133

Leu Met Val Ile
1

<210> SEQ ID NO 134
<211> LENGTH: 4
<212> TYPE: PRT
<213> ORGANISM: Artificial Sequence
<220> FEATURE:
<223> OTHER INFORMATION: peptide motif

<400> SEQUENCE: 134

Leu Thr Val Ile
1

<210> SEQ ID NO 135
<211> LENGTH: 4
<212> TYPE: PRT
<213> ORGANISM: Artificial Sequence
<220> FEATURE:
<223> OTHER INFORMATION: peptide motif

<400> SEQUENCE: 135

Leu Val Val Ile
1

<210> SEQ ID NO 136
<211> LENGTH: 4
<212> TYPE: PRT
<213> ORGANISM: Artificial Sequence
<220> FEATURE:
<223> OTHER INFORMATION: peptide motif

<400> SEQUENCE: 136

Leu Ala Ala Ile
1

<210> SEQ ID NO 137
<211> LENGTH: 8
<212> TYPE: PRT
<213> ORGANISM: Artificial Sequence
<220> FEATURE:
<223> OTHER INFORMATION: peptide motif

```
<400> SEQUENCE: 137

Asn Val Lys Met Pro Val Ile Asp
1               5

<210> SEQ ID NO 138
<211> LENGTH: 8
<212> TYPE: PRT
<213> ORGANISM: Artificial Sequence
<220> FEATURE:
<223> OTHER INFORMATION: peptide motif

<400> SEQUENCE: 138

Lys Glu Lys Met Pro Val Ile Asp
1               5

<210> SEQ ID NO 139
<211> LENGTH: 8
<212> TYPE: PRT
<213> ORGANISM: Artificial Sequence
<220> FEATURE:
<223> OTHER INFORMATION: peptide motif

<400> SEQUENCE: 139

Lys His Lys Met Pro Val Ile Asp
1               5

<210> SEQ ID NO 140
<211> LENGTH: 8
<212> TYPE: PRT
<213> ORGANISM: Artificial Sequence
<220> FEATURE:
<223> OTHER INFORMATION: peptide motif

<400> SEQUENCE: 140

Lys Lys Lys Met Pro Val Ile Asp
1               5

<210> SEQ ID NO 141
<211> LENGTH: 8
<212> TYPE: PRT
<213> ORGANISM: Artificial Sequence
<220> FEATURE:
<223> OTHER INFORMATION: peptide motif

<400> SEQUENCE: 141

Lys Trp Lys Met Pro Val Ile Asp
1               5

<210> SEQ ID NO 142
<211> LENGTH: 8
<212> TYPE: PRT
<213> ORGANISM: Artificial Sequence
<220> FEATURE:
<223> OTHER INFORMATION: peptide motif

<400> SEQUENCE: 142

Lys Val Lys Met Pro Val Gln Asp
1               5

<210> SEQ ID NO 143
<211> LENGTH: 8
<212> TYPE: PRT
<213> ORGANISM: Artificial Sequence
<220> FEATURE:
<223> OTHER INFORMATION: peptide motif
```

<400> SEQUENCE: 143

Lys Val Lys Met Pro Val Ile Asn
1               5

<210> SEQ ID NO 144
<211> LENGTH: 4
<212> TYPE: PRT
<213> ORGANISM: Artificial Sequence
<220> FEATURE:
<223> OTHER INFORMATION: peptide motif

<400> SEQUENCE: 144

His Val Gly Gly
1

<210> SEQ ID NO 145
<211> LENGTH: 4
<212> TYPE: PRT
<213> ORGANISM: Artificial Sequence
<220> FEATURE:
<223> OTHER INFORMATION: peptide motif

<400> SEQUENCE: 145

Gln Val Gly Met
1

<210> SEQ ID NO 146
<211> LENGTH: 4
<212> TYPE: PRT
<213> ORGANISM: Artificial Sequence
<220> FEATURE:
<223> OTHER INFORMATION: peptide motif

<400> SEQUENCE: 146

Gln Val Gly Ser
1

<210> SEQ ID NO 147
<211> LENGTH: 4
<212> TYPE: PRT
<213> ORGANISM: Artificial Sequence
<220> FEATURE:
<223> OTHER INFORMATION: peptide motif

<400> SEQUENCE: 147

Gln Val Gly Tyr
1

<210> SEQ ID NO 148
<211> LENGTH: 5
<212> TYPE: PRT
<213> ORGANISM: Artificial Sequence
<220> FEATURE:
<223> OTHER INFORMATION: peptide motif

<400> SEQUENCE: 148

Gly Val Glu Glu Glu
1               5

<210> SEQ ID NO 149
<211> LENGTH: 7
<212> TYPE: PRT
<213> ORGANISM: Artificial Sequence
<220> FEATURE:
<223> OTHER INFORMATION: peptide motif

<400> SEQUENCE: 149

Asp Ala Tyr Glu Asp Val Cys
1               5

<210> SEQ ID NO 150
<211> LENGTH: 7
<212> TYPE: PRT
<213> ORGANISM: Artificial Sequence
<220> FEATURE:
<223> OTHER INFORMATION: peptide motif

<400> SEQUENCE: 150

Asn Ala Tyr Glu Asp Gly Cys
1               5

<210> SEQ ID NO 151
<211> LENGTH: 7
<212> TYPE: PRT
<213> ORGANISM: Artificial Sequence
<220> FEATURE:
<223> OTHER INFORMATION: peptide motif

<400> SEQUENCE: 151

Asn Ala Tyr Glu Asp Lys Cys
1               5

<210> SEQ ID NO 152
<211> LENGTH: 7
<212> TYPE: PRT
<213> ORGANISM: Artificial Sequence
<220> FEATURE:
<223> OTHER INFORMATION: peptide motif

<400> SEQUENCE: 152

Asn Ala Tyr Glu Asp Arg Cys
1               5

<210> SEQ ID NO 153
<211> LENGTH: 7
<212> TYPE: PRT
<213> ORGANISM: Artificial Sequence
<220> FEATURE:
<223> OTHER INFORMATION: peptide motif

<400> SEQUENCE: 153

Asn Ala Tyr Glu Asp Ser Cys
1               5

<210> SEQ ID NO 154
<211> LENGTH: 7
<212> TYPE: PRT
<213> ORGANISM: Artificial Sequence
<220> FEATURE:
<223> OTHER INFORMATION: peptide motif

<400> SEQUENCE: 154

Asn Ala Tyr Glu Asp Val Arg
1               5

<210> SEQ ID NO 155
<211> LENGTH: 59
<212> TYPE: DNA
<213> ORGANISM: Artificial Sequence
<220> FEATURE:
<223> OTHER INFORMATION: oligonucleotide primer

```
<400> SEQUENCE: 155
gacgaattcg ctagcaagag gagaagtcga catgtccaat tcactggccg tcgttttac         59

<210> SEQ ID NO 156
<211> LENGTH: 47
<212> TYPE: DNA
<213> ORGANISM: Artificial Sequence
<220> FEATURE:
<223> OTHER INFORMATION: oligonucleotide primer

<400> SEQUENCE: 156
gaccctagga agctttctag agtcgaccta tgcggcatca gagcaga                      47

<210> SEQ ID NO 157
<211> LENGTH: 185
<212> TYPE: PRT
<213> ORGANISM: Bacillus methanolicus

<400> SEQUENCE: 157

Met Gly Lys Leu Phe Glu Glu Lys Thr Ile Lys Thr Glu Gln Ile Phe
1               5                   10                  15

Ser Gly Arg Val Val Lys Leu Gln Val Asp Asp Val Glu Leu Pro Asn
            20                  25                  30

Gly Gln Thr Ser Lys Arg Glu Ile Val Arg His Pro Gly Ala Val Ala
        35                  40                  45

Val Ile Ala Ile Thr Asn Glu Asn Lys Ile Val Met Val Glu Gln Tyr
    50                  55                  60

Arg Lys Pro Leu Glu Lys Ser Ile Val Glu Ile Pro Ala Gly Lys Leu
65                  70                  75                  80

Glu Lys Gly Glu Asp Pro Arg Ile Thr Ala Leu Arg Glu Leu Glu Glu
                85                  90                  95

Glu Thr Gly Tyr Glu Cys Glu Gln Met Glu Trp Leu Ile Ser Phe Ala
            100                 105                 110

Thr Ser Pro Gly Phe Ala Asp Glu Ile Ile His Ile Tyr Val Ala Lys
        115                 120                 125

Gly Leu Ser Lys Lys Glu Asn Ala Ala Gly Leu Asp Glu Asp Glu Phe
    130                 135                 140

Val Asp Leu Ile Glu Leu Thr Leu Asp Glu Ala Leu Gln Tyr Ile Lys
145                 150                 155                 160

Glu Gln Arg Ile Tyr Asp Ser Lys Thr Val Ile Ala Val Gln Tyr Leu
                165                 170                 175

Gln Leu Gln Glu Ala Leu Lys Asn Lys
            180                 185
```

What is claimed is:

1. An NAD$^+$-dependent non-natural alcohol dehydrogenase comprising at least one amino acid substitution as compared to a corresponding alcohol dehydrogenase and capable of greater conversion of methanol or ethanol to formaldehyde or acetaldehyde, respectively, as compared to the corresponding alcohol dehydrogenase without amino acid substitution, and having a sequence identity of 55% or greater, 65% or greater, 75% or greater, 85% or greater, 90% or greater, 92.5% or greater, 95% or greater, 96% or greater, 97% or greater, 98% or greater, or 99% or greater to an NAD$^+$-dependent alcohol dehydrogenase amino acid template selected from the group consisting of SEQ ID NO:1 (MDH MGA3_17392), SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, and SEQ ID NO:77, or a fragment of said template having said dehydrogenase activity with an amino-terminal deletion, carboxy-terminal deletion, or both, the fragment having a sequence identity of 55% or greater, 65% or greater, 75% or greater, 85% or greater, 90% or greater, 92.5% or greater, 95% or greater, 96% or greater, 97% or greater, 98% or greater, or 99% or greater to the template, and wherein the at least one amino acid substitution is based on formula: $R^1XR^2$, where $R^1$ is an original amino acid at position X of the template, and $R^2$ is the variant amino acid that replaces $R^1$ at a position on the template corresponding to X, wherein $XR^2$ is selected from the group consisting of 11T, 38N, 42Q, 48D, 53I, 56K, 60E, 61A, 63F, 65Q, 70N, 71I, 71T, 71V, 74S, 81G, 84R, 86K, 87K, 94V, 99P, 99T, 103V, 106L, 107S, 108V, 108W, 109Y, 112K, 112R, 115H, 116F, 117D, 117Q, 117Y, 120H, 120R, 121A, 121D, 121E, 121L, 121M, 121R, 121S, 121T, 121V, 121W, 121Y, 122A, 122P, 123D, 123I, 123L, 123R, 123Y, 124I, 124L, 124R, 125C, 125G, 125V, 125W, 126G, 126V, 127C, 127R, 128A, 128R, 128S, 129A, 129M, 129P, 129S, 129V, 130F, 130I, 130Y, 134T, 143T, 145M, 146N, 147R, 148A, 148F, 148G, 148I, 148T, 148V, 148W, 149L, 149M, 149T, 149V, 150A, 150I, 152M, 155V, 157N, 158E, 158H, 158K, 158W, 161A, 161G, 161Q, 161S, 161V, 163F, 163N, 163Q, 163T, 164G, 164N, 165G, 181R, 184T, 186M, 190A, 190S, 199V, 217K, 226M, 256C, 267H, 269S, 270M, 270S, 270Y, 296S, 298H, 300T, 302V, 312V, 316V, 323M, 333L, 336L, 337C, 343D, 344A, 344G, 345E, 350K, 354M, 355D, 355I, 355K, 358G, 360A, 360G, 360K, 360R, 360S, 361N, 361R, 363K, and 379M.

2. The NAD$^+$-dependent non-natural alcohol dehydrogenase of claim 1, wherein said template is selected from the group consisting of SEQ ID NO:1, SEQ ID NO:11, SEQ ID NO:15, SEQ ID NO:19, SEQ ID NO:29, SEQ ID NO:31 SEQ ID NO:43, SEQ ID NO:45 SEQ ID NO:47, SEQ ID NO:53, SEQ ID NO:55, SEQ ID NO:63, and SEQ ID NO:67.

3. The NAD$^+$-dependent non-natural alcohol dehydrogenase of claim 1, wherein the alcohol dehydrogenase is a methanol dehydrogenase.

4. The NAD$^+$-dependent non-natural alcohol dehydrogenase of claim 3, wherein the methanol dehydrogenase is from bacteria.

5. The NAD$^+$-dependent non-natural alcohol dehydrogenase of claim 4, wherein the methanol dehydrogenase is from *Bacillus methanolicus* MGA3 or *Bacillus methanolicus* PB1.

6. The NAD$^+$-dependent non-natural alcohol dehydrogenase of claim 1, wherein the non-natural alcohol dehydrogenase has a sequence identity of 55% or greater, 65% or greater, 75% or greater, 85% or greater, 90% or greater, 92.5% or greater, 95% or greater, 96% or greater, 97% or greater, 98% or greater, or 99% or greater to any one of the templates of claim 1, wherein $XR^2$ is selected from the group consisting of 38N, 60E, 71I, 71V, 87K, 99T, 103V, 107S, 108V, 108W, 109Y, 115H, 116F, 117D, 117Q, 121D, 121E, 121L, 121M, 121R, 121S, 121T, 121V, 121W, 121Y, 122P, 123D, 123I, 123L, 123R, 123Y, 124I, 124L, 125C, 125G, 125V, 125W, 126G, 127C, 127R, 128A, 128R, 128S, 129A, 129M, 129P, 129S, 129V, 130F, 130I, 130Y, 134T, 143T, 146N, 149L, 149M, 149T, 149V, 150A, 157N, 158E, 158H, 158K, 158W, 163Q, 164N, 267H, 270M, 270S, 270Y, 345E, 355D, 360G, 360K, 360R, 360S, and 361R.

7. The NAD$^+$-dependent non-natural alcohol dehydrogenase of claim 6, wherein $XR^2$ is selected from the group consisting of 107S, 121D, 123D, 123I, 123L, 123R, 123Y, 129A, 129M, 129P, 129S, 129V, 130F, 130I, 130Y, 143T, 146N, 149L, 149M, 149T, 149V, 158E, 158H, 158K, 158W, 267H, 270M, 270S, 270Y, 355D, 360G, 360K, 360R, and 360S.

8. The NAD$^+$-dependent non-natural alcohol dehydrogenase of claim 1, wherein the template is selected from the group consisting of SEQ ID NO:1, SEQ ID NO:3, and SEQ ID NO:5, and wherein $R^1XR^2$ is selected from the group consisting of (a) S11T, D38N, H42Q, E48D, N53I, E56K, D60E, V61A, I63F, P65Q, D70N, P71I, P71T, P71V, T74S, D81G, K84R, E86K, N87K, I94V, S99P, S99T, A103V, I106L, G107S, L108V, L108W, V109Y, N112K, N112R, R115H, I116F, N117D, N117Q, N117Y, Q120H, Q120R, G121A, G121D, G121E, G121L, G121M, G121R, G121S, G121T, G121V, G121W, G121Y, V122A, V122P, N123D, N123I, N123L, N123R, N123Y, S124I, S124L, S124R, V125C, V125G, V125W, E126G, E126V, K127C, K127R, P128A, P128R, P128S, V129A, V129M, V129P, V129S, V130F, V130I, V130Y, A134T, S143T, T145M, T146N, S147R, L148A, L148F, L148G, L148I, L148T, L148V, L148W, A149L, A149M, A149T, A149V, V150A, V150I, T152M, A155V, K157N, V158E, V158H, V158K, V158W, P161A, P161G, P161Q, P161S, P161V, I163F, I163N, I163Q, I163T, D164G, D164N, E165G, K181R, A184T, L186M, T190A, T190S, I199V, Q217K, L226M, G256C, Q267H, G269S, G270M, G270S, G270Y, T296S, R298H, A300T, I302V, G312V, A316V, I323M, F333L, P336L, S337C, G343D, V344A, V344G, K345E, E350K, K/N354M, N355D, N355I, N355K, E/Q358G, V360A, V360G, V360K, V360R, V360S, C361N, C361R, Q/L363K, and K379M; or (b) D38N, D60E, P71I, P71V, N87K, S99T, A103V, G107S, L108V, L108W, V109Y, R115H, I116F, N117D, N117Q, G121D, G121E, G121L, G121M, G121R, G121S, G121T, G121V, G121W, G121Y, V122P, N123D, N123I, N123L, N123R, N123Y, S124I, S124L, V125C, V125G, V125W, E126G, K127C, K127R, P128A, P128R, P128S, V129A, V129M, V129P, V129S, V130F, V130I, V130Y, A134T, S143T, T146N, A149L, A149M, A149T, A149V, V150A, K157N, V158E, V158H, V158K, V158W, I163Q, D164N, Q267H, G270M, G270S, G270Y, K345E, N355D, V360G, V360K, V360R, V360S, and C361R.

9. The NAD$^+$-dependent non-natural alcohol dehydrogenase of claim 1 having a sequence identity of 55% or greater, 65% or greater, 75% or greater, 85% or greater, 90% or greater, 92.5% or greater, 95% or greater, 96% or greater, 97% or greater, 98% or greater, or 99% or greater to any one of the templates of claim 1, and comprising original amino acids at all positions other than selected from the group consisting of 11, 38, 42, 48, 53, 56, 60, 61, 63, 65, 70, 71, 74, 81, 84, 86, 87, 94, 99, 103, 106, 107, 108, 109, 112, 115, 116, 117, 117, 120, 121, 122, 123, 124, 125, 126, 127, 128, 129, 130, 134, 143, 145, 146, 147, 148, 149, 150, 152, 155, 157, 158, 161, 163, 164, 165, 181, 184, 186, 190, 199, 217, 226, 256, 267, 269, 270, 296, 298, 300, 302, 312, 316, 323, 333, 336, 337, 343, 344, 345, 350, 354, 355, 358, 360, 361, 363 and 379; or 38, 60, 71, 87, 99, 103, 107, 108, 109, 115, 116, 117, 121, 122, 123, 124, 125, 126, 127, 128, 129, 130, 134, 143, 146, 149, 150, 157, 158, 163, 164, 267, 270, 345, 355, 360, and 361.

10. The NAD$^+$-dependent non-natural alcohol dehydrogenase of claim 1 having a sequence identity of 55% or greater, 65% or greater, 75% or greater, 85% or greater, 90% or greater, 92.5% or greater, 95% or greater, 96% or greater, 97% or greater, 98% or greater, or 99% or greater to any one of the templates of claim 1, and comprising original amino acids at all positions other than 107, 121, 123, 129, 130, 143, 146, 149, 158, 267, 270, 355, and 360.

11. The NAD$^+$-dependent non-natural alcohol dehydrogenase of claim 8 comprising two, three, four, five, six, seven, eight, nine, ten, eleven or twelve amino acid substitutions selected from the group consisting of: (a) S11T, D38N, H42Q, E48D, N53I, E56K, D60E, V61A, I63F, P65Q, D70N, P71I, P71T, P71V, T74S, D81G, K84R, E86K, N87K, I94V, S99P, S99T, A103V, I106L, G107S, L108V, L108W, V109Y, N112K, N112R, R115H, I116F, N117D, N117Q, N117Y, Q120H, Q120R, G121A, G121D, G121E, G121L, G121M, G121R, G121S, G121T, G121V, G121W, G121Y, V122A, V122P, N123D, N123I, N123L, N123R, N123Y, S124I, S124L, S124R, V125C, V125G, V125W, E126G, E126V, K127C, K127R, P128A, P128R, P128S, V129A, V129M, V129P, V129S, V130F, V130I, V130Y, A134T, S143T, T145M, T146N, S147R, L148A, L148F, L148G, L148I, L148T, L148V, L148W, A149L, A149M, A149T, A149V, V150A, V150I, T152M, A155V, K157N, V158E, V158H, V158K, V158W, P161A, P161G, P161Q, P161S, P161V, I163F, I163N, I163Q, I163T, D164G, D164N, E165G, K181R, A184T, L186M, T190A, T190S, I199V, Q217K, L226M, G256C, Q267H, G269S, G270M, G270S, G270Y, T296S, R298H, A300T, I302V, G312V, A316V, I323M, F333L, P336L, S337C, G343D, V344A, V344G, K345E, E350K, K/N354M, N355D, N355I, N355K, E/Q358G, V360A, V360G, V360K, V360R, V360S, C361N, C361R, Q/L363K, and K379M; or (b) D38N, D60E, P71I, P71V, N87K, S99T, A103V, G107S, L108V, L108W, V109Y, R115H, I116F, N117D, N117Q, G121D, G121E, G121L, G121M, G121R, G121S, G121T, G121V, G121W, G121Y, V122P, N123D, N123I, N123L, N123R, N123Y, S124I, S124L, V125C, V125G, V125W, E126G, K127C, K127R, P128A, P128R, P128S, V129A, V129M, V129P, V129S, V130F, V130I, V130Y, A134T, S143T, T146N, A149L, A149M, A149T, A149V, V150A, K157N, V158E, V158H, V158K, V158W, I163Q, D164N, Q267H, G270M, G270S, G270Y, K345E, N355D, V360G, V360K, V360R, V360S, and C361R.

12. The NAD⁺-dependent non-natural alcohol dehydrogenase of claim 8 comprising a set of amino acid substitutions selected from the group consisting of (a) D70N, L148G, P161G, V360A; (b) D70N, L148G, V360A, C361N; (c) D70N, L148V, V150I, P161A, V360G; (d) D70N, L148V, V360G; (e) D70N, P161A, V360A; (f) D70N, P161V, V360G, C361N; (g) D70N, V150I, P161A, V360A; (h) D70N, V150I, P161V, V360G, C361N; (i) E48D, L148V, P161A, V360A; (j) L148G, P161A, V360A, C361N; (k) L148G, P161A, V360G; (l) L148G, P161A, V360G, C361N; (m) L148G, P161G, V360A; (n) L148G, P161G, V360G, C361N; (o) L148G, V360A, C361N; (p) L148G, V360G, C361N; (q) L148I, P161G, V360G; (r) L148I, P161V, V360G; (s) L148T, V150I, V360A; (t) L148T, V360G; (u) L148V, P161A, V360A; (v) L148V, V150I, P161A, V360A; (w) L148V, V150I, P161A, V360A, C361N; (x) L148V, V150I, P161A, V360G; (y) L148V, V150I, P161A, V360G, C361N; (z) L148V, V150I, P161A, V360G, C361N; (aa) L148V, V150I, P161G, V360A; (ab) L148V, V150I, P161V, V360G, C361N; (ac) L148W, P161A, V360A, C361N; (ad) N112K, S147R, P161A, V360A; (ae) P161A, Q217K, V360A, C361N; (af) P161A, V360A, C361N; (ag) P161A, V360G; (ah) P161V, E358G, V360G; (ai) P161V, V360A, C361N; (aj) L148W, P161A, V360A, C361N; (ak) N112K, S147R, P161A, V360A; (al) P161A, Q217K, V360A, C361N; (am) P161A, V360A, C361N; (an) P161A, V360G; (ao) P161V, E358G, V360G; (ap) P161V, V360A, C361N; (aq) P161V, V360G; (ar) P65Q, L148G, V150I, P161A, V360G, C361N; (as) S147R, L148A, V150I, P161A, V360G; (at) S147R, L148F, V150I, P161G, V360G; (au) S147R, L148V, P161G, V360A; (av) P161V, V360G; (aw) P65Q, L148G, V150I, P161A, V360G, C361N; (ax) S147R, L148A, V150I, P161A, V360G; (ay) S147R, L148F, V150I, P161G, V360G; (az) S147R, L148V, P161G, V360A; (aaa) S147R, L148V, P161V, V360G; (aab) S147R, L148V, V150I, P161A, C361N; (aac) S147R, L148V, V150I, P161G, V360G; (aad) S147R, P161A, V360A; (aae) S147R, P161A, V360A, C361N; (aaf) S147R, P161A, V360G; (aag) S147R, P161V, V360G; (aah) S147R, P161V, V360G, C361N; (aai) S147R, V150I, P161V, V360A; (aaj) S147R, V150I, V360A, C361N; (aak) T145M, L148I, V360G; (aal) V150I, I302V, V360G, C361N; (aam) V150I, P161A, C361N; (aan) V150I, P161G, V360A, C361N; (aao) V150I, P161G, V360G; (aap) V150I, P161G, V360G, C361N; (aaq) V150I, P161V, C361N; (aar) V150I, P161V, K/N354R, V360A, C361N; (aas) V150I, P161V, V360A, C361N; (aat) V150I, P161V, V360G, C361N; (aau) V150I, V360A, C361N; (aav) V150I, V360G; (aaw) S11T, T74S, G269S, V344A; (aax) K84R, I163T; (aay) V122A, I163N; (aaz) G107S, F333L; (aaaa) V129M, T152M, G343D; (aaab) I63F, N355K; (aaac) G107S, F333L; (aaad) E86K, S99T, A149V; (aaae) N53I, V158E; (aaaf) N355I, K379M; (aaag) H42Q, G107S; (aaah) Q120H, I163N; (aaai) A149V, I323M; (aaaj) G107S, F333L; (aaak) D164G, K181R; (aaal) A155V, R298H, N355D; (aaam) N123D, E165G; (aaan) I163F, L186M; (aaao) G121A, T296S; (aaap) I94V, S99P, N123I; (aaaq) E126V, V129M, V344G; (aaar) Q120R, S143T; (aaas) G256C, A316V; (aaat) P161Q, G312V; (aaau) L226M, A300T, V360A; (aaav) S337C, E350K, N355D, Q/L363K; (aaaw) D81G, V158E; (aaax) I106L, N117Y, E126V; (aaay) G107S, G121D; (aaaz) V61A, V158E; (aaaaa) N53I, V158E; (aaaab) N117Y, T190S; (aaaac) S124R, I199V; (aaaad) K/N354M, C361R; (aaaae) A184T, C361R; (aaaaf) E56K, Q267H; (aaaag) S124R, E126G; (aaaah) T190A, N355K; (aaaai) P71T, F333L; (aaaaj) G107S, F333L; and (aaaak) N123I, P336L, (aaaal) D38D/A149V, (aaaam) D38N/V163V, (aaaan) D73D/L108V, (aaaao) G121R/P161S; and (aaaap) N112R/P161S.

13. The NAD⁺-dependent non-natural alcohol dehydrogenase of claim 1 comprising a sequence motif selected from one of groups (i)-(xv) as follows:
  (i) TNA and VTNAF (SEQ ID NO: 79);
  (ii) VEV and GVEVA (SEQ ID NO: 80);
  (iii) DIA, PDIAD (SEQ ID NO: 81), DVA, and PDVAD (SEQ ID NO: 82);
  (iv) EKC and QEKCD (SEQ ID NO: 83);
  (v) STH and GSTHD (SEQ ID NO: 84);
  (vi) TVK and DTVKA (SEQ ID NO: 85);
  (vii) SLV, GVV, GWV, GLY, ISLVA (SEQ ID NO: 86), IGVVA (SEQ ID NO: 87), IGWVA (SEQ ID NO: 88), and IGLYA (SEQ ID NO: 89);
  (viii) HIN, RFN, RID, RIQ, GHIND (SEQ ID NO: 90), GRFND (SEQ ID NO: 91), GRIDD (SEQ ID NO: 92), and GRIQD (SEQ ID NO: 93);
  (ix) DVNSVEKPVV (SEQ ID NO: 94), EVNSVEKPVV (SEQ ID NO: 95), LVNSVEKPVV (SEQ ID NO: 96), MVNSVEKPVV (SEQ ID NO: 97), RVNSVEKPVV (SEQ ID NO: 98), SVNSVEKPVV (SEQ ID NO: 99), TVNSVEKPVV (SEQ ID NO: 100), VVNSVEKPVV (SEQ ID NO: 101), WVNSVEKPVV (SEQ ID NO: 102), YVNSVEKPVV (SEQ ID NO: 103), GPNSVEKPVV (SEQ ID NO: 104), GVDSVEKPVV (SEQ ID NO: 105), GVISVEKPVV (SEQ ID NO: 106), GVLSVEKPVV (SEQ ID NO: 107), GVRSVEKPVV (SEQ ID NO: 108), GVYSVEKPVV (SEQ ID NO: 109), GVNIVEKPVV (SEQ ID NO: 110), GVNLVEKPVV (SEQ ID NO: 111), GVNSCEKPVV (SEQ ID NO: 112), GVNSGEKPVV (SEQ ID NO: 113), GVNSWEKPVV (SEQ ID NO: 114), GVNSVGKPVV (SEQ ID NO: 115), GVNSVECPVV (SEQ ID NO: 116), GVNSVERPVV (SEQ ID NO: 117), GVNSVEKAVV (SEQ ID NO: 118), GVNSVEKRVV (SEQ ID NO: 119), GVNSVEKSVV (SEQ ID NO: 120), GVNSVEKPAV (SEQ ID NO: 121), GVNSVEKPMV (SEQ ID NO: 122), GVNSVEKPPV (SEQ ID NO: 123), GVNSVEKPSV (SEQ ID NO: 124), GVNSVEKPVF (SEQ ID NO: 125), GVNSVEKPVI (SEQ ID NO: 126), and GVNSVEKPVY (SEQ ID NO: 127);

(x) TETT (SEQ ID NO: 128), SETN (SEQ ID NO: 129) GTETTS (SEQ ID NO: 130), and GSETNS (SEQ ID NO: 131);

(xi) LLVI (SEQ ID NO: 132), LMVI (SEQ ID NO: 133), LTVI (SEQ ID NO: 134), LVVI (SEQ ID NO: 135), and LAAI (SEQ ID NO: 136);

(xii) NVKMPVID (SEQ ID NO: 137), KEKMPVID (SEQ ID NO: 138), KHKMPVID (SEQ ID NO: 139), KKKMPVID (SEQ ID NO: 140), KWKMPVID (SEQ ID NO: 141), KVKMPVQD (SEQ ID NO: 142), and KVKMPVIN (SEQ ID NO: 143);

(xiii) HVGG (SEQ ID NO: 144), QVGM (SEQ ID NO: 145), QVGS (SEQ ID NO: 146), and QVGY (SEQ ID NO: 147);

(xiv) VEE and GVEEE (SEQ ID NO: 148);

(xv) DAYEDVC (SEQ ID NO: 149), NAYEDGC (SEQ ID NO: 150), NAYEDKC (SEQ ID NO: 151), and NAYEDRC (SEQ ID NO: 152), and NAYEDSC (SEQ ID NO: 153), and NAYEDVR (SEQ ID NO: 154).

14. The NAD$^+$-dependent non-natural alcohol dehydrogenase of claim 1 having a sequence identity of 75% or greater, 85% or greater, 90% or greater, 92.5% or greater, 95% or greater, 96% or greater, 97% or greater, 98% or greater, or 99% or greater to one of said NAD$^+$-dependent alcohol dehydrogenase templates.

15. The NAD$^+$-dependent non-natural alcohol dehydrogenase of claim 1 that is a) capable, when expressed in a cell, of at least two-fold greater conversion of methanol or ethanol to formaldehyde or acetaldehyde respectively, or b) having a catalytic efficiency ($k_{cat}/K_m$) for the conversion of methanol to formaldehyde of $8.6 \times 10^{-4}$ or greater, as compared to the corresponding alcohol dehydrogenase without amino acid substitution.

16. The NAD$^+$-dependent non-natural alcohol dehydrogenase of claim 15 wherein the methanol is converted to formaldehyde.

17. The NAD$^+$-dependent non-natural alcohol dehydrogenase of claim 15 capable of at least three-fold greater, of at least-four fold, of at least five-fold, of at least six-fold, of at least seven-fold, at least 8-fold, at least 9-fold, at least 10-fold, or at least 11-fold conversion of methanol or ethanol to formaldehyde or acetaldehyde, respectively, in vivo, as compared to the corresponding alcohol dehydrogenase without amino acid substitution.

18. The NAD$^+$-dependent non-natural alcohol dehydrogenase of claim 15 capable of an increase in the rate of conversion of methanol or ethanol to formaldehyde or acetaldehyde respectively, as compared to the corresponding alcohol dehydrogenase without amino acid substitution, in the range of two-fold to twelve-fold greater, in the range of two-fold to eleven-fold greater, in the range of two-fold to ten-fold greater, in the range of two-fold to nine-fold greater, in the range of two-fold to eight-fold greater, in the range of two-fold to seven-fold greater, in the range of two-fold to six-fold greater, in the range of two-fold to five-fold greater, or in the range of two-fold to four-fold greater.

* * * * *